(12) United States Patent
Ohtsuka et al.

(10) Patent No.: US 8,436,012 B2
(45) Date of Patent: May 7, 2013

(54) IMIDAZOPYRIDIN-2-ONE DERIVATIVES

(75) Inventors: Masami Ohtsuka, Tokyo (JP); Noriyasu Haginoya, Chiba (JP); Masanori Ichikawa, Shizuoka (JP); Hironori Matsunaga, Tokyo (JP); Hironao Saito, Tokyo (JP); Yoshihiro Shibata, Chiba (JP); Tomoyuki Tsunemi, Tokyo (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 279 days.

(21) Appl. No.: 12/954,408

(22) Filed: Nov. 24, 2010

(65) Prior Publication Data

US 2011/0082138 A1   Apr. 7, 2011

Related U.S. Application Data

(63) Continuation of application No. PCT/JP2009/063807, filed on Aug. 4, 2009.

(30) Foreign Application Priority Data

Aug. 5, 2008 (JP) ................................. 2008-201670
Mar. 27, 2009 (JP) ................................. 2009-078540

(51) Int. Cl.
    *A61K 31/5377* (2006.01)
    *A61K 31/437* (2006.01)
    *A61K 31/496* (2006.01)
    *A61K 31/519* (2006.01)
    *A61K 31/4985* (2006.01)
    *A61K 31/5025* (2006.01)
    *A61P 35/00* (2006.01)

(52) U.S. Cl.
    USPC .............. 514/303; 514/234.2; 514/253.04; 514/259.31; 514/249; 514/248; 546/118; 544/127; 544/362; 544/281; 544/350; 544/236

(58) Field of Classification Search ............. 514/234.2, 514/303, 253.04, 259.31, 249, 248; 546/118; 544/127, 362, 281, 350, 236
    See application file for complete search history.

(56) References Cited

U.S. PATENT DOCUMENTS 4,294,837 A   10/1981   Lesher

FOREIGN PATENT DOCUMENTS

| JP | 2003-221386 A | 8/2003 |
|---|---|---|
| WO | 99/57103 A1 | 11/1999 |
| WO | 2004/043913 A2 | 5/2004 |
| WO | 2005/100353 A1 | 10/2005 |
| WO | 2006/015123 A1 | 2/2006 |
| WO | 2006/030031 A1 | 3/2006 |
| WO | 2006099268 * | 9/2006 |
| WO | 2007/135398 A1 | 11/2007 |
| WO | 2008/011560 A2 | 1/2008 |
| WO | 2008/023161 A1 | 2/2008 |
| WO | 2008/051493 A2 | 5/2008 |
| WO | 2008/051494 A1 | 5/2008 |
| WO | 2010/008847 A2 | 1/2010 |
| WO | 2010/021693 A2 | 2/2010 |
| WO | 2010/068483 A2 | 6/2010 |
| WO | 2011/096490 A1 | 8/2011 |

OTHER PUBLICATIONS

Meanwell, N. A., et al., "Regiospecific Functionalization of 1,3-Dihydro-2H-benzimidazol-2-one and Structurally Related Cyclic Urea Derivatives," Journal of Organic Chemistry 60(6):1565-1582, Mar. 1995.
Sarbassov, D. D., et al., "Phosphorylation and Regulation of Akt/PKB by the Rictor-mTOR Complex," Science 307(5712):1098-1101, Feb. 2005.
Shaw, J., and L. C. Cantley, "Ras, (PI(3)K and mTOR Signalling Controls Tumour Cell Growth," Nature 441:424-430, May 2006.
Tsang, C. K., et al., "Targeting Mammalian Target of Rapamycin (mTOR) for Health and Diseases," Drug Discovery Today 12(3/4):112-124, Feb. 2007.
Extended European Search Report mailed Feb. 9, 2012, issued in corresponding European Application No. EP 09 80 4973, filed Aug. 4, 2009, 5 pages.

* cited by examiner

*Primary Examiner* — Niloofar Rahmani
(74) *Attorney, Agent, or Firm* — Christensen O'Connor Johnson Kindness PLLC

(57) ABSTRACT

A compound represented by formula (I) having mTOR inhibitory activity or a pharmacologically acceptable salt thereof.

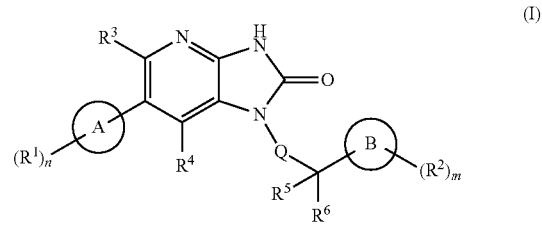

(I)

23 Claims, No Drawings

IMIDAZOPYRIDIN-2-ONE DERIVATIVES

TECHNICAL FIELD

The present invention relates to a novel compound or a pharmacologically acceptable salt thereof, or a pharmaceutical composition comprising the compound or the salt as an active ingredient, having an effect of inhibiting mTOR kinase activity.

BACKGROUND ART

Mammalian target of rapamaycin (mTOR) is a 289 kD serine/threonine kinase identified as a target of rapamycin, a macrolide antimicrobial agent.

mTOR (also referred to as FRAP, RAPT1 or RAFT1) is expressed in almost all organs and tissues and is involved in the PI3K-Akt signaling system. mTOR forms mTORC1 and mTORC2 complexes together with adaptor proteins such as raptor and rictor, respectively, and transduces extracellular signals. mTORC1 activates translation of cancer-related proteins (such as cyclin D1, myc and HIF-10α) by phosphorylating its downstream targets such as S6K and 4EBP-1. On the other hand, mTORC2 is assumed to activate survival signals of cancer cells by phosphorylating its downstream target Ser473 of Akt.

Clinically, the mTOR signaling system has also been observed to be enhanced in many cancer types including renal cancer, osteosarcoma, lung cancer, ovarian cancer, prostate cancer, breast cancer, colon cancer and liver cancer.

Rapamycin, an mTOR inhibitor, binds intracellularly to FKBP12 (FK-506 binding protein) and forms a complex. Then rapamycin/FKBP12 complex binds to mTOR; mTOR kinase activity is assumed to be inhibited by this binding, and protein synthesis and cell proliferation are also inhibited as the results. Rapamycin has in fact been reported as having an antitumor effect in tumor patients. Currently, clinical trials have been performed for mTOR inhibitors including CCI-779, a rapamycin derivative.

As described above, it is thought that mTOR is an effective molecular target for cancer therapy, and that compounds having an effect of inhibiting mTOR kinase activity (hereinafter sometimes referred to as mTOR inhibitory activity) can be pharmacologically useful in cancer therapy, in particular, for cancer with enhanced mTOR signaling, e.g., cancer with LKB mutations or TSC2 mutations, or cancer with inactivated PTEN (Non-patent References 1 to 3).

Compounds such as pyridopyrimidine derivatives and imidazopyrazine derivatives have been known to inhibit mTOR activity.

CITATION LIST

Patent References

Patent Reference 1: WO 2007/051493
Patent Reference 2: WO 2008/023161
Patent Reference 3: WO 2008/051493

Non-Patent References

Non-patent Reference 1: Science, vol. 307, no. 18, 1098-1101, 2005
Non-patent Reference 2: Nature, vol. 441, no. 25, 424-430, 2006
Non-patent Reference 3: Drug Discovery Today, vol. 12, no. 3/4, 112-124, 2007

SUMMARY OF INVENTION

Technical Problem

As a result of conducting extensive studies relating to compounds having mTOR inhibitory activity, the present inventors have found that a compound, represented by the formula (I) according to the present invention, strongly inhibits mTOR kinase activity with an excellent cell proliferation inhibitory effect. Thus, the inventors have completed the present invention.

Accordingly, an object of the present invention is to provide a compound or a pharmacologically acceptable salt thereof having excellent mTOR inhibitory activity.

Another object of the present invention is to provide a pharmaceutical composition or an mTOR inhibitor, in particular, an antitumor agent, comprising the aforementioned compound or pharmacologically acceptable salt thereof as an active ingredient.

Means to Solve Problem

Specifically, the present invention relates to:
(1) A compound represented by the following formula (I):

[Formula 1]

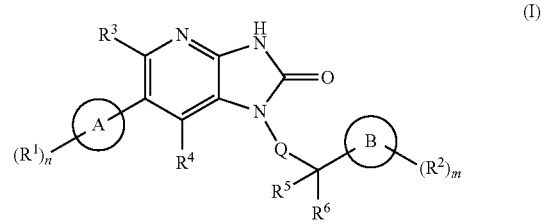

wherein in the general formula (I),
A is an 8- to 10-membered partially saturated or aromatic fused bicyclic nitrogen-containing heterocyclic group having 1 to 3 nitrogen atoms,
A may have the same or different n $R^1$s as substituents,
$R^1$ is a substituent selected from the group consisting of a hydroxy group, a halogen atom, a cyano group, an oxo group, a $C_{1-4}$ alkyl group (wherein the $C_{1-4}$ alkyl group may be substituted with one or two same or different two $C_{1-4}$ alkoxy groups or —$NR^{7a}R^{7b}$s), a $C_{1-4}$ alkoxy group, a halogeno-$C_{1-4}$ alkyl group, —$NR^{7a}R^{7b}$, —C(O)$R^8$ and —C(O)$NR^{9a}R^{9b}$,
n is any integer of 0 to 3,
$R^{7a}$, $R^{7b}$, $R^{9a}$ and $R^{9b}$ are the same or different and are each a hydrogen atom or a $C_{1-4}$ alkyl group (wherein the $C_{1-4}$ alkyl group may be substituted with 1 or 2 hydroxy groups),
$R^8$ is a hydrogen atom, a hydroxy group, a $C_{1-4}$ alkyl group or a $C_{1-4}$ alkoxy group,
B is a 3- to 7-membered saturated or partially saturated monocyclic hydrocarbon group and may contain 1 or 2 oxygen atoms, sulfur atoms, nitrogen atoms, sulfinyl groups and/or sulfonyl groups as ring constituents,
B may have the same or different m $R^2$s as substituents,
$R^2$ is a substituent present on a carbon atom or nitrogen atom forming B,
$R^2$ is a substituent selected from the group consisting of a hydroxy group, a halogen atom, a cyano group, an oxo group, a C$_{1-4}$ alkyl group (wherein the C$_{1-4}$ alkyl group may be substituted with 1 or 2 C$_{1-4}$ alkoxy groups), a C$_{1-4}$ alkoxy group, a halogeno-C$_{1-4}$ alkyl group, a C$_{1-4}$ alkylsulfonyl group, a C$_{1-4}$ alkylcarbonyl group and —NR$^{10a}$R$^{10b}$ when R$^2$ is a substituent present on a carbon atom forming B, and R$^2$ is a substituent selected from the group consisting of a hydroxy group, a C$_{1-4}$ alkyl group (wherein the C$_{1-4}$ alkyl group may be substituted with 1 or 2 C$_{1-4}$ alkoxy groups), a C$_{1-4}$ alkoxy group, a halogeno-C$_{1-4}$ alkyl group, a C$_{1-4}$ alkylsulfonyl group, a C$_{1-4}$ alkylcarbonyl group and —NR$^{10a}$R$^{10b}$ when R$^2$ is a substituent present on a nitrogen atom forming B, R$^{10a}$ and R$^{10b}$ are the same or different and are each a hydrogen atom or a C$_{1-4}$ alkyl group, m is any integer of 0 to 3, Q is a bond or a C$_{1-4}$ alkylene group, R$^3$ and R$^4$ are the same or different and are each a hydrogen atom, a halogen atom, a C$_{1-4}$ alkyl group, a halogeno-C$_{1-4}$ alkyl group or a cyano group, and R$^5$ and R$^6$ are the same or different and are each a hydrogen atom, a halogen atom or a C$_{1-4}$ alkyl group, or R$^5$ and R$^6$ together may form an oxo group or together with the carbon atom to which R$^5$ and R$^6$ are bonded may form a C$_{3-8}$ cycloalkyl group, or a pharmacologically acceptable salt thereof;

(2) The compound or pharmacologically acceptable salt thereof according to (1) above, wherein A is a fused bicyclic nitrogen-containing heterocyclic group having 1 to 3 nitrogen atoms in which:

(a) the ring directly bonded to the imidazopyridine ring is a partially saturated or aromatic 6-membered ring containing 0 to 2 nitrogen atoms and (b) the ring not directly bonded to the imidazopyridine ring is a partially saturated or aromatic 5-membered ring containing 1 or 2 nitrogen atoms;

(3) The compound or pharmacologically acceptable salt thereof according to (1) above, wherein A is an indolyl group, an isoindolyl group, an indazolyl group, a pyrrolopyridyl group, a pyrazolopyridyl group, an imidazopyridyl group, a pyrrolopyridazinyl group, a pyrazolopyridazinyl group, an imidazopyridazinyl group, a pyrrolopyrimidinyl group, a pyrazolopyrimidinyl group, an imidazopyrimidinyl group, a pyrrolopyrazinyl group, a pyrazolopyrazinyl group or an imidazopyrazinyl group;

(4) The compound or pharmacologically acceptable salt thereof according to any one of (1) to (3) above, wherein R$^1$ is a substituent identically or differently selected from the group consisting of a fluorine atom, a chlorine atom, a cyano group, a methyl group, an ethyl group, an isopropyl group, a methoxy group, an ethoxy group, a trifluoromethyl group, a methoxymethyl group, an ethoxymethyl group, an amino group, a methylamino group, a dimethylamino group, a methylethylamino group, a propylamino group, a (2-hydroxyethyl)(methyl)amino group, a formyl group, an acetyl group, an ethylcarbonyl group, an ethoxycarbonyl group, a carboxyl group, a carbamoyl group and a methylcarbamoyl group and n is any integer of 0 to 2;

(5) The compound or pharmacologically acceptable salt thereof according to any one of (1) to (4) above, wherein R$^3$ is a hydrogen atom, a fluorine atom, a chlorine atom, a cyano group or a methyl group and R$^4$ is a hydrogen atom;

(6) The compound or pharmacologically acceptable salt thereof according to any one of (1) to (5) above, wherein Q is a bond or a methylene group;

(7) The compound or pharmacologically acceptable salt thereof according to any one of (1) to (6) above, wherein R$^5$ and R$^6$ are the same or different and are each a hydrogen atom, a halogen atom or a C$_{1-4}$ alkyl group;

(8) The compound or pharmacologically acceptable salt thereof according to any one of (1) to (7) above, wherein B is a C$_{3-7}$ cycloalkyl group, a tetrahydrofuryl group, a dihydropyranyl group, a tetrahydropyranyl group, a dioxanyl group, a piperidyl group, a piperazinyl group or a 1,1-dioxidotetrahydrothiopyranyl group;

(9) The compound or pharmacologically acceptable salt thereof according to any one of (1) to (8) above, wherein R$^2$ is a hydroxy group, a halogen atom, a cyano group, an oxo group, a C$_{1-4}$ alkyl group, a C$_{1-4}$ alkoxy-C$_{1-4}$ alkyl group, a C$_{1-4}$ alkoxy group, a C$_{1-4}$ alkylsulfonyl group or a C$_{1-4}$ alkylcarbonyl group when R$^2$ is a substituent present on a carbon atom forming B, R$^2$ is a C$_{1-4}$ alkyl group, a C$_{1-4}$ alkylsulfonyl group or a C$_{1-4}$ alkylcarbonyl group when R$^2$ is a substituent present on a nitrogen atom forming B, and m is any integer of 0 to 2;

(10) The compound according to (1) above, wherein the compound is any one compound selected from:

1-[(2S)-1,4-dioxan-2-ylmethyl]-6-(1H-pyrrolo[2,3-b]pyridin-5-yl)-1,3-dihydro-imidazo[4,5-b]pyridin-2-one, 1-[(2S)-1,4-dioxan-2-ylmethyl]-6-(4-methyl-1H-pyrrolo[2,3-b]pyridin-5-yl)-1,3-dihydro-imidazo[4,5-b]pyridin-2-one, 6-(3,4-dimethyl-1H-pyrrolo[2,3-b]pyridin-5-yl)-1-[(2S)-1,4-dioxan-2-ylmethyl]-1,3-dihydro-2H-imidazo[4,5-b]pyridin-2-one, 6-(3-chloro-4-methyl-1H-pyrrolo[2,3-b]pyridin-5-yl)-1-[(2S)-1,4-dioxan-2-ylmethyl]-1,3-dihydro-2H-imidazo[4,5-b]pyridin-2-one, 1-[(2S)-1,4-dioxan-2-ylmethyl]-6-(3-fluoro-4-methyl-1H-pyrrolo[2,3-b]pyridin-5-yl)-1,3-dihydro-2H-imidazo[4,5-b]pyridin-2-one, 2,6-anhydro-1,3,5-trideoxy-4-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol, 2,6-anhydro-1,3,4-trideoxy-5-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol, 2,6-anhydro-1,3,4-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-5-O-methyl-L-threo-hexitol, 2,6-anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,4-trideoxy-5-O-methyl-L-threo-hexitol, 2,6-anhydro-1,3,5-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-4-O-methyl-L-threo-hexitol and 2,6-anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,5-trideoxy-4-O-methyl-L-threo-hexitol;

(11) 1-[(2S)-1,4-Dioxan-2-ylmethyl]-6-(1H-pyrrolo[2,3-b]pyridin-5-yl)-1,3-dihydro-imidazo[4,5-b]pyridin-2-one;

(12) 1-[(2S)-1,4-Dioxan-2-ylmethyl]-6-(4-methyl-1H-pyrrolo[2,3-b]pyridin-5-yl)-1,3-dihydro-imidazo[4,5-b]pyridin-2-one;

(13) 6-(3,4-Dimethyl-1H-pyrrolo[2,3-b]pyridin-5-yl)-1-[(2S)-1,4-dioxan-2-ylmethyl]-1,3-dihydro-2H-imidazo[4,5-b]pyridin-2-one;

(14) 6-(3-Chloro-4-methyl-1H-pyrrolo[2,3-b]pyridin-5-yl)-1-[(2S)-1,4-dioxan-2-ylmethyl]-1,3-dihydro-2H-imidazo[4,5-b]pyridin-2-one;

(15) 1-[(2S)-1,4-Dioxan-2-ylmethyl]-6-(3-fluoro-4-methyl-1H-pyrrolo[2,3-b]pyridin-5-yl)-1,3-dihydro-2H-imidazo[4,5-b]pyridin-2-one;

(16) 2,6-Anhydro-1,3,5-trideoxy-4-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol;

(17) 2,6-Anhydro-1,3,4-trideoxy-5-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol;
(18) 2,6-Anhydro-1,3,4-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-5-O-methyl-L-threo-hexitol;
(19) 2,6-Anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,4-trideoxy-5-O-methyl-L-threo-hexitol;
(20) 2,6-Anhydro-1,3,5-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-4-O-methyl-L-threo-hexitol;
(21) 2,6-Anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,5-trideoxy-4-O-methyl-L-threo-hexitol;
(22) A pharmacologically acceptable salt of the compound according to any one of (10) to (21) above;
(23) A pharmaceutical composition comprising the compound or pharmacologically acceptable salt thereof according to any one of (1) to (21) above as an active ingredient;
(24) An antitumor agent comprising the compound or pharmacologically acceptable salt thereof according to any one of (1) to (21) above as an active ingredient;
(25) An mTOR inhibitor comprising the compound or pharmacologically acceptable salt thereof according to any one of (1) to (21) above as an active ingredient; and
(26) The antitumor agent according to 24 above, wherein the tumor is leukemia, lymphoma, multiple myeloma, brain tumor, head and neck cancer, esophageal cancer, gastric cancer, appendiceal cancer, colon cancer, anal cancer, gallbladder cancer, bile duct cancer, pancreatic cancer, gastrointestinal stromal tumor, lung cancer, liver cancer, mesothelioma, thyroid cancer, renal cancer, prostate cancer, neuroendocrine tumor, melanoma, breast cancer, endometrial cancer, cervical cancer, ovarian cancer, osteosarcoma, soft tissue sarcoma, Kaposi's sarcoma, myosarcoma, renal cancer, bladder cancer and/or testicular cancer.

The present invention also provides a method for preventing, treating or preventing tumor recurrence, comprising administering to a warm-blooded animal (preferably a human) the compound or pharmacologically acceptable salt thereof according to any one selected from (1) to (21) above, the pharmaceutical composition according to (23) above, the mTOR inhibitor according to (25) above, or the antitumor agent according to (24) or (26) above.

The present invention further relates to:
(27) A compound represented by the following formula (II):

[Formula 2]

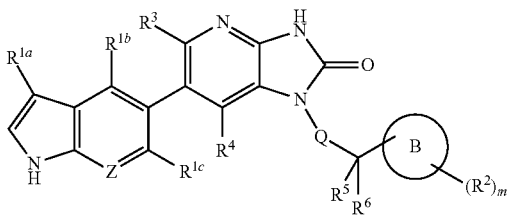

(II)

wherein in the general formula (II),
$R^{1a}$, $R^{1b}$ and $R^{1c}$ are the same or different and are each a substituent selected from the group consisting of a hydrogen atom, a hydroxy group, a halogen atom, a cyano group, a $C_{1-4}$ alkyl group (wherein the $C_{1-4}$ alkyl group may be substituted with one or two same or different $C_{1-4}$ alkoxy groups or —$NR^{7a}R^{7b}$s), a $C_{1-4}$ alkoxy group, a halogeno-$C_{1-4}$ alkyl group, —$NR^{7a}R^{7b}$, —$C(O)R^8$ and —$C(O)NR^{9a}R^{9b}$,
Z is C—$R^{1d}$ or a nitrogen atom,
$R^{1d}$ is a hydrogen atom, a halogen atom or a $C_{1-4}$ alkyl group,
$R^{7a}$, $R^{7b}$, $R^{9a}$ and $R^{9b}$ are the same or different and are each a hydrogen atom or a $C_{1-4}$ alkyl group (wherein the $C_{1-4}$ alkyl group may be substituted with 1 or 2 hydroxy groups),
$R^8$ is a hydrogen atom, a hydroxy group, a $C_{1-4}$ alkyl group or a $C_{1-4}$ alkoxy group,
B is a 3- to 7-membered saturated or partially saturated monocyclic hydrocarbon group and may contain 1 or 2 oxygen atoms, sulfur atoms, nitrogen atoms, sulfinyl groups and/or sulfonyl groups as ring constituents,
B may have the same or different m $R^2$s as substituents,
$R^2$ is a substituent present on a carbon atom or nitrogen atom forming B,
$R^2$ is a substituent selected from the group consisting of a hydroxy group, a halogen atom, a cyano group, an oxo group, a $C_{1-4}$ alkyl group (wherein the $C_{1-4}$ alkyl group may be substituted with 1 or 2 $C_{1-4}$ alkoxy groups), a $C_{1-4}$ alkoxy group, a halogeno-$C_{1-4}$ alkyl group, a $C_{1-4}$ alkylsulfonyl group, a $C_{1-4}$ alkylcarbonyl group and —$NR^{10a}R^{10b}$ when $R^2$ is a substituent present on a carbon atom forming B, and $R^2$ is a substituent selected from the group consisting of a hydroxy group, a $C_{1-4}$ alkyl group (wherein the $C_{1-4}$ alkyl group may be substituted with 1 or 2 $C_{1-4}$ alkoxy groups), a $C_{1-4}$ alkoxy group, a halogeno-$C_{1-4}$ alkyl group, a $C_{1-4}$ alkylsulfonyl group, a $C_{1-4}$ alkylcarbonyl group and —$NR^{10a}R^{10b}$ when $R^2$ is a substituent present on a nitrogen atom forming B,
$R^{10a}$ and $R^{10b}$ are the same or different and are each a hydrogen atom or a $C_{1-4}$ alkyl group,
m is any integer of 0 to 3,
Q is a bond or a $C_{1-4}$ alkylene group,
$R^3$ and $R^4$ are the same or different and are each a hydrogen atom, a halogen atom, a $C_{1-4}$ alkyl group, a halogeno-$C_{1-4}$ alkyl group or a cyano group, and
$R^5$ and $R^6$ are the same or different and are each a hydrogen atom, a halogen atom or a $C_{1-4}$ alkyl group, or $R^5$ and $R^6$ together may form an oxo group or together with the carbon atom to which $R^5$ and $R^6$ are bonded may form a $C_{3-8}$ cycloalkyl group,
or a pharmacologically acceptable salt thereof;
(28) The compound or pharmacologically acceptable salt thereof according to (27) above, wherein $R^{1a}$, $R^{1b}$ and $R^{1c}$ are the same or different and are each a hydrogen atom, a halogen atom, a $C_{1-4}$ alkyl group or a $C_{1-4}$ alkoxy group;
(29) The compound or pharmacologically acceptable salt thereof according to (27) or (28) above, wherein $R^3$ is a hydrogen atom, a fluorine atom, a chlorine atom, a cyano group or a methyl group and $R^4$ is a hydrogen atom;
(30) The compound or pharmacologically acceptable salt thereof according to any one of (27) to (29) above, wherein Q is a bond or a methylene group;
(31) The compound or pharmacologically acceptable salt thereof according to any one of (27) to (30) above, wherein $R^5$ and $R^6$ are the same or different and are each a hydrogen atom, a halogen atom or a $C_{1-4}$ alkyl group;
(32) The compound or pharmacologically acceptable salt thereof according to any one of (27) to (31) above, wherein B is a $C_{3-7}$ cycloalkyl group, a tetrahydrofuryl group, a dihydropyranyl group, a tetrahydropyranyl group, a dioxanyl group, a piperidyl group, a piperazinyl group or a 1,1-dioxidotetrahydrothiopyranyl group;

(33) The compound or pharmacologically acceptable salt thereof according to any one of (27) to (32) above, wherein $R^2$ is a hydroxy group, a halogen atom, a cyano group, an oxo group, a $C_{1-4}$ alkyl group, a $C_{1-4}$ alkoxy-$C_{1-4}$ alkyl group, a $C_{1-4}$ alkoxy group, a $C_{1-4}$ alkylsulfonyl group or a $C_{1-4}$ alkylcarbonyl group when $R^2$ is a substituent present on a carbon atom forming B, $R^2$ is a $C_{1-4}$ alkyl group, a $C_{1-4}$ alkylsulfonyl group or a $C_{1-4}$ alkylcarbonyl group when $R^2$ is a substituent present on a nitrogen atom forming B, and m is any integer of 0 to 2;

(34) A pharmaceutical composition comprising the compound or pharmacologically acceptable salt thereof according to any one of (27) to (33) above as an active ingredient;

(35) An antitumor agent comprising the compound or pharmacologically acceptable salt thereof according to any one of (27) to (33) above as an active ingredient;

(36) An mTOR inhibitor comprising the compound or pharmacologically acceptable salt thereof according to any one of (27) to (33) above as an active ingredient; and

(37) The antitumor agent according to (35) above, wherein the tumor is leukemia, lymphoma, multiple myeloma, brain tumor, head and neck cancer, esophageal cancer, gastric cancer, appendiceal cancer, colon cancer, anal cancer, gallbladder cancer, bile duct cancer, pancreatic cancer, gastrointestinal stromal tumor, lung cancer, liver cancer, mesothelioma, thyroid cancer, renal cancer, prostate cancer, neuroendocrine tumor, melanoma, breast cancer, endometrial cancer, cervical cancer, ovarian cancer, osteosarcoma, soft tissue sarcoma, Kaposi's sarcoma, myosarcoma, renal cancer, bladder cancer and/or testicular cancer.

The present invention also provides a method for preventing, treating or preventing tumor recurrence, comprising administering to a warm-blooded animal (preferably human) the compound or pharmacologically acceptable salt thereof according to any one selected from (27) to (33) above, the pharmaceutical composition according to (34) above, the mTOR inhibitor according to (36) above, or the antitumor agent according to (35) or (37) above.

Advantageous Effects of Invention

The compound or pharmacologically acceptable salt thereof having the formula (I) according to the present invention has strong mTOR inhibitory activity and inhibits cell proliferation. Moreover, in tumor transplantation model animals, the compound or salt inhibits phosphorylation of S6 and Akt in tumor tissue and has an excellent antitumor effect. Accordingly, the compound or pharmacologically acceptable salt thereof according to the present invention, or a pharmaceutical composition comprising the compound or pharmacologically acceptable salt thereof according to the present invention as an active ingredient is useful as an antitumor agent, in particular, a therapeutic agent for tumors such as blood cancer such as leukemia, lymphoma or multiple myeloma, brain tumor, head and neck cancer, esophageal cancer, gastric cancer, appendiceal cancer, colon cancer, anal cancer, gallbladder cancer, bile duct cancer, pancreatic cancer, gastrointestinal stromal tumor, lung cancer, liver cancer, mesothelioma, thyroid cancer, renal cancer, prostate cancer, neuroendocrine tumor, melanoma, breast cancer, endometrial cancer, cervical cancer, ovarian cancer, osteosarcoma, soft tissue sarcoma, Kaposi's sarcoma, myosarcoma, renal cancer, bladder cancer and/or testicular cancer. The compound or salt, or the pharmaceutical composition, is effective as a therapeutic agent for tumors with mutations of genes involved in signaling pathways involving mTOR, e.g., tumors with LKB mutations or TSC2 mutations, or tumors with inactivated PTEN, among the aforementioned tumors.

DESCRIPTION OF EMBODIMENTS

As used herein, the "$C_{1-4}$ alkyl group" is a linear or branched alkyl group having 1 to 4 carbon atoms. Examples of the group include a methyl group, an ethyl group, a propyl group, an isopropyl group, a butyl group, an isobutyl group, a sec-butyl group and a tert-butyl group. The "$C_{3-8}$ cycloalkyl group" is an alicyclic hydrocarbon group having 3 to 8 carbon atoms, and the "$C_{3-7}$ cycloalkyl group" is an alicyclic hydrocarbon group having 3 to 7 carbon atoms. Examples of such groups include a cyclopropyl group, a cyclobutyl group, a cyclopentyl group and a cyclohexyl group, respectively. Examples of the "halogen atom" include a fluorine atom, a chlorine atom, a bromine atom and an iodine atom. The "halogeno-$C_{1-4}$ alkyl group" is a group in which the aforementioned $C_{1-4}$ alkyl group substituted with the same or different 1 to 3 aforementioned halogen atoms. Examples of the group include a fluoromethyl group, a difluoromethyl group, a trifluoromethyl group, a chloromethyl group, a dichloromethyl group, a trichloromethyl group, a 2-fluoroethyl group, a 1,2-difluoroethyl group, a 2-trifluoroethyl group, a 2-chloroethyl group, a 1,2-dichloroethyl group, a 1,1,2-trichloroethyl group, a 1,2,2-trichloroethyl group and a 2,2,2-trichloroethyl group. The "$C_{1-4}$ alkoxy group" is a group formed by the aforementioned "$C_{1-4}$ alkyl group" and an oxygen atom. Examples of the group include a methoxy group, an ethoxy group, a propoxy group and an isopropoxy group. The "$C_{1-4}$ alkylcarbonyl group" is a group formed by the aforementioned "$C_{1-4}$ alkyl group" and a carbonyl group. Examples of the group include an acetyl group, an ethylcarbonyl group and a propylcarbonyl group. The "$C_{1-4}$ alkylsulfonyl group" is a group in which the aforementioned $C_{1-4}$ alkyl group is substituted or a sulfonyl group. Examples of the group include a methylsulfonyl group, an ethylsulfonyl group, a propylsulfonyl group and an isopropylsulfonyl group. The "$C_{1-4}$ alkylene group" is a linear or branched alkylene group having 1 to 4 carbon atoms. Examples of the group include a methylene group, an ethylene group, a propylene group and a methylmethylene group.

As used herein, the "8- to 10-membered partially saturated or aromatic fused bicyclic nitrogen-containing heterocyclic group" in the definition of A is a 8- to 10-membered bicyclic aromatic ring containing 1 to 3 nitrogen atoms which may be partially saturated. The two monocycles forming the bicyclic nitrogen-containing heterocyclic group are identically or differently selected from 5-membered or 6-membered rings. Examples of such fused bicyclic nitrogen-containing heterocyclic groups include an indolizinyl group, an isoindolyl group, an indolyl group, an indolinyl group, an indazolyl group, a pyrrolopyridyl group, a pyrazolopyridyl group, an imidazopyridyl group, a pyrazolopyrimidinyl group, a purinyl group, a quinolizinyl group, an isoquinolyl group, a quinolyl group and a naphthidinyl group.

The "3- to 7-membered monocyclic saturated or partially saturated cyclic hydrocarbon group" in the definition of B refers to a 3- to 7-membered saturated or partially saturated cyclic hydrocarbon group which may contain the same or different 1 or 2 nitrogen atoms, oxygen atoms, sulfur atoms, sulfoxide groups and/or sulfonyl groups as ring constituents. Examples of such cyclic hydrocarbon groups include $C_{3-7}$ cycloalkyl groups such as a cyclopropyl group, a cyclobutyl group, a cyclopentyl group or a cyclohexyl group, a pyrrolidinyl group, an imidazolidinyl group, a pyrazolidinyl group, a piperidyl group, a piperazinyl group, a morpholinyl group, a dihydrofuryl group, a tetrahydrofuryl group, a dihydropyranyl group, a tetrahydropyranyl group, a dioxanyl group, a tetrahydrothienyl group, a 1-oxidotetrahydrothiopyranyl group and a 1,1-dioxidotetrahydrothiopyranyl group.

The substituents and partial structures in the general formula (I) will be described below.

A is an 8- to 10-membered partially saturated or aromatic fused bicyclic nitrogen-containing heterocyclic group containing 1 to 3 nitrogen atoms. Preferably, the ring directly bonded to the imidazopyridine ring among two rings forming A is a partially saturated or aromatic 6-membered ring containing 0 to 2 nitrogen atoms, and the ring not directly bonded to the imidazopyridine ring is a partially saturated or aromatic 5-membered ring containing 1 or 2 nitrogen atoms. A may have a nitrogen atom at the fusion site.

More specifically, A is an indolyl group, an isoindolyl group, an indazolyl group, a pyrrolopyridyl group, a pyrazolopyridyl group, an imidazopyridyl group, a pyrrolopyridazinyl group, a pyrazolopyridazinyl group, an imidazopyridazinyl group, a pyrrolopyrimidinyl group, a pyrazolopyrimidinyl group, an imidazopyrimidinyl group, a pyrrolopyrazinyl group, a pyrazolopyrazinyl group or an imidazopyrazinyl group, for example. A is preferably an indolyl group, an indazolyl group, a pyrrolopyridyl group, a pyrazolopyridyl group, an imidazopyridyl group, a pyrrolopyridazinyl group, a pyrazolopyrimidinyl group or a pyrrolopyrazinyl group. A is more preferably a 1H-indol-5-yl group, a 1H-indol-2-yl group, a 1H-indazol-5-yl group, a 1H-pyrrolo[2,3-b]pyridin-5-yl group, a 2,3-dihydro-1H-pyrrolo[2,3-b]pyridin-5-yl group, a 1H-pyrrolo[3,2-b]pyridin-5-yl group, a 1H-pyrrolo[3,2-b]pyridin-6-yl group, a 1H-pyrrolo[2,3-c]pyridin-5-yl group, a 1H-pyrazolo[3,4-b]pyridin-5-yl group, a 3H-imidazo[4,5-b]pyridin-6-yl group, a 7H-pyrrolo[2,3-c]pyridazin-3-yl group, a pyrazolo[1,5-a]pyrimidin-6-yl group or a 5H-pyrrolo[2,3-b]pyrazin-2-yl group. A is particularly preferably a 1H-indol-5-yl group or a 1H-pyrrolo[2,3-b]pyridin-5-yl group.

In the general formula (I), —($R^1$)n indicates that A is substituted with the same or different n $R^1$s. A is preferably substituted with $R^1$ on a carbon atom forming A.

$R^1$ is a substituent selected from the group consisting of a hydroxy group, a halogen atom, a cyano group, an oxo group, a $C_{1-4}$ alkyl group (wherein the $C_{1-4}$ alkyl group may be substituted with one or two same or different $C_{1-4}$ alkoxy groups or —$NR^{7a}R^{7b}$s), a $C_{1-4}$ alkoxy group, a halogeno-$C_{1-4}$ alkyl group, —$NR^{7a}R^{7b}$, —C(O)$R^8$ and —C(O)$NR^{9a}R^{9b}$.

$R^{7a}$, $R^{7b}$, $R^{9a}$ and $R^{9b}$ are the same or different and are each a hydrogen atom or a $C_{1-4}$ alkyl group (wherein the $C_{1-4}$ alkyl group may be substituted with 1 or 2 hydroxy groups). Preferably, $R^{7a}$, $R^{7b}$, $R^{9a}$ and $R^{9b}$ are the same or different and are each a hydrogen atom, a methyl group, an ethyl group, a hydroxymethyl group, or a hydroxyethyl group. More preferably, $R^{7a}$, $R^{7b}$, $R^{9a}$ and $R^{9b}$ are the same or different and are each a hydrogen atom, a methyl group or a hydroxyethyl group.

$R^8$ is a hydrogen atom, a hydroxy group, a $C_{1-4}$ alkyl group or a $C_{1-4}$ alkoxy group, preferably a hydrogen atom, a hydroxy group or a $C_{1-4}$ alkoxy group, and more preferably a hydroxy group, a methoxy group or an ethoxy group.

$R^1$ is preferably a substituent identically or differently selected from the group consisting of a fluorine atom, a chlorine atom, a cyano group, a methyl group, an ethyl group, an isopropyl group, a methoxy group, an ethoxy group, a trifluoromethyl group, a methoxymethyl group, an ethoxymethyl group, an amino group, a methylamino group, a dimethylamino group, a methylethylamino group, a propylamino group, a (2-hydroxyethyl)(methyl)amino group, a formyl group, an acetyl group, an ethylcarbonyl group, an ethoxycarbonyl group, a carboxyl group, a carbamoyl group and a methylcarbamoyl group. $R^1$ is more preferably a substituent identically or differently selected from the group consisting of a fluorine atom, a chlorine atom and a methyl group.

n is preferably any integer of 0 to 3, and more preferably any integer of 0 to 2.

The partial structure represented by the following formula (III):

[Formula 3]

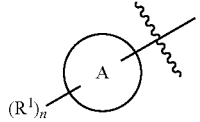

(III)

is preferably a 1H-indol-5-yl group, a 4-fluoro-1H-indol-5-yl group, a 6-fluoro-1H-indol-5-yl group, a 7-fluoro-1H-indol-5-yl group, a 7-fluoro-3-methyl-1H-indol-5-yl group, a 7-fluoro-4-methyl-1H-indol-5-yl group, a 3,4-dimethyl-7-fluoro-1H-indol-5-yl group, a 1H-indazol-5-yl group, a 1H-pyrrolo[2,3-b]pyridin-5-yl group, a 3-chloro-1H-pyrrolo[2,3-b]pyridin-5-yl group, a 4-chloro-1H-pyrrolo[2,3-b]pyridin-5-yl group, a 6-chloro-1H-pyrrolo[2,3-b]pyridin-5-yl group, a 3-fluoro-1H-pyrrolo[2,3-b]pyridin-5-yl group, a 4-fluoro-1H-pyrrolo[2,3-b]pyridin-5-yl group, a 6-fluoro-1H-pyrrolo[2,3-b]pyridin-5-yl group, a 3-methyl-1H-pyrrolo[2,3-b]pyridin-5-yl group, a 4-methyl-1H-pyrrolo[2,3-b]pyridin-5-yl group, a 6-methyl-1H-pyrrolo[2,3-b]pyridin-5-yl group, a 3,4-dimethyl-1H-pyrrolo[2,3-b]pyridin-5-yl group, a 3-chloro-4-methyl-1H-pyrrolo[2,3-b]pyridin-5-yl group, a 3-fluoro-4-methyl-1H-pyrrolo[2,3-b]pyridin-5-yl group, a 3-methoxy-1H-pyrrolo[2,3-b]pyridin-5-yl group, a 3-trifluoromethyl-1H-pyrrolo[2,3-b]pyridin-5-yl group, a 4-trifluoromethyl-1H-pyrrolo[2,3-b]pyridin-5-yl group, a 3-amino-1H-pyrrolo[2,3-b]pyridin-5-yl group, a 4-amino-1H-pyrrolo[2,3-b]pyridin-5-yl group, a 1H-pyrrolo[3,2-b]pyridin-5-yl group, a pyrazolo[1,5-a]pyrimidin-6-yl group, a 1H-pyrazolo[3,4-b]pyridin-5-yl group, a 5H-pyrrolo[2,3-b]pyrazin-2-yl group, a 7H-pyrrolo[2,3-c]pyridazin-3-yl group or a 2-oxo-2,3-dihydro-1H-pyrrolo[2,3-b]pyridin-5-yl group.

The partial structure is more preferably a 1H-pyrrolo[2,3-b]pyridin-5-yl group, a 3-chloro-1H-pyrrolo[2,3-b]pyridin-5-yl group, a 4-chloro-1H-pyrrolo[2,3-b]pyridin-5-yl group, a 3-fluoro-1H-pyrrolo[2,3-b]pyridin-5-yl group, a 4-fluoro-1H-pyrrolo[2,3-b]pyridin-5-yl group, a 3-methyl-1H-pyrrolo[2,3-b]pyridin-5-yl group, a 4-methyl-1H-pyrrolo[2,3-b]pyridin-5-yl group, a 3,4-dimethyl-1H-pyrrolo[2,3-b]pyridin-5-yl group, a 3-fluoro-4-methyl-1H-pyrrolo[2,3-b]pyridin-5-yl group or a 3-chloro-4-methyl-1H-pyrrolo[2,3-b]pyridin-5-yl group.

B is a 3- to 7-membered monocyclic saturated or partially saturated cyclic hydrocarbon group and may contain 1 or 2 oxygen atoms, sulfur atoms, nitrogen atoms, sulfinyl groups and/or sulfonyl groups as ring constituents. B also includes stereoisomeric structures if such structures exist.

More specifically, B is a $C_{3-7}$ cycloalkyl group, a furyl group, a pyranyl group, a dioxanyl group, a piperidyl group, a piperazinyl group, a thiopyranyl group, a 1-oxidothiopyranyl group or a 1,1-dioxidothiopyranyl group, for example. B is a preferably $C_{3-7}$ cycloalkyl group, a tetrahydrofuryl group, a dihydropyranyl group, a tetrahydropyranyl group, a dioxanyl group, a piperidyl group, a piperazinyl group or a 1,1-dioxidotetrahydrothiopyranyl group. B is more preferably a cyclopropyl group, a cyclohexyl group, a tetrahydrofuran-3- yl group, a 3,6-dihydro-2H-pyran-4-yl group, a 5,6-dihydro-2H-pyran-3-yl group, a tetrahydro-2H-pyran-2-yl group, a tetrahydro-2H-pyran-3-yl group, a tetrahydro-2H-pyran-4-yl group, a piperidin-4-yl group, a piperazin-1-yl group, a morpholin-3-yl group, a morpholin-4-yl group, a 1,1-dioxidotetrahydro-2H-thiopyran-4-yl group or a 1,4-dioxan-2-yl group. B is particularly preferably a cyclohexyl group, a tetrahydro-2H-pyran-2-yl group, a tetrahydro-2H-pyran-3-yl group, a tetrahydro-2H-pyran-4-yl group, a 5,6-dihydro-2H-pyran-3-yl group or a 1,4-dioxan-2-yl group.

In the general formula (I), $-(R^2)_m$ indicates that B is substituted with the same or different m $R^2$s. The structure in which B is substituted with $R^2$ also includes stereoisomeric structures if such structures exist.

$R^2$ is a substituent present on a carbon atom or nitrogen atom forming B. When B is substituted with $R^2$ on a carbon atom, B may be substituted with the same or different two $R^2$s on the carbon atom.

$R^2$ is a substituent selected from the group consisting of a hydroxy group, a halogen atom, a cyano group, an oxo group, a $C_{1-4}$ alkyl group (wherein the $C_{1-4}$ alkyl group may be substituted with 1 or 2 $C_{1-4}$ alkoxy groups), a $C_{1-4}$ alkoxy group, a halogeno-$C_{1-4}$ alkyl group, a $C_{1-4}$ alkylsulfonyl group, a $C_{1-4}$ alkylcarbonyl group and $-NR^{10a}R^{10b}$ when $R^2$ is a substituent present on a carbon atom forming B. $R^{10a}$ and $R^{10b}$ are the same or different and are each a hydrogen atom or a alkyl group. Preferably, $R^{10a}$ and $R^{10b}$ are the same or different and are each a hydrogen atom, a methyl group or an ethyl group. More preferably, $R^{10a}$ and $R^{10b}$ are both hydrogen atoms.

$R^2$ when it is a substituent on a carbon atom forming B is preferably a hydroxy group, a halogen atom, a cyano group, an oxo group, a $C_{1-4}$ alkyl group, a $C_{1-4}$ alkoxy-$C_{1-4}$ alkyl group, a $C_{1-4}$ alkoxy group, a $C_{1-4}$ alkylsulfonyl group or a $C_{1-4}$ alkylcarbonyl group. $R^2$ is more preferably a hydroxy group, a fluorine atom, a chlorine atom, a cyano group, an oxo group, a methyl group, an ethyl group, a methoxymethyl group, a methoxy group, an ethoxy group, a methylsulfonyl group, an ethylsulfonyl group or an acetyl group. $R^2$ is particularly preferably a hydroxy group, a fluorine atom, a cyano group, a methyl group, a methoxymethyl group or a methoxy group.

$R^2$ is a substituent selected from the group consisting of a hydroxy group, a $C_{1-4}$ alkyl group (wherein the $C_{1-4}$ alkyl group may be substituted with 1 or 2 $C_{1-4}$ alkoxy groups), a $C_{1-4}$ alkoxy group, a halogeno-$C_{1-4}$ alkyl group, a $C_{1-4}$ alkylsulfonyl group, a $C_{1-4}$ alkylcarbonyl group and $-NR^{10a}R^{10b}$ when $R^2$ is a substituent present on a nitrogen atom forming B. $R^{10a}$ and $R^{10b}$ are the same as described above.

$R^2$ when it is a substituent on a nitrogen atom forming B is preferably a $C_{1-4}$ alkyl group, a $C_{1-4}$ alkylsulfonyl group or a $C_{1-4}$ alkylcarbonyl group. $R^2$ is more preferably a methyl group, a methylsulfonyl group or an acetyl group.

m represents any integer of 0 to 3, and is preferably any integer of 0 to 2, and more preferably 0 or 1.

The partial structure containing B which is represented by the following formula (IV):

[Formula 4]

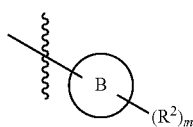

(IV)

also includes stereoisomeric structures that may exist.

The partial structure represented by the formula (IV) is preferably a cyclopropyl group, a cyclohexyl group, a 4-hydroxycyclohexyl group, a 3-methoxycyclohexyl group, a 4-methoxycyclohexyl group, a 4,4-difluorocyclohexyl group, a tetrahydrofuran-3-yl group, a 4-hydroxytetrahydrofuran-3-yl group, a 4-methoxytetrahydrofuran-3-yl group, a tetrahydro-2H-pyran-2-yl group, a tetrahydro-2H-pyran-3-yl group, a tetrahydro-2H-pyran-4-yl group, a 4-hydroxytetrahydro-2H-pyran-2-yl group, a 5-hydroxytetrahydro-2H-pyran-2-yl group, a 5-hydroxytetrahydro-2H-pyran-3-yl group, a 4-cyanotetrahydro-2H-pyran-4-yl group, a 3-fluorotetrahydro-2H-pyran-3-yl group, a 4-fluorotetrahydro-2H-pyran-4-yl group, a 3-methyltetrahydro-2H-pyran-3-yl group, a 4-methyltetrahydro-2H-pyran-4-yl group, a 2,2-dimethyltetrahydro-2H-pyran-4-yl group, a 2,6-dimethyltetrahydro-2H-pyran-4-yl group, a 3-methoxytetrahydro-2H-pyran-3-yl group, a 4-methoxytetrahydro-2H-pyran-2-yl group, a 4-methoxytetrahydro-2H-pyran-4-yl group, a 5-methoxytetrahydro-2H-pyran-2-yl group, a 5-methoxytetrahydro-2H-pyran-3-yl group, a 4-oxotetrahydro-2H-pyran-3-yl group, a 3,6-dihydro-2H-pyran-4-yl group, a 5,6-dihydro-2H-pyran-3-yl group, a 1,4-dioxan-2-yl group, a 5-methoxymethyl-1,4-dioxan-2-yl group, a 6-methoxymethyl-1,4-dioxan-2-yl group, a piperidin-4-yl group, a 1-methylpiperidin-4-yl group, a 1-(methylsulfonyl)piperidin-4-yl group, a piperazin-1-yl group, a 4-methylpiperazin-1-yl group, a 4-acetylpiperazin-1-yl group, a 4-(methylsulfonyl)piperazin-1-yl group, a morpholin-4-yl group, a morpholin-3-yl group, a 3-methylmorpholin-4-yl group, a 2,6-dimethylmorpholin-4-yl group, a 5-oxomorpholin-2-yl group, a 4-methyl-5-oxo-morpholin-4-yl group or a 1,1-dioxidotetrahydro-2H-thiopyran-4-yl group.

The partial structure is more preferably a cyclohexyl group, a 4-hydroxycyclohexyl group, a 3-methoxycyclohexyl group, a 4-methoxycyclohexyl group, a 4,4-difluorocyclohexyl group, a tetrahydro-2H-pyran-2-yl group, a tetrahydro-2H-pyran-3-yl group, a tetrahydro-2H-pyran-4-yl group, a 4-hydroxytetrahydro-2H-pyran-2-yl group, a 5-hydroxytetrahydro-2H-pyran-2-yl group, a 5-hydroxytetrahydro-2H-pyran-3-yl group, a 4-cyanotetrahydro-2H-pyran-4-yl group, a 3-fluorotetrahydro-2H-pyran-3-yl group, a 4-fluorotetrahydro-2H-pyran-4-yl group, a 3-methyltetrahydro-2H-pyran-3-yl group, a 4-methyltetrahydro-2H-pyran-4-yl group, a 2,2-dimethyltetrahydro-2H-pyran-4-yl group, a 2,6-dimethyltetrahydro-2H-pyran-4-yl group, a 3-methoxytetrahydro-2H-pyran-3-yl group, a 4-methoxytetrahydro-2H-pyran-2-yl group, a 4-methoxytetrahydro-2H-pyran-4-yl group, a 5-methoxytetrahydro-2H-pyran-2-yl group, a 5-methoxytetrahydro-2H-pyran-3-yl group, a 4-oxotetrahydro-2H-pyran-3-yl group, a 3,6-dihydro-2H-pyran-4-yl group, a 5,6-dihydro-2H-pyran-3-yl group, a 1,4-dioxan-2-yl group, a 5-methoxymethyl-1,4-dioxan-2-yl group or a 6-methoxymethyl-1,4-dioxan-2-yl group.

$R^3$ and $R^4$ are the same or different and are each a hydrogen atom, a halogen atom, a $C_{1-4}$ alkyl group, a halogeno-$C_{1-4}$ alkyl group or a cyano group. Preferably, $R^3$ is a hydrogen atom, a fluorine atom, a chlorine atom, a cyano group or a methyl group and $R^4$ is a hydrogen atom. More preferably, $R^3$ is a hydrogen atom or a methyl group and $R^4$ is a hydrogen atom.

$R^5$ and $R^6$ are the same or different and are each a hydrogen atom, a halogen atom or a $C_{1-4}$ alkyl group, or $R^5$ and $R^6$ together may form an oxo group or together with the carbon atom to which $R^5$ and $R^6$ are bonded may form a $C_{3-8}$ cycloalkyl group. Preferably, $R^5$ and $R^6$ are the same or different and are each a hydrogen atom, a halogen atom or a $C_{1-4}$ alkyl group. More preferably, $R^5$ is a hydrogen atom, a fluorine atom or a methyl group and $R^6$ is a hydrogen atom or a fluorine atom. Particularly preferably, $R^5$ is a hydrogen atom, a fluorine atom or a methyl group and $R^6$ is a hydrogen atom.

Q is a bond or a $C_{1-4}$ alkylene group, more preferably a bond, a methylene group or an ethylene group, and particularly preferably a bond or a methylene group.

The partial structure containing Q, $R^5$, $R^6$ and B which is represented by the following formula (V):

[Formula 5]

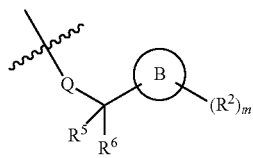

(V)

also includes stereoisomeric structures that may exist.

The partial structure represented by the formula (V) is preferably a cyclohexylmethyl group, a 4-hydroxycyclohexylmethyl group, a 3-methoxycyclohexylmethyl group, a 4-methoxycyclohexylmethyl group, a 4,4-difluorocyclohexylmethyl group, a tetrahydro-2H-pyran-2-ylmethyl group, a tetrahydro-2H-pyran-3-ylmethyl group, a tetrahydro-2H-pyran-4-ylmethyl group, a 2-(tetrahydro-2H-pyran-4-yl)ethyl group, a 2-fluoro-2-(tetrahydro-2H-pyran-4-yl)ethyl group, a 2-(tetrahydro-2H-pyran-4-yl)propyl group, a tetrahydro-2H-pyran-3-ylmethyl group, a 4-hydroxytetrahydro-2H-pyran-2-ylmethyl group, a 5-hydroxytetrahydro-2H-pyran-2-ylmethyl group, a 5-hydroxytetrahydro-2H-pyran-3-ylmethyl group, a 4-cyanotetrahydro-2H-pyran-4-ylmethyl group, a 3-fluorotetrahydro-2H-pyran-3-ylmethyl group, a 4-fluorotetrahydro-2H-pyran-4-ylmethyl group, a 3-methyltetrahydro-2H-pyran-3-ylmethyl group, a 4-methyltetrahydro-2H-pyran-4-ylmethyl group, a 2,2-dimethyltetrahydro-2H-pyran-4-ylmethyl group, a 2,6-dimethyltetrahydro-2H-pyran-4-ylmethyl group, a 3-methoxytetrahydro-2H-pyran-3-ylmethyl group, a 4-methoxytetrahydro-2H-pyran-2-ylmethyl group, a 4-methoxytetrahydro-2H-pyran-4-ylmethyl group, a 5-methoxytetrahydro-2H-pyran-2-ylmethyl group, a 5-methoxytetrahydro-2H-pyran-3-ylmethyl group, a 4-oxotetrahydro-2H-pyran-3-ylmethyl group, a 3,6-dihydro-2H-pyran-4-ylmethyl group, a 2-(3,6-dihydro-2H-pyran-4-yl)ethyl group, a 5,6-dihydro-2H-pyran-3-ylmethyl group, a 2-(5,6-dihydro-2H-pyran-3-yl)ethyl group, a 1,4-dioxan-2-ylmethyl group, a 5-methoxymethyl-1,4-dioxan-2-ylmethyl group or a 6-methoxymethyl-1,4-dioxan-2-ylmethyl group.

In the general formula (I), in preferred combinations of the partial structures represented by the formulas (III) and (V), when the partial structure represented by the formula (III) is a 1H-indol-5-yl group, a 4-fluoro-1H-indol-5-yl group, a 6-fluoro-1H-indol-5-yl group, a 7-fluoro-1H-indol-5-yl group, a 7-fluoro-3-methyl-1H-indol-5-yl group, a 7-fluoro-4-methyl-1H-indol-5-yl group, a 3,4-dimethyl-7-fluoro-1H-indol-5-yl group, a 1H-indazol-5-yl group, a 1H-pyrrolo[2,3-b]pyridin-5-yl group, a 3-chloro-1H-pyrrolo[2,3-b]pyridin-5-yl group, a 4-chloro-1H-pyrrolo[2,3-b]pyridin-5-yl group, a 6-chloro-1H-pyrrolo[2,3-b]pyridin-5-yl group, a 3-fluoro-1H-pyrrolo[2,3-b]pyridin-5-yl group, a 4-fluoro-1H-pyrrolo[2,3-b]pyridin-5-yl group, a 6-fluoro-1H-pyrrolo[2,3-b]pyridin-5-yl group, a 3-methyl-1H-pyrrolo[2,3-b]pyridin-5-yl group, a 4-methyl-1H-pyrrolo[2,3-b]pyridin-5-yl group, a 6-methyl-1H-pyrrolo[2,3-b]pyridin-5-yl group, a 3,4-dimethyl-1H-pyrrolo[2,3-b]pyridin-5-yl group, a 3-chloro-4-methyl-1H-pyrrolo[2,3-b]pyridin-5-yl group, a 3-fluoro-4-methyl-1H-pyrrolo[2,3-b]pyridin-5-yl group, a 3-methoxy-1H-pyrrolo[2,3-b]pyridin-5-yl group, a 3-trifluoromethyl-1H-pyrrolo[2,3-b]pyridin-5-yl group, a 4-trifluoromethyl-1H-pyrrolo[2,3-b]pyridin-5-yl group, a 3-amino-1H-pyrrolo[2,3-b]pyridin-5-yl group, a 4-amino-1H-pyrrolo[2,3-b]pyridin-5-yl group, a 1H-pyrrolo[3,2-b]pyridin-5-yl group, a pyrazolo[1,5-a]pyrimidin-6-yl group, a 1H-pyrazolo[3,4-b]pyridin-5-yl group, a 5H-pyrrolo[2,3-b]pyrazin-2-yl group, a 7H-pyrrolo[2,3-c]pyridazin-3-yl group or a 2-oxo-2,3-dihydro-1H-pyrrolo[2,3-b]pyridin-5-yl group, the partial structure represented by the formula (V) is a cyclohexylmethyl group, a 4-hydroxycyclohexylmethyl group, a 3-methoxycyclohexylmethyl group, a 4-methoxycyclohexylmethyl group, a 4,4-difluorocyclohexylmethyl group, a tetrahydro-2H-pyran-4-ylmethyl group, a tetrahydro-2H-pyran-4-ylmethyl group, a 2-(tetrahydro-2H-pyran-4-yl)ethyl group, a 2-fluoro-2-(tetrahydro-2H-pyran-4-yl)ethyl group, a 2-(tetrahydro-2H-pyran-4-yl)propyl group, a tetrahydro-2H-pyran-3-ylmethyl group, a 4-hydroxytetrahydro-2H-pyran-2-ylmethyl group, a 5-hydroxytetrahydro-2H-pyran-2-ylmethyl group, a 5-hydroxytetrahydro-2H-pyran-3-ylmethyl group, a 4-cyanotetrahydro-2H-pyran-4-ylmethyl group, a 3-fluorotetrahydro-2H-pyran-3-ylmethyl group, a 4-fluorotetrahydro-2H-pyran-4-ylmethyl group, a 3-methyltetrahydro-2H-pyran-3-ylmethyl group, a 4-methyltetrahydro-2H-pyran-4-ylmethyl group, a 2,2-dimethyltetrahydro-2H-pyran-4-ylmethyl group, a 2,6-dimethyltetrahydro-2H-pyran-4-ylmethyl group, a 3-methoxytetrahydro-2H-pyran-3-ylmethyl group, a 4-methoxytetrahydro-2H-pyran-2-ylmethyl group, a 4-methoxytetrahydro-2H-pyran-4-ylmethyl group, a 5-methoxytetrahydro-2H-pyran-2-ylmethyl group, a 5-methoxytetrahydro-2H-pyran-3-ylmethyl group, a 4-oxotetrahydro-2H-pyran-3-ylmethyl group, a 3,6-dihydro-2H-pyran-4-ylmethyl group, a 2-(3,6-dihydro-2H-pyran-4-yl)ethyl group, a 5,6-dihydro-2H-pyran-3-ylmethyl group, a 2-(5,6-dihydro-2H-pyran-3-yl)ethyl group, a 1,4-dioxan-2-ylmethyl group, a 5-methoxymethyl-1,4-dioxan-2-ylmethyl group or a 6-methoxymethyl-1,4-dioxan-2-ylmethyl group.

The following general formula (II) can be illustrated as another preferred embodiment of the compound represented by the general formula (I) according to the present invention.

[Formula 2]

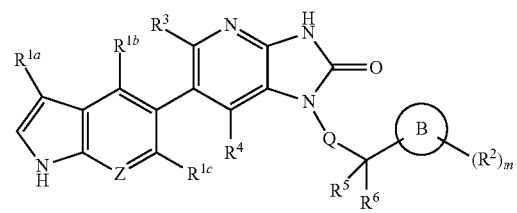

(II)

Here, in the general formula (II), B, Q, $R^2$, $R^3$, $R^4$, $R^5$, $R^6$ and m are as described above. The formulas (IV) and (V) each representing a partial structure containing B in the general formula (II) are also as described above.

In the general formula (II), Z is C—$R^{1d}$ or a nitrogen atom. $R^{1d}$ is a hydrogen atom, a halogen atom or a $C_{1-4}$ alkyl group, and preferably a hydrogen atom, a fluorine atom or a methyl group.

R$^{1a}$, R$^{1b}$ and R$^{1c}$ are the same or different and are each a substituent selected from the group consisting of a hydrogen atom, a hydroxy group, a halogen atom, a cyano group, a C$_{1-4}$ alkyl group (wherein the C$_{1-4}$ alkyl group may be substituted with one or two same or different C$_{1-4}$ alkoxy groups or —NR$^{7a}$R$^{7b}$s) a C$_{1-4}$ alkoxy group, a halogeno-C$_{1-4}$ alkyl group, —NR$^{7a}$R$^{7b}$, —C(O)R$^8$ and —C(O)NR$^{9a}$R$^{9b}$. R$^{7a}$, R$^{7b}$, R$^8$, R$^{9a}$ and R$^{9b}$ are as described above.

Preferably, R$^{1a}$, R$^{1b}$ and R$^{1c}$ are the same or different and are each a hydrogen atom, a halogen atom, a C$_{1-4}$ alkyl group or a C$_{1-4}$ alkoxy group, and more preferably a hydrogen atom, a fluorine atom, a chlorine atom, a methyl group or a methoxy group. In a particularly preferred combination of R$^{1a}$, R$^{1b}$ and R$^{1c}$, R$^{1a}$ and R$^{1b}$ are the same or different and are each a hydrogen atom, a fluorine atom, a chlorine atom or a methyl group and R$^{1c}$ is a hydrogen atom or a fluorine atom.

Preferred examples of the compound represented by the general formula (I) or (II) according to the present invention include 6-(1H-pyrrolo[2,3-b]pyridin-5-yl)-1-(tetrahydro-2H-pyran-4-ylmethyl)-1,3-dihydro-2H-imidazo[4,5-b]pyridin-2-one, 6-(7-fluoro-1H-indol-5-yl)-1-(tetrahydro-2H-pyran-4-ylmethyl)-1,3-dihydro-2H-imidazo[4,5-b]pyridin-2-one, 6-(4-methyl-1H-pyrrolo[2,3-b]pyridin-5-yl)-1-(tetrahydro-2H-pyran-4-ylmethyl)-1,3-dihydro-2H-imidazo[4,5-b]pyridin-2-one, 6-(3-methyl-1H-pyrrolo[2,3-b]pyridin-5-yl)-1-(tetrahydro-2H-pyran-4-ylmethyl)-1,3-dihydro-2H-imidazo[4,5-b]pyridin-2-one, 1-[(2S)-1,4-dioxan-2-ylmethyl]-6-(1H-pyrrolo[2,3-b]pyridin-5-yl)-1,3-dihydro-imidazo[4,5-b]pyridin-2-one, 6-(3-chloro-1H-pyrrolo[2,3-b]pyridin-5-yl)-1-[(2S)-1,4-dioxan-2-ylmethyl]-1,3-dihydro-imidazo[4,5-b]pyridin-2-one, 1-[(2S)-1,4-dioxan-2-ylmethyl]-6-(4-methyl-1H-pyrrolo[2,3-b]pyridin-5-yl)-1,3-dihydro-imidazo[4,5-b]pyridin-2-one, 1-[(2S)-1,4-dioxan-2-ylmethyl]-6-(3-methyl-1H-pyrrolo[2,3-b]pyridin-5-yl)-1,3-dihydro-imidazo[4,5-b]pyridin-2-one, 6-(3-chloro-1H-pyrrolo[2,3-b]pyridin-5-yl)-1-[(2S)-1,4-dioxan-2-ylmethyl]-5-methyl-1,3-dihydro-imidazo[4,5-b]pyridin-2-one, 1-[(2S)-1,4-dioxan-2-ylmethyl]-5-methyl-6-(3-methyl-1H-pyrrolo[2,3-b]pyridin-5-yl)-1,3-dihydro-imidazo[4,5-b]pyridin-2-one, 6-(3,4-dimethyl-1H-pyrrolo[2,3-b]pyridin-5-yl)-1-[(2S)-1,4-dioxan-2-ylmethyl]-1,3-dihydro-2H-imidazo[4,5-b]pyridin-2-one, 6-(3-chloro-4-methyl-1H-pyrrolo[2,3-b]pyridin-5-yl)-1-[(2S)-1,4-dioxan-2-ylmethyl]-1,3-dihydro-2H-imidazo[4,5-b]pyridin-2-one, 1-[(2S)-1,4-dioxan-2-ylmethyl]-6-(3-fluoro-4-methyl-1H-pyrrolo[2,3-b]pyridin-5-yl)-1,3-dihydro-2H-imidazo[4,5-b]pyridin-2-one, 2,6-anhydro-1,3,4-trideoxy-5-O-methyl-1-[2-oxo-6-(1H-pyrrolo[2,3-b]pyridin-5-yl)-2,3-dihydro-1H-imidazo[4,5-b]pyridin-1-yl]-L-threo-hexitol, 2,6-anhydro-1,3,5-trideoxy-4-O-methyl-1-[2-oxo-6-(1H-pyrrolo[2,3-b]pyridin-5-yl)-2,3-dihydro-1H-imidazo[4,5-b]pyridin-1-yl]-L-threo-hexitol, 2,6-anhydro-1,3,5-trideoxy-4-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol, 2,6-anhydro-1,3,4-trideoxy-1-[6-(4-methyl-1H-pyrrolo[2,3-b]pyridin-5-yl)-2-oxo-2,3-dihydro-1H-imidazo[4,5-b]pyridin-1-yl]-L-threo-hexitol, 2,6-anhydro-1,3,4-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-L-threo-hexitol, 2,6-anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,4-trideoxy-L-threo-hexitol, 2,6-anhydro-1,3,4-trideoxy-5-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol, 2,6-anhydro-1,3,4-trideoxy-1-[5-methyl-2-oxo-6-(1H-pyrrolo[2,3-b]pyridin-5-yl)-2,3-dihydro-1H-imidazo[4,5-b]pyridin-1-yl]-L-threo-hexitol, 2,6-anhydro-1,3,5-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-L-threo-hexitol, 2,6-anhydro-1,3,5-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-4-O-methyl-L-threo-hexitol and 2,6-anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,5-trideoxy-4-O-methyl-L-threo-hexitol.

More preferred examples of the compound include 1-[(2S)-1,4-dioxan-2-ylmethyl]-6-(1H-pyrrolo[2,3-b]pyridin-5-yl)-1,3-dihydro-imidazo[4,5-b]pyridin-2-one, 1-[(2S)-1,4-dioxan-2-ylmethyl]-6-(4-methyl-1H-pyrrolo[2,3-b]pyridin-5-yl)-1,3-dihydro-imidazo[4,5-b]pyridin-2-one, 6-(3,4-dimethyl-1H-pyrrolo[2,3-b]pyridin-5-yl)-1-[(2S)-1,4-dioxan-2-ylmethyl]-1,3-dihydro-2H-imidazo[4,5-b]pyridin-2-one, 6-(3-chloro-4-methyl-1H-pyrrolo[2,3-b]pyridin-5-yl)-1-[(2S)-1,4-dioxan-2-ylmethyl]-1,3-dihydro-2H-imidazo[4,5-b]pyridin-2-one, 1-[(2S)-1,4-dioxan-2-ylmethyl]-6-(3-fluoro-4-methyl-1H-pyrrolo[2,3-b]pyridin-5-yl)-1,3-dihydro-2H-imidazo[4,5-b]pyridin-2-one, 2,6-anhydro-1,3,5-trideoxy-4-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol, 2,6-anhydro-1,3,4-trideoxy-5-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol, 2,6-anhydro-1,3,4-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-5-O-methyl-L-threo-hexitol, 2,6-anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,4-trideoxy-5-O-methyl-L-threo-hexitol, 2,6-anhydro-1,3,5-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-4-O-methyl-L-threo-hexitol and 2,6-anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,5-trideoxy-4-O-methyl-L-threo-hexitol.

In the present invention, the "pharmacologically acceptable salt thereof" refers to a salt that can be obtained by converting a compound having the formula (I) according to the present invention which has a basic substituent or contains a nitrogen atom in A and/or B to a salt according to a conventional method as desired.

Examples of such salts include salts of inorganic acids such as hydrochlorides, hydrobromides, sulfates, nitrates and phosphates; salts of carboxylic acids such as acetates, fumarates, maleates, oxalates, malonates, succinates, citrates and malates; salts of sulfonic acids such as methanesulfonates, ethanesulfonates, benzenesulfonates and toluenesulfonates; and salts of amino acids such as glutamates and aspartates.

The compound or pharmacologically acceptable salt thereof having the formula (I) according to the present invention may absorb moisture, adsorb water or form a hydrate when left to stand in the air or recrystallized; such hydrates are also included in the present invention.

The compound or pharmacologically acceptable salt thereof having the formula (I) according to the present invention may form a solvate when left to stand in a solvent or recrystallized; such solvates are also included in the present invention.

Further, stereoisomers may exist for the compound or pharmacologically acceptable salt thereof having the formula (I) according to the present invention; isomers of the compound and the salt and mixtures of these isomers are all included in the present invention.

The present invention also includes compounds labeled with various radioisotopes or non-radioactive isotopes.

The compound having the formula (I) according to the present invention can easily be produced according to the method of Processes 1 to 3 described below. The compound can also be produced without implementing protecting group introduction and deprotection steps in the schemes.

(Process 1)

The compound represented by the formula (I) which is shown below can be produced according to the following reaction scheme, for example.

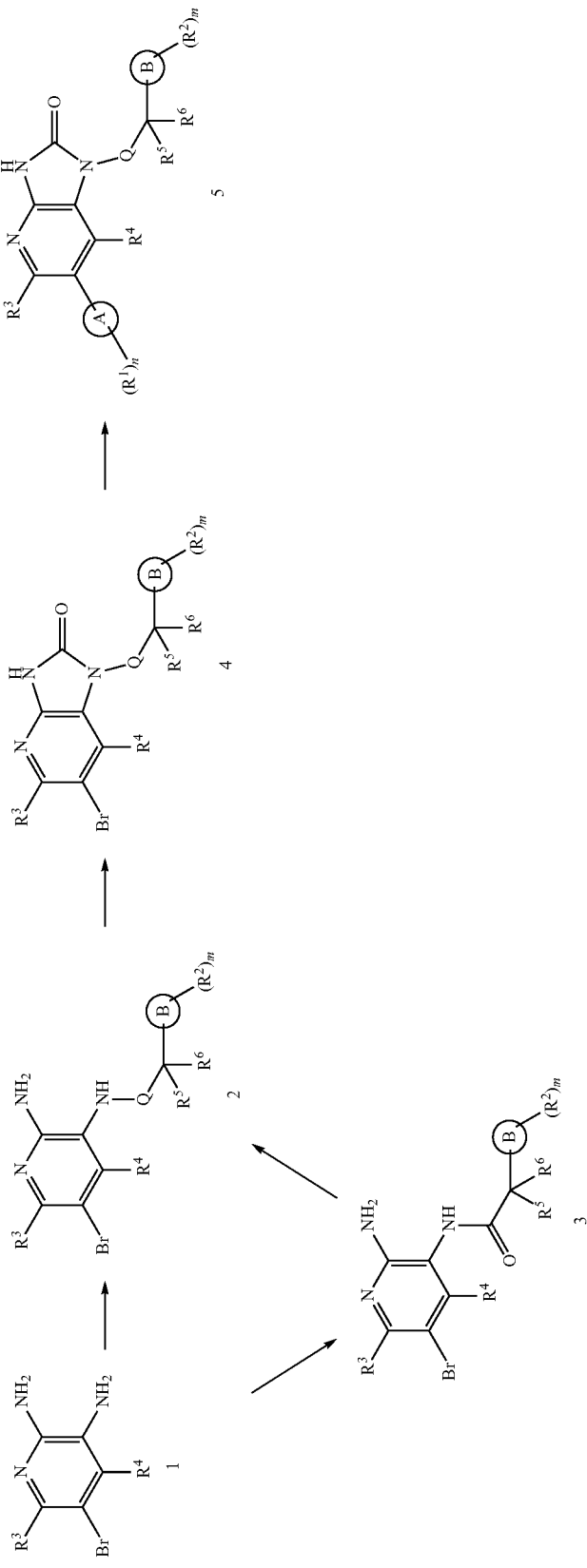

In this scheme, $R^1$, $R^2$, $R^3$, $R^4$, $R^5$, $R^6$, Q, A, B, m and n are as described above.

Each step in Process 1 will be shown below.

[Formula 7]

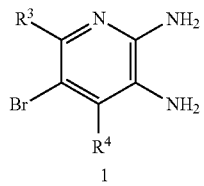
1

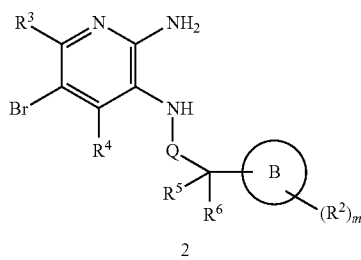
2

Compound 1 is converted to Compound 2 by reductive amination reaction of Compound 1 with a carbonyl compound using a known organic chemistry technique. The reaction is performed by treating Compound 1 and a carbonyl compound with sodium cyanoborohydride, sodium borohydride or sodium triacetoxyborohydride in an appropriate solvent not adversely affecting the reaction (such as methanol, dichloromethane or acetic acid) at −20° C. to 100° C., preferably 0° C. to 50° C., in the presence of an appropriate acid (such as acetic acid, hydrochloric acid or trifluoroacetic acid), for example. The carbonyl compound may be used in an amount of 1 mole to excess moles, preferably 1 to 5 moles, per mole of Compound 1. The reaction time is 5 minutes to 150 hours, usually 15 minutes to 100 hours.

Compound 2 can also be obtained by alkylation reaction of Compound 1 using a known organic chemistry technique. The reaction is performed by treating Compound 1 with an alkyl halide compound, a methanesulfonyloxyalkyl compound or the like in an appropriate solvent not adversely affecting the reaction (such as N,N-dimethylformamide, dimethyl sulfoxide, 1,4-dioxane or acetonitrile) or a mixed solvent thereof at 0° C. to 300° C., preferably room temperature to 150° C., in the presence of an organic or inorganic base (such as potassium carbonate, potassium tert-butoxide or triethylamine) with the addition of an appropriate additive (such as triethylbenzylammonium chloride), for example. The alkyl halide compound, methanesulfonyloxyalkyl compound or the like may be used in an amount of 1 mole to excess moles, preferably 1 to 5 moles, per mole of Compound 1. The reaction time is 1 minute to 72 hours, usually 5 minutes to 48 hours.

[Formula 8]

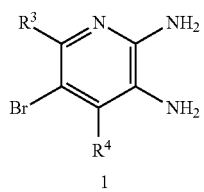
1

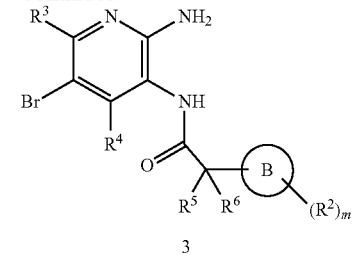
3

Compound 1 is converted to Compound 3 by amidation reaction of Compound 1 with a carbonyl compound using a known organic chemistry technique. The reaction is performed by reacting Compound 1 with a carboxylic acid compound in an appropriate solvent not adversely affecting the reaction (such as benzene, toluene, diethyl ether, dichloromethane, tetrahydrofuran or N,N-dimethylformamide) or a mixed solvent thereof at −30° C. to boiling point of the solvent used for the reaction, preferably 0° C. to 50° C., in the presence of an appropriate condensing agent such as N,N-dicyclohexylcarbodiimide, 1-ethyl-3-(3-dimethylaminopropyl)carbodiimide or diethyl cyanophosphate. The condensing agent may be used in an amount of 1 mole to excess moles, preferably 1 to 5 moles, per mole of Compound 1. The reaction may also be performed with the addition of a base (such as triethylamine, diisopropylethylamine, N-methylmorpholine or 4-dimethylaminopyridine) as required. The base can be used in a catalytic amount or in an excess amount. The reaction time is 10 minutes to 72 hours, usually 30 minutes to 24 hours. The reaction can also be performed by reacting Compound 1 with a carboxylic halide compound in an appropriate solvent not adversely affecting the reaction (such as benzene, toluene, diethyl ether, dichloromethane, tetrahydrofuran or dichloromethane) or a mixed solvent thereof at −30° C. to boiling point of the solvent used for the reaction, preferably 0° C. to 100° C., in the presence of an appropriate base (such as triethylamine, diisopropylethylamine, N-methylmorpholine or 4-dimethylaminopyridine). The base can be used in a catalytic amount or in an excess amount. The reaction time is 10 minutes to 72 hours, usually 30 minutes to 24 hours. Alternatively, the reaction can be performed by reacting Compound 1 with a carboxylic acid compound in an acidic solvent (such as polyphosphoric acid) at 0° C. to boiling point of the solvent used for the reaction, preferably 10° C. to 120° C. The reaction time is 10 minutes to 72 hours, usually 30 minutes to 24 hours.

[Formula 9]

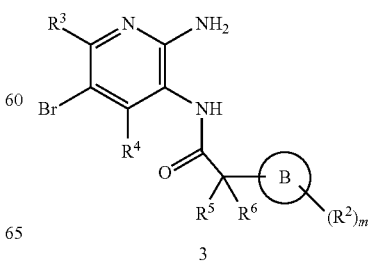
3

-continued

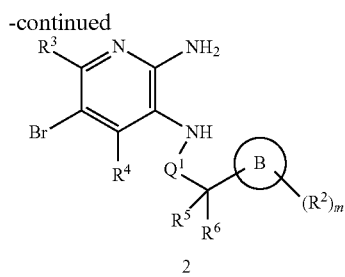
2

In this scheme, $Q^1$ represents a methylene group. Compound 3 is converted to Compound 2 by reduction reaction of Compound 3 using a known organic chemistry technique. The reaction is performed by treating Compound 3 with an appropriate reducing agent (such as lithium aluminum hydride, diborane, lithium borohydride, a borane-tetrahydrofuran complex or a borane-dimethyl sulfide complex) in an appropriate solvent not adversely affecting the reaction (such as dichloromethane, tetrahydrofuran, dichloromethane or toluene) or a mixed solvent thereof at −78° C. to boiling point used for the reaction, preferably 0° C. to 100° C., for example. The reducing agent may be used in an amount of 1 mole to excess moles, preferably 1 to 5 moles, per mole of Compound 3. The reaction is performed with the addition of a Lewis acid (such as tin chloride or a trifluoroborane-ether complex) as required. The reaction time is 1 minute to 60 hours, usually 5 minutes to 24 hours.

[Formula 10]

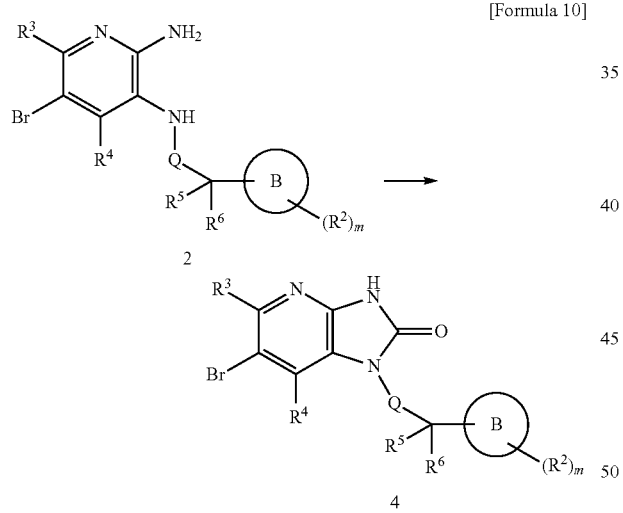

Compound 2 is converted to Compound 4 by introducing a carbonyl group into Compound 2 using a known organic chemistry technique. The reaction is performed by treating Compound 2 with 1,1'-carbonyldiimidazole, N,N'-disuccinimidyl carbonate, triphosgene or the like in an appropriate solvent not adversely affecting the reaction (such as 1,4-dioxane, tetrahydrofuran or dichloromethane) or a mixed solvent thereof at −10° C. to boiling point of the solvent used for the reaction, preferably 0° C. to 100° C., for example. The 1,1'-carbonyldiimidazole, N,N'-disuccinimidyl carbonate, triphosgene or the like may be used in an amount of 1 mole to excess moles, preferably 1 to 5 moles, per mole of Compound 2. The reaction time is 5 minutes to 60 hours, usually 1 to 24 hours.

[Formula 11]

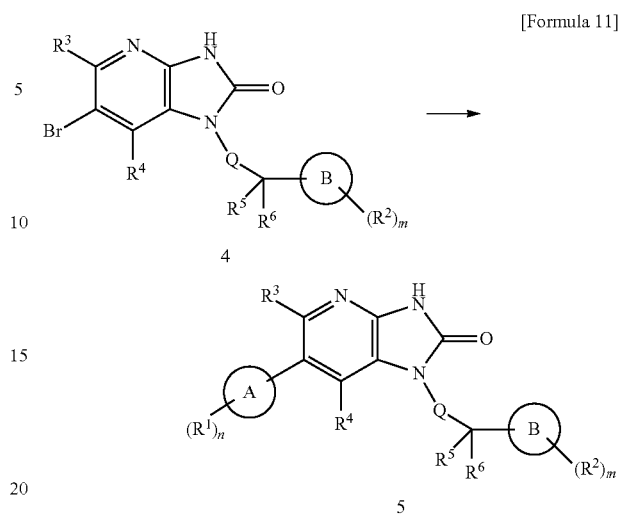

Compound 4 is converted to Compound 5 by coupling reaction of Compound 4 with a compound forming a partial structure containing A which is represented by the above formula (III) using a known organic chemistry technique. The reaction is performed by treating Compound 4 in the presence of an appropriate organoboronic acid, organoboronate, organotin, organozinc or organomagnesium compound and an appropriate transition metal catalyst (such as a palladium compound) with the addition of an organic or inorganic base (such as sodium bicarbonate, tripotassium phosphate or diisopropylethylamine), a ligand (such as triphenylphosphine) and a known reaction promoting additive (such as lithium chloride or copper iodide) as required, for example.

The above coupling reaction is performed using an appropriate solvent not adversely affecting the reaction (such as N,N-dimethylformamide, tetrahydrofuran, toluene, 1,4-dioxane or water) or a mixed solvent thereof at a reaction temperature of 0° C. to 300° C., preferably room temperature to 200° C. The above reaction is also performed by treatment in a sealed tube or under microwave irradiation. The organoboronic acid or the like and the base may be used in an amount of 1 mole to excess moles, preferably 1 to 5 moles, per mole of Compound 3. The reaction time is 1 minute to 60 hours, usually 5 minutes to 24 hours.

(Process 2)

The compound represented by the formula (I) which is shown below can be produced according to the following reaction scheme, for example.

[Formula 12]

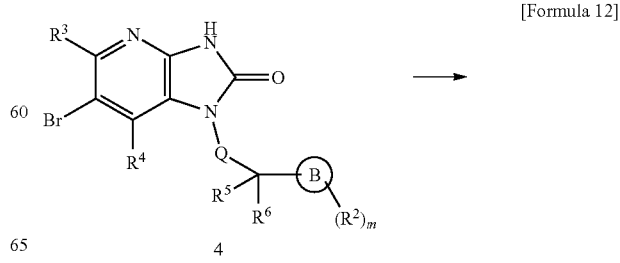

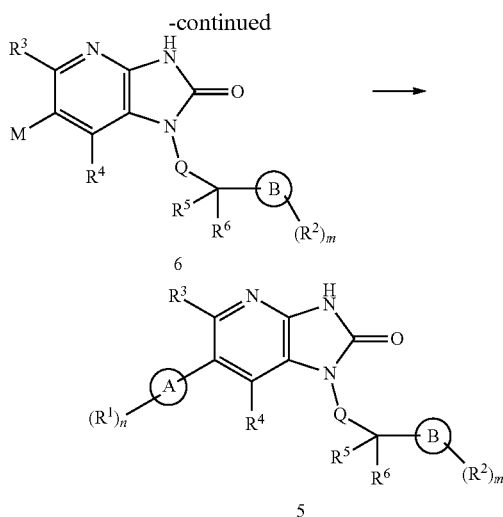

In this scheme, $R^1$, $R^2$, $R^3$, $R^4$, $R^5$, $R^6$, Q, A, B, m and n are as described above and M represents an alkyltin, borate or the like.

Each step in Process 2 will be shown below.

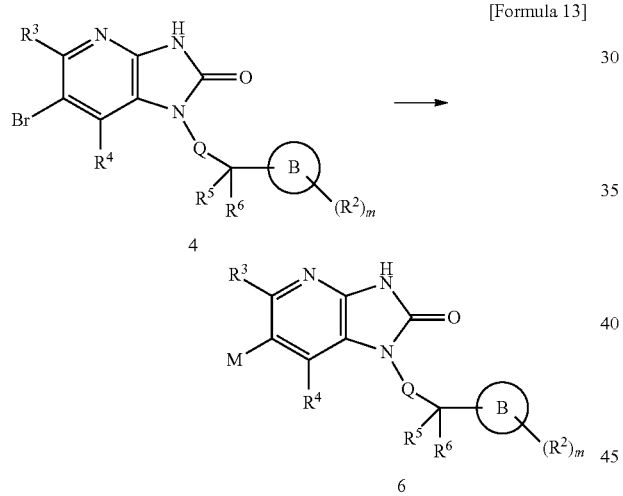

[Formula 13]

Compound 4 is converted to Compound 6 by halogen-metal exchange reaction of Compound 4 using a known organic chemistry technique. The reaction is performed by treating Compound 4 in the presence of an appropriate diboronate or alkylditin compound and an appropriate transition metal catalyst (such as a palladium compound) with the addition of an organic or inorganic base (such as potassium acetate, sodium carbonate or diisopropylethylamine), a ligand (such as triphenylphosphine) and a known reaction promoting additive (such as lithium chloride or copper iodide) as required, for example.

The above reaction is performed using an appropriate solvent not adversely affecting the reaction (such as N,N-dimethylformamide, tetrahydrofuran, toluene, 1,4-dioxane or water) or a mixed solvent thereof at a reaction temperature of 0° C. to 300° C., preferably room temperature to 200° C. The above reaction is also performed by treatment in a sealed tube or under microwave irradiation. The diboronate or the like and the base may be used in an amount of 1 mole to excess moles, preferably 1 to 5 moles, per mole of Compound 4. The reaction time is 1 minute to 60 hours, usually 5 minutes to 24 hours.

The reaction is also performed by treating Compound 4 with 1 mole to excess moles, preferably 1 to 1.5 moles, of a base such as n-butyllithium, sec-butyllithium or tert-butyllithium in an appropriate solvent not adversely affecting the reaction (such as benzene, toluene, diethyl ether or tetrahydrofuran) or a mixed solvent thereof at −100° C. to 50° C., preferably −85° C. to 10° C., and then reacting with a metal halide such as tributyltin chloride, a trialkyl borate, or the like. The reaction time is 1 minute to 24 hours, usually 10 minutes to 8 hours.

[Formula 14]

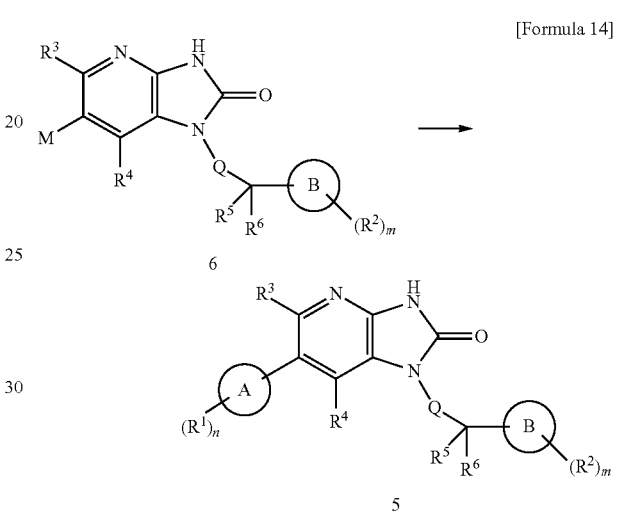

Compound 6 is converted to Compound 5 by coupling reaction of Compound 6 with a compound forming a partial structure containing A which is represented by the formula (III) using a known organic chemistry technique. The reaction is performed by treating Compound 6 in the presence of an appropriate organohalogen compound and an appropriate transition metal catalyst (such as a palladium compound) with the addition of an organic or inorganic base (such as sodium bicarbonate, tripotassium phosphate or diisopropylethylamine), a ligand (such as triphenylphosphine) and a known reaction promoting additive (such as lithium chloride or copper iodide) as required, for example.

The above coupling reaction is performed using an appropriate solvent not adversely affecting the reaction (such as N,N-dimethylformamide, tetrahydrofuran, toluene, 1,4-dioxane or water) or a mixed solvent thereof at a reaction temperature of 0° C. to 300° C., preferably room temperature to 200° C. The above reaction is performed by treatment in a sealed tube or under microwave irradiation. The organoboronic acid or the like and the base is used in an amount of 1 mole to excess moles, preferably 1 to 5 moles, per mole of Compound 3. The reaction time is 1 minute to 60 hours, preferably 5 minutes to 24 hours.

(Process 3)

The compound represented by the formula (I) which is shown below can be produced according to the following reaction scheme, for example.

[Formula 15]

In this scheme, $R^1$, $R^2$, $R^3$, $R^4$, $R^5$, $R^6$, M, Q, A, B, m and n are as described above and Pro represents a protecting group.

Each step in Process 3 will be shown below.

[Formula 16]

Compound 1 is converted to Compound 7 by introducing a protecting group (such as a cyclohexene group, a trimethylsilylethoxymethyl group, a trimethylsilylethyl group or a cyanoethyl group) into an appropriate position of Compound 1 using a known organic chemistry technique. For example, when Pro is a cyclohexene group, the reaction is performed by treating Compound 1 with ethyl 2-cyclohexanonecarboxylate in an appropriate solvent not adversely affecting the reaction (such as toluene, benzene or xylene) with heating under reflux. Ethyl 2-cyclohexanonecarboxylate is used in an amount of 1 mole to excess moles, preferably 1 to 5 moles, per mole of Compound 1. The reaction time is 5 minutes to 150 hours, preferably 60 minutes to 100 hours.

[Formula 17]

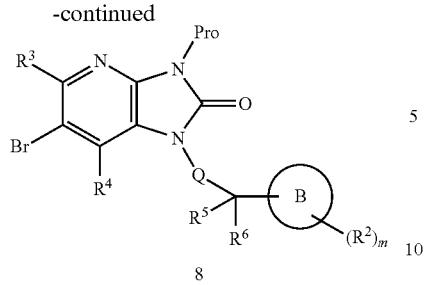

8

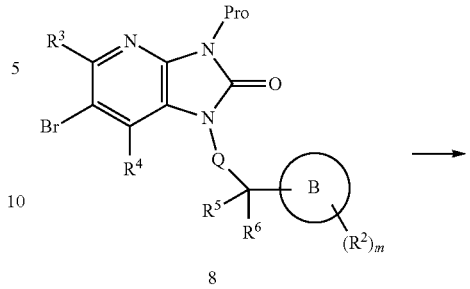

8

Compound 7 can be converted to Compound 8 according to the method of the alkylation reaction shown in Process 1. The reaction is also performed by Mitsunobu reaction of Compound 7 using a known organic chemistry technique. The reaction is performed by reacting Compound 7 with an alcohol compound in an appropriate solvent not adversely affecting the reaction (such as benzene, toluene, diethyl ether, dichloromethane or tetrahydrofuran) or a mixed solvent thereof at −30° C. to boiling point of the solvent used for the reaction, preferably 0° C. to 50° C., in the presence of cyanomethylenetributylphosphorane or triphenylphosphine and an appropriate Mitsunobu reagent such as diethyl azodicarboxylate or diisopropyl azodicarboxylate. The triphenylphosphine and the Mitsunobu reagent are used in an amount of 1 mole to excess moles, preferably 1 to 5 moles, per mole of Compound 7. The reaction time is 10 minutes to 72 hours, preferably 30 minutes to 24 hours.

[Formula 18]

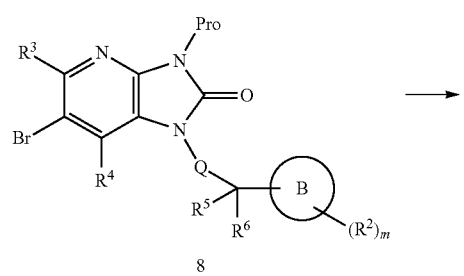

8

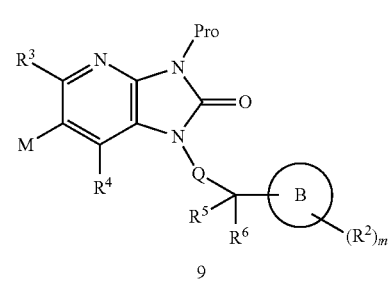

9

Compound 8 can be converted to Compound 9 according to the method of the halogen-metal exchange reaction shown in Process 2.

[Formula 19]

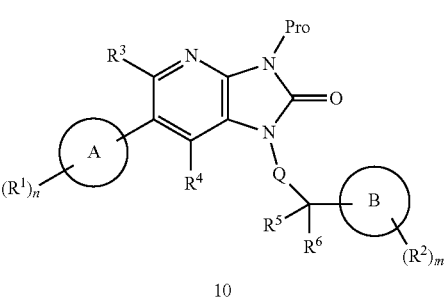

10

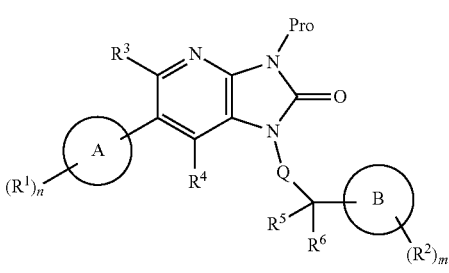

9

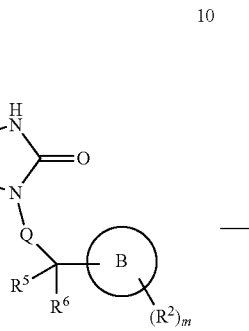

10

6

-continued

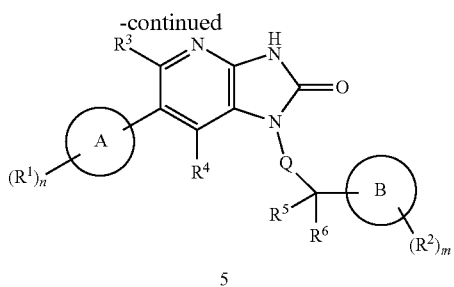

5

Compound 8 can be converted to Compound 10 according to the method of the coupling reaction shown in Process 1. Compound 9 can be converted to Compound 10 and Compound 6 can be converted to Compound 5 according to the method of the coupling reaction shown in Process 2.

[Formula 20]

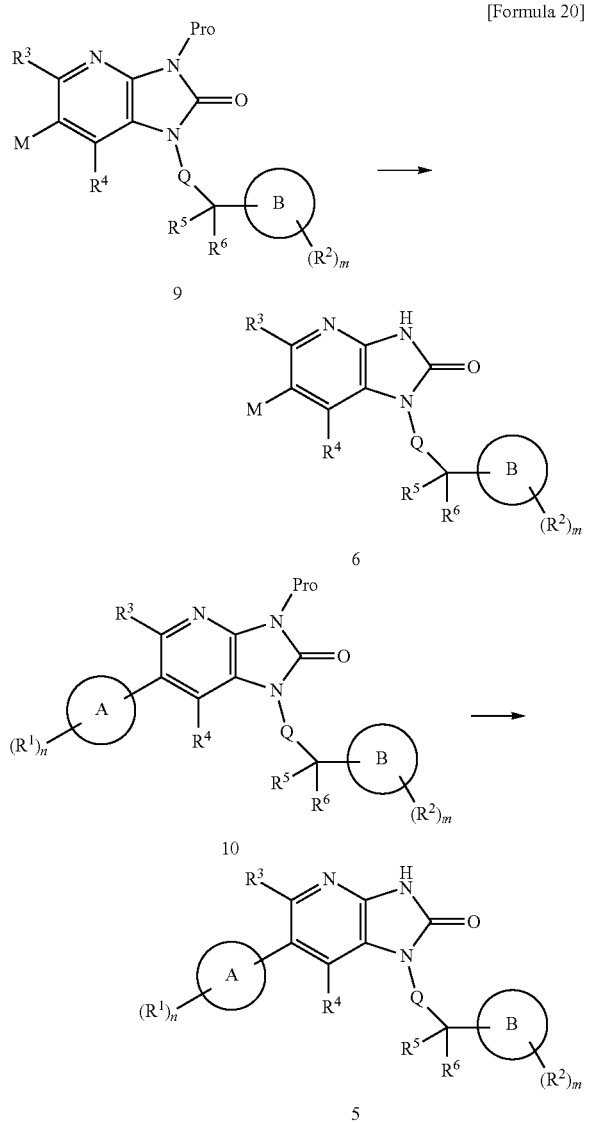

Compound 9 is converted to Compound 6 and Compound 10 is converted to Compound 5 by deprotection reaction of Compound 9 or 10 using a known organic chemistry technique. For example, when Pro is a cyclohexene group, the reaction is performed by treating Compound 9 or 10 with an appropriate acid (such as sulfuric acid, hydrochloric acid or trifluoroacetic acid) in an appropriate solvent not adversely affecting the reaction (such as ethanol, methanol, propanol or water) or a mixed solvent thereof at a reaction temperature of 0° C. to 200° C., preferably room temperature to 150° C. The acid is used in an amount of 1 mole to excess moles per mole of Compound 9 or 10. The reaction time is 1 minute to 500 hours, preferably 5 minutes to 200 hours.

The compound having the formula (I) according to the present invention can also be produced using an intermediate described in WO 2008/051493.

The compound or pharmacologically acceptable salt thereof having the formula (I) according to the present invention used as the aforementioned therapeutic agent or prophylactic agent can be orally administered as tablets, capsules, granules, powder or syrup or parenterally administered as an injection or suppository, for example, alone or in a mixture with an appropriate pharmacologically acceptable excipient, diluent or the like.

These preparations are produced by well-known methods using additives such as excipients (whose examples include organic excipients such as sugar derivatives such as lactose, sucrose, glucose, mannitol and sorbitol; starch derivatives such as corn starch, potato starch, α-starch and dextrin; cellulose derivatives such as crystalline cellulose; gum arabic; dextran; and pullulan; and inorganic excipients such as silicate derivatives such as light silicic anhydride, converted aluminum silicate, calcium silicate and magnesium aluminometasilicate; phosphates such as calcium hydrogenphosphate; carbonates such as calcium carbonate; and sulfates such as calcium sulfate), lubricants (whose examples include stearic acid and stearic acid metal salts such as calcium stearate and magnesium stearate; talc; colloidal silica; waxes such as veegum and spermaceti; boric acid; adipic acid; sulfates such as sodium sulfate; glycol; fumaric acid; sodium benzoate; DL-leucine; fatty acid sodium salts; lauryl sulfates such as sodium lauryl sulfate and magnesium lauryl sulfate; silicic acids such as silicic anhydride and silicic acid hydrate; and the aforementioned starch derivatives), binders (whose examples include hydroxypropylcellulose, hydroxypropylmethylcellulose, polyvinylpyrrolidone, macrogol and the same compounds as the aforementioned excipients), disintegrants (whose examples include cellulose derivatives such as low-substituted hydroxypropylcellulose, carboxymethylcellulose, calcium carboxymethylcellulose and internally crosslinked sodium carboxymethylcellulose; and chemically modified starches such as carboxymethyl starch, sodium carboxymethyl starch and crosslinked polyvinylpyrrodidone), stabilizers (whose examples include parahydroxybenzoates such as methylparaben and propylparaben; alcohols such as chlorobutanol, benzyl alcohol and phenylethyl alcohol; benzalkonium chloride; phenols such as phenol and cresol; thimerosal; dehydroacetic acid; and sorbic acid), corrigents (whose examples include commonly used sweeteners, acidulants and flavors) and diluents.

The dosage of the compound of the present invention may greatly vary according to various conditions such as the activity of the agent and the symptoms, age and body weight of the patient (warm-blooded animal, in particular, human). It is desirable to orally administer the compound at a single dosage of 0.01 mg/kg body weight at minimum to 5000 mg/kg body weight at maximum or intravenously administer the compound at a single dosage of 0.001 mg/kg body weight at minimum to 5000 mg/kg body weight at maximum once to

EXAMPLES

The present invention will be described in more detail by the following examples, preparation examples and test examples; however, these examples are illustrative only and may be changed without departing from the scope of the present invention.

Example 1

1-(Cyclopropylmethyl)-6-(1H-indol-5-yl)-1,3-dihydro-2H-imidazo[4,5-b]pyridin-2-one

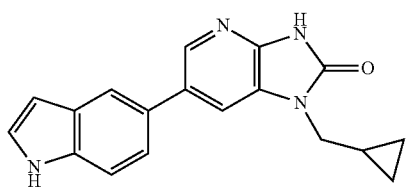

[Formula 21]

Step 1

5-Bromo-$N^3$-(cyclopropylmethyl)pyridine-2,3-diamine

Acetic acid (304 μl) and cyclopropanecarbaldehyde (406 μl) were added to a solution of 2,3-diamino-5-bromopyridine (1000 mg) in dichloromethane (25 ml) at room temperature, followed by stirring for 1 hour. Sodium tetrahydroborate (604 mg) was added to the reaction solution under ice-cooling, and the mixture was stirred with warming to room temperature for 22 hours. The reaction solution was extracted by adding a saturated aqueous sodium bicarbonate solution and dichloromethane. The resulting organic layer was washed with brine and dried over anhydrous sodium sulfate. The solvent was evaporated under reduced pressure. The resulting residue was purified by flash column chromatography to give the title compound (286 mg).

MS (ESI) m/z: 243 (M+H)$^+$.

$^1$H-NMR (CDCl$_3$) δ: 0.24-0.30 (2H, m), 0.57-0.64 (2H, m), 1.06-1.19 (1H, m), 2.86-2.93 (2H, m), 3.38 (1H, brs), 4.16 (2H, brs), 6.84 (1H, d, J=1.8 Hz), 7.62 (1H, d, J=1.8 Hz).

Step 2

6-Bromo-1-(cyclopropylmethyl)-1,3-dihydro-2H-imidazo[4,5-b]pyridin-2-one 1,1'-Carbonylbis-1H-imidazole (281 mg) was added to a solution of the compound obtained in the above Step 1 (280 mg) in tetrahydrofuran (11 ml), and the mixture was heated under reflux for 8 hours. After cooling to room temperature, the solvent was evaporated under reduced pressure. The resulting residue was solidified by adding dichloromethane and hexane. This was collected by filtration, washed with hexane and then dried under reduced pressure to give the title compound (273 mg).

MS (ESI) m/z: 268 (M+H)$^+$.

$^1$H-NMR (CDCl$_3$) δ: 0.40-0.47 (2H, m), 0.58-0.64 (2H, m), 1.14-1.26 (1H, m), 3.73 (2H, d, J=7.3 Hz), 7.38 (1H, d, J=1.8 Hz), 8.10 (1H, d, J=1.8 Hz), 9.08 (1H, brs).

Step 3

1-(Cyclopropylmethyl)-6-(1H-indol-5-yl)-1,3-dihydro-2H-imidazo[4,5-b]pyridin-2-one Potassium carbonate (63 mg), 5-(4,4,5,5-tetramethyl-1,3,2-dioxaborolan-2-yl)-1H-indole (37 mg) and tetrakistriphenylphosphine palladium (18 mg) were added to a mixed solution of the compound obtained in the above Step 2 (41 mg) in 1,4-dioxane-distilled water (1.6 ml-0.4 ml), and the mixture was heated under reflux at 170° C. for 30 minutes using a microwave reactor. The reaction solution was cooled to room temperature and separated by adding ethyl acetate and distilled water. The resulting organic layer was washed with brine and dried over anhydrous sodium sulfate. The solvent was evaporated under reduced pressure. The resulting residue was purified by thin-layer chromatography (developed with dichloromethane-methanol) to give the title compound (37 mg).

HRMS (ESI) [(M+H)$^+$] calculated: $C_{18}H_{17}N_4O$ 305.14024. found: 305.14092.

$^1$H-NMR (DMSO-d$_6$) δ: 0.34-0.52 (4H, m), 1.21-1.32 (1H, m), 3.78 (2H, d, J=6.9 Hz), 6.46-6.51 (1H, m), 7.37-7.44 (2H, m), 7.48 (1H, d, J=8.3 Hz), 7.84 (2H, dd, J=9.4, 1.8 Hz), 8.20 (1H, d, J=1.8 Hz), 11.16 (1H, brs), 11.52 (1H, brs).

Example 2

6-(1H-Indol-5-yl)-1-(tetrahydro-2H-pyran-4-yl)-1,3-dihydro-2H-imidazo[4,5-b]pyridin-2-one

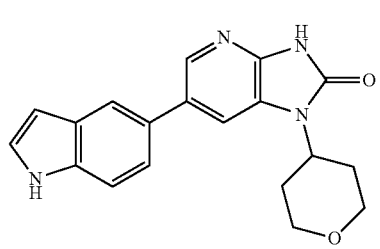

[Formula 22]

Step 1

5-Bromo-$N^3$-(tetrahydro-2H-pyran-4-yl)pyridine-2,3-diamine 2,3-Diamino-5-bromopyridine (1.0 g) and tetrahydro-4-pyran-4-one (0.69 g) were dissolved in acetic acid (20 ml). After stirring at room temperature for a while, sodium tetrahydroborate (0.6 g) was added and the mixture was stirred at room temperature for 16 hours. The reaction solution was concentrated, diluted with ethyl acetate, washed with a saturated aqueous sodium bicarbonate solution and brine and dried over anhydrous sodium sulfate. The solvent was evaporated under reduced pressure. The resulting residue was purified by flash column chromatography (developed with ethyl acetate-hexane) to give the title compound (254 mg).

MS (ESI) m/z: 272 (M+H)$^+$.

$^1$H-NMR (CDCl$_3$) δ: 1.50-1.54 (2H, m), 2.01-2.04 (2H, m), 3.15-3.18 (1H, m), 3.40-3.43 (1H, m), 3.52-3.55 (2H, m), 4.01-4.04 (2H, m), 4.12-4.13 (2H, m), 6.90 (1H, d, J=2.2 Hz), 7.64 (1H, d, J=2.2 Hz).

Step 2

6-Bromo-1-(tetrahydro-2H-pyran-4-yl)-1,3-dihydro-2H-imidazo[4,5-b]pyridin-2-one

The title compound (167 mg) was obtained by the same procedure as in Step 2 of Example 1 using the compound obtained in the above Step 1 (287 mg).
MS (ESI) m/z: 298 (M+H)$^+$.
$^1$H-NMR (CDCl$_3$) δ: 1.80-1.83 (2H, m), 2.31-2.38 (2H, m), 3.54-3.57 (2H, m), 4.14-4.17 (2H, m), 4.58-4.62 (1H, m), 7.55 (1H, d, J=2.0 Hz), 8.11 (1H, d, J=2.0 Hz), 9.51 (1H, brs).

Step 3

6-(1H-Indol-5-yl)-1-(tetrahydro-2H-pyran-4-yl)-1,3-dihydro-2H-imidazo[4,5-b]pyridin-2-one The title compound (10 mg) was obtained by the same procedure as in Step 3 of Example 1 using the compound obtained in the above Step 2 (48 mg).
HRMS (ESI) [(M+H)$^+$] calculated: C$_{19}$H$_{19}$N$_4$O$_2$ 335.15080.
found: 335.15316.
$^1$H-NMR (DMSO-d$_6$) δ: 1.66-1.76 (2H, m), 2.36-2.49 (2H, m), 3.49 (2H, t, J=11.0 Hz), 4.00 (2H, dd, J=11.0, 4.1 Hz), 4.45-4.56 (1H, m), 6.47-6.52 (1H, m), 7.37-7.44 (2H, m), 7.48 (1H, d, J=8.3 Hz), 7.81 (1H, d, J=1.8 Hz), 7.84-7.88 (1H, m), 8.19 (1H, d, J=1.8 Hz), 11.15 (1H, brs), 11.55 (1H, brs).

Example 3

6-(1H-Indol-5-yl)-1-[2-(tetrahydro-2H-pyran-4-yl)ethyl]-1,3-dihydro-2H-imidazo[4,5-b]pyridin-2-one

[Formula 23]

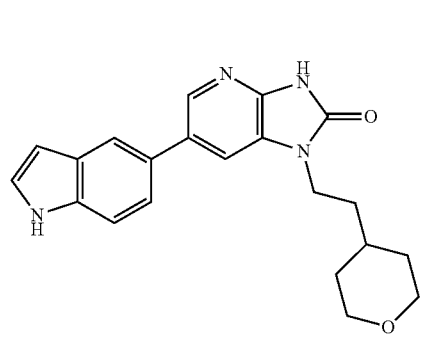

Step 1

5-Bromo-N$^3$-[2-(tetrahydro-2H-pyran-4-yl)ethyl]pyridine-2,3-diamine

The title compound (445 mg) was obtained by the same procedure as in Step 1 of Example 2 using 2,3-diamino-5-bromopyridine (1.0 g) and tetrahydro-2H-pyran-4-ylacetaldehyde (0.89 g).
MS (ESI) m/z: 300 (M+H)$^+$.

Step 2

6-Bromo-1-(tetrahydro-2H-pyran-4-yl)-1,3-dihydro-2H-imidazo[4,5-b]pyridin-2-one

The title compound (707 mg) was obtained by the same procedure as in Step 2 of Example 1 using the compound obtained in the above Step 1 (966 mg).
MS (ESI) m/z: 326 (M+H)$^+$.
$^1$H-NMR (CDCl$_3$) δ: 1.32-1.71 (7H, m), 3.35-3.41 (2H, m), 3.89-3.91 (2H, m), 3.98-4.01 (2H, m), 7.30 (1H, d, J=2.0 Hz), 8.12 (1H, d, J=2.0 Hz), 10.32 (1H, brs).

Step 3

6-(1H-Indol-5-yl)-1-[2-(tetrahydro-2H-pyran-4-yl)ethyl]-1,3-dihydro-2H-imidazo[4,5-b]pyridin-2-one The title compound (16 mg) was obtained by the same procedure as in Step 3 of Example 1 using the compound obtained in the above Step 2 (61 mg).
HRMS (ESI) [(M+H)$^+$] calculated: C$_{21}$H$_{23}$N$_4$O$_2$ 363.18210.
found: 363.18482.
$^1$H-NMR (DMSO-d$_6$) δ: 1.12-1.29 (2H, m), 1.45-1.73 (5H, m), 3.19-3.31 (2H, m), 3.76-3.96 (4H, m), 6.47-6.51 (1H, m), 7.38-7.43 (2H, m), 7.48 (1H, d, J=8.7 Hz), 7.74 (1H, d, J=1.8 Hz), 7.84 (1H, s), 8.19 (1H, d, J=1.8 Hz), 11.16 (1H, brs), 11.51 (1H, brs).

Example 4

6-(1H-Indol-5-yl)-1-(tetrahydro-2H-pyran-4-ylmethyl)-1,3-dihydro-2H-imidazo[4,5-b]pyridin-2-one

[Formula 24]

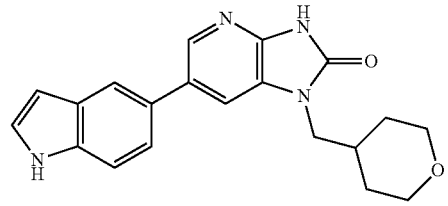

Step 1

6-Bromo-1-(tetrahydro-2H-pyran-4-ylmethyl)-1,3-dihydro-2H-imidazo[4,5-b]pyridin-2-one The title compound (809 mg) was obtained as a colorless amorphous solid by the same procedure as in Step 2 of Example 1 using 5-bromo-N$^3$-(tetrahydro-2H-pyran-4-ylmethyl)pyridine-2,3-diamine obtained by the method described in WO 2006/126081 (830 mg).
MS (FAB) m/z: 311M$^+$.
$^1$H-NMR (CDCl$_3$) δ: 1.39-1.51 (2H, m), 1.55-1.67 (3H, m), 2.05-2.17 (1H, m), 3.36 (2H, t, J=11.5 Hz), 3.73 (2H, d, J=7.2 Hz), 3.99 (2H, dd, J=11.5, 3.2 Hz), 7.31 (1H, d, J=1.7 Hz), 8.12 (1H, d, J=1.7 Hz), 10.01 (1H, brs).

Step 2

6-(1H-Indol-5-yl)-1-(tetrahydro-2H-pyran-4-ylmethyl)-1,3-dihydro-2H-imidazo[4,5-b]pyridin-2-one The compound obtained in the above Step 1 (50 mg) was suspended in 1,4-dioxane (2 ml), and 5-(4,4,5,5-tetramethyl-1,3,2-dioxaborolan-2-yl)-1H-indole (39 mg), sodium carbonate (17 mg), tetrabutylammonium bromide (5 mg), tetrakistriphenylphosphine palladium (18 mg) and water (1 ml) were added. The mixture was heated with stirring under nitrogen atmosphere at 85° C. overnight. The reaction solution was cooled to room temperature, and separated by adding ethyl acetate and water. The organic layer was dried over anhydrous sodium sulfate and then the solvent was evaporated under reduced pressure. The residue was purified by thin-layer silica gel chromatography (developed with chloroform-methanol) to give the title compound (36 mg) as a colorless amorphous solid.

HRMS (ESI) [(M+H)$^+$] calculated: $C_{20}H_{21}N_4O_2$ 349.16645.

found: 349.16738.

Example 5

6-Quinolin-3-yl-1-(tetrahydro-2H-pyran-4-ylmethyl)-1,3-dihydro-2H-imidazo[4,5-b]pyridin-2-one

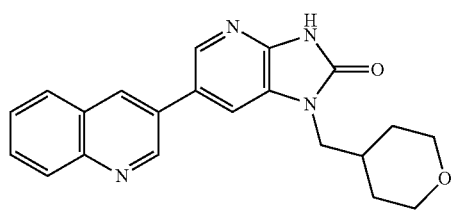

[Formula 25]

The title compound (34 mg) was obtained by the same procedure as in Step 3 of Example 1 using the compound obtained in Step 1 of Example 4 (46 mg).

HRMS (ESI) [(M+H)$^+$] calculated: $C_{21}H_{21}N_4O_2$ 361.16645.

found: 361.16530 $^1$H-NMR (DMSO-d$_6$) δ: 1.26-1.41 (2H, m), 1.47-1.57 (2H, m), 2.05-2.20 (1H, m), 3.19-3.30 (2H, m), 3.76-3.87 (4H, m), 7.63-7.71 (1H, m), 7.75-7.81 (1H, m), 8.03-8.12 (3H, m), 8.45 (1H, d, J=1.8 Hz), 8.69 (1H, d, J=2.3 Hz), 9.31 (1H, d, J=2.3 Hz), 11.75 (1H, brs).

Example 6

1-(Cyclohexylmethyl)-6-(1H-indol-5-yl)-1,3-dihydro-2H-imidazo[4,5-b]pyridin-2-one

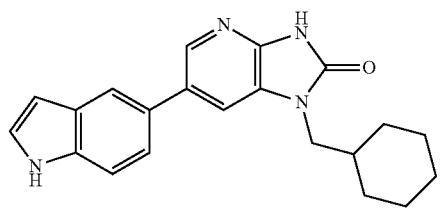

[Formula 26]

Step 1

5-Bromo-N$^3$-(cyclohexylmethyl)pyridine-2,3-diamine

The title compound (263 mg) was obtained by the same procedure as in Step 1 of Example 1 using 2,3-diamino-5-bromopyridine (1.0 g) and cyclohexanecarbaldehyde (591 mg).

MS (ESI) m/z: 284 (M+H)$^+$.

$^1$H-NMR (CDCl$_3$) δ: 0.95-1.08 (2H, m), 1.16-1.35 (4H, m), 1.67-1.88 (4H, m), 2.89 (2H, d, J=6.9 Hz), 4.11 (1H, brs), 5.51 (2H, brs), 7.13 (1H, d, J=1.8 Hz), 7.91 (1H, d, J=1.8 Hz).

Step 2

6-Bromo-1-(cyclohexylmethyl)-1,3-dihydro-2H-imidazo[4,5-b]pyridin-2-one

The title compound (116 mg) was obtained by the same procedure as in Step 2 of Example 1 using the compound obtained in the above Step 1 (260 mg).

$^1$H-NMR (CDCl$_3$) δ: 0.96-1.11 (2H, m), 1.14-1.35 (4H, m), 1.64-1.88 (4H, m), 3.65 (2H, d, J=7.3 Hz), 4.15 (1H, brs), 7.29 (1H, d, J=1.8 Hz), 8.07 (1H, d, J=1.8 Hz).

Step 3

1-(Cyclohexylmethyl)-6-(1H-indol-5-yl)-1,3-dihydro-2H-imidazo[4,5-b]pyridin-2-one The title compound (23 mg) was obtained by the same procedure as in Step 3 of Example 1 using the compound obtained in the above Step 2 (47 mg).

HRMS (ESI) [(M+H)$^+$] calculated: $C_{21}H_{23}N_4O$ 347.18719. found: 347.18864.

$^1$H-NMR (DMSO-d$_6$) δ: 0.96-1.25 (6H, m), 1.55-1.71 (4H, m), 1.77-1.90 (1H, m), 3.71 (2H, d, J=7.3 Hz), 6.47-6.51 (1H, m), 7.37-7.43 (2H, m), 7.48 (1H, d, J=8.3 Hz), 7.76 (1H, d, J=1.8 Hz), 7.84 (1H, d, J=1.8 Hz), 8.18 (1H, d, J=1.8 Hz), 11.16 (1H, brs), 11.50 (1H, brs).

Example 7

6-(1H-Indol-5-yl)-5-methyl-1-(tetrahydro-2H-pyran-4-ylmethyl)-1,3-dihydro-2H-imidazo[4,5-b]pyridin-2-one

[Formula 27]

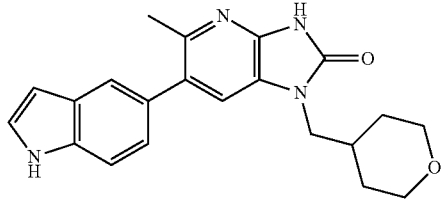

Step 1

5-Bromo-6-methyl-3-nitropyridin-2-amine

Nitric acid (2.9 ml) was added dropwise to a solution of 6-amino-3-bromo-2-methylpyridine (7.2 g) in concentrated sulfuric acid (39 ml) under ice-cooling over 30 minutes, and the mixture was stirred at the same temperature for one hour. After further stirring at room temperature for one hour, the reaction solution was poured into ice water. A 50% aqueous sodium hydroxide solution was added, and the resulting precipitate was collected by filtration, washed with distilled water and then dried under reduced pressure to give the title compound (9.0 g).
$^1$H-NMR (CDCl$_3$) δ: 2.57 (3H, s), 8.51 (1H, s).

Step 2

5-Bromo-6-methylpyridine-2,3-diamine

Distilled water (9 ml) and iron powder (21.6 g) were added to a solution of the compound obtained in the above Step 1 (8.9 mg) in ethanol (36 ml). Concentrated hydrochloric acid (0.4 ml) was further added and the mixture was heated under reflux for one hour. Iron powder (21.6 g) was further added and the mixture was heated under reflux for one hour. The reaction solution was cooled to room temperature, filtered through Celite 545 and washed with ethanol. The filtrate was concentrated under reduced pressure to give the title compound (5.5 g).
$^1$H-NMR (CDCl$_3$) δ: 2.42 (3H, s), 3.22 (2H, brs), 4.20 (2H, brs), 7.03 (1H, s).

Step 3

5-Bromo-6-methyl-N$^3$-(tetrahydro-2H-pyran-4-ylmethyl)pyridine-2,3-diamine

The title compound (619 mg) was obtained by the same procedure as in Step 1 of Example 1 using the compound obtained in the above Step 2 (1500 mg) and tetrahydro-2H-pyran-4-carbaldehyde (915 mg).
$^1$H-NMR (CDCl$_3$) δ: 1.33-1.47 (2H, m), 1.68-1.77 (2H, m), 1.79-1.92 (1H, m), 2.42 (3H, s), 2.95 (2H, d, J=6.9 Hz), 3.07 (1H, brs), 3.37-3.46 (2H, m), 3.97-4.05 (2H, m), 4.11 (2H, brs), 6.91 (1H, s).

Step 4

6-Bromo-5-methyl-1-(tetrahydro-2H-pyran-4-ylmethyl)-1,3-dihydro-2H-imidazo[4,5-b]pyridin-2-one The title compound (462 mg) was obtained by the same procedure as in Step 2 of Example 1 using the compound obtained in the above Step 3 (618 mg).
$^1$H-NMR (CDCl$_3$) δ: 1.37-1.50 (2H, m), 1.55-1.63 (2H, m), 2.03-2.18 (1H, m), 2.65 (3H, s), 3.31-3.41 (2H, m), 3.70 (2H, d, J=7.3 Hz), 4.02-3.94 (2H, m), 7.32 (1H, s).

Step 5

6-(1H-Indol-5-yl)-5-methyl-1-(tetrahydro-2H-pyran-4-ylmethyl)-1,3-dihydro-2H-imidazo[4,5-b]pyridin-2-one The title compound (33 mg) was obtained by the same procedure as in Step 3 of Example 1 using the compound obtained in the above Step 4 (60 mg).
HRMS (ESI) [(M+H)$^+$] calculated: C$_{21}$H$_{23}$N$_4$O$_2$ 363.18210.
found: 363.18238.
$^1$H-NMR (DMSO-d$_6$) δ: 1.18-1.33 (2H, m), 1.42-1.52 (2H, m), 1.94-2.08 (1H, m), 2.37 (3H, s), 3.15-3.26 (2H, m), 3.66-3.72 (2H, m), 3.76-3.84 (2H, m), 6.47 (1H, brs), 7.09 (1H, d, J=8.7 Hz), 7.37-7.41 (2H, m), 7.46 (1H, d, J=8.3 Hz), 7.51 (1H, s), 11.16 (1H, brs), 11.40 (1H, brs).

Example 8

6-(1H-Indol-5-yl)-7-methyl-1-(tetrahydro-2H-pyran-4-ylmethyl)-1,3-dihydro-2H-imidazo[4,5-b]pyridin-2-one

[Formula 28]

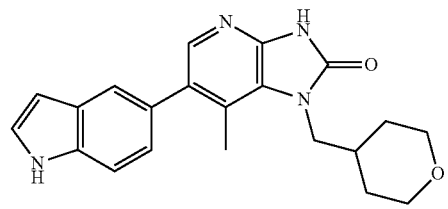

Step 1

5-Bromo-4-methyl-3-nitropyridin-2-amine

Nitric acid (0.7 ml) was added dropwise to a solution of 5-bromo-4-methylpyridine-2-amine (2.0 g) in concentrated sulfuric acid (8.7 ml) at 55° C. over 30 minutes, and the mixture was stirred at the same temperature for 3 hours. After further stirring at room temperature for 2 hours, the reaction solution was poured into ice water. A 50% aqueous sodium hydroxide solution was added, and the resulting precipitate was collected by filtration, washed with distilled water and then dried under reduced pressure to give the title compound (2.5 g).
MS (ESI) m/z: 268 (M+H)$^+$.
$^1$H-NMR (CDCl$_3$) δ: 2.54 (3H, s), 5.83 (2H, brs), 8.29 (1H, s).

Step 2

5-Bromo-4-methylpyridine-2,3-diamine

Distilled water (4 ml) and iron powder (3260 mg) were added to a solution of the compound obtained in the above Step 1 (1354 mg) in ethanol (20 ml). Concentrated hydrochloric acid (2.0 ml) was further added and the mixture was heated under reflux for one hour. The reaction solution was cooled to room temperature and then adjusted to pH 9 by adding a 1 N aqueous sodium hydroxide solution. The mixed solution was filtered through Celite 545 and washed with ethanol. The filtrate was concentrated under reduced pressure to give the title compound (934 mg).

$^1$H-NMR (CDCl$_3$) δ: 2.28 (3H, s), 3.39 (2H, brs), 4.10 (2H, brs), 7.77 (1H, s).

Step 3

5-Bromo-4-methyl-N$^3$-(tetrahydro-2H-pyran-4-ylmethyl)pyridine-2,3-diamine

The title compound (390 mg) was obtained by the same procedure as in Step 1 of Example 1 using the compound obtained in the above Step 2 (1410 mg) and tetrahydro-2H-pyran-4-carbaldehyde (860 mg).

$^1$H-NMR (CDCl$_3$) δ: 1.32-1.50 (2H, m), 1.71-1.81 (3H, m), 2.32 (3H, s), 2.73-2.79 (2H, m), 3.38-3.48 (2H, m), 3.98-4.06 (2H, m), 4.72 (2H, brs), 7.89 (1H, d, J=4.1 Hz).

Step 4

6-Bromo-7-methyl-1-(tetrahydro-2H-pyran-4-ylmethyl)-1,3-dihydro-2H-imidazo[4,5-b]pyridin-2-one The title compound (190 mg) was obtained by the same procedure as in Step 2 of Example 1 using the compound obtained in the above Step 3 (288 mg).

MS (ESI) m/z: 326 (M+H)$^+$.

$^1$H-NMR (CDCl$_3$) δ: 1.45-1.57 (4H, m), 1.89-2.04 (1H, m), 2.60 (3H, s), 3.29-3.39 (2H, m), 3.93-4.03 (4H, m), 8.15 (1H, s), 8.77 (1H, brs).

Step 5

6-(1H-Indol-5-yl)-7-methyl-1-(tetrahydro-2H-pyran-4-ylmethyl)-1,3-dihydro-2H-imidazo[4,5-b]pyridin-2-one The title compound (33 mg) was obtained by the same procedure as in Step 3 of Example 1 using the compound obtained in the above Step 4 (92 mg).

HRMS (ESI) [(M+H)$^+$] calculated: C$_{22}$H$_{23}$N$_4$O$_2$ 363.18210.

found: 363.18512.

$^1$H-NMR (DMSO-d$_6$) δ: 1.21-1.37 (2H, m), 1.45-1.54 (2H, m), 1.91-2.07 (1H, m), 2.39 (3H, s), 3.21-3.33 (2H, m), 3.78-3.92 (4H, m), 6.44-6.49 (1H, m), 7.04 (1H, dd, J=8.3, 1.4 Hz), 7.38-7.42 (1H, m), 7.43-7.49 (2H, m), 7.77 (1H, s), 11.19 (1H, brs), 11.53 (1H, brs).

Example 9

6-(1H-Indol-5-yl)-1-{[1-(methanesulfonyl)piperidin-4-yl]methyl}-1,3-dihydro-2H-imidazo[4,5-b]pyridin-2-one

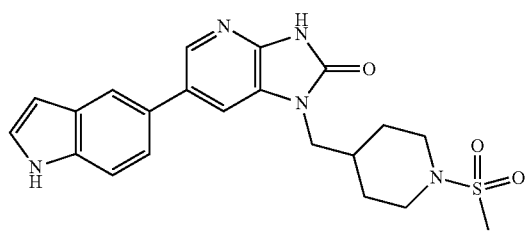

[Formula 29]

Step 1

1-(Methanesulfonyl)piperidine-4-carbaldehyde

[1-(Methanesulfonyl)piperidin-4-yl]methanol obtained by the method described in US 2002/895374 (1.00 g) was dissolved in dichloromethane (20 ml). Dess-Martin reagent (2.19 g) was added and the mixture was stirred at room temperature for one hour. An aqueous sodium thiosulfate solution and a saturated aqueous sodium bicarbonate solution were added to the reaction solution, followed by extraction with chloroform. The organic layer was dried over anhydrous sodium sulfate and then the solvent was evaporated under reduced pressure to give the title compound (1.04 g).

Step 2

5-Bromo-N$^3$-{[1-(methanesulfonyl)piperidin-4-yl]methyl}pyridine-2,3-diamine The title compound (92 mg) was obtained by the same procedure as in Step 1 of Example 2 using 2,3-diamino-5-bromopyridine (0.75 g) and the compound obtained in the above Step 1 (0.99 g).

MS (ESI) m/z: 363 (M+H)$^+$.

Step 3

6-Bromo-1-{[1-(methanesulfonyl)piperidin-4-yl]methyl}-1,3-dihydro-2H-imidazo[4,5-b]pyridin-2-one The title compound (59 mg) was obtained by the same procedure as in Step 2 of Example 1 using the compound obtained in the above Step 2 (92 mg).

MS (ESI) m/z: 389 (M+H)$^+$.

Step 4

6-(1H-Indol-5-yl)-1-{[1-(methanesulfonyl)piperidin-4-yl]methyl}-1,3-dihydro-2H-imidazo[4,5-b]pyridin-2-one The title compound (1.6 mg) was obtained by the same procedure as in Step 2 of Example 4 using the compound obtained in the above Step 3 (28 mg).

HRMS (ESI) [(M+H)+] calculated: C22H24N5O3S 426.15998.

found: 426.16272.

Example 10

6-Quinolin-6-yl-1-(tetrahydro-2H-pyran-4-ylmethyl)-1,3-dihydro-2H-imidazo[4,5-b]pyridin-2-one

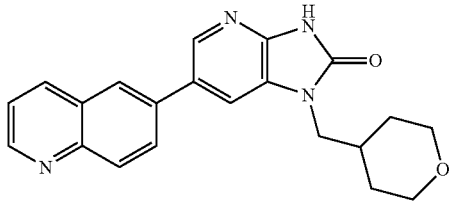

[Formula 30]

The title compound (54 mg) was obtained by the same procedure as in Step 3 of Example 1 using the compound obtained in Step 1 of Example 4 (60 mg) and 5-(4,4,5,5-tetramethyl-1,3,2-dioxaborolan-2-yl)quinoline (54 mg).

HRMS (ESI) [(M+H)+] calculated: C21H21N4O2 361.16645. found: 361.16722.

1H-NMR (DMSO-d6) δ: 1.22-1.40 (2H, m), 1.46-1.56 (2H, m), 2.03-2.18 (1H, m), 3.18-3.30 (2H, m), 3.75-3.86 (4H, m), 7.53-7.61 (1H, m), 8.01 (1H, d, J=1.8 Hz), 8.07-8.18 (2H, m), 8.31 (1H, d, J=1.8 Hz), 8.37-8.45 (2H, m), 8.87-8.93 (1H, m), 11.69 (1H, brs).

Example 11

6-Isoquinolin-4-yl-1-(tetrahydro-2H-pyran-4-ylmethyl)-1,3-dihydro-2H-imidazo[4,5-b]pyridin-2-one

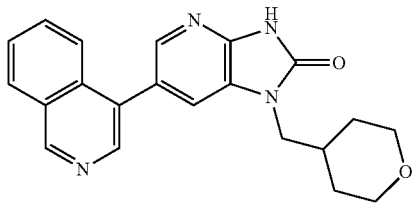

[Formula 31]

The title compound (40 mg) was obtained by the same procedure as in Step 3 of Example 1 using the compound obtained in Step 1 of Example 4 (60 mg) and isoquinolin-4-ylboric acid (37 mg).

HRMS (ESI) [(M+H)+] calculated: C21H21N4O2 361.16645.

found: 361.16727.

1H-NMR (DMSO-d6) δ: 1.19-1.34 (2H, m), 1.44-1.53 (2H, m), 1.95-2.12 (1H, m), 3.15-3.27 (2H, m), 3.70-3.85 (4H, m), 7.71-7.84 (3H, m), 7.86-7.92 (1H, m), 8.04 (1H, d, J=1.8 Hz), 8.23 (1H, d, J=8.3 Hz), 8.49 (1H, s), 9.36 (1H, s), 11.76 (1H, brs).

Example 12

6-Quinolin-4-yl-1-(tetrahydro-2H-pyran-4-ylmethyl)-1,3-dihydro-2H-imidazo[4,5-b]pyridin-2-one

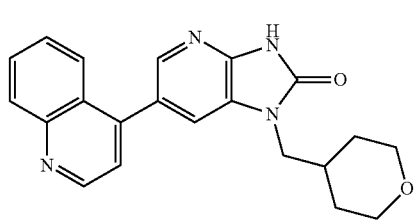

[Formula 32]

The title compound (6 mg) was obtained by the same procedure as in Step 3 of Example 1 using the compound obtained in Step 1 of Example 4 (60 mg) and quinolin-4-ylboric acid (37 mg).

HRMS (ESI) [(M+H)+] calculated: C21H21N4O2 361.16645.

found: 361.16471.

1H-NMR (DMSO-d6) δ: 1.21-1.36 (2H, m), 1.43-1.55 (2H, m), 1.95-2.12 (1H, m), 3.17-3.27 (2H, m), 3.72-3.87 (4H, m), 7.54 (1H, d, J=4.6 Hz), 7.60-7.66 (1H, m), 7.78-7.85 (2H, m), 7.94 (1H, d, J=8.3 Hz), 8.08 (1H, s), 8.13 (1H, d, J=8.7 Hz), 8.97 (1H, d, J=4.6 Hz), 11.80 (1H, brs).

Example 13

6-Quinolin-5-yl-1-(tetrahydro-2H-pyran-4-ylmethyl)-1,3-dihydro-2H-imidazo[4,5-b]pyridin-2-one

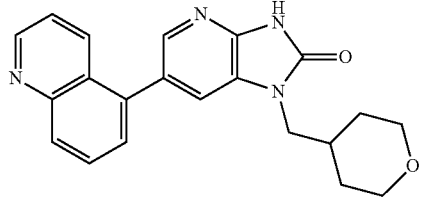

[Formula 33]

The title compound (45 mg) was obtained by the same procedure as in Step 3 of Example 1 using the compound obtained in Step 1 of Example 4 (60 mg) and quinolin-5-ylboric acid (37 mg).

HRMS (ESI) [(M+H)+] calculated: C21H21N4O2 361.16645.

found: 361.16582.

1H-NMR (DMSO-d6) δ: 1.20-1.35 (2H, m), 1.44-1.55 (2H, m), 1.97-2.11 (1H, m), 3.16-3.27 (2H, m), 3.70-3.86 (4H, m), 7.55 (1H, dd, J=8.7, 4.1 Hz), 7.60-7.64 (1H, m), 7.73 (1H, s), 7.82-7.89 (1H, m), 8.01 (1H, d, J=1.8 Hz), 8.09 (1H, d, J=8.3 Hz), 8.24 (1H, d, J=8.3 Hz), 8.95 (1H, dd, J=4.1, 1.4 Hz), 11.74 (1H, brs).

Example 14

6-(1H-Indazol-5-yl)-1-(tetrahydro-2H-pyran-4-ylmethyl)-1,3-dihydro-2H-imidazo[4,5-b]pyridin-2-one

[Formula 34]

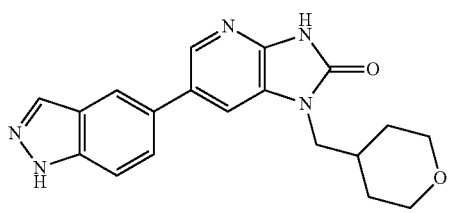

Step 1

5-(4,4,5,5-Tetramethyl-1,3,2-dioxaborolan-2-yl)-1H-indazole

5-Bromo-1H-indazole (1.00 g) was dissolved in N,N-dimethylformamide (20 ml), and bis(pinacolato)diboron (3.87 g), potassium acetate (2.49 g) and a [1,1'-bis(diphenylphosphino)ferrocene]palladium(II) chloride-dichloromethane complex (0.12 g) were added. The mixture was stirred with heating under nitrogen atmosphere at 100° C. overnight. The reaction solution was cooled to room temperature and then concentrated under reduced pressure. The residue was purified by silica gel column chromatography (developed with ethyl acetate-hexane) to give the title compound (1.99 g).

MS (ESI) m/z: 245 (M+H)$^+$.

Step 2

6-(1H-Indazol-5-yl)-1-(tetrahydro-2H-pyran-4-ylmethyl)-1,3-dihydro-2H-imidazo[4,5-b]pyridin-2-one The title compound (9 mg) was obtained by the same procedure as in Step 3 of Example 1 using the compound obtained in Step 1 of Example 4 (60 mg) and 5-(4,4,5,5-tetramethyl-1,3,2-dioxaborolan-2-yl)-1H-indazole obtained in the above Step 1 (49 mg).

HRMS (ESI) [(M+H)$^+$] calculated: $C_{19}H_{20}N_5O_2$ 350.16170.

found: 350.16170.

$^1$H-NMR (DMSO-d$_6$) δ: 1.21-1.39 (2H, m), 1.45-1.56 (2H, m), 2.02-2.17 (1H, m), 3.19-3.30 (2H, m), 3.73-3.88 (4H, m), 7.64 (1H, d, J=8.7 Hz), 7.70 (1H, dd, J=8.7, 1.4 Hz), 7.87 (1H, d, J=1.8 Hz), 8.06 (1H, s), 8.14 (1H, s), 8.23 (1H, d, J=1.8 Hz), 11.58 (1H, brs).

Example 15

6-(1H-Pyrrolo[2,3-b]pyridin-5-yl)-1-(tetrahydro-2H-pyran-4-ylmethyl)-1,3-dihydro-2H-imidazo[4,5-b]pyridin-2-one

[Formula 35]

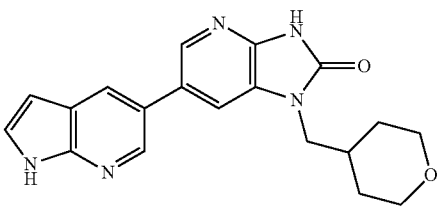

The title compound (45 mg) was obtained by the same procedure as in Step 2 of Example 4 using the compound obtained in Step 1 of Example 4 (75 mg) and 5-(4,4,5,5-tetramethyl-1,3,2-dioxaborolan-2-yl)-1H-pyrrolo[2,3-b]pyridine (59 mg).

HRMS (ESI) [(M+H)$^+$] calculated: $C_{19}H_{20}N_5O_2$ 350.16170.

found: 350.16275.

$^1$H-NMR (DMSO-d$_6$) δ: 1.25-1.38 (2H, m), 1.51 (2H, d, J=11.7 Hz), 2.10 (1H, brs), 3.24 (2H, t, J=11.7 Hz), 3.74-3.86 (4H, m), 6.49-6.53 (1H, m), 7.50-7.54 (1H, m), 7.91 (1H, d, J=2.0 Hz), 8.22-8.26 (2H, m), 8.55 (1H, d, J=2.0 Hz), 11.59 (1H, s), 11.74 (1H, s).

Example 16

6-(6-Methyl-1H-pyrrolo[2,3-b]pyridin-5-yl)-1-(tetrahydro-2H-pyran-4-ylmethyl)-1,3-dihydro-2H-imidazo[4,5-b]pyridin-2-one

[Formula 36]

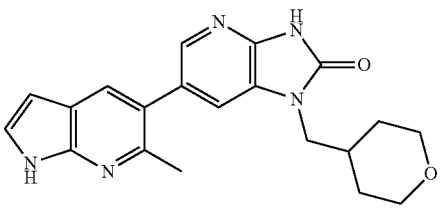

The title compound (44 mg) was obtained by the same procedure as in Step 3 of Example 1 using the compound obtained in Step 1 of Example 4 (110 mg) and tert-butyl 6-methyl-5-(4,4,5,5-tetramethyl-1,3,2-dioxaborolan-2-yl)-1H-pyrrolo[2,3-b]pyridine-1-carboxylate obtained by the method described in WO 2007/135398 (151 mg).

HRMS (ESI) [(M+H)$^+$] calculated: $C_{20}H_{22}N_5O_2$ 364.17735.

found: 364.17844.

$^1$H-NMR (DMSO-d$_6$) δ: 1.17-1.35 (2H, m), 1.44-1.54 (2H, m), 1.95-2.11 (1H, m), 2.48 (3H, s), 3.15-3.30 (2H, m), 3.70-3.86 (4H, m), 6.40-6.44 (1H, m), 7.39-7.44 (1H, m), 7.62-7.66 (2H, m), 7.79 (1H, s), 7.90 (1H, d, J=1.8 Hz), 11.61 (1H, brs), 11.54 (1H, brs).

Example 17

5-Methyl-6-(1H-pyrrolo[2,3-b]pyridin-5-yl)-1-(tetrahydro-2H-pyran-4-ylmethyl)-1,3-dihydro-2H-imidazo[4,5-b]pyridin-2-one

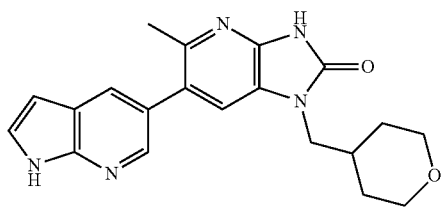

[Formula 37]

The title compound (47 mg) was obtained by the same procedure as in Step 3 of Example 1 using the compound obtained in Step 4 of Example 7 (80 mg) and 5-(4,4,5,5-tetramethyl-1,3,2-dioxaborolan-2-yl)-1H-pyrrolo[2,3-b]pyridine (66 mg).

HRMS (ESI) [(M+H)$^+$] calculated: $C_{20}H_{22}N_5O_2$ 364.17735.

found: 364.17731.

$^1$H-NMR (DMSO-d$_6$) δ: 1.19-1.33 (2H, m), 1.41-1.51 (2H, m), 1.95-2.10 (1H, m), 2.38 (3H, s), 3.16-3.33 (2H, m), 3.66-3.84 (4H, m), 6.47-6.52 (1H, m), 7.47 (1H, s), 7.51-7.55 (1H, m), 7.96 (1H, d, J=1.8 Hz), 8.21 (1H, d, J=1.8 Hz), 11.48 (1H, brs), 11.74 (1H, brs).

Example 18

7-Methyl-6-(1H-pyrrolo[2,3-b]pyridin-5-yl)-1-(tetrahydro-2H-pyran-4-ylmethyl)-1,3-dihydro-2H-imidazo[4,5-b]pyridin-2-one

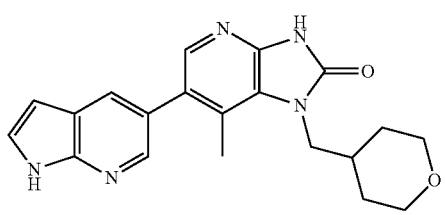

[Formula 38]

The title compound (64 mg) was obtained by the same procedure as in Step 3 of Example 1 using the compound obtained in Step 4 of Example 8 (88 mg) and 5-(4,4,5,5-tetramethyl-1,3,2-dioxaborolan-2-yl)-1H-pyrrolo[2,3-b]pyridine (72 mg).

HRMS (ESI) [(M+H)$^+$] calculated: $C_{20}H_{22}N_5O_2$ 364.17735.

found: 364.17698.

$^1$H-NMR (DMSO-d$_6$) δ: 1.22-1.37 (2H, m), 1.43-1.54 (2H, m), 1.92-2.07 (1H, m), 2.39 (3H, s), 3.26-3.43 (2H, m), 3.78-3.94 (4H, m), 6.47-6.52 (1H, m), 7.51-7.57 (1H, m), 7.80 (1H, s), 7.93 (1H, d, J=1.8 Hz), 8.17 (1H, d, J=1.8 Hz), 11.61 (1H, brs), 11.76 (1H, brs).

Example 19

6-(1H-Pyrrolo[2,3-b]pyridin-5-yl)-1-(tetrahydro-2H-pyran-4-yl)-1,3-dihydro-2H-imidazo[4,5-b]pyridin-2-one

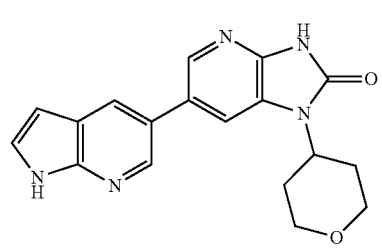

[Formula 39]

The title compound (46 mg) was obtained by the same procedure as in Step 3 of Example 1 using the compound obtained in Step 2 of Example 2 (61 mg) and 5-(4,4,5,5-tetramethyl-1,3,2-dioxaborolan-2-yl)-1H-pyrrolo[2,3-b]pyridine (55 mg).

HRMS (ESI) [(M+H)$^+$] calculated: $C_{18}H_{18}N_5O_2$ 336.14605.

found: 336.14456.

$^1$H-NMR (DMSO-d$_6$) δ: 1.66-1.75 (2H, m), 2.39-2.49 (2H, m), 3.42-3.53 (2H, m), 3.96-4.05 (2H, m), 4.44-4.57 (1H, m), 6.48-6.53 (1H, m), 7.50-7.55 (1H, m), 7.91 (1H, d, J=1.8 Hz), 8.23 (1H, d, J=1.8 Hz), 8.27 (1H, d, J=1.8 Hz), 8.55 (1H, d, J=1.8 Hz), 11.62 (1H, brs), 11.74 (1H, brs).

Example 20

6-(1H-Pyrrolo[2,3-b]pyridin-5-yl)-1-[2-(tetrahydro-2H-pyran-4-yl)ethyl]-1,3-dihydro-2H-imidazo[4,5-b]pyridin-2-one

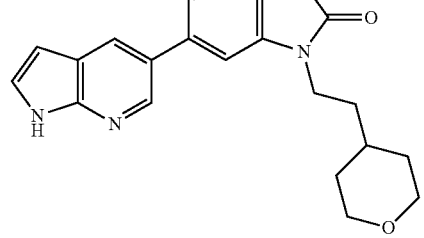

[Formula 40]

The title compound (36 mg) was obtained by the same procedure as in Step 3 of Example 1 using the compound obtained in Step 2 of Example 3 (60 mg) and 5-(4,4,5,5-tetramethyl-1,3,2-dioxaborolan-2-yl)-1H-pyrrolo[2,3-b]pyridine (49 mg).

HRMS (ESI) [(M+H)$^+$] calculated: $C_{20}H_{22}N_5O_2$ 364.17735.

found: 364.17712.

$^1$H-NMR (DMSO-d$_6$) δ: 1.12-1.27 (2H, m), 1.42-1.56 (1H, m), 1.58-1.71 (4H, m), 3.25-3.35 (1H, m), 3.76-3.84 (2H, m), 3.86-3.94 (2H, m), 6.48-6.52 (1H, m), 7.49-7.52 (1H, m), 7.81 (1H, d, J=2.3 Hz), 8.20-8.25 (2H, m), 8.52 (1H, d, J=2.3 Hz), 11.57 (1H, brs), 11.70 (1H, brs).

Example 21

1-(Cyclopropylmethyl)-6-(1H-pyrrolo[2,3-b]pyridin-5-yl)-1,3-dihydro-2H-imidazo[4,5-b]pyridin-2-one

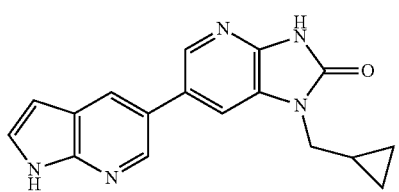

[Formula 41]

The title compound (51 mg) was obtained by the same procedure as in Step 3 of Example 1 using the compound obtained in Step 2 of Example 1 (60 mg) and 5-(4,4,5,5-tetramethyl-1,3,2-dioxaborolan-2-yl)-1H-pyrrolo[2,3-b]pyridine (60 mg).

HRMS (ESI) [(M+H)$^+$] calculated: $C_{17}H_{16}N_5O$ 306.13548. found: 306.13866.

$^1$H-NMR (DMSO-d$_6$) δ: 0.39-0.54 (4H, m), 1.23-1.36 (1H, m), 3.79 (2H, d, J=6.9 Hz), 6.50-6.55 (1H, m), 7.51-7.56 (1H, m), 7.93 (1H, d, J=1.8 Hz), 8.25-8.28 (2H, m), 8.56 (1H, d, J=1.8 Hz), 11.61 (1H, brs), 11.75 (1H, brs).

Example 22

1-(Tetrahydro-2H-pyran-4-ylmethyl)-1,3-dihydro-2H,3'H-6,6'-biimidazo[4,5-b]pyridin-2-one

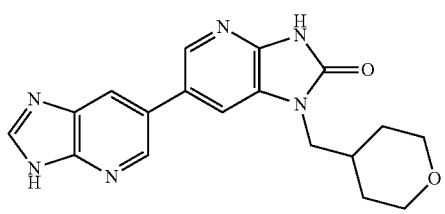

[Formula 42]

Bis(triphenylphosphine)palladium(II) dichloride (17 mg) and 6-(trimethylstannyl)-3H-imidazo[4,5-b]pyridine obtained by the method described in WO 2008/051493 (75 mg) were added to a solution of the compound obtained in Step 1 of Example 5 (75 mg) in N,N-dimethylformamide (2.5 ml), and the mixture was stirred at 110° C. for 2 hours. The reaction solvent was evaporated under reduced pressure. The resulting residue was purified by HPLC chromatography to give the title compound (6 mg).

HRMS (ESI) [(M+H)$^+$] calculated: $C_{18}H_{19}N_6O_2$ 351.15695.

found: 351.15798.

$^1$H-NMR (DMSO-d$_6$) δ: 1.21-1.36 (2H, m), 1.45-1.54 (2H, m), 3.17-3.27 (2H, m), 3.72-3.86 (4H, m), 6.56-6.61 (1H, m), 7.95 (1H, d, J=1.7 Hz), 8.27 (2H, d, J=1.7 Hz), 8.30 (1H, brs), 8.47 (1H, s), 8.69 (1H, d, J=2.3 Hz).

Example 23

6-(1H-Indol-2-yl)-1-(tetrahydro-2H-pyran-4-ylmethyl)-1,3-dihydro-2H-imidazo[4,5-b]pyridin-2-one

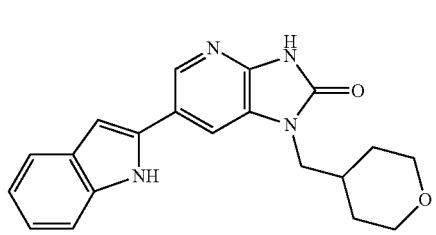

[Formula 43]

The title compound (23 mg) was obtained by the same procedure as in Step 3 of Example 1 using the compound obtained in Step 1 of Example 4 (60 mg) and [1-(tert-butoxycarbonyl)-1H-indol-2-yl]boric acid (55 mg).

HRMS (ESI) [(M+H)$^+$] calculated: $C_{20}H_{21}N_4O_2$ 349.16645.

found: 349.16844.

$^1$H-NMR (DMSO-d$_6$) δ: 1.26-1.38 (2H, m), 1.47-1.55 (2H, m), 2.03-2.15 (1H, m), 3.17-3.29 (2H, m), 3.73 (2H, d, J=7.4 Hz), 3.79-3.87 (2H, m), 6.94 (1H, d, J=1.7 Hz), 6.97-7.01 (1H, m), 7.05-7.11 (1H, m), 7.37-7.42 (1H, m), 7.51 (1H, d, J=7.4 Hz), 7.93 (1H, d, J=1.7 Hz), 8.44 (1H, d, J=1.7 Hz), 11.50 (1H, brs).

Example 24

6-(1H-Pyrrolo[2,3-b]pyridin-5-yl)-1-[1-(tetrahydro-2H-pyran-4-yl)ethyl]-1,3-dihydro-2H-imidazo[4,5-b]pyridin-2-one

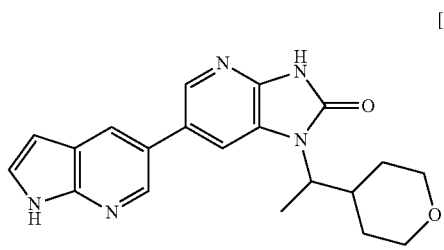

[Formula 44]

Step 1

5-Bromo-N$^3$-[1-(tetrahydro-2H-pyran-4-yl)ethyl]pyridine-2,3-diamine 2,3-Diamino-5-bromopyridine (1.07 g) and 1-(tetrahydro-2H-pyran-4-yl)ethanone (0.80 g) were dissolved in methanol (20 ml), and acetic acid (0.98 ml) was added. After stirring at room temperature for a while, sodium cyanoborohydride (1.08 g) was added and the mixture was stirred at room temperature for 20 hours. A saturated aqueous sodium bicarbonate solution was added to the reaction solution, followed by extraction with ethyl acetate. Then, the organic layer was dried over anhydrous sodium sulfate. The solvent was evaporated under reduced pressure. The resulting residue was purified by flash column chromatography (developed with ethyl acetate-hexane) to give the title compound (334 mg).
MS (ESI) m/z: 300 (M+H)+.

Step 2

6-Bromo-1-[1-(tetrahydro-2H-pyran-4-yl)ethyl]-1,3-dihydro-2H-imidazo[4,5-b]pyridin-2-one The title compound (345 mg) was obtained by the same procedure as in Step 2 of Example 1 using the compound obtained in the above Step 1 (344 mg).
MS (ESI) m/z: 326 (M+H)+.
$^1$H-NMR (CDCl$_3$) δ: 1.27-1.31 (1H, m), 1.52 (3H, d, J=7.1 Hz), 1.77-1.81 (1H, m), 2.16-2.19 (1H, m), 3.29-3.31 (1H, m), 3.40-3.43 (1H, m), 3.90-3.92 (1H, m), 4.04-4.06 (1H, m), 4.15-4.17 (1H, m), 7.39 (1H, d, J=2.0 Hz), 8.10 (1H, d, J=2.0 Hz), 9.35 (1H, s).

Step 3

6-(1H-Pyrrolo[2,3-b]pyridin-5-yl)-1-[1-(tetrahydro-2H-pyran-4-yl)ethyl]-1,3-dihydro-2H-imidazo[4,5-b]pyridin-2-one The title compound (33 mg) was obtained by the same procedure as in Step 3 of Example 1 using the compound obtained in the above Step 2 (60 mg) and 5-(4,4,5,5-tetramethyl-1,3,2-dioxaborolan-2-yl)-1H-pyrrolo[2,3-b]pyridine (49 mg).
HRMS (ESI) [(M+H)+] calculated: C$_{20}$H$_{22}$N$_5$O$_2$ 364.17735.
found: 364.17814.
$^1$H-NMR (DMSO-d$_6$) δ: 1.11-1.20 (2H, m), 1.24-1.37 (1H, m), 1.49 (3H, d, J=6.9 Hz), 1.72-1.82 (1H, m), 2.26-2.40 (1H, m), 3.09-3.21 (1H, m), 3.28-3.33 (1H, m), 3.71-3.79 (1H, m), 3.86-3.95 (1H, m), 4.11-4.22 (1H, m), 6.49-6.53 (1H, m), 7.50-7.54 (1H, m), 7.90 (1H, d, J=1.8 Hz), 8.24 (2H, dd, J=11.9, 1.8 Hz), 8.54 (1H, d, J=2.3 Hz), 11.58 (1H, brs), 11.73 (1H, brs).

Example 25

1-[(4-Methyltetrahydro-2H-pyran-4-yl)methyl]-6-(1H-pyrrolo[2,3-b]pyridin-5-yl)-1,3-dihydro-2H-imidazo[4,5-b]pyridin-2-one

[Formula 45]

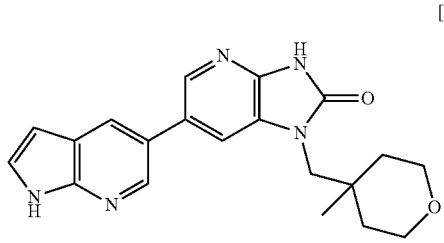

Step 1

4-Methyltetrahydro-2H-pyran-4-carbaldehyde (4-Methyltetrahydro-2H-pyran-4-yl)methanol obtained by the method described in EP 1431285 (1.02 g) was dis-solved in dichloromethane (20 ml). Dimethyl sulfoxide (5.01 ml), triethylamine (5.46 ml) and a sulfur trioxide-pyridine complex (3.74 g) were added and the mixture was stirred at room temperature for one hour. A saturated aqueous ammonium chloride solution was added to the reaction solution, followed by extraction with chloroform. The organic layer was washed with 1 N hydrochloric acid, a saturated aqueous sodium bicarbonate solution and brine and dried over anhydrous sodium sulfate. The solvent was evaporated under reduced pressure to give the title compound (647 mg).

Step 2

5-Bromo-N$^3$-[(4-methyltetrahydro-2H-pyran-4-yl)methyl]pyridine-2,3-diamine

The title compound (574 mg) was obtained by the same procedure as in Step 1 of Example 24 using 2,3-diamino-5-bromopyridine (0.85 g) and the compound obtained in the above Step 1 (0.64 g).
MS (ESI) m/z: 300 (M+H)+.

Step 3

6-Bromo-1-[(4-methyltetrahydro-2H-pyran-4-yl)methyl]-1,3-dihydro-2H-imidazo[4,5-b]pyridin-2-one The title compound (636 mg) was obtained by the same procedure as in Step 2 of Example 1 using the compound obtained in the above Step 2 (574 mg).
MS (ESI) m/z: 326 (M+H)+.
$^1$H-NMR (CDCl$_3$) δ: 1.14 (3H, s), 1.36-1.39 (2H, m), 1.68-1.75 (2H, m), 3.61-3.65 (2H, m), 3.83-3.86 (2H, m), 4.04 (2H, s), 7.32 (1H, d, J=2.0 Hz), 8.10 (1H, d, J=2.0 Hz), 9.35 (1H, s).

Step 4

1-[(4-Methyltetrahydro-2H-pyran-4-yl)methyl]-6-(1H-pyrrolo[2,3-b]pyridin-5-yl)-1,3-dihydro-2H-imidazo[4,5-b]pyridin-2-one The title compound (36 mg) was obtained by the same procedure as in Step 3 of Example 1 using the compound obtained in the above Step 3 (60 mg) and 5-(4,4,5,5-tetramethyl-1,3,2-dioxaborolan-2-yl)-1H-pyrrolo[2,3-b]pyridine (49 mg).
HRMS (ESI) [(M+H)+] calculated: C$_{20}$H$_{22}$N$_5$O$_2$ 364.17735.
found: 364.17621.
$^1$H-NMR (DMSO-d$_6$) δ: 1.07 (3H, s), 1.26-1.35 (2H, m), 1.57-1.70 (2H, m), 3.46-3.56 (2H, m), 3.66-3.80 (4H, m), 6.48-6.54 (1H, m), 7.50-7.55 (1H, m), 7.88 (1H, s), 8.20-8.26 (2H, m), 8.53 (1H, s), 11.62 (1H, brs), 11.74 (1H, brs).

Example 26

1-{[1-(Methanesulfonyl)piperidin-4-yl]methyl}-6-(1H-pyrrolo[2,3-b]pyridin-5-yl)-1,3-dihydro-2H-imidazo[4,5-b]pyridin-2-one

[Formula 46]

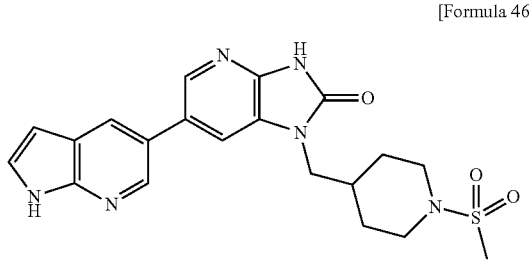 [SMILES: CS(=O)(=O)N1CCC(Cn2c(=O)[nH]c3ncc(-c4cnc5[nH]ccc5c4)cc32)CC1]

The title compound (4.3 mg) was obtained by the same procedure as in Step 2 of Example 4 using the compound obtained in Step 3 of Example 9 (28 mg) and 5-(4,4,5,5-tetramethyl-1,3,2-dioxaborolan-2-yl)-1H-pyrrolo[2,3-b]pyridine (21 mg).

HRMS (ESI) [(M+H)$^+$] calculated: $C_{22}H_{23}N_6O_3S$ 427.15523.

found: 427.15738.

Example 27

6-(4-Fluoro-1H-indol-5-yl)-1-(tetrahydro-2H-pyran-4-ylmethyl)-1,3-dihydro-2H-imidazo[4,5-b]pyridin-2-one

[Formula 47]

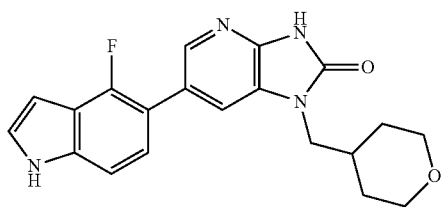

Step 1

4-Fluoro-5-(4,4,5,5-tetramethyl-1,3,2-dioxaborolan-2-yl)-1H-indole

5-Bromo-4-fluoro-1H-indole obtained by the method described in Eur. J. Org. Chem. 2956-2969, 2006 (793 mg) was dissolved in N,N-dimethylformamide (30 ml), and bis(pinacolato)diboron (1.88 g), potassium acetate (1.82 g) and a [1,1'-bis(diphenylphosphino)ferrocene]palladium(II) chloride-dichloromethane complex (151 mg) were added. The mixture was stirred with heating under nitrogen atmosphere at 100° C. overnight. The reaction solution was cooled to room temperature and then concentrated under reduced pressure. The residue was purified by silica gel column chromatography (developed with ethyl acetate-hexane). The resulting colorless oil was slurry washed with hexane to give the title compound (481 mg) as a colorless solid.

MS (EI) m/z: 261M$^+$.

$^1$H-NMR (CDCl$_3$) δ: 1.38 (12H, s), 6.65-6.68 (1H, m), 7.14-7.17 (1H, m), 7.18 (1H, s), 7.51 (1H, dd, J=8.3, 5.5 Hz), 8.27 (1H, brs).

Step 2

6-(4-Fluoro-1H-indol-5-yl)-1-(tetrahydro-2H-pyran-4-ylmethyl)-1,3-dihydro-2H-imidazo[4,5-b]pyridin-2-one The title compound (35 mg) was obtained as a colorless amorphous solid by the same procedure as in Step 2 of Example 4 using the compound obtained in Step 1 of Example 4 (50 mg) and the compound obtained in the above Step 1 (46 mg).

HRMS (ESI) [(M+H)$^+$] calculated: $C_{20}H_{20}FN_4O_2$ 367.15703.

found: 367.15767.

$^1$H-NMR (DMSO-d$_6$) δ: 1.24-1.35 (2H, m), 1.50 (2H, d, J=11.7 Hz), 2.00-2.11 (1H, m), 3.23 (2H, t, J=11.7 Hz), 3.75 (2H, d, J=6.9 Hz), 3.82 (2H, dd, J=11.7, 2.8 Hz), 6.54-6.56 (1H, m), 7.22 (1H, t, J=8.0 Hz), 7.34 (1H, d, J=8.0 Hz), 7.44 (1H, t, J=2.8 Hz), 7.71 (1H, s), 8.07 (1H, t, J=1.6 Hz), 11.48 (1H, s), 11.61 (1H, s).

Example 28

6-(6-Fluoro-1H-indol-5-yl)-1-(tetrahydro-2H-pyran-4-ylmethyl)-1,3-dihydro-2H-imidazo[4,5-b]pyridin-2-one

[Formula 48]

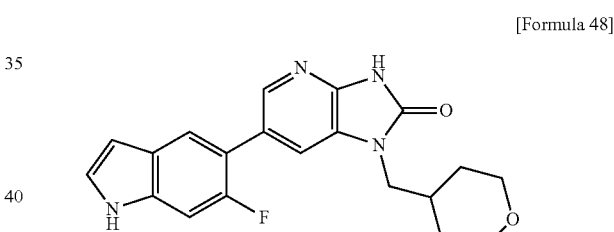

Step 1

6-Fluoro-5-(4,4,5,5-tetramethyl-1,3,2-dioxaborolan-2-yl)-1H-indole

The title compound (867 mg) was obtained as a colorless solid by the same procedure as in Step 1 of Example 27 using 5-bromo-6-fluoro-1H-indole obtained by the method described in Eur. J. Org. Chem. 2956-2969, 2006 (1.22 g).

MS (EI) m/z: 261M$^+$.

$^1$H-NMR (CDCl$_3$) δ: 1.38 (12H, s), 6.53 (1H, s), 7.04 (1H, d, J=10.1 Hz), 7.17 (1H, t, J=2.6 Hz), 8.04 (1H, d, J=5.5 Hz), 8.17 (1H, brs).

MS (ESI) m/z: 262 (M+H)$^+$.

Step 2

6-(6-Fluoro-1H-indol-5-yl)-1-(tetrahydro-2H-pyran-4-ylmethyl)-1,3-dihydro-2H-imidazo[4,5-b]pyridin-2-one The title compound (35 mg) was obtained as a colorless amorphous solid by the same procedure as in Step 2 of Example 4 using the compound obtained in Step 1 of Example 4 (50 mg) and 6-fluoro-5-(4,4,5,5-tetramethyl-1,3,2-dioxaborolan-2-yl)-1H-indole obtained in the above Step 1 (46 mg).

HRMS (ESI) [(M+H)$^+$] calculated: $C_{20}H_{20}FN_4O_2$ 367.15703.

found: 367.15850.

$^1$H-NMR (DMSO-d$_6$) δ: 1.22-1.35 (2H, m), 1.49 (2H, d, J=11.5 Hz), 2.04 (1H, brs), 3.21 (2H, t, J=11.5 Hz), 3.74 (2H, d, J=7.3 Hz), 3.81 (2H, d, J=11.5 Hz), 6.48 (1H, s), 7.29 (1H, d, J=11.5 Hz), 7.38 (1H, t, J=2.8 Hz), 7.65 (1H, d, J=8.3 Hz), 7.68 (1H, s), 8.04 (1H, s), 11.21 (1H, s), 11.60 (1H, s).

Example 29

6-(7-Fluoro-1H-indol-5-yl)-1-(tetrahydro-2H-pyran-4-ylmethyl)-1,3-dihydro-2H-imidazo[4,5-b]pyridin-2-one

[Formula 49]

![Structure of Example 29 compound]

Step 1

7-Fluoro-5-(4,4,5,5-tetramethyl-1,3,2-dioxaborolan-2-yl)-1H-indole

The title compound (189 mg) was obtained as a white solid by the same procedure as in Step 1 of Example 27 using 5-bromo-7-fluoro-1H-indole obtained by the method described in Eur. J. Org. Chem. 2956-2969, 2006 (0.596 g).

MS (EI) m/z: 261M$^+$.

$^1$H-NMR (CDCl$_3$) δ: 1.38 (12H, s), 6.53 (1H, s), 7.04 (1H, d, J=10.1 Hz), 7.17 (1H, t, J=2.6 Hz), 8.04 (1H, d, J=5.5 Hz), 8.17 (1H, brs).

Step 2

6-(7-Fluoro-1H-indol-5-yl)-1-(tetrahydro-2H-pyran-4-ylmethyl)-1,3-dihydro-2H-imidazo[4,5-b]pyridin-2-one The title compound (41 mg) was obtained as a colorless amorphous solid by the same procedure as in Step 2 of Example 4 using the compound obtained in Step 1 of Example 4 (50 mg) and the compound obtained in the above Step 1 (48 mg).

HRMS (ESI) [(M+H)$^+$] calculated: $C_{20}H_{20}FN_4O_2$ 367.15703.

found: 367.15743.

$^1$H-NMR (DMSO-d$_6$) δ: 1.26-1.39 (2H, m), 1.51 (2H, d, J=11.7 Hz), 2.10 (1H, brs), 3.24 (2H, t, J=11.7 Hz), 3.78 (2H, d, J=7.2 Hz), 3.83 (2H, d, J=11.7 Hz), 6.59 (1H, s), 7.32 (1H, d, J=12.7 Hz), 7.46 (1H, t, J=2.4 Hz), 7.72 (1H, s), 7.87 (1H, d, J=1.5 Hz), 8.24 (1H, d, J=1.5 Hz), 11.56 (1H, s), 11.67 (1H, s).

Example 30

6-(2-Oxo-2,3-dihydro-1H-pyrrolo[2,3-b]pyridin-5-yl)-1-(tetrahydro-2H-pyran-4-ylmethyl)-1,3-dihydro-2H-imidazo[4,5-b]pyridin-2-one

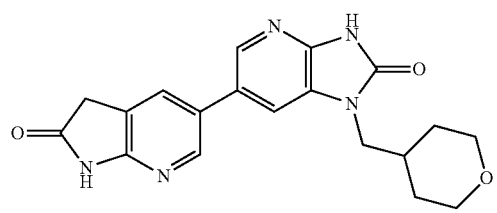

[Formula 50]

Step 1

5-(4,4,5,5-Tetramethyl-1,3,2-dioxaborolan-2-yl)-1,3-dihydro-2H-pyrrolo[2,3-b]pyridin-2-one The title compound (39 mg) was obtained as a colorless solid by the same procedure as in Step 1 of Example 27 using 5-bromo-1,3-dihydro-2H-pyrrolo[2,3-b]pyridin-2-one obtained by the method described in J. Am. Chem. Soc. 14426, 2006 (300 mg).

MS (EI) m/z: 260M$^+$.

$^1$H-NMR (CDCl$_3$) δ: 1.35 (12H, s), 3.55 (2H, s), 7.84 (1H, d, J=1.4 Hz), 8.53-8.55 (1H, m), 8.67 (1H, brs).

Step 2

6-(2-Oxo-2,3-dihydro-1H-pyrrolo[2,3-b]pyridin-5-yl)-1-(tetrahydro-2H-pyran-4-ylmethyl)-1,3-dihydro-2H-imidazo[4,5-b]pyridin-2-one The title compound (22 mg) was obtained as a colorless amorphous solid by the same procedure as in Step 2 of Example 4 using the compound obtained in Step 1 of Example 4 (38 mg) and the compound obtained in the above Step 1 (33 mg).

HRMS (ESI) [(M+H)$^+$] calculated: $C_{19}H_{20}N_5O_3$ 366.15661.

found: 366.15792.

$^1$H-NMR (DMSO-d$_6$) δ: 1.25-1.38 (2H, m), 1.49 (2H, d, J=11.7 Hz), 2.02-2.14 (1H, m), 3.23 (2H, t, J=11.7 Hz), 3.63 (2H, s), 3.75 (2H, d, J=7.2 Hz), 3.82 (2H, d, J=11.7 Hz), 7.84 (1H, d, J=1.7 Hz), 7.92 (1H, s), 8.19 (1H, d, J=1.7 Hz), 8.40 (1H, d, J=1.7 Hz), 11.09 (1H, s), 11.62 (1H, s).

Example 31

1-(5,6-Dihydro-2H-pyran-3-ylmethyl)-6-(1H-pyrrolo[2,3-b]pyridin-5-yl)-1,3-dihydro-2H-imidazo[4,5-b]pyridin-2-one

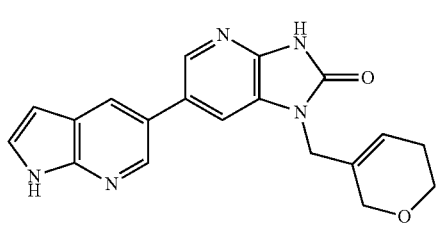

[Formula 51]

Step 1

5-Bromo-$N^3$-(5,6-dihydro-2H-pyran-3-ylmethyl)pyridine-2,3-diamine

The title compound (434 mg) was obtained by the same procedure as in Step 1 of Example 24 using 2,3-diamino-5-bromopyridine (0.85 g) and 5,6-dihydro-2H-pyran-3-carbaldehyde obtained by the method described in U.S. Pat. No. 4,532,337 (0.58 g).
MS (ESI) m/z: 284 (M+H)$^+$.

Step 2

6-Bromo-1-(5,6-dihydro-2H-pyran-3-ylmethyl)-1,3-dihydro-2H-imidazo[4,5-b]pyridin-2-one The title compound (290 mg) was obtained by the same procedure as in Step 2 of Example 1 using the compound obtained in the above Step 1 (434 mg).
MS (ESI) m/z: 310 (M+H)$^+$.
$^1$H-NMR (CDCl$_3$) δ: 2.18-2.19 (2H, m), 3.75 (2H, t, J=5.5 Hz), 4.06-4.06 (2H, m), 4.34-4.37 (2H, m), 5.84-5.85 (1H, m), 7.30 (1H, d, J=2.0 Hz), 8.11 (1H, d, J=2.0 Hz), 9.12-9.15 (1H, m).

Step 3

1-(5,6-Dihydro-2H-pyran-3-ylmethyl)-6-(1H-pyrrolo[2,3-b]pyridin-5-yl)-1,3-dihydro-2H-imidazo[4,5-b]pyridin-2-one The title compound (33 mg) was obtained by the same procedure as in Step 3 of Example 1 using the compound obtained in the above Step 2 (60 mg) and 5-(4,4,5,5-tetramethyl-1,3,2-dioxaborolan-2-yl)-1H-pyrrolo[2,3-b]pyridine (47 mg).
HRMS (ESI) [(M+H)$^+$] calculated: $C_{19}H_{18}N_5O_2$ 348.14605.
found: 348.14610.
$^1$H-NMR (DMSO-d$_6$) δ: 1.97-2.08 (2H, m), 3.58-3.64 (2H, m), 4.00 (2H, d, J=1.8 Hz), 4.40 (2H, s), 5.77 (1H, s), 6.48-6.53 (1H, m), 7.50-7.55 (1H, m), 7.77 (1H, d, J=1.8 Hz), 8.20-8.27 (2H, m), 8.49-8.53 (1H, m), 11.66 (1H, brs), 11.74 (1H, brs).

Example 32

6-(1H-Pyrrolo[2,3-b]pyridin-5-yl)-1-(tetrahydro-2H-pyran-3-ylmethyl)-1,3-dihydro-2H-imidazo[4,5-b]pyridin-2-one

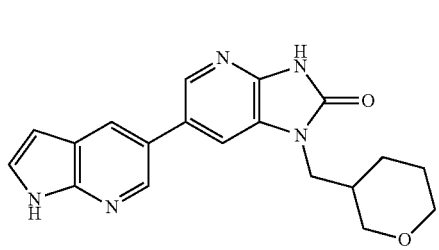

[Formula 52]

Step 1

5-Bromo-$N^3$-(tetrahydro-2H-pyran-3-ylmethyl)pyridine-2,3-diamine

The title compound (743 mg) was obtained by the same procedure as in Step 1 of Example 27 using 2,3-diamino-5-bromopyridine (2.00 g) and tetrahydro-2H-pyran-3-carbaldehyde obtained by the method described in U.S. Pat. No. 5,071,863 (1.34 g).
MS (ESI) m/z: 286 (M+H)$^+$.

Step 2

6-Bromo-1-(tetrahydro-2H-pyran-4-ylmethyl)-1,3-dihydro-2H-imidazo[4,5-b]pyridin-2-one The title compound (741 mg) was obtained by the same procedure as in Step 2 of Example 1 using the compound obtained in the above Step 1 (743 mg).
MS (ESI) m/z: 312 (M+H)$^+$.
$^1$H-NMR (CDCl$_3$) δ: 1.42-1.43 (1H, m), 1.58-1.61 (1H, m), 1.71-1.72 (1H, m), 1.80-1.83 (1H, m), 2.16-2.17 (1H, m), 3.33 (1H, dd, J=11.5, 8.3 Hz), 3.50-3.56 (1H, m), 3.77-3.80 (4H, m), 7.12 (1H, d, J=0.7 Hz), 7.34 (1H, d, J=2.0 Hz), 8.11 (1H, d, J=2.0 Hz).

Step 3

6-(1H-Pyrrolo[2,3-b]pyridin-5-yl)-1-(tetrahydro-2H-pyran-3-ylmethyl)-1,3-dihydro-2H-imidazo[4,5-b]pyridin-2-one The title compound (33 mg) was obtained by the same procedure as in Step 3 of Example 1 using the compound obtained in the above Step 2 (60 mg) and 5-(4,4,5,5-tetramethyl-1,3,2-dioxaborolan-2-yl)-1H-pyrrolo[2,3-b]pyridine (47 mg).
HRMS (ESI) [(M+H)$^+$] calculated: $C_{19}H_{20}N_5O_2$ 350.16330.
found: 350.16330.
$^1$H-NMR (DMSO-d$_6$) 1.24-1.37 (1H, m), 1.38-1.51 (1H, m), 1.58-1.67 (1H, m), 1.68-1.78 (1H, m), 2.04-2.17 (1H, m), 3.19-3.28 (2H, m), 3.65-3.81 (4H, m), 6.48-6.54 (1H, m), 7.50-7.55 (1H, m), 7.88 (1H, d, J=1.8 Hz), 8.24 (2H, d, J=1.8 Hz), 8.54 (1H, d, J=2.3 Hz), 11.60 (1H, brs), 11.74 (1H, brs).

Example 33

6-(7-Fluoro-1H-indol-5-yl)-1-(2-morpholin-4-yl-ethyl)-1,3-dihydro-2H-imidazo[4,5-b]pyridin-2-one

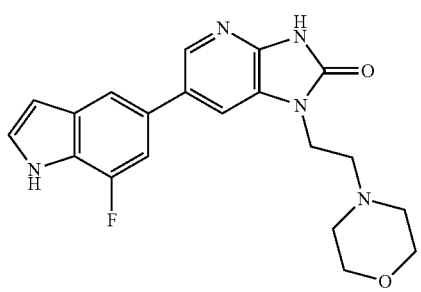

[Formula 53]

Step 1

N-(2-Amino-5-bromopyridin-3-yl)-2-morpholin-4-ylacetamide 2,3-Diamino-5-bromopyridine (2.00 g) and morpholin-4-ylacetic acid hydrochloride obtained by the method described in U.S. Pat. No. 6,352,993 (1.34 g) were dissolved in acetonitrile (15 ml). 1-Ethyl-3-(3-dimethylaminopropyl)carbodiimide hydrochloride (1.22 g), 1-hydroxybenzotriazole (0.98 g) and N-methylmorpholine (1.29 ml) were added and the mixture was stirred at room temperature overnight. The reaction solution was diluted with chloroform and washed with brine. The organic layer was dried over anhydrous sodium sulfate and then the solvent was evaporated under reduced pressure. The resulting solid was washed with diethyl ether to give the title compound (1.40 g) as a pale yellow solid.

MS (ESI) m/z: 315 (M+H)$^+$.

$^1$H-NMR (DMSO-d$_6$) δ: 2.52 (4H, t, J=4.6 Hz), 3.62 (4H, t, J=4.6 Hz), 6.01 (2H, s), 7.84 (1H, d, J=2.2 Hz), 7.87 (1H, d, J=2.2 Hz), 9.20 (1H, s).

Step 2

5-Bromo-N$^3$-(2-morpholin-4-ylethyl)pyridine-2,3-diamine

Lithium aluminum hydride (120 mg) was suspended in tetrahydrofuran (10 m). A solution of the compound obtained in the above Step 1 (500 mg) in tetrahydrofuran (3 ml) was slowly added dropwise with stirring at 0° C., followed by stirring for one hour. Lithium aluminum hydride (120 mg) was added, and the mixture was stirred at room temperature for 2.5 hours and then heated under reflux for one hour. The reaction solution was left to cool to room temperature and then water (0.3 ml), and a 15% aqueous sodium hydroxide solution (0.3 ml) and water (0.6 ml) were added. The precipitated insoluble matter was filtered off through Celite. The filtrate was concentrated to give the title compound (397 mg).

MS (ESI) m/z: 301 (M+H)$^+$.

Step 3

6-Bromo-1-(2-morpholin-4-ylethyl)-1,3-dihydro-2H-imidazo[4,5-b]pyridin-2-one

The title compound (79 mg) was obtained by the same procedure as in Step 2 of Example 1 using the compound obtained in the above Step 2 (397 mg).

MS (ESI) m/z: 327 (M+H)$^+$.

Step 4

6-(7-Fluoro-1H-indol-5-yl)-1-(2-morpholin-4-yl-ethyl)-1,3-dihydro-2H-imidazo[4,5-b]pyridin-2-one The title compound (2.8 mg) was obtained as a colorless amorphous solid by the same procedure as in Step 2 of Example 4 using the compound obtained in the above Step 3 (79 mg) and the compound obtained in Step 1 of Example 29 (54 mg).

HRMS (ESI) [(M+H)$^+$] calculated: C$_{20}$H$_{21}$FN$_5$O$_2$ 382.16793.

found: 382.16871.

Example 34

6-(4-Chloro-1H-pyrrolo[2,3-b]pyridin-5-yl)-1-(tetrahydro-2H-pyran-4-ylmethyl)-1,3-dihydro-2H-imidazo[4,5-b]pyridin-2-one

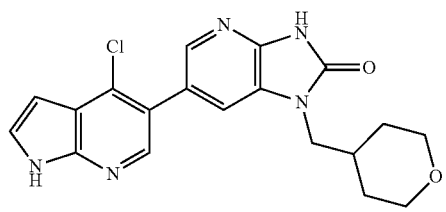

[Formula 54]

The title compound (26 mg) was obtained by the same procedure as in Step 3 of Example 1 using the compound obtained in Step 1 of Example 4 (60 mg) and [4-chloro-1-(triisopropylsilyl)-1H-pyrrolo[2,3-b]pyridin-5-yl]boric acid obtained by the method described in Tetrahedron Lett. (45), 2317-2319, 2004 (75 mg).

HRMS (ESI) [(M+H)$^+$] calculated: C$_{19}$H$_{19}$ClN$_5$O$_2$ C$_{19}$H$_{19}$ClN$_5$O$_2$.

found: 384.12663.

$^1$H-NMR (DMSO-d$_6$) δ: 1.20-1.37 (2H, m), 1.46-1.54 (2H, m), 1.99-2.15 (1H, m), 3.19-3.28 (2H, m), 3.70-3.87 (4H, m), 6.55-6.59 (1H, m), 7.64-7.68 (1H, m), 7.72 (1H, d, J=1.7 Hz), 8.01 (1H, d, J=1.7 Hz), 8.26-8.26 (1H, m), 11.69 (1H, brs), 12.13 (1H, brs).

Example 35

6-(3-Chloro-1H-pyrrolo[2,3-b]pyridin-5-yl)-1-(tetrahydro-2H-pyran-4-ylmethyl)-1,3-dihydro-2H-imidazo[4,5-b]pyridin-2-one

[Formula 55]

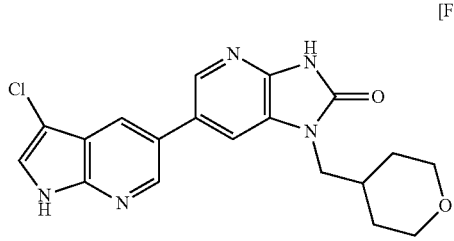

Step 1 tert-Butyl 5-bromo-3-chloro-1H-pyrrolo[2,3-b]pyridine-1-carboxylate

5-Bromo-3-chloro-1H-pyrrolo[2,3-b]pyridine (235 mg) was dissolved in dichloromethane (5 ml). Di-tert-butyl dicarbonate (248 mg) and N,N-dimethylaminopyridine (1.2 mg) were added and the mixture was stirred at room temperature overnight. The reaction solution was concentrated under reduced pressure. The residue was purified by silica gel column chromatography (developed with ethyl acetate-hexane) to give the title compound (297 mg).

MS (ESI) m/z: 331 (M+H)$^+$.
$^1$H-NMR (CDCl$_3$) δ: 1.67 (9H, s), 7.65 (1H, s), 8.05 (1H, d, J=2.2 Hz), 8.58 (1H, d, J=2.2 Hz).

Step 2

6-Bromo-3-cyclohex-1-en-1-yl-1,3-dihydro-2H-imidazo[4,5-b]pyridin-2-one 2,3-Diamino-5-bromopyridine (50 g) and 2-cyclohexanonecarboxylic acid ethyl ester (63.5 ml) were heated under reflux in xylene (2000 ml) for 64 hours. The reaction solution was cooled to room temperature and the precipitated crystals were collected by filtration. The resulting crude crystals were recrystallized from toluene to give the title compound (30 g).

MS (ESI) m/z: 294 (M+H)$^+$.
$^1$H-NMR (DMSO-d$_6$) δ: 1.61-1.64 (2H, m), 1.72-1.75 (2H, m), 2.19-2.21 (2H, m), 2.31-2.32 (2H, m), 5.89-5.90 (1H, m), 7.50 (1H, d, J=2.0 Hz), 8.02 (1H, d, J=2.0 Hz), 11.34 (1H, s).

Step 3

6-Bromo-3-cyclohex-1-en-1-yl-1-(tetrahydro-2H-pyran-4-ylmethyl)-1,3-dihydro-2H-imidazo[4,5-b]pyridin-2-one The compound obtained in the above Step 2 (1 g), tetrahydro-2H-pyran-4-ylmethanol (0.43 g) and triphenylphosphine (1.1 g) were dissolved in tetrahydrofuran (30 ml). Diisopropyl azodicarboxylate (0.74 ml) was added dropwise in a nitrogen atmosphere and then the mixture was stirred at room temperature for 30 minutes. The reaction solution was concentrated under reduced pressure. The residue was purified by silica gel column chromatography (developed with ethyl acetate-hexane) to give the title compound (0.89 g).

MS (ESI) m/z: 392 (M+H)$^+$.
$^1$H-NMR (CDCl$_3$) δ: 1.44-1.49 (2H, m), 1.61-1.62 (2H, m), 1.73-1.77 (2H, m), 1.85-1.88 (2H, m), 2.10-2.12 (1H, m), 2.30-2.32 (2H, m), 2.39-2.44 (2H, m), 3.35-3.38 (2H, m), 3.73 (2H, d, J=7.3 Hz), 3.97-4.00 (2H, m), 6.00-6.02 (1H, m), 7.28 (1H, d, J=2.0 Hz), 8.09 (1H, d, J=2.0 Hz).

Step 4

3-Cyclohex-1-en-1-yl-1-(tetrahydro-2H-pyran-4-ylmethyl)-6-(4,4,5,5-tetramethyl-1,3,2-dioxaboran-2-yl)-1,3-dihydro-2H-imidazo[4,5-b]pyridin-2-one Bis(pinacolato)diboron (925 mg), potassium acetate (715 mg) and a [1,1'-bis(diphenylphosphino)ferrocene]palladium(II) chloride-dichloromethane complex (93 mg) were added to a solution of the compound obtained in the above Step 3 (893 mg) in N,N-dimethylformamide (20 ml), and the mixture was heated with stirring under nitrogen atmosphere at 80° C. for 6.5 hours. The reaction solution was cooled to room temperature, diluted with ethyl acetate and washed with brine. The organic layer was dried and then concentrated under reduced pressure. The residue was purified by silica gel column chromatography (developed with ethyl acetate-hexane) to give the title compound (723 mg).

MS (ESI) m/z: 440 (M+H)$^+$.
$^1$H-NMR (CDCl$_3$) δ: 1.36 (12H, s), 1.45-1.48 (2H, m), 1.58-1.61 (2H, m), 1.75-1.77 (2H, m), 1.84-1.89 (2H, m), 2.12-2.14 (1H, m), 2.31-2.32 (2H, m), 2.43-2.43 (2H, m), 3.33-3.39 (2H, m), 3.77 (2H, d, J=7.3 Hz), 3.96-3.99 (2H, m), 6.00-6.02 (1H, m), 7.48 (1H, d, J=1.2 Hz), 8.45 (1H, d, J=1.2 Hz).

Step 5

6-(3-Chloro-1H-pyrrolo[2,3-b]pyridin-5-yl)-3-cyclohex-1-en-1-yl-1-(tetrahydro-2H-pyran-4-ylmethyl)-1,3-dihydro-2H-imidazo[4,5-b]pyridin-2-one The title compound (60 mg) was obtained by the same procedure as in Step 3 of Example 1 using the compound obtained in the above Step 4 (120 mg) and the compound obtained in the above Step 1 (95 mg).

MS (ESI) m/z: 464 (M+H)$^+$.
$^1$H-NMR (CDCl$_3$) δ: 1.45-1.56 (2H, m), 1.62-1.69 (2H, m), 1.75-1.81 (2H, m), 1.87-1.92 (2H, m), 2.13-2.24 (1H, m), 2.31-2.38 (2H, m), 2.46-2.53 (2H, m), 3.33-3.41 (2H, m), 3.84 (2H, d, J=7.4 Hz), 3.95-4.02 (2H, m), 6.06-6.10 (1H, m), 7.37 (1H, d, J=1.7 Hz), 8.07 (1H, d, J=1.7 Hz), 8.29 (1H, d, J=2.3 Hz), 8.54 (1H, d, J=2.3 Hz), 8.94 (1H, brs).

Step 6

6-(3-Chloro-1H-pyrrolo[2,3-b]pyridin-5-yl)-1-(tetrahydro-2H-pyran-4-ylmethyl)-1,3-dihydro-2H-imidazo[4,5-b]pyridin-2-one Distilled water (1.5 ml) was added to a solution of the compound obtained in the above Step 5 (58 mg) in ethanol (5 ml), and concentrated sulfuric acid (1.5 ml) was added under ice-cooling. The reaction solution was stirred at 70° C. for 89 hours. After cooling to room temperature, the reaction solution was poured into a saturated aqueous sodium bicarbonate solution and the unwanted material was filtered off. The resulting filtrate was separated by adding ethyl acetate and distilled water. The resulting organic layer was washed with brine and dried over anhydrous sodium sulfate. The solvent was evaporated under reduced pressure. The resulting residue was solidified from a dichloromethane-hexane mixed solvent and suspended by adding a small amount of ethyl acetate, followed by stirring overnight. The solid component was collected from the mixed solution by filtration and dried to give the title compound (17 mg).

MS (ESI) m/z: 384 (M+H)$^+$.

HRMS (ESI) [(M+H)$^+$] calculated: $C_{19}H_{19}ClN_5O_2$ 384.12273.

found: 384.12365.

$^1$H-NMR (DMSO-d$_6$) δ: 1.27-1.38 (2H, m), 1.46-1.55 (2H, m), 2.03-2.17 (1H, m), 3.19-3.28 (2H, m), 3.79 (2H, d, J=7.4 Hz), 3.80-3.86 (2H, m), 7.74 (1H, d, J=2.9 Hz), 7.97 (1H, d, J=1.7 Hz), 8.18 (1H, d, J=1.7 Hz), 8.28 (1H, d, J=1.7 Hz), 8.65 (1H, d, J=2.3 Hz), 11.63 (1H, brs), 12.09 (1H, brs).

Example 36

6-(4-Methyl-1H-pyrrolo[2,3-b]pyridin-5-yl)-1-(tetrahydro-2H-pyran-4-ylmethyl)-1,3-dihydro-2H-imidazo[4,5-b]pyridin-2-one

[Formula 56]

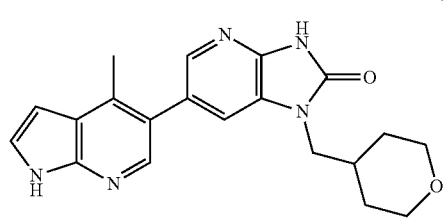

Step 1

5-Bromo-3-iodo-4-methylpyridin-2-amine

5-Bromo-4-methylpyridine-2-amine (3.1 g) was dissolved in acetic acid (20 ml). N-Iodosuccinimide (3.8 g) and trifluoroacetic acid (0.2 ml) were added and the mixture was stirred at room temperature for 2.5 hours. The reaction solution was poured into ice water and neutralized with 28% aqueous ammonia. Then, the precipitated solid was collected by filtration, washed with water and dried to give the title compound (4.9 g).

MS (ESI) m/z: 313 (M+H)$^+$.

$^1$H-NMR (DMSO-d$_6$) δ: 2.59 (3H, s), 5.01 (1H, brs), 8.02 (1H, s).

Step 2

5-Bromo-4-methyl-3-[(trimethylsilyl)ethynyl]methylpyridin-2-amine

The compound obtained in the above Step 1 (3.0 g) was dissolved in tetrahydrofuran (12 ml), and triethylamine (60 ml) and copper iodide (0.04 g) were added. The atmosphere was replaced with nitrogen. Trimethylsilylacetylene (1.1 g) and bis(triphenylphosphine)palladium(II) dichloride (0.1 g) were further added and the mixture was stirred at room temperature overnight. The reaction solution was partitioned between ethyl acetate and water, and the organic layer was washed with brine. The organic layer was dried and then concentrated under reduced pressure. The residue was purified by silica gel column chromatography (developed with ethyl acetate-hexane) to give the title compound (2.5 g).

MS (ESI) m/z: 283 (M+H)$^+$.

$^1$H-NMR (CDCl$_3$) δ: 0.28 (9H, s), 2.44 (3H, s), 4.99 (1H, brs), 8.04 (1H, s).

Step 3

5-Bromo-4-methyl-1H-pyrrolo[2,3-b]pyridine

A solution of the compound obtained in the above Step 2 (14.0 g) in N-methylpyrrolidone (200 ml) was slowly added dropwise to a solution of potassium tert-butoxide (11.6 g) in N-methylpyrrolidone (300 ml) at 80° C., and then the mixture was stirred at 80° C. for 30 minutes. The reaction solution was cooled to room temperature, diluted with ethyl acetate and washed with water. The organic layer was dried and then concentrated under reduced pressure. The precipitated solid was collected by filtration with diethyl ether-hexane to give the title compound (8.6 g).

MS (ESI) m/z: 211 (M+H)$^+$.

$^1$H-NMR (CDCl$_3$) δ: 2.62 (3H, s), 6.50-6.54 (1H, m), 7.29-7.32 (1H, m), 8.35 (1H, s) 9.36 (1H, brs).

Step 4 tert-Butyl 5-bromo-4-methyl-1H-pyrrolo[2,3-b]pyridine-1-carboxylate

The title compound (339 mg) was obtained by the same procedure as in Step 1 of Example 35 using the compound obtained in the above Step 3 (276 mg).

MS (ESI) m/z: 311 (M+H)$^+$.

$^1$H-NMR (CDCl$_3$) δ: 1.67 (9H, s), 2.58 (3H, s), 6.53 (1H, d, J=4.0 Hz), 7.61 (1H, d, J=4.0 Hz), 8.52 (1H, s).

Step 5

3-Cyclohex-1-en-1-yl-6-(4-methyl-1H-pyrrolo[2,3-b]pyridin-5-yl)-1-(tetrahydro-2H-pyran-4-ylmethyl)-1,3-dihydro-2H-imidazo[4,5-b]pyridin-2-one The title compound (136 mg) was obtained by the same procedure as in Step 3 of Example 1 using the compound obtained in Step 4 of Example 35 (179 mg) and the compound obtained in the above Step 4 (126 mg).

MS (ESI) m/z: 444 (M+H)$^+$.

Step 6

6-(4-Methyl-1H-pyrrolo[2,3-b]pyridin-5-yl)-1-(tetrahydro-2H-pyran-4-ylmethyl)-1,3-dihydro-2H-imidazo[4,5-b]pyridin-2-one The title compound (54 mg) was obtained by the same procedure as in Step 6 of Example 35 using the compound obtained in the above Step 5 (136 mg).

MS (ESI) m/z: 364 (M+H)$^+$.

HRMS (ESI) [(M+H)$^+$] calculated: $C_{20}H_{22}N_5O_2$ 364.17735.

found: 364.17525.

$^1$H-NMR (DMSO-d$_6$) δ: 1.27-1.32 (2H, m), 1.50 (2H, d, J=11.5 Hz), 2.03-2.05 (1H, m), 2.47 (3H, s), 3.21-3.24 (2H, m), 3.70-3.75 (2H, m), 3.79-3.84 (2H, m), 6.56-6.58 (1H, m), 7.47-7.49 (1H, m), 7.63 (1H, s), 7.91 (1H, d, J=1.7 Hz), 8.10 (1H, s), 11.62 (1H, brs), 11.66 (1H, brs).

Example 37

6-(3-Methyl-1H-pyrrolo[2,3-b]pyridin-5-yl)-1-(tetrahydro-2H-pyran-4ylmethyl)-1,3-dihydro-2H-imidazo[4,5-b]pyridin-2-one

[Formula 57]

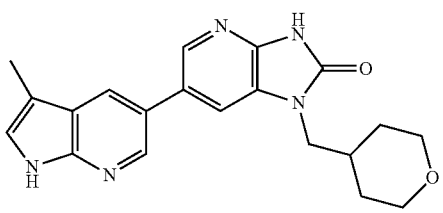

Step 1

5-[3-Cyclohex-1-en-1-yl-2-oxo-1-(tetrahydro-2H-pyran-4-ylmethyl)-2,3-dihydro-2H-imidazo[4,5-b]pyridin-6-yl]-1H-pyrrolo[2,3-b]pyridine-3-carbaldehyde The title compound (173 mg) was obtained by the same procedure as in Step 3 of Example 1 using the compound obtained in Step 4 of Example 35 (296 mg) and 5-bromo-1H-pyrrolo[2,3-b]pyridine-3-carbaldehyde obtained by the method described in WO 2004/101565 (159 mg).

MS (ESI) m/z: 458 (M+H)$^+$.

$^1$H-NMR (CDCl$_3$) δ: 1.26-1.41 (2H, m), 1.48-1.57 (2H, m), 1.62-1.71 (2H, m), 1.73-1.82 (2H, m), 2.05-2.18 (1H, m), 2.20-2.28 (2H, m), 2.36-2.44 (2H, m), 3.19-3.29 (2H, m), 3.79-3.88 (4H, m), 5.94-6.00 (1H, m), 7.77-7.83 (1H, m), 8.04 (1H, d, J=2.3 Hz), 8.29 (1H, d, J=2.3 Hz), 8.55 (1H, s), 8.63 (1H, d, J=2.3 Hz), 8.69 (1H, d, J=2.3 Hz), 9.97 (1H, s).

Step 2

3-Cyclohex-1-en-1-yl-6-(3-methyl-1H-pyrrolo[2,3-b]pyridin-5-yl)-1-(tetrahydro-2H-pyran-4-ylmethyl)-1,3-dihydro-2H-imidazo[4,5-b]pyridin-2-one The compound obtained in the above Step 1 (120 mg) was dissolved in methanol (4 ml). Dimethylamine hydrochloride (43 mg) and sodium acetate (34 mg) were added and the mixture was stirred at room temperature for 1.5 hours. Sodium cyanoborohydride (46 mg) was further added and the mixture was stirred at room temperature overnight. The reaction solution was diluted with ethyl acetate and washed with brine. The organic layer was dried and then concentrated under reduced pressure. The residue was purified by silica gel column chromatography (developed with methanol-chloroform) to give the title compound (50 mg).

MS (ESI) m/z: 444 (M+H)$^+$.

$^1$H-NMR (CDCl$_3$) δ: 1.46-1.56 (2H, m), 1.65 (2H, d, J=13.2 Hz), 1.75-1.80 (2H, m), 1.88-1.93 (2H, m), 2.15-2.22 (1H, m), 2.33-2.36 (2H, m), 2.39 (3H, d, J=1.1 Hz), 2.49-2.52 (2H, m), 3.35-3.39 (2H, m), 3.85 (2H, d, J=6.9 Hz), 3.97-4.01 (2H, m), 6.08-6.09 (1H, m), 7.17-7.18 (1H, m), 7.38 (1H, d, J=1.7 Hz), 8.00 (1H, d, J=2.3 Hz), 8.30 (1H, d, J=2.3 Hz), 8.47 (1H, d, J=2.3 Hz), 9.36 (1H, s).

Step 3

6-(3-Methyl-1H-pyrrolo[2,3-b]pyridin-5-yl)-1-(tetrahydro-2H-pyran-4ylmethyl)-1,3-dihydro-2H-imidazo[4,5-b]pyridin-2-one The title compound (26 mg) was obtained by the same procedure as in Step 6 of Example 35 using the compound obtained in the above Step 2 (50 mg).

MS (ESI) m/z: 364 (M+H)$^+$.

HRMS (ESI) [M+H]$^+$ calculated: C$_{20}$H$_{22}$N$_5$O$_2$ 364.17735. found: 364.17567. $^1$H-NMR (DMSO-d$_6$) δ: 1.27-1.35 (2H, m), 1.47-1.51 (2H, m), 2.07-2.11 (1H, m), 2.31 (3H, s), 3.23 (2H, t, J=10.9 Hz), 3.77 (2H, d, J=7.4 Hz), 3.79-3.83 (2H, m), 7.27 (1H, s), 7.90 (1H, d, J=1.7 Hz), 8.17 (1H, d, J=1.7 Hz), 8.24 (1H, d, J=1.7 Hz), 8.49-8.51 (1H, m), 11.37 (1H, s), 11.58 (1H, s).

Example 38

1-(1,4-Dioxan-2-ylmethyl)-6-(1H-pyrrolo[2,3-b]pyridin-5-yl)-1,3-dihydro-2H-imidazo[4,5-b]pyridin-2-one

[Formula 58]

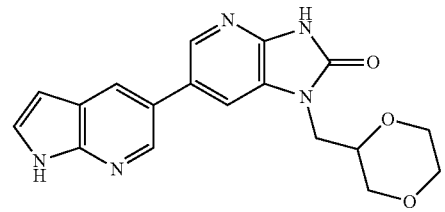

Step 1

6-Bromo-3-cyclohex-1-en-1-yl-1-(1,4-dioxan-2-ylmethyl)-1,3-dihydro-2H-imidazo[4,5-b]pyridin-2-one The title compound (312 mg) was obtained by the same method as in Step 3 of Example 35 using the compound obtained in Step 2 of Example 35 (280 mg) and 1,4-dioxan-2-ylmethanol obtained by the method described in Bioorg. Med. Chem. 15, 2667-2679 (2007) (135 mg).

MS (APCI) m/z: 394 [M+H]$^+$ $^1$H-NMR (CDCl$_3$) δ: 1.73-1.76 (2H, m), 1.84-1.88 (2H, m), 2.30-2.31 (2H, m), 2.41-2.43 (2H, m), 3.35-3.93 (9H, m), 6.02 (1H, m), 7.49 (1H, d, J=2.3 Hz), 8.09 (1H, d, J=2.3 Hz).

Step 2

3-Cyclohex-1-en-1-yl-1-(1,4-dioxan-2-ylmethyl)-6-(1H-pyrrolo[2,3-b]pyridin-5-yl)-1,3-dihydro-2H-imidazo[4,5-b]pyridin-2-one The title compound (47 mg) was obtained by the same procedure as in Step 3 of Example 1 using the compound obtained in the above Step 1 (122 mg) and 5-(4,4,5,5-tetramethyl-1,3,2-dioxaborolan-2-yl)-1H-pyrrolo[2,3-b]pyridine (83 mg).

MS (APCI) m/z: 432 [M+H]$^+$.

Step 3

1-(1,4-Dioxan-2-ylmethyl)-6-(1H-pyrrolo[2,3-b]pyridin-5-yl)-1,3-dihydro-2H-imidazo[4,5-b]pyridin-2-one The title compound (32 mg) was obtained by the same procedure as in Step 6 of Example 35 using the compound obtained in the above Step 2 (47 mg).

HRMS (ESI) [M+H]$^+$ calculated: $C_{18}H_{17}N_5O_3$ 352.14096. found: 352.14017.

$^1$H-NMR (DMSO-$d_6$) δ: 3.29-4.01 (9H, m), 6.51-6.52 (1H, m), 7.52-7.54 (1H, m), 7.84-7.85 (1H, m), 8.22-8.25 (2H, m), 8.53 (1H, d, J=2.3 Hz), 11.62 (1H, s), 11.74 (1H, s).

Example 39

1-[(2R)-1,4-Dioxan-2-ylmethyl]-6-(1H-pyrrolo[2,3-b]pyridin-5-yl)-1,3-dihydro-2H-imidazo[4,5-b]pyridin-2-one

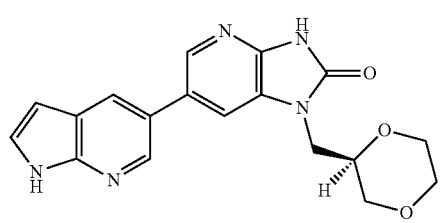

[Formula 59]

Step 1

6-Bromo-3-cyclohex-1-en-1-yl-1-[(2R)-1,4-dioxan-2-ylmethyl]-1,3-dihydro-2H-imidazo[4,5-b]pyridin-2-one The title compound (602 mg) was obtained by the same method as in Step 3 of Example 35 using the compound obtained in Step 2 of Example 35 (300 mg) and (2R)-1,4-dioxan-2-ylmethanol obtained by the method described in Bioorg. Med. Chem. 15, 2667-2679 (2007) (169 mg).

MS (ESI) m/z: 394 (M+H)$^+$.

$^1$H-NMR (CDCl$_3$) δ: 1.73-1.76 (2H, m), 1.84-1.88 (2H, m), 2.30-2.31 (2H, m), 2.41-2.43 (2H, m), 3.37 (1H, m), 3.56-3.60 (1H, m), 3.66-3.73 (2H, m), 3.78-3.83 (2H, m), 3.86-3.94 (3H, m), 6.00-6.03 (1H, m), 7.49 (1H, d, J=2.3 Hz), 8.09 (1H, d, J=2.3 Hz).

Step 2

3-Cyclohex-1-en-1-yl-1-[(2R)-1,4-dioxan-2-ylmethyl]-6-(1H-pyrrolo[2,3-b]pyridin-5-yl)-1,3-dihydro-2H-imidazo[4,5-b]pyridin-2-one The title compound (91 mg) was obtained by the same procedure as in Step 3 of Example 1 using the compound obtained in the above Step 1 (180 mg) and 5-(4,4,5,5-tetramethyl-1,3,2-dioxaborolan-2-yl)-1H-pyrrolo[2,3-b]pyridine (69 mg).

MS (ESI) m/z: 432 (M+H)$^+$.

$^1$H-NMR (CDCl$_3$) δ: 1.75-1.80 (2H, m), 1.88-1.93 (2H, m), 2.32-2.36 (2H, m), 2.49-2.52 (2H, m), 3.41-3.45 (1H, m), 3.57-3.60 (1H, m), 3.68-3.74 (2H, m), 3.77-3.80 (1H, m), 3.90-4.02 (4H, m), 6.08-6.09 (1H, m), 6.60 (1H, dd, J=3.4, 1.7 Hz), 7.41 (1H, dd, J=3.4, 2.3 Hz), 7.58 (1H, d, J=1.7 Hz), 8.09 (1H, d, J=1.7 Hz), 8.30 (1H, d, J=2.3 Hz), 8.50 (1H, d, J=1.7 Hz), 9.63 (1H, brs).

Step 3

1-[(2R)-1,4-Dioxan-2-ylmethyl]-6-(1H-pyrrolo[2,3-b]pyridin-5-yl)-1,3-dihydro-2H-imidazo[4,5-b]pyridin-2-one The title compound (31 mg) was obtained by the same procedure as in Step 6 of Example 35 using the compound obtained in the above Step 2 (91 mg).

MS (ESI) m/z: 352 (M+H)$^+$.

HRMS (ESI) [M+H]$^+$ calculated: $C_{18}H_{18}N_5O_3$ 352.14096. found: 352.13790.

$^1$H-NMR (DMSO-$d_6$) δ: 3.29-4.01 (9H, m), 6.51-6.52 (1H, m), 7.52-7.54 (1H, m), 7.84-7.85 (1H, m), 8.22-8.25 (2H, m), 8.53 (1H, d, J=2.3 Hz), 11.62 (1H, s), 11.74 (1H, s).

Example 40

1-[(2S)-1,4-Dioxan-2-ylmethyl]-6-(1H-pyrrolo[2,3-b]pyridin-5-yl)-1,3-dihydro-2H-imidazo[4,5-b]pyridin-2-one

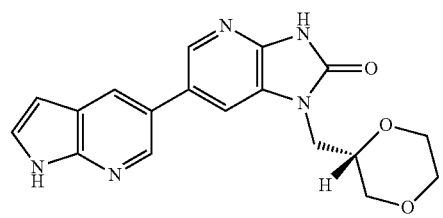

[Formula 60]

Step 1

6-Bromo-3-cyclohex-1-en-1-yl-1-[(2S)-1,4-dioxan-2-ylmethyl]-1,3-dihydro-2H-imidazo[4,5-b]pyridin-2-one The title compound (593 mg) was obtained by the same method as in Step 3 of Example 35 using the compound obtained in Step 2 of Example 35 (300 mg) and (2S)-1,4-dioxan-2-ylmethanol obtained by the method described in Bioorg. Med. Chem. 15, 2667-2679 (2007) (169 mg).

MS (ESI) m/z: 394 (M+H)$^+$.

$^1$H-NMR (CDCl$_3$) δ: 1.73-1.76 (2H, m), 1.84-1.88 (2H, m), 2.30-2.31 (2H, m), 2.41-2.43 (2H, m), 3.37 (1H, m), 3.56-3.60 (1H, m), 3.66-3.73 (2H, m), 3.78-3.83 (2H, m), 3.86-3.94 (3H, m), 6.00-6.03 (1H, m), 7.49 (1H, d, J=2.3 Hz), 8.09 (1H, d, J=2.3 Hz).

Step 2

3-Cyclohex-1-en-1-yl-1-[(2S)-1,4-dioxan-2-ylmethyl]-6-(1H-pyrrolo[2,3-b]pyridin-5-yl)-1,3-dihydro-2H-imidazo[4,5-b]pyridin-2-one The title compound (89 mg) was obtained by the same procedure as in Step 3 of Example 1 using the compound obtained in the above Step 1 (180 mg) and 5-(4,4,5,5-tetramethyl-1,3,2-dioxaborolan-2-yl)-1H-pyrrolo[2,3-b]pyridine (69 mg).

MS (ESI) m/z: 432 (M+H)+.

Step 3

1-[(2S)-1,4-Dioxan-2-ylmethyl]-6-(1H-pyrrolo[2,3-b]pyridin-5-yl)-1,3-dihydro-2H-imidazo[4,5-b]pyridin-2-one The title compound (32 mg) was obtained by the same procedure as in Step 6 of Example 35 using the compound obtained in the above Step 2 (89 mg).

MS (ESI) m/z: 352 (M+H)+.
HRMS (ESI) [M+H]+ calculated: $C_{18}H_{18}N_5O_3$ 352.14096. found: 352.14104.
1H-NMR (DMSO-d6) δ: 3.29-4.01 (9H, m), 6.51-6.52 (1H, m), 7.52-7.54 (1H, m), 7.84-7.85 (1H, m), 8.22-8.25 (2H, m), 8.53 (1H, d, J=2.3 Hz), 11.62 (1H, s), 11.74 (1H, s).

Example 41

6-(3-Chloro-1H-pyrrolo[2,3-b]pyridin-5-yl)-1-[(2S)-1,4-dioxan-2-ylmethyl]-1,3-dihydro-imidazo[4,5-b]pyridin-2-one

[Formula 61]

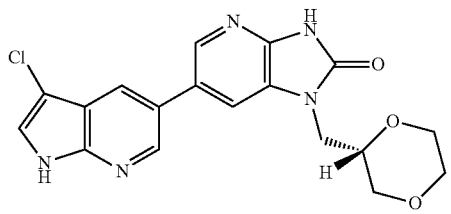

Step 1

3-Cyclohex-1-en-1-yl-1-[(2S)-1,4-dioxan-2-ylmethyl]-6-(4,4,5,5-tetramethyl-1,3,2-dioxaboran-2-yl)-1,3-dihydro-2H-imidazo[4,5-b]pyridin-2-one The title compound (240 mg) was obtained by the same procedure as in Step 4 of Example 35 using the compound obtained in Step 1 of Example 40 (353 mg).

MS (ESI) m/z: 442 (M+H)+.
1H-NMR (CDCl3) δ: 1.36 (12H, s), 1.74-1.76 (2H, m), 1.86-1.89 (2H, m), 2.31-2.32 (2H, m), 2.43-2.45 (2H, m), 3.43 (1H, dd, J=11.5, 9.6 Hz), 3.62 (1H, dd, J=11.5, 2.7 Hz), 3.68-3.70 (2H, m), 3.78-3.87 (2H, m), 3.89-3.90 (2H, m), 3.95-3.97 (1H, m), 6.01-6.03 (1H, m), 7.61 (1H, d, J=1.2 Hz), 8.45 (1H, d, J=1.2 Hz).

Step 2

6-(3-Chloro-1H-pyrrolo[2,3-b]pyridin-5-yl)-3-cyclohex-1-en-1-yl-1-[(2S)-1,4-dioxan-2-ylmethyl]-1,3-dihydro-2H-imidazo[4,5-b]pyridin-2-one The title compound (122 mg) was obtained by the same procedure as in Step 3 of Example 1 using the compound obtained in the above Step 1 (240 mg) and the compound obtained in Step 1 of Example 35 (198 mg).

MS (ESI) m/z: 466 (M+H)+.

Step 3

6-(3-Chloro-1H-pyrrolo[2,3-b]pyridin-5-yl)-1-[(2S)-1,4-dioxan-2-ylmethyl]-1,3-dihydro-imidazo[4,5-b]pyridin-2-one The title compound (54 mg) was obtained by the same procedure as in Step 6 of Example 35 using the compound obtained in the above Step 2 (122 mg).

MS (ESI) m/z: 386 (M+H)+.
HRMS (ESI) [M+H]+ calculated: $C_{18}H_{17}ClN_5O_3$ 386.10199.
found: 386.10009.
1H-NMR (DMSO-d6) δ: 3.33-4.02 (9H, m), 7.74-7.76 (1H, m), 7.91 (1H, d, J=1.7 Hz), 8.18 (1H, d, J=1.7 Hz), 8.29 (1H, d, J=2.3 Hz), 8.64 (1H, d, J=2.3 Hz), 11.66 (1H, s), 12.10 (1H, brs).

Example 42

1-[(2S)-1,4-Dioxan-2-ylmethyl]-6-(4-methyl-1H-pyrrolo[2,3-b]pyridin-5-yl)-1,3-dihydro-imidazo[4,5-b]pyridin-2-one

[Formula 62]

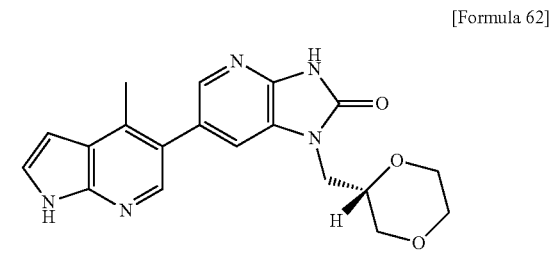 [SMILES: Cc1c(-c2cnc3[nH]c(=O)n(C[C@H]4COCCO4)c3c2)cnc2[nH]ccc12]

Step 1

3-Cyclohex-1-en-1-yl-1-[(2S)-1,4-dioxan-2-ylmethyl]-6-(4-methyl-1H-pyrrolo[2,3-b]pyridin-5-yl)-1,3-dihydro-2H-imidazo[4,5-b]pyridin-2-one The title compound (41 mg) was obtained by the same procedure as in Step 3 of Example 1 using the compound obtained in Step 1 of Example 41 (153 mg) and the compound obtained in Step 4 of Example 36 (108 mg).

MS (ESI) m/z: 446 (M+H)+.

Step 2

1-[(2S)-1,4-Dioxan-2-ylmethyl]-6-(4-methyl-1H-pyrrolo[2,3-b]pyridin-5-yl)-1,3-dihydro-imidazo[4,5-b]pyridin-2-one The title compound (20 mg) was obtained by the same procedure as in Step 6 of Example 35 using the compound obtained in the above Step 2 (41 mg).

MS (ESI) m/z: 366 (M+H)+.
HRMS (ESI) [M+H]+ calculated: $C_{19}H_{20}N_5O_3$ 366.15661. found: 366.15640.

$^1$H-NMR (DMSO-d$_6$) δ: 2.47 (3H, s), 3.33-3.95 (9H, m), 6.56-6.58 (1H, m), 7.47-7.50 (1H, m), 7.56 (1H, s), 7.92-7.93 (1H, m), 8.09 (1H, s), 11.64-11.67 (2H, m).

Example 43

1-[(2S)-1,4-Dioxan-2-ylmethyl]-6-(3-methyl-1H-pyrrolo[2,3-b]pyridin-5-yl)-1,3-dihydro-imidazo[4,5-b]pyridin-2-one

[Formula 63]

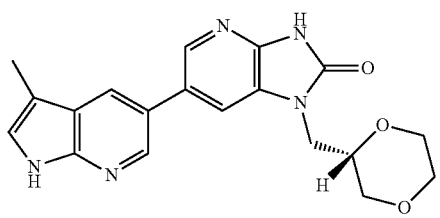

Step 1

5-[3-Cyclohex-1-en-1-yl-1-[(2S)-1,4-dioxan-2-ylmethyl]-2-oxo-2,3-dihydro-2H-imidazo[4,5-b]pyridin-6-yl]-1H-pyrrolo[2,3-b]pyridine-3-carbaldehyde The title compound (41 mg) was obtained by the same procedure as in Step 3 of Example 1 using the compound obtained in Step 1 of Example 41 (190 mg) and 5-bromo-1H-pyrrolo[2,3-b]pyridine-3-carbaldehyde obtained by the method described in WO 2004/101565 (97 mg).
MS (ESI) m/z: 460 (M+H)$^+$.

Step 2

3-Cyclohex-1-en-1-yl-1-[(2S)-1,4-dioxan-2-ylmethyl]-6-(3-methyl-1H-pyrrolo[2,3-b]pyridin-5-yl)-1,3-dihydro-2H-imidazo[4,5-b]pyridin-2-one The title compound (27 mg) was obtained by the same procedure as in Step 2 of Example 37 using the compound obtained in the above Step 1 (41 mg).
MS (ESI) m/z: 446 (M+H)$^+$.

Step 3

1-[(2S)-1,4-Dioxan-2-ylmethyl]-6-(3-methyl-1H-pyrrolo[2,3-b]pyridin-5-yl)-1,3-dihydro-imidazo[4,5-b]pyridin-2-one The title compound (26 mg) was obtained by the same procedure as in Step 6 of Example 35 using the compound obtained in the above Step 2 (49 mg).
MS (ESI) m/z: 366 (M+H)$^+$.
HRMS (ESI) [M+H]$^+$ calculated: C$_{19}$H$_{20}$N$_5$O$_3$ 366.15661. found: 366.15790.
$^1$H-NMR (DMSO-d$_6$) δ: 2.32 (3H, s), 3.33-4.04 (9H, m), 7.28 (1H, s), 7.85 (1H, d, J=1.2 Hz), 8.17-8.18 (1H, m), 8.26 (1H, d, J=1.2 Hz), 8.50-8.50 (1H, m), 11.38 (1H, brs), 11.61 (1H, brs).

Example 44

1-[(2S)-1,4-Dioxan-2-ylmethyl]-5-methyl-6-(1H-pyrrolo[2,3-b]pyridin-5-yl)-1,3-dihydro-imidazo[4,5-b]pyridin-2-one

[Formula 64]

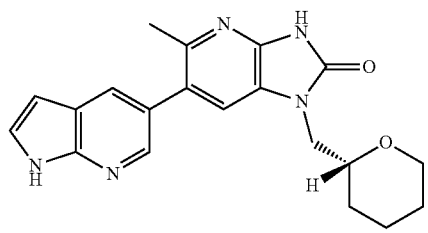

Step 1

6-Bromo-3-cyclohex-1-en-1-yl-5-methyl-1,3-dihydro-2H-imidazo[4,5-b]pyridin-2-one The title compound (0.64 g) was obtained by the same procedure as in Step 2 of Example 35 using the compound obtained in Step 2 of Example 7 (1.0 g).
MS (ESI) m/z: 410 (M+H)$^+$.

Step 2

6-Bromo-3-cyclohex-1-en-1-yl-1-[(2S)-1,4-dioxan-2-ylmethyl]-5-methyl-1,3-dihydro-2H-imidazo[4,5-b]pyridin-2-one (2S)-1,4-Dioxan-2-ylmethanol (319 mg) and triphenylphosphine (817 mg) were added to a solution of the compound obtained in the above Step 1 (640 mg) in tetrahydrofuran (20 ml). Thereafter, a solution of di-2-methoxyethyl azodicarboxylate (730 mg) in tetrahydrofuran (5 ml) was added dropwise at 0° C., and the mixture was stirred for 11 hours while gradually warming to room temperature. The reaction solution was diluted with diethyl ether, washed with water and brine in this order and dried over anhydrous sodium sulfate. The solvent was evaporated under reduced pressure. The resulting residue was purified by silica gel column chromatography (developed with ethyl acetate-hexane) to give the title compound (480 mg).
MS (ESI) m/z: 308 (M+H)$^+$.
$^1$H-NMR (CDCl$_3$) δ: 1.72-1.76 (2H, m), 1.83-1.88 (2H, m), 2.28-2.32 (2H, m), 2.43-2.46 (2H, m), 2.60 (3H, s), 3.36 (1H, dd, J=11.5, 9.7 Hz), 3.54-3.60 (1H, m), 3.66-3.71 (2H, m), 3.77-3.81 (2H, m), 3.85-3.92 (3H, m), 5.99-6.01 (1H, m), 7.47 (1H, s).

Step 3

3-Cyclohex-1-en-1-yl-1-[(2S)-1,4-dioxan-2-ylmethyl]-5-methyl-6-(1H-pyrrolo[2,3-b]pyridin-5-yl)-1,3-dihydro-2H-imidazo[4,5-b]pyridin-2-one The title compound (180 mg) was obtained by the same procedure as in Step 3 of Example 1 using the compound obtained in the above Step 2 (150 mg) and 5-(4,4,5,5-tetramethyl-1,3,2-dioxaborolan-2-yl)-1H-pyrrolo[2,3-b]pyridine (107 mg).

MS (ESI) m/z: 446 (M+H)⁺.
¹H-NMR (CDCl₃) δ: 1.75-1.79 (2H, m), 1.87-1.93 (2H, m), 2.31-2.35 (2H, m), 2.48 (3H, s), 2.52-2.55 (2H, m), 3.39 (1H, dd, J=11.5, 9.7 Hz), 3.55-3.76 (4H, m), 3.83-3.95 (4H, m), 6.06-6.08 (1H, m), 6.57 (1H, dd, J=3.7, 2.0 Hz), 7.24 (1H, s), 7.39-7.39 (1H, m), 7.89 (1H, d, J=1.2 Hz), 8.27 (1H, d, J=1.7 Hz), 8.97 (1H, s).

Step 4

1-[(2S)-1,4-Dioxan-2-ylmethyl]-5-methyl-6-(1H-pyrrolo[2,3-b]pyridin-5-yl)-1,3-dihydro-imidazo[4,5-b]pyridin-2-one The title compound (75 mg) was obtained by the same procedure as in Step 6 of Example 35 using the compound obtained in the above Step 3 (180 mg).
MS (ESI) m/z: 366 (M+H)⁺.
¹H-NMR (DMSO-d₆) δ: 2.38 (3H, s), 3.28-3.30 (1H, m), 3.40-3.52 (2H, m), 3.59 (1H, d, J=10.5 Hz), 3.68-3.80 (3H, m), 3.82-3.93 (2H, m), 6.49 (1H, dd, J=3.4, 1.7 Hz), 7.41 (1H, s), 7.53-7.53 (1H, m), 7.95 (1H, d, J=2.0 Hz), 8.21 (1H, d, J=2.2 Hz), 11.49 (1H, brs), 11.74 (1H, brs).

Example 45

1-[(2S)-1,4-Dioxan-2-ylmethyl]-5-methyl-6-(4-methyl-1H-pyrrolo[2,3-b]pyridin-5-yl)-1,3-dihydro-imidazo[4,5-b]pyridin-2-one

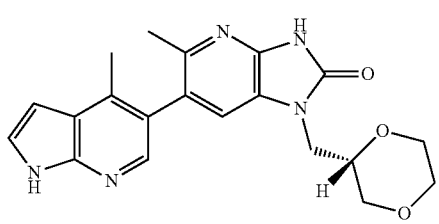

[Formula 65]

Step 1

3-Cyclohex-1-en-1-yl-1-[(2S)-1,4-dioxan-2-ylmethyl]-5-methyl-6-(4,4,5,5-tetramethyl-1,3,2-dioxaboran-2-yl)-1,3-dihydro-2H-imidazo[4,5-b]pyridin-2-one The title compound (433 mg) was obtained by the same procedure as in Step 4 of Example 35 using the compound obtained in Step 2 of Example 44 (470 mg).
MS (ESI) m/z: 456 (M+H)⁺.
¹H-NMR (CDCl₃) δ: 1.36 (6H, s), 1.58 (6H, s), 1.71-1.76 (2H, m), 1.83-1.88 (2H, m), 1.93 (6H, s), 2.28-2.31 (2H, m), 2.45-2.49 (2H, m), 2.72 (3H, s), 3.43 (1H, dd, J=12.0, 9.7 Hz), 3.58-3.63 (1H, m), 3.67-3.72 (2H, m), 3.78-3.97 (5H, m), 4.07-4.09 (2H, m), 6.00-6.02 (1H, m), 7.58 (1H, s).

Step 2

3-Cyclohex-1-en-1-yl-1-[(2S)-1,4-dioxan-2-ylmethyl]-5-methyl-6-(4-methyl-1H-pyrrolo[2,3-b]pyridin-5-yl)-1,3-dihydro-2H-imidazo[4,5-b]pyridin-2-one The title compound (74 mg) was obtained by the same procedure as in Step 3 of Example 1 using the compound obtained in the above Step 1 (130 mg) and the compound obtained in Step 4 of Example 36 (106 mg).
MS (ESI) m/z: 460 (M+H)⁺.

Step 3

1-[(2S)-1,4-Dioxan-2-ylmethyl]-5-methyl-6-(4-methyl-1H-pyrrolo[2,3-b]pyridin-5-yl)-1,3-dihydro-imidazo[4,5-b]pyridin-2-one The title compound (13 mg) was obtained by the same procedure as in Step 6 of Example 35 using the compound obtained in the above Step 2 (70 mg).
MS (ESI) m/z: 380 (M+H)⁺.
¹H-NMR (DMSO-d₆) δ: 2.15-2.15 (3H, m), 2.25-2.26 (3H, m), 3.39-3.51 (3H, m), 3.56-3.61 (1H, m), 3.67-3.91 (5H, m), 6.55-6.56 (1H, m), 7.29-7.30 (1H, m), 7.47-7.48 (1H, m), 7.95-7.97 (1H, m), 11.50-11.52 (1H, m), 11.64-11.66 (1H, m).

Example 46

6-(3-Chloro-1H-pyrrolo[2,3-b]pyridin-5-yl)-1-[(2S)-1,4-dioxan-2-ylmethyl]-5-methyl-1,3-dihydro-imidazo[4,5-b]pyridin-2-one

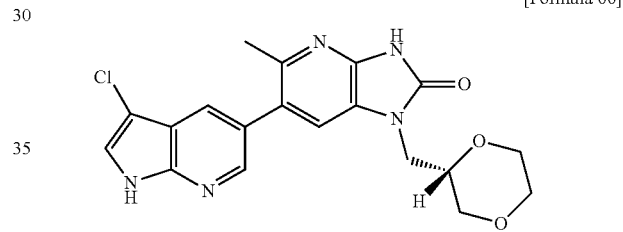

[Formula 66]

Step 1

6-(3-Chloro-1H-pyrrolo[2,3-b]pyridin-5-yl)-3-cyclohex-1-en-1-yl-1-[(2S)-1,4-dioxan-2-ylmethyl]-5-methyl-1,3-dihydro-2H-imidazo[4,5-b]pyridin-2-one The title compound (35 mg) was obtained by the same procedure as in Step 3 of Example 1 using the compound obtained in Step 1 of Example 45 (130 mg) and the compound obtained in Step 1 of Example 35 (113 mg).
MS (ESI) m/z: 480 (M+H)⁺.

Step 2

6-(3-Chloro-1H-pyrrolo[2,3-b]pyridin-5-yl)-1-[(2S)-1,4-dioxan-2-ylmethyl]-5-methyl-1,3-dihydro-imidazo[4,5-b]pyridin-2-one The title compound (17 mg) was obtained by the same procedure as in Step 6 of Example 35 using the compound obtained in the above Step 1 (35 mg).
MS (ESI) m/z: 400 (M+H)⁺.
¹H-NMR (DMSO-d₆) δ: 2.38 (3H, s), 3.27-3.31 (1H, m), 3.41-3.52 (2H, m), 3.59 (1H, d, J=10.9 Hz), 3.68-3.80 (3H, m), 3.84-3.88 (1H, m), 3.89-3.94 (1H, m), 7.45 (1H, s), 7.76 (1H, d, J=2.9 Hz), 7.90 (1H, d, J=1.7 Hz), 8.32 (1H, d, J=2.3 Hz), 11.53 (1H, s), 12.11 (1H, s).

Example 47

1-[(2S)-1,4-Dioxan-2-ylmethyl]-5-methyl-6-(3-methyl-1H-pyrrolo[2,3-b]pyridin-5-yl)-1,3-dihydroimidazo[4,5-b]pyridin-2-one

[Formula 67]

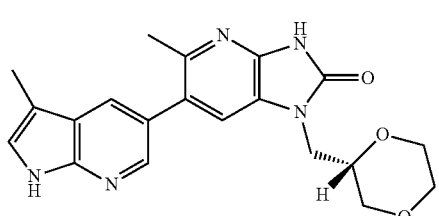

Step 1 tert-Butyl 5-bromo-3-methyl-1H-pyrrolo[2,3-b]pyridine-1-carboxylate

The title compound (385 mg) was obtained by the same procedure as in Step 1 of Example 35 using 5-bromo-3-methyl-1H-pyrrolo[2,3-b]pyridine obtained by the method described in WO 2009/016460 (365 mg).
MS (ESI) m/z: 311 (M+H)$^+$.
$^1$H-NMR (CDCl$_3$) δ: 1.66 (9H, s), 2.23 (3H, d, J=1.5 Hz), 7.41-7.41 (1H, m), 7.94 (1H, d, J=2.2 Hz), 8.51 (1H, d, J=2.2 Hz).

Step 2

3-Cyclohex-1-en-1-yl-1-[(2S)-1,4-dioxan-2-ylmethyl]-5-methyl-6-(3-methyl-1H-pyrrolo[2,3-b]pyridin-5-yl)-1,3-dihydro-2H-imidazo[4,5-b]pyridin-2-one The title compound (105 mg) was obtained by the same procedure as in Step 2 of Example 4 using the compound obtained in Step 1 of Example 45 (160 mg) and the compound obtained in the above Step 1 (100 mg).
MS (ESI) m/z: 460 (M+H)$^+$.
$^1$H-NMR (CDCl$_3$) δ: 1.75-1.79 (2H, m), 1.87-1.92 (2H, m), 2.32-2.34 (2H, m), 2.35 (3H, d, J=1.15 Hz), 2.47 (3H, s), 2.52-2.55 (2H, m), 3.39 (1H, dd, J=11.5, 9.7 Hz), 3.55 (1H, td, J=11.7, 2.9 Hz), 3.65-3.70 (2H, m), 3.72-3.76 (1H, m), 3.84-3.94 (4H, m), 6.06-6.08 (1H, m), 7.14 (1H, s), 7.24 (1H, s), 7.81 (1H, d, J=2.3 Hz), 8.24 (1H, d, J=2.3 Hz), 8.59 (1H, brs).

Step 3

1-[(2S)-1,4-Dioxan-2-ylmethyl]-5-methyl-6-(3-methyl-1H-pyrrolo[2,3-b]pyridin-5-yl)-1,3-dihydroimidazo[4,5-b]pyridin-2-one The title compound (42 mg) was obtained by the same procedure as in Step 6 of Example 35 using the compound obtained in the above Step 2 (103 mg).
MS (ESI) m/z: 380 (M+H)$^+$.
$^1$H-NMR (DMSO-d$_6$) δ: 2.28 (3H, s), 2.38 (3H, s), 3.27-3.31 (1H, m), 3.40-3.52 (2H, m), 3.59 (1H, d, J=10.9 Hz), 3.68-3.93 (5H, m), 7.29 (1H, s), 7.41 (1H, s), 7.89 (1H, d, J=2.3 Hz), 8.18 (1H, d, J=1.7 Hz), 11.39 (1H, s), 11.49 (1H, s).

Example 48

1-[2-(3,6-Dihydro-2H-pyran-4-yl)ethyl]-6-(1H-pyrrolo[2,3-b]pyridin-5-yl)-1,3-dihydro-2H-imidazo[4,5-b]pyridin-2-one

[Formula 68]

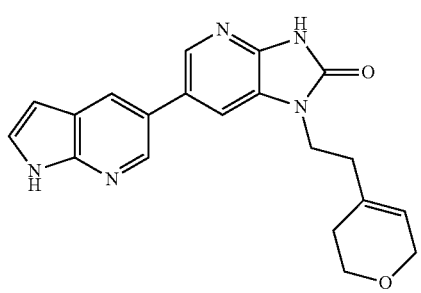

Step 1

Ethyl tetrahydro-4H-pyran-4-ylideneacetate

Ethyl 3,6-dihydro-2H-pyran-4-ylacetate

55% Sodium hydride (2.6 g) was suspended in dimethoxyethane (150 ml). Ethyl diethylphosphonoacetate (9.6 ml) was added dropwise under nitrogen atmosphere under ice-cooling over five minutes, and the mixture was stirred at the same temperature for 45 minutes. A solution of tetrahydro-4H-pyran-4-one (4.0 g) in dimethoxyethane (10 ml) was added dropwise thereto over five minutes. The mixture was stirred at room temperature for 10 minutes and then heated under reflux for one hour. The reaction solution was poured into water, followed by extraction with ethyl acetate. The organic layer was washed with brine and then dried over anhydrous sodium sulfate, and the solvent was evaporated. The residue was purified by silica gel column chromatography (developed with ethyl acetate-hexane) to give the title compounds ethyl tetrahydro-4H-pyran-4-ylideneacetate (1.7 g) and ethyl 3,6-dihydro-2H-pyran-4-ylacetate (2.2 g) both as colorless oils.

Ethyl tetrahydro-4H-pyran-4-ylideneacetate $^1$H-NMR (CDCl$_3$) δ: 1.28 (3H, t, J=7.1 Hz), 2.30-2.35 (2H, m), 2.98-3.03 (2H, m), 3.74 (2H, t, J=5.6 Hz), 3.77 (2H, t, J=5.6 Hz), 4.16 (2H, q, J=7.1 Hz), 5.68 (1H, s).

Ethyl 3,6-dihydro-2H-pyran-4-ylacetate $^1$H-NMR (CDCl$_3$) δ: 1.27 (3H, t, J=7.1 Hz), 2.12-2.19 (2H, m), 3.01 (2H, s), 3.80 (2H, t, J=5.5 Hz), 4.11-4.19 (4H, m), 5.58-5.62 (1H, m).

Step 2

2-(3,6-Dihydro-2H-pyran-4-yl)ethanol

The title compound (1.6 g) was obtained as a colorless oil by the same procedure as in Step 2 of Example 33 using ethyl 3,6-dihydro-2H-pyran-4-ylacetate obtained in the above Step 1.

$^1$H-NMR (CDCl$_3$) δ: 1.55 (1H, br s), 2.06-2.12 (2H, m), 2.28 (2H, t, J=6.2 Hz), 3.72 (2H, t, J=6.3 Hz), 3.80 (2H, t, J=5.5 Hz), 4.11-4.15 (2H, m), 5.53-5.57 (1H, m).

Step 3

6-Bromo-3-cyclohex-1-en-1-yl-1-[2-(3,6-dihydro-2H-pyran-4-yl)ethyl]-1,3-dihydro-2H-imidazo[4,5-b]pyridin-2-one The title compound (705 mg) was obtained as a mixture by the same procedure as in Step 3 of Example 35 using the compound obtained in Step 2 of Example 35 (280 mg) and the compound obtained in the above Step 2 (146 mg).

$^1$H-NMR (CDCl$_3$) δ: 1.70-1.78 (2H, m), 1.81-1.90 (2H, m), 2.11-2.18 (2H, m), 2.26-2.33 (2H, m), 2.36-2.45 (4H, m), 3.78 (2H, t, J=5.5 Hz), 3.97 (2H, t, J=7.2 Hz), 4.00-4.04 (2H, m), 5.37 (1H, s), 5.96-6.00 (1H, m), 7.30 (1H, d, J=2.0 Hz), 8.09 (1H, d, J=2.0 Hz).

Step 4

6-Bromo-1-[2-(3,6-dihydro-2H-pyran-4-yl)ethyl]-1,3-dihydro-2H-imidazo[4,5-b]pyridin-2-one The title compound (192 mg) was obtained as a colorless powder by the same procedure as in Step 6 of Example 35 using the compound obtained in the above Step 3 (705 mg).

$^1$H-NMR (CDCl$_3$) δ: 2.13-2.19 (2H, m), 2.42 (2H, t, J=7.0 Hz), 3.78 (2H, t, J=5.4 Hz), 3.95 (2H, t, J=7.3 Hz), 4.02-4.06 (2H, m), 5.39-5.43 (1H, m), 7.31 (1H, d, J=1.8 Hz), 8.10 (1H, d, J=1.8 Hz), 8.95 (1H, br s).

Step 5

1-[2-(3,6-Dihydro-2H-pyran-4-yl)ethyl]-6-(1H-pyrrolo[2,3-b]pyridin-5-yl)-1,3-dihydro-2H-imidazo[4,5-b]pyridin-2-one The title compound (55 mg) was obtained by the same procedure as in Step 3 of Example 1 using the compound obtained in the above Step 4 (100 mg) and 5-(4,4,5,5-tetramethyl-1,3,2-diaxaborolan-2-yl)-1H-pyrrolo[2,3-b]pyridine (90 mg).

MS (ESI) m/z: 362 (M+H)$^+$.
HRMS (ESI) [M+H]$^+$ calculated: C$_{20}$H$_{19}$N$_5$O$_2$ 362.16170. found: 362.16021.

$^1$H-NMR (DMSO-d$_6$) δ: 2.07-2.14 (2H, m), 2.36-2.42 (2H, m), 3.63 (2H, t, J=5.7 Hz), 3.86-3.90 (2H, m), 3.99 (2H, t, J=6.6 Hz), 5.35-5.38 (1H, m), 6.49-6.52 (1H, m), 7.51-7.54 (1H, m), 7.86 (1H, d, J=1.2 Hz), 8.22-8.26 (2H, m), 8.55 (1H, d, J=2.0 Hz), 11.56 (1H, br s), 11.72 (1H, br s).

Example 49

1-[2-(3,6-Dihydro-2H-pyran-4-yl)ethyl]-6-(1H-indol-5-yl)-1,3-dihydro-2H-imidazo[4,5-b]pyridin-2-one

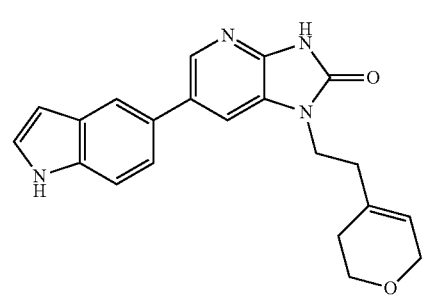

[Formula 69]

The title compound (42 mg) was obtained by the same procedure as in Step 3 of Example 1 using the compound obtained in Step 4 of Example 48 (92 mg) and 5-(4,4,5,5-tetramethyl-1,3,2-dioxaborolan-2-yl)-1H-indole (33 mg).

MS (ESI) m/z: 361 (M+H)$^+$.
HRMS (ESI) [M+H]$^+$ calculated: C$_{20}$H$_{20}$N$_4$O$_2$ 361.16645. found: 361.16597.

$^1$H-NMR (DMSO-d$_6$) δ: 2.07-2.14 (2H, m), 2.35-2.41 (2H, m), 3.63 (2H, t, J=5.4 Hz), 3.85-3.90 (2H, m), 3.99 (2H, t, J=7.0 Hz), 5.34-5.38 (1H, m), 6.47-6.50 (1H, m), 7.37-7.44 (2H, m), 7.48 (1H, d, J=8.5 Hz), 7.76-7.78 (1H, m), 7.84-7.86 (1H, m), 8.19 (1H, d, J=1.7 Hz), 11.14 (1H, br s), 11.49 (1H, br s).

Example 50

6-(1H-Pyrrolo[2,3-b]pyridin-5-yl)-1-[2-(tetrahydro-2H-pyran-4-yl)propyl]-1,3-dihydro-2H-imidazo[4,5-b]pyridin-2-one

[Formula 70]

Step 1

Ethyl 2-(tetrahydro-2H-pyran-4-yl)propanoate

Diisopropylamine (2.8 g) was dissolved in tetrahydrofuran (20 ml). A solution of n-butyllithium in hexane (2.64 N, 11 ml) was added dropwise under nitrogen atmosphere under ice-cooling, and the mixture was stirred at the same temperature for 15 minutes. The reaction solution was cooled to −78° C. A solution of ethyl 2-(tetrahydro-2H-pyran-4-yl)acetate (4.0 g) in tetrahydrofuran (15 ml) was added dropwise and the mixture was stirred at the same temperature for 15 minutes. Methyl iodide (2.2 ml) was subsequently added dropwise. The mixture was stirred at the same temperature for 10 minutes, and then warmed to room temperature and stirred for 3 hours. A 1 N aqueous hydrochloric acid solution was added under ice-cooling, followed by extraction with ethyl acetate. The organic layer was washed with a saturated aqueous sodium bicarbonate solution and brine and then dried over anhydrous sodium sulfate, and the solvent was evaporated. The residue was purified by silica gel column chromatography (developed with ethyl acetate-hexane) to give the title compound (4.0 g) as a colorless oil.

$^1$H-NMR (CDCl$_3$) δ: 1.13 (3H, d, J=6.8 Hz), 1.26 (3H, t, J=7.2 Hz), 1.30-1.46 (2H, m), 1.47-1.55 (1H, m), 1.58-1.66 (1H, m), 1.72-1.84 (1H, m), 2.21-2.30 (1H, m), 3.37 (2H, tt, J=11.8, 2.9 Hz), 3.92-4.03 (2H, m), 4.14 (2H, q, J=7.2 Hz).

Step 2

2-(Tetrahydro-2H-pyran-4-yl)propan-1-ol

The title compound (1.4 g) was obtained as a colorless oil by the same procedure as in Step 2 of Example 33 using the compound obtained in the above Step 1 (1.8 g).

$^1$H-NMR (CDCl$_3$) δ: 0.93 (3H, d, J=6.8 Hz), 1.20-1.72 (7H, m), 3.33-3.45 (2H, m), 3.49-3.58 (1H, m), 3.59-3.69 (1H, m), 3.95-4.07 (2H, m).

Step 3

6-Bromo-3-cyclohex-1-en-1-yl-1-[2-(tetrahydro-2H-pyran-4-yl)propyl]-1,3-dihydro-2H-imidazo[4,5-b]pyridin-2-one The title compound (255 mg) was obtained as a mixture by the same procedure as in Step 3 of Example 35 using the compound obtained in Step 2 of Example 35 (200 mg) and the compound obtained in the above Step 2 (147 mg).

$^1$H-NMR (CDCl$_3$) δ: 0.91 (3H, d, J=6.8 Hz), 1.43-1.60 (3H, m), 1.63-1.78 (4H, m), 1.81-1.90 (2H, m), 1.90-1.98 (1H, m), 2.26-2.34 (2H, m), 2.36-2.44 (2H, m), 3.31-3.42 (2H, m), 3.63 (1H, dd, J=14.1, 8.9 Hz), 3.89 (1H, dd, J=14.1, 6.1 Hz), 3.96-4.06 (2H, m), 5.97-6.03 (1H, m), 7.25 (1H, d, J=2.0 Hz), 8.10 (1H, d, J=2.0 Hz).

Step 4

6-Bromo-1-[2-(tetrahydro-2H-pyran-4-yl)propyl]-1,3-dihydro-2H-imidazo[4,5-b]pyridin-2-one The title compound (73 mg) was obtained as a colorless solid by the same procedure as in Step 6 of Example 35 using the compound obtained in the above Step 3 (255 mg).

$^1$H-NMR (CDCl$_3$) δ: 0.90 (3H, d, J=6.8 Hz), 1.48-1.59 (3H, m), 1.63-1.70 (1H, m), 1.88-1.99 (2H, m), 3.33-3.42 (3H, m), 3.63 (1H, dd, J=14.0, 8.9 Hz), 3.85 (1H, dd, J=13.3, 5.7 Hz), 3.97-4.07 (2H, m), 7.23-7.26 (1H, m), 8.06-8.09 (1H, m).

Step 5

6-(1H-Pyrrolo[2,3-b]pyridin-5-yl)-1-[2-(tetrahydro-2H-pyran-4-yl)propyl]-1,3-dihydro-2H-imidazo[4,5-b]pyridin-2-one The title compound (45 mg) was obtained as a colorless solid by the same procedure as in Step 3 of Example 1 using the compound obtained in the above Step 4 (73 mg) and 5-(4,4,5,5-tetramethyl-1,3,2-dioxaborolan-2-yl)-1H-pyrrolo[2,3-b]pyridine (63 mg).

MS (ESI) m/z: 378 (M+H)$^+$.

HRMS (ESI) [M+H]$^+$ calculated: C$_{21}$H$_{23}$N$_5$O$_2$ 378.19300. found: 378.19239.

$^1$H-NMR (DMSO-d$_6$) δ: 0.81 (3H, d, J=6.6 Hz), 1.22-1.58 (4H, m), 1.61-1.70 (1H, m), 1.94-2.05 (1H, m), 3.19-3.30 (2H, m), 3.66-3.76 (1H, m), 3.82-3.94 (3H, m), 6.50-6.53 (1H, m), 7.50-7.54 (1H, m), 7.81 (1H, s), 8.22-8.25 (2H, m), 8.53 (1H, d, J=1.7 Hz), 11.60 (1H, br s), 11.73 (1H, br s).

Example 51

1-[2-Fluoro-2-(tetrahydro-2H-pyran-4-yl)ethyl]-6-(1H-pyrrolo[2,3-b]pyridin-5-yl)-1,3-dihydro-2H-imidazo[4,5-b]pyridin-2-one

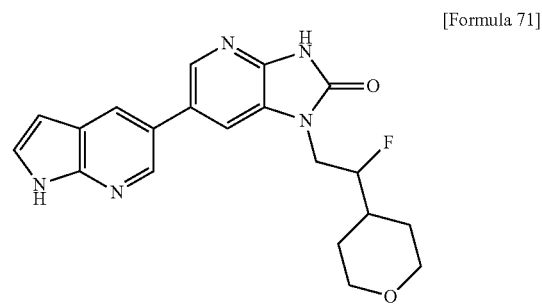 [SMILES: O=c1[nH]c2ncc(-c3cnc4[nH]ccc4c3)cc2n1CC(F)C1CCOCC1]

[Formula 71]

Step 1

Ethyl fluoro(tetrahydro-2H-pyran-4-yl)acetate

Ethyl 2-(tetrahydro-2H-pyran-4-yl)acetate (2.0 g) was dissolved in tetrahydrofuran (20 ml). A solution of lithium bis(trimethylsilyl)amide in tetrahydrofuran (1.0 M, 17 ml) was added dropwise under nitrogen atmosphere under ice-cooling, and the mixture was stirred at the same temperature for 15 minutes. Then, a solution of N-fluorobenzenesulfonimide (7.3 g) in tetrahydrofuran (20 ml) was added and the mixture was stirred at the same temperature for 3 hours. A saturated aqueous ammonium chloride solution and water were added under ice-cooling, followed by extraction with ethyl acetate. The organic layer was washed with brine and then dried over anhydrous sodium sulfate, and the solvent was evaporated. Chloroform-diethyl ether was added to the residue, and insoluble matter was removed by filtration. Thereafter, the solvent was evaporated and the residue was purified by silica gel column chromatography (developed with ethyl acetate-hexane and with chloroform) to give the title compound containing insoluble matter (0.9 g) as a pale orange oil.

MS (ESI) m/z: 191 (M+H)$^+$.

Step 2

2-Fluoro(tetrahydro-2H-pyran-4-yl)ethanol

The title compound (0.4 g) was obtained as a colorless oil by the same procedure as in Step 2 of Example 33 using the compound obtained in the above Step 1 (0.9 g).

¹H-NMR (CDCl₃) δ: 1.42-1.66 (3H, m), 1.74-2.05 (3H, m), 3.35-3.44 (2H, m), 3.68-3.88 (2H, m), 3.95-4.05 (2H, m), 4.21-4.28 (0.5H, m), 4.34-4.39 (0.5H, m).

Step 3

6-Bromo-3-cyclohex-1-en-1-yl-1-[2-fluoro-2-(tetrahydro-2H-pyran-4-yl)ethyl]-1,3-dihydro-2H-imidazo[4,5-b]pyridin-2-one The title compound (196 mg) was obtained as a mixture by the same procedure as in Step 3 of Example 35 using the compound obtained in Step 2 of Example 35 (200 mg) and the compound obtained in the above Step 2 (151 mg).

¹H-NMR (CDCl₃) δ: 1.48-1.61 (2H, m), 1.70-1.95 (7H, m), 2.28-2.34 (2H, m), 2.39-2.44 (2H, m), 3.35-3.45 (2H, m), 3.92-4.06 (3H, m), 4.17 (1H, ddd, J=29.4, 15.2, 2.2 Hz), 4.49 (0.5H, td, J=7.2, 2.2 Hz), 4.61 (0.5H, td, J=7.2, 2.2 Hz), 5.99-6.03 (1H, m), 7.43-7.45 (1H, m), 8.11 (1H, d, J=2.0 Hz).

Step 4

6-Bromo-1-[2-fluoro-2-(tetrahydro-2H-pyran-4-yl)ethyl]-1,3-dihydro-2H-imidazo[4,5-b]pyridin-2-one The title compound (145 mg) was obtained as a pale yellow amorphous material by the same procedure as in Step 6 of Example 35 using the compound obtained in the above Step 3 (196 mg).

¹H-NMR (CDCl₃-CD₃OD (10:1)) δ: 1.23-1.34 (2H, m), 1.49-1.62 (2H, m), 1.70-1.96 (2H, m), 3.35-3.47 (2H, m), 3.91-4.19 (4H, m), 4.42-4.50 (0.5H, m), 4.53-4.62 (0.5H, m), 7.30 (1H, d, J=2.0 Hz), 7.93 (1H, d, J=2.0 Hz).

Step 5

1-[2-Fluoro-2-(tetrahydro-2H-pyran-4-yl)ethyl]-6-(1H-pyrrolo[2,3-b]pyridin-5-yl)-1,3-dihydro-2H-imidazo[4,5-b]pyridin-2-one The title compound (27 mg) was obtained as a colorless solid by the same procedure as in Step 3 of Example 1 using the compound obtained in the above Step 4 (71 mg) and 5-(4,4,5,5-tetramethyl-1,3,2-dioxaborolan-2-yl)-1H-pyrrolo[2,3-b]pyridine (60 mg).

MS (ESI) m/z: 382 (M+H)⁺.

HRMS (ESI) [M+H]⁺ calculated: C₂₀H₂₀FN₅O₂ 382.16793. found: 382.16778.

¹H-NMR (DMSO-d₆) δ: 0.81 (3H, d, J=6.6 Hz), 1.22-1.58 (4H, m), 1.61-1.70 (1H, m), 1.94-2.05 (1H, m), 3.19-3.30 (2H, m), 3.66-3.76 (1H, m), 3.82-3.94 (3H, m), 6.50-6.53 (1H, m), 7.50-7.54 (1H, m), 7.81 (1H, s), 8.22-8.25 (2H, m), 8.53 (1H, d, J=1.7 Hz), 11.60 (1H, br s), 11.73 (1H, br s).

Example 52

1-{2-[cis-2,6-Dimethylmorpholin-4-yl]ethyl}-6-(1H-indol-5-yl)-1,3-dihydro-2H-imidazo[4,5-b]pyridin-2-one

[Formula 72]

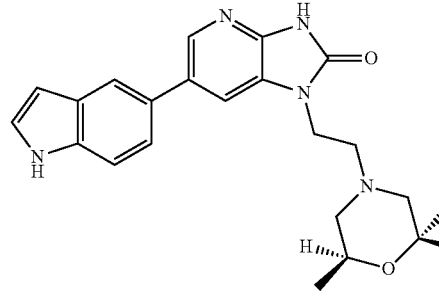

Step 1

Ethyl [cis-2,6-dimethylmorpholin-4-yl]acetate cis-2,6-Dimethylmorpholine (2.0 g) was dissolved in acetonitrile (70 ml). Ethyl bromoacetate (2.5 ml) and potassium carbonate (3.1 g) were added and the mixture was heated with stirring at 60° C. for 12 hours. The solvent was evaporated and then ethyl acetate was added to the residue. The organic layer was washed with brine and then dried over anhydrous sodium sulfate, and the solvent was evaporated. The residue was purified by silica gel column chromatography (developed with ethyl acetate-hexane) to give the title compound (2.9 g) as a colorless oil.

¹H-NMR (CDCl₃) δ: 1.16 (6H, d, J=6.1 Hz), 1.28 (3H, t, J=7.1 Hz), 1.93 (2H, t, J=10.6 Hz), 2.76-2.83 (2H, m), 3.18 (2H, s), 3.71-3.81 (2H, m), 4.19 (2H, q, J=7.1 Hz).

Step 2

2-[cis-2,6-Dimethylmorpholin-4-yl]ethanol

The title compound (2.3 g) was obtained as a colorless oil by the same procedure as in Step 2 of Example 33 using the compound obtained in the above Step 1 (2.9 g).

¹H-NMR (CDCl₃) δ: 1.16 (6H, d, J=6.3 Hz), 1.80-1.88 (2H, m), 2.52 (2H, t, J=5.5 Hz), 2.70-2.76 (2H, m), 2.71 (1H, br s), 3.62 (2H, t, J=5.5 Hz), 3.63-3.72 (2H, m).

Step 3

6-Bromo-3-cyclohex-1-en-1-yl-1-{2-[cis-2,6-dimethylmorpholin-4-yl]ethyl}-1,3-dihydro-2H-imidazo[4,5-b]pyridin-2-one The title compound (248 mg) was obtained by the same procedure as in Step 3 of Example 35 using the compound obtained in Step 2 of Example 35 (280 mg) and the compound obtained in the above Step 2 (182 mg).

¹H-NMR (CDCl₃) δ: 1.15 (6H, d, J=6.3 Hz), 1.70-1.91 (6H, m), 2.27-2.34 (2H, m), 2.37-2.44 (2H, m), 2.64 (2H, t, J=6.5 Hz), 2.77 (2H, d, J=10.5 Hz), 3.55-3.65 (2H, m), 3.96 (2H, t, J=6.5 Hz), 5.97-6.02 (1H, m), 7.37 (1H, d, J=2.0 Hz), 8.08 (1H, d, J=2.0 Hz).

Step 4

6-Bromo-1-{2-[cis-2,6-dimethylmorpholin-4-yl]ethyl}-1,3-dihydro-2H-imidazo[4,5-b]pyridin-2-one The title compound (165 mg) was obtained as a colorless amorphous material by the same procedure as in Step 6 of Example 35 using the compound obtained in the above Step 3 (249 mg).

$^1$H-NMR (CDCl$_3$) δ: 1.16 (6H, d, J=6.3 Hz), 1.85 (2H, t, J=10.6 Hz), 2.67 (2H, t, J=6.3 Hz), 2.82 (2H, d, J=10.5 Hz), 3.58-3.68 (2H, m), 3.97 (2H, t, J=6.3 Hz), 7.39 (1H, d, J=1.8 Hz), 8.08 (1H, d, J=1.8 Hz), 10.53 (1H, br s).

Step 5

1-{2-[cis-2,6-Dimethylmorpholin-4-yl]ethyl}-6-(1H-indol-5-yl)-1,3-dihydro-2H-imidazo[4,5-b]pyridin-2-one The title compound (33 mg) was obtained as a colorless solid by the same procedure as in Step 3 of Example 1 using the compound obtained in the above Step 4 (100 mg) and 5-(4,4,5,5-tetramethyl-1,3,2-dioxaborolan-2-yl)-1H-indole (96 mg).

MS (ESI) m/z: 392 (M+H)$^+$.
HRMS (ESI) [M+H]$^+$ calculated: C$_{22}$H$_{25}$N$_5$O$_2$ 392.20865. found: 392.20833.

$^1$H-NMR (CDCl$_3$) δ: 1.15 (6H, d, J=6.1 Hz), 1.85 (3H, t, J=10.7 Hz), 2.72 (2H, t, J=6.6 Hz), 2.86 (2H, d, J=10.5 Hz), 3.60-3.71 (2H, m), 4.06 (2H, t, J=6.6 Hz), 6.60-6.64 (1H, m), 7.29 (1H, t, J=2.7 Hz), 7.35-7.40 (1H, m), 7.45-7.51 (2H, m), 7.79 (1H, d, J=1.2 Hz), 8.30 (1H, d, J=1.2 Hz), 8.39 (1H, br s).

Example 53

1-{2-[cis-2,6-Dimethylmorpholin-4-yl]ethyl}-6-(1H-pyrrolo[2,3-b]pyridin-5-yl)-1,3-dihydro-2H-imidazo[4,5-b]pyridin-2-one

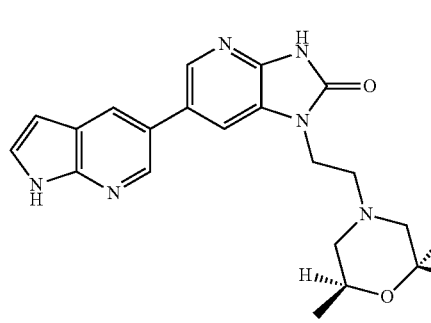

[Formula 73]

The title compound (53 mg) was obtained as a colorless solid by the same procedure as in Step 3 of Example 1 using the compound obtained in Step 4 of Example 52 (65 mg) and 5-(4,4,5,5-tetramethyl-1,3,2-dioxaborolan-2-yl)-1H-pyrrolo[2,3-b]pyridine (54 mg).

MS (ESI) m/z: 393 (M+H)$^+$.
HRMS (ESI) [M+H]$^+$ calculated: C$_{21}$H$_{24}$N$_6$O$_2$ 393.20390. found: 393.20452.

$^1$H-NMR (DMSO-d$_6$) δ: 1.02 (6H, d, J=6.3 Hz), 1.66 (2H, t, J=10.5 Hz), 2.60 (2H, t, J=6.1 Hz), 2.88 (2H, d, J=11.0 Hz), 3.38-3.47 (2H, m), 3.96-4.03 (2H, m), 6.48-6.52 (1H, m), 7.51-7.55 (1H, m), 7.86 (1H, s), 8.23-8.26 (2H, m), 8.54 (1H, d, J=1.5 Hz), 11.56 (1H, br s), 11.73 (1H, br s).

Example 54

1-{2-[(3S)-3-Methylmorpholin-4-yl]ethyl}-6-(1H-pyrrolo[2,3-b]pyridin-5-yl)-1,3-dihydro-2H-imidazo[4,5-b]pyridin-2-one

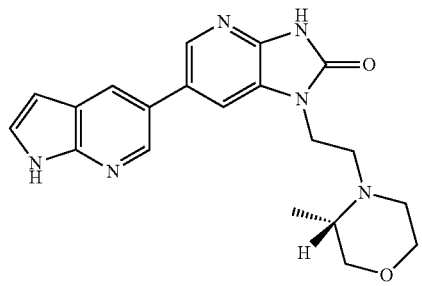

[Formula 74]

Step 1

Ethyl [(3S)-3-methylmorpholin-4-yl]acetate

The title compound (1.6 g) was obtained as a colorless oil by the same procedure as in Step 1 of Example 52 using (3S)-3-methylmorpholine (1.0 g).

$^1$H-NMR (CDCl$_3$) δ: 0.98 (3H, d, J=6.3 Hz), 1.28 (3H, t, J=7.1 Hz), 2.65-2.74 (2H, m), 2.77 (1H, dt, J=11.7, 2.2 Hz), 3.23-3.27 (1H, m), 3.27 (1H, d, J=16.3 Hz), 3.43 (1H, d, J=16.3 Hz), 3.64-3.72 (2H, m), 3.77-3.83 (1H, m), 4.19 (2H, q, J=7.2 Hz).

Step 2

2-[(3S)-3-Methylmorpholin-4-yl]ethanol

The title compound (1.3 g) was obtained as a colorless oil by the same procedure as in Step 2 of Example 33 using the compound obtained in the above Step 1 (1.6 g).

$^1$H-NMR (CDCl$_3$) δ: 1.00 (3H, d, J=6.1 Hz), 2.25-2.38 (2H, m), 2.49-2.59 (1H, m), 2.73 (1H, br s), 2.78-2.85 (1H, m), 2.93-3.02 (1H, m), 3.28 (1H, dd, J=11.1, 8.4 Hz), 3.49-3.58 (1H, m), 3.61-3.73 (3H, m), 3.75-3.82 (1H, m).

Step 3

6-Bromo-3-cyclohex-1-en-1-yl-1-{2-[(3S)-3-methylmorpholin-4-yl]ethyl}-1,3-dihydro-2H-imidazo[4,5-b]pyridin-2-one The title compound (443 mg) was obtained by the same procedure as in Step 3 of Example 35 using the compound obtained in Step 2 of Example 35 (400 mg) and the compound obtained in the above Step 2 (296 mg).

$^1$H-NMR (CDCl$_3$) δ: 0.85 (3H, d, J=6.3 Hz), 1.71-1.78 (2H, m), 1.83-1.90 (2H, m), 2.27-2.34 (2H, m), 2.37-2.54 (5H, m), 2.85 (1H, dt, J=11.5, 2.9 Hz), 3.01-3.16 (2H, m), 3.55-3.64 (2H, m), 3.78 (1H, dt, J=11.0, 2.7 Hz), 3.87-3.98 (2H, m), 5.97-6.02 (1H, m), 7.38 (1H, d, J=2.0 Hz), 8.08 (1H, d, J=2.0 Hz).

Step 4

6-Bromo-1-{2-[(3S)-3-methylmorpholin-4-yl]ethyl}-1,3-dihydro-2H-imidazo[4,5-b]pyridin-2-one The title compound (364 mg) was obtained as a pale yellow amorphous material by the same procedure as in Step 6 of Example 35 using the compound obtained in the above Step 3 (443 mg).

$^1$H-NMR (CDCl$_3$) δ: 0.84 (3H, d, J=6.3 Hz), 2.39-2.52 (3H, m), 2.77-2.86 (1H, m), 2.95-3.08 (1H, m), 3.08-3.17 (1H, m), 3.53-3.64 (2H, m), 3.71-3.80 (1H, m), 3.81-3.94 (2H, m), 7.34-7.41 (1H, m), 8.01-8.08 (1H, m).

Step 5

1-{2-[(3S)-3-Methylmorpholin-4-yl]ethyl}-6-(1H-pyrrolo[2,3-b]pyridin-5-yl)-1,3-dihydro-2H-imidazo[4,5-b]pyridin-2-one The title compound (78 mg) was obtained as a colorless solid by the same procedure as in Step 3 of Example 1 using the compound obtained in the above Step 4 (147 mg) and 5-(4,4,5,5-tetramethyl-1,3,2-dioxaborolan-2-yl)-1H-pyrrolo[2,3-b]pyridine (126 mg).

MS (ESI) m/z: 379 (M+H)$^+$.

HRMS (ESI) [M+H]$^+$ calculated: C$_{20}$H$_{22}$N$_6$O$_2$ 379.18825. found: 379.18744.

$^1$H-NMR (DMSO-d$_6$) δ: 0.75 (3H, d, J=6.1 Hz), 2.27-2.47 (2H, m), 2.87-2.96 (2H, m), 3.02-3.12 (1H, m), 3.34-3.42 (1H, m), 3.49 (2H, dd, J=11.0, 2.8 Hz), 3.61-3.68 (1H, m), 3.86-3.96 (1H, m), 3.97-4.08 (1H, m), 6.49-6.53 (1H, m), 7.53 (1H, t, J=2.9 Hz), 7.86-7.88 (1H, m), 8.22-8.25 (2H, m), 8.54 (1H, d, J=2.0 Hz), 11.56 (1H, br s), 11.73 (1H, br s).

Example 55

1-(2-Morpholin-4-ylethyl)-6-(1H-pyrrolo[2,3-b]pyridin-5-yl)-1,3-dihydro-2H-imidazo[4,5-b]pyridin-2-one

[Formula 75]

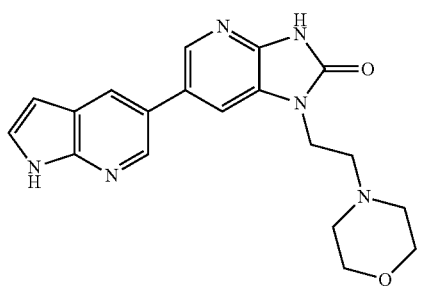

Step 1

6-Bromo-3-cyclohex-1-en-1-yl-1-(2-morpholin-4-ylethyl)-1,3-dihydro-2H-imidazo[4,5-b]pyridin-2-one The title compound (340 mg) was obtained by the same procedure as in Step 3 of Example 35 using the compound obtained in Step 2 of Example 35 (300 mg) and N-(2-hydroxyethyl)morpholine (201 mg).

$^1$H-NMR (CDCl$_3$) δ: 1.71-1.78 (2H, m), 1.83-1.90 (2H, m), 2.27-2.34 (2H, m), 2.39-2.45 (2H, m), 2.53 (4H, t, J=4.6 Hz), 2.68 (2H, t, J=6.4 Hz), 3.67 (4H, t, J=4.6 Hz), 3.97 (2H, t, J=6.4 Hz), 5.99-6.02 (1H, m), 7.39 (1H, d, J=2.0 Hz), 8.08 (1H, d, J=2.0 Hz).

Step 2

3-Cyclohex-1-en-1-yl-1-(2-morpholin-4-ylethyl)-6-(1H-pyrrolo[2,3-b]pyridin-5-yl)-1,3-dihydro-2H-imidazo[4,5-b]pyridin-2-one The title compound (308 mg) was obtained as a pale yellow amorphous material by the same procedure as in Step 3 of Example 1 using the compound obtained in the above Step 1 (325 mg) and 5-(4,4,5,5-tetramethyl-1,3,2-dioxaborolan-2-yl)-1H-pyrrolo[2,3-b]pyridine (234 mg).

$^1$H-NMR (CDCl$_3$) δ: 1.74-1.82 (2H, m), 1.86-1.95 (2H, m), 2.31-2.38 (2H, m), 2.47-2.53 (2H, m), 2.53-2.59 (4H, m), 2.75 (2H, t, J=6.6 Hz), 3.65-3.70 (4H, m), 4.08 (2H, t, J=6.6 Hz), 6.05-6.09 (1H, m), 6.59 (1H, dd, J=3.7, 2.0 Hz), 7.38-7.41 (1H, m), 7.43 (1H, d, J=2.0 Hz), 8.07 (1H, d, J=1.7 Hz), 8.28 (1H, d, J=2.0 Hz), 8.49 (1H, d, J=2.2 Hz), 9.09 (1H, s).

Step 3

1-(2-Morpholin-4-ylethyl)-6-(1H-pyrrolo[2,3-b]pyridin-5-yl)-1,3-dihydro-2H-imidazo[4,5-b]pyridin-2-one The title compound (143 mg) was obtained as a colorless solid by the same procedure as in Step 6 of Example 35 using the compound obtained in the above Step 2 (308 mg).

MS (ESI) m/z: 365 (M+H)$^+$.

HRMS (ESI) [M+H]$^+$ calculated: C$_{19}$H$_{20}$N$_6$O$_2$ 365.17260. found: 365.17207.

$^1$H-NMR (DMSO-d$_6$) δ: 2.44-2.49 (4H, m), 2.63 (2H, t, J=6.3 Hz), 3.48-3.53 (4H, m), 4.00 (2H, t, J=6.2 Hz), 6.51 (1H, d, J=3.4 Hz), 7.51-7.54 (1H, m), 7.87 (1H, s), 8.22-8.25 (2H, m), 8.54 (1H, d, J=2.0 Hz), 11.57 (1H, br s), 11.73 (1H, br s).

Example 56

1-[(1-Methylpiperidin-4-yl)methyl]-6-(1H-pyrrolo[2,3-b]pyridin-5-yl)-1,3-dihydro-2H-imidazo[4,5-b]pyridin-2-one

[Formula 76]

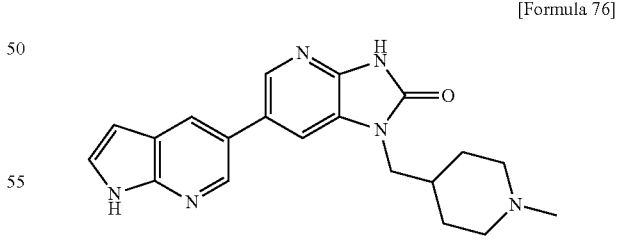

Step 1

6-Bromo-3-cyclohex-1-en-1-yl-1-[(1-methylpiperidin-4-yl)methyl]-1,3-dihydro-2H-imidazo[4,5-b]pyridin-2-one The title compound (126 mg) was obtained by the same procedure as in Step 3 of Example 35 using the compound obtained in Step 2 of Example 35 (200 mg) and (1-methylpiperidin-4-yl)methanol (132 mg).

¹H-NMR (CDCl₃) δ: 1.36-1.50 (2H, m), 1.63-1.96 (9H, m), 2.26-2.34 (2H, m), 2.27 (3H, s), 2.38-2.44 (2H, m), 2.82-2.90 (2H, m), 3.73 (2H, d, J=7.1 Hz), 5.97-6.03 (1H, m), 7.25-7.28 (1H, m), 8.08 (1H, d, J=2.0 Hz).

Step 2

3-Cyclohex-1-en-1-yl-1-[(1-methylpiperidin-4-yl)methyl]-6-(1H-pyrrolo[2,3-b]pyridin-5-yl)-1,3-dihydro-2H-imidazo[4,5-b]pyridin-2-one The title compound (132 mg) was obtained as a pale yellow amorphous material by the same procedure as in Step 3 of Example 1 using the compound obtained in the above Step 1 (126 mg) and 5-(4,4,5,5-tetramethyl-1,3,2-dioxaborolan-2-yl)-1H-pyrrolo[2,3-b]pyridine (91 mg).

¹H-NMR (CDCl₃) δ: 1.40-1.55 (2H, m), 1.69-1.81 (4H, m), 1.84-1.95 (6H, m), 2.25 (3H, s), 2.29-2.38 (2H, m), 2.45-2.52 (2H, m), 2.80-2.89 (2H, m), 3.83 (2H, d, J=6.8 Hz), 6.04-6.09 (1H, m), 6.57-6.61 (1H, m), 7.35 (1H, d, J=1.7 Hz), 7.36-7.40 (1H, m), 8.06 (1H, d, J=2.1 Hz), 8.28 (1H, d, J=2.1 Hz), 8.49 (1H, d, J=2.1 Hz), 8.91 (1H, br s).

Step 3

1-[(1-Methylpiperidin-4-yl)methyl]-6-(1H-pyrrolo[2,3-b]pyridin-5-yl)-1,3-dihydro-2H-imidazo[4,5-b]pyridin-2-one The title compound (50 mg) was obtained as a colorless solid by the same procedure as in Step 6 of Example 35 using the compound obtained in the above Step 2 (132 mg).

MS (ESI) m/z: 363 (M+H)⁺.

HRMS (ESI) [M+H]⁺ calculated: $C_{20}H_{22}N_6O$ 363.19333. found: 363.19277.

¹H-NMR (DMSO-d₆) δ: 1.22-1.39 (2H, m), 1.52-1.62 (2H, m), 1.75-1.91 (3H, m), 2.15 (3H, s), 2.77 (2H, d, J=10.0 Hz), 3.76 (2H, d, J=7.1 Hz), 6.49-6.54 (1H, m), 7.51-7.55 (1H, m), 7.87-7.91 (1H, m), 8.22-8.26 (2H, m), 8.53-8.56 (1H, m), 11.58 (1H, br s), 11.73 (1H, br s).

Example 57

1-[2-piperazin-1-ylethyl]-6-(1H-pyrrolo[2,3-b]pyridin-5-yl)-1,3-dihydro-2H-imidazo[4,5-b]pyridin-2-one

[Formula 77]

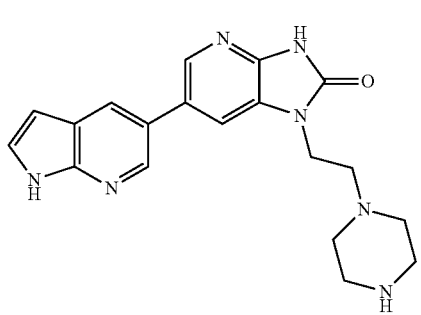

Step 1

1-[2-(4-Acetylpiperazin-1-yl)ethyl]-6-bromo-3-cyclohex-1-en-1-yl-1,3-dihydro-2H-imidazo[4,5-b]pyridin-2-one The title compound (174 mg) was obtained by the same procedure as in Step 3 of Example 35 using the compound obtained in Step 2 of Example 35 (200 mg) and 2-(4-acetylpiperazin-1-yl)ethanol (176 mg).

¹H-NMR (CDCl₃) δ: 1.70-1.78 (2H, m), 1.82-1.90 (2H, m), 2.08 (3H, s), 2.27-2.34 (2H, m), 2.37-2.44 (2H, m), 2.49 (2H, t, J=4.9 Hz), 2.53 (2H, t, J=4.9 Hz), 2.70 (2H, t, J=6.3 Hz), 3.41 (2H, t, J=5.0 Hz), 3.57 (2H, t, J=5.0 Hz), 3.98 (2H, t, J=6.3 Hz), 5.98-6.02 (1H, m), 7.35 (1H, d, J=2.0 Hz), 8.09 (1H, d, J=2.0 Hz).

Step 2

1-[2-(4-Acetylpiperazin-1-yl)ethyl]-3-cyclohex-1-en-1-yl-6-(1H-pyrrolo[2,3-b]pyridin-5-yl)-1,3-dihydro-2H-imidazo[4,5-b]pyridin-2-one The title compound (156 mg) was obtained as a pale yellow amorphous material by the same procedure as in Step 3 of Example 1 using the compound obtained in the above Step 1 (174 mg) and 5-(4,4,5,5-tetramethyl-1,3,2-dioxaborolan-2-yl)-1H-pyrrolo[2,3-b]pyridine (114 mg).

¹H-NMR (CDCl₃) δ: 1.73-1.82 (2H, m), 1.82-1.94 (2H, m), 2.07 (3H, s), 2.30-2.38 (2H, m), 2.45-2.60 (6H, m), 2.77 (2H, t, J=6.5 Hz), 3.42 (2H, t, J=4.9 Hz), 3.58 (2H, t, J=4.9 Hz), 4.09 (2H, t, J=6.5 Hz), 6.04-6.10 (1H, m), 6.59 (1H, dd, J=3.5, 1.8 Hz), 7.40-7.44 (2H, m), 8.08 (1H, d, J=2.0 Hz), 8.30 (1H, d, J=2.0 Hz), 8.50 (1H, d, J=2.0 Hz), 10.04 (1H, br s).

Step 3

1-[2-piperazin-1-ylethyl]-6-(1H-pyrrolo[2,3-b]pyridin-5-yl)-1,3-dihydro-2H-imidazo[4,5-b]pyridin-2-one The title compound (34 mg) was obtained as a colorless solid by the same procedure as in Step 6 of Example 35 using the compound obtained in the above Step 2 (156 mg).

MS (ESI) m/z: 364 (M+H)⁺.

HRMS (ESI) [M+H]⁺ calculated: $C_{21}H_{23}N_7O_2$ 364.18858. found: 364.18800.

¹H-NMR (DMSO-d₆) δ: 2.34-2.45 (4H, m), 2.55-2.67 (6H, m), 3.93-4.02 (2H, m), 6.49-6.53 (1H, m), 7.50-7.56 (1H, m), 7.82-7.87 (1H, m), 8.21-8.26 (2H, m), 8.52-8.57 (1H, m), 11.73 (1H, br s).

Example 58

1-[2-(4-Methylpiperazin-1-yl)ethyl]-6-(1H-pyrrolo[2,3-b]pyridin-5-yl)-1,3-dihydro-2H-imidazo[4,5-b]pyridin-2-one

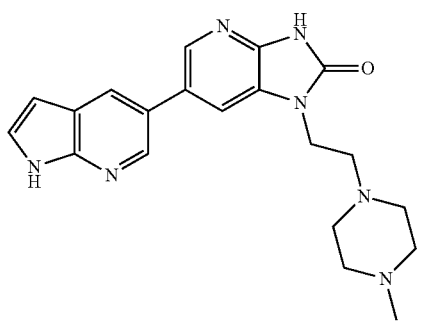

[Formula 78]

Step 1

6-Bromo-3-cyclohex-1-en-1-yl-1-[2-(4-methylpiperazin-1-yl)ethyl]-1,3-dihydro-2H-imidazo[4,5-b]pyridin-2-one The title compound (177 mg) was obtained by the same procedure as in Step 3 of Example 35 using the compound obtained in Step 2 of Example 35 (200 mg) and 2-(4-methylpiperazin-1-yl)ethanol (147 mg).
$^1$H-NMR (CDCl$_3$) δ: 1.70-1.79 (2H, m), 1.81-1.91 (2H, m), 2.25-2.34 (2H, m), 2.28 (3H, s), 2.36-2.48 (6H, m), 2.50-2.62 (4H, m), 2.67 (2H, t, J=6.4 Hz), 3.96 (2H, t, J=6.4 Hz), 5.98-6.02 (1H, m), 7.42 (1H, d, J=2.0 Hz), 8.08 (1H, d, J=2.0 Hz).

Step 2

3-Cyclohex-1-en-1-yl-1-[2-(4-methylpiperazin-1-yl)ethyl]-6-(1H-pyrrolo[2,3-b]pyridin-5-yl)-1,3-dihydro-2H-imidazo[4,5-b]pyridin-2-one The title compound (173 mg) was obtained as a pale yellow amorphous material by the same procedure as in Step 3 of Example 1 using the compound obtained in the above Step 1 (177 mg) and 5-(4,4,5,5-tetramethyl-1,3,2-dioxaborolan-2-yl)-1H-pyrrolo[2,3-b]pyridine (123 mg).
$^1$H-NMR (CDCl$_3$) δ: 1.72-1.81 (2H, m), 1.86-1.94 (2H, m), 2.27 (3H, s), 2.30-2.38 (2H, m), 2.38-2.70 (10H, m), 2.76 (2H, t, J=6.8 Hz), 4.07 (2H, t, J=6.8 Hz), 6.05-6.09 (1H, m), 6.59 (1H, dd, J=3.4, 2.0 Hz), 7.38-7.42 (1H, m), 7.47 (1H, d, J=2.0 Hz), 8.08 (1H, d, J=2.0 Hz), 8.28 (1H, d, J=1.7 Hz), 8.50 (1H, d, J=2.2 Hz), 9.37 (1H, br s).

Step 3

1-[2-(4-Methylpiperazin-1-yl)ethyl]-6-(1H-pyrrolo[2,3-b]pyridin-5-yl)-1,3-dihydro-2H-imidazo[4,5-b]pyridin-2-one The title compound (74 mg) was obtained as a colorless solid by the same procedure as in Step 6 of Example 35 using the compound obtained in the above Step 2 (173 mg).
MS (ESI) m/z: 378 (M+H)$^+$.

HRMS (ESI) [M+H]$^+$ calculated: C$_{20}$H$_{23}$N$_7$O 378.20290. found: 378.20325.
$^1$H-NMR (DMSO-d$_6$) δ: 2.10 (3H, s), 2.17-2.35 (4H, m), 2.62 (2H, t, J=6.2 Hz), 3.28-3.30 (4H, m), 3.97 (2H, t, J=6.2 Hz), 6.49-6.52 (1H, m), 7.51-7.54 (1H, m), 7.85-7.87 (1H, m), 8.23 (2H, dd, J=5.7, 1.8 Hz), 8.54 (1H, d, J=2.0 Hz), 11.55 (1H, br s), 11.73 (1H, br s).

Example 59

1-[2-(4-Acetylpiperazin-1-yl)ethyl]-6-(1H-pyrrolo[2,3-b]pyridin-5-yl)-1,3-dihydro-2H-imidazo[4,5-b]pyridin-2-one

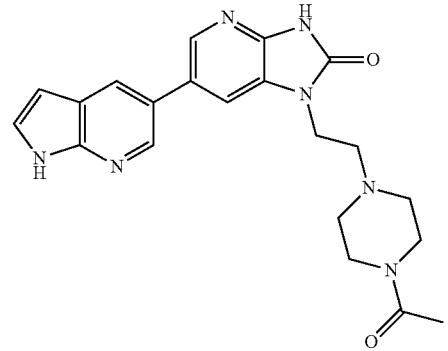

[Formula 79]

Step 1 tert-Butyl 4-[2-(6-bromo-3-cyclohex-1-en-1-yl-2-oxo-2,3-dihydro-1H-imidazo[4,5-b]pyridin-1-yl)-ethyl]piperazine-1-carboxylate The title compound (551 mg) was obtained by the same procedure as in Step 3 of Example 35 using the compound obtained in Step 2 of Example 35 (400 mg) and tert-butyl 4-(2-hydroxyethyl)piperazine-1-carboxylate (468 mg).
$^1$H-NMR (CDCl$_3$) δ: 1.45 (9H, s), 1.70-1.78 (2H, m), 1.82-1.90 (2H, m), 2.27-2.34 (2H, m), 2.38-2.44 (2H, m), 2.44-2.50 (4H, m), 2.68 (2H, t, J=6.5 Hz), 3.36-3.41 (4H, m), 3.97 (2H, t, J=6.5 Hz), 5.98-6.02 (1H, m), 7.37 (1H, d, J=2.0 Hz), 8.08 (1H, d, J=2.0 Hz).

Step 2

6-Bromo-1-(2-piperazin-4-ylethyl]-1,3-dihydro-2H-imidazo[4,5-b]pyridin-2-one

The title compound (249 mg) was obtained as a colorless amorphous material by the same procedure as in Step 6 of Example 35 using the compound obtained in the above Step 1 (551 mg).
$^1$H-NMR (CDCl$_3$) δ: 2.49-2.57 (4H, m), 2.68 (2H, t, J=6.2 Hz), 2.88 (4H, t, J=4.9 Hz), 3.95 (2H, t, J=6.2 Hz), 7.41 (1H, d, J=2.0 Hz), 8.04 (1H, d, J=2.0 Hz).

Step 3

1-[2-(4-Acetylpiperazin-1-yl)ethyl]-6-bromo-1,3-dihydro-2H-imidazo[4,5-b]pyridin-2-one The compound obtained in the above Step 2 (100 mg) was dissolved in chloroform (10 ml). Triethylamine (0.128 ml)

and acetyl chloride (0.026 ml) were added dropwise under ice-cooling, and the mixture was stirred at the same temperature for 30 minutes and then stirred at room temperature for 1.5 hours. The reaction solution was concentrated, and the residue was purified by silica gel column chromatography (developed with methanol-chloroform) to give the title compound (114 mg) as a colorless solid.

$^1$H-NMR (CDCl$_3$) δ: 2.08 (3H, s), 2.52 (2H, t, J=5.1 Hz), 2.57 (2H, t, J=5.0 Hz), 2.72 (2H, t, J=6.2 Hz), 3.44 (2H, t, J=4.8 Hz), 3.60 (2H, t, J=5.0 Hz), 3.98 (2H, t, J=6.2 Hz), 7.37 (1H, d, J=2.0 Hz), 8.08 (1H, d, J=2.0 Hz), 10.70 (1H, br s).

Step 4

1-[2-(4-Acetylpiperazin-1-yl)ethyl]-6-(1H-pyrrolo[2,3-b]pyridin-5-yl)-1,3-dihydro-2H-imidazo[4,5-b]pyridin-2-one The title compound (38 mg) was obtained as a colorless solid by the same procedure as in Step 3 of Example 1 using the compound obtained in the above Step 3 (114 mg) and 5-(4,4,5,5-tetramethyl-1,3,2-dioxaborolan-2-yl)-1H-pyrrolo[2,3-b]pyridine (91 mg).

MS (ESI) m/z: 406 (M+H)$^+$.

HRMS (ESI) [M+H]$^+$ calculated: C$_{21}$H$_{23}$N$_7$O$_2$ 406.19915. found: 406.19850.

$^1$H-NMR (DMSO-d$_6$) δ: 1.96 (3H, s), 2.38-2.50 (4H, m), 2.63-2.71 (2H, m), 3.32-3.38 (4H, m), 3.97-4.05 (2H, m), 6.49-6.53 (1H, m), 7.51-7.55 (1H, m), 7.85-7.90 (1H, m), 8.22-8.27 (2H, m), 8.53-8.57 (1H, m), 11.57 (1H, br s), 11.73 (1H, br s).

Example 60

1-{2-[4-(Methylsulfonyl)piperazin-1-yl]ethyl}-6-(1H-pyrrolo[2,3-b]pyridin-5-yl)-1,3-dihydro-2H-imidazo[4,5-b]pyridin-2-one

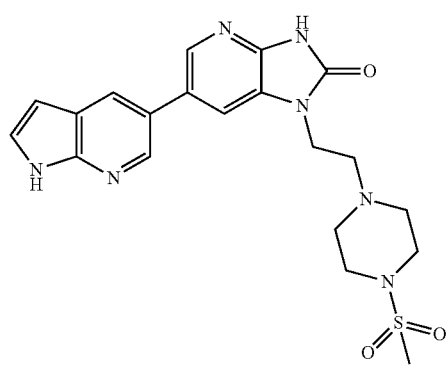

[Formula 80]

Step 1

6-Bromo-1-{2-[4-(methylsulfonyl)piperazin-1-yl]ethyl}-1,3-dihydro-2H-imidazo[4,5-b]pyridin-2-one The compound obtained in Step 2 of Example 59 (100 mg) was dissolved in chloroform (10 ml). Triethylamine (0.128 ml) and methanesulfonyl chloride (0.036 ml) were added dropwise under ice-cooling, and the mixture was stirred at the same temperature for 10 minutes and then stirred at room temperature for 1.5 hours. The reaction solution was concentrated, and the residue was purified by silica gel column chromatography (developed with methanol-chloroform) to give the title compound (82 mg) as a colorless solid.

$^1$H-NMR (CD$_3$OD) δ: 2.63 (4H, t, J=4.9 Hz), 2.74 (2H, t, J=6.1 Hz), 2.80 (3H, s), 3.15 (4H, t, J=4.9 Hz), 4.02 (2H, t, J=6.1 Hz), 7.71-7.73 (1H, m), 7.88 (1H, br s), 8.02 (1H, d, J=2.0 Hz).

Step 2

1-{2-[4-(Methylsulfonyl)piperazin-1-yl]ethyl}-6-(1H-pyrrolo[2,3-b]pyridin-5-yl)-1,3-dihydro-2H-imidazo[4,5-b]pyridin-2-one The title compound (68 mg) was obtained as a colorless solid by the same procedure as in Step 3 of Example 1 using the compound obtained in the above Step 1 (82 mg) and 5-(4,4,5,5-tetramethyl-1,3,2-dioxaborolan-2-yl)-1H-pyrrolo[2,3-b]pyridine (59 mg).

MS (ESI) m/z: 442 (M+H)$^+$.

HRMS (ESI) [M+H]$^+$ calculated: C$_{20}$H$_{23}$N$_7$O$_3$S 442.16613. found: 442.16415.

$^1$H-NMR (DMSO-d$_6$) δ: 2.55-2.62 (4H, m), 2.68-2.75 (2H, m), 2.80 (3H, s), 3.00-3.07 (4H, m), 3.97-4.04 (2H, m), 6.49-6.53 (1H, m), 7.53 (1H, t, J=2.7 Hz), 7.86-7.90 (1H, m), 8.22-8.26 (2H, m), 8.54-8.56 (1H, m), 11.57 (1H, br s), 11.73 (1H, br s).

Example 61

1-{[trans-4-Hydroxytetrahydrofuran-3-yl]methyl}-3-cyclohex-1-en-1-yl-6-(1H-pyrrolo[2,3-b]pyridin-5-yl)-1,3-dihydro-2H-imidazo[4,5-b]pyridin-2-one

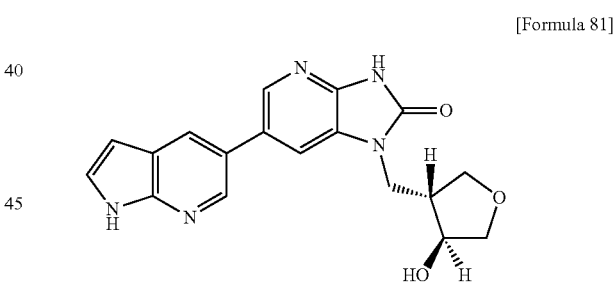

[Formula 81]

and an enantiomer thereof

Step 1

Methyl 4-oxotetrahydrofuran-3-carboxylate

55% Sodium hydride (1.9 g) was suspended in tetrahydrofuran (30 ml), and a solution of methyl glycolate (3.6 g) in tetrahydrofuran (10 ml) was added dropwise over 10 minutes. After stirring at room temperature for 30 minutes, the solvent was evaporated to give a colorless solid. This was suspended in dimethyl sulfoxide (20 ml), and methyl acrylate (4.3 ml) was added under ice-cooling. The mixture was stirred at the same temperature for 15 minutes and then stirred at room temperature for 45 minutes. The reaction solution was poured into a 5% aqueous sulfuric acid solution (50 ml), followed by extraction with ethyl acetate. The organic layer was washed with brine and then dried over anhydrous sodium sulfate, and the solvent was evaporated. The residue was purified by silica gel column chromatography (developed with ethyl acetate-hexane) to give the title compound (3.0 g) as a colorless solid.

$^1$H-NMR (CDCl$_3$) δ: 3.54 (1H, t, J=8.3 Hz), 3.79 (3H, s), 3.97 (1H, d, J=17.1 Hz), 4.05 (1H, d, J=17.1 Hz), 4.43-4.54 (2H, m).

Step 2

Methyl 4-hydroxytetrahydrofuran-3-carboxylate

The compound obtained in the above Step 1 (1.6 g) was dissolved in methanol (150 ml). Sodium borohydride (0.6 g) was added under ice-cooling and the mixture was stirred at the same temperature for 2 hours. Water was added to the reaction solution, followed by extraction with chloroform. The organic layer was washed with brine and then dried over anhydrous sodium sulfate, and the solvent was evaporated to give the title compound (1.3 g).

Step 3

Methyl trans-4-{[tert-butyl(dimethyl)silyl]oxy}tetrahydrofuran-3-carboxylate

Methyl cis-4-{[tert-butyl(dimethyl)silyl]oxy}tetrahydrofuran-3-carboxylate

The compound obtained in the above Step 2 (1.3 g) was dissolved in N,N-dimethylformamide (10 ml). Imidazole (1.2 g) and tert-butyldimethylsilyl chloride (1.7 g) were added and the mixture was stirred at room temperature for 17 hours. Water was added, followed by extraction with ethyl acetate. The organic layer was washed with water and brine and then dried over anhydrous sodium sulfate, and the solvent was evaporated. The residue was separated and purified by silica gel column chromatography (developed with ethyl acetate-hexane) to give the title compound trans isomer (0.6 g) and cis isomer (1.4 g) as colorless oils, respectively.

trans isomer $^1$H-NMR (CDCl$_3$) δ: 0.07 (3H, s), 0.08 (3H, s), 0.88 (9H, s), 2.95-3.01 (1H, m), 3.62 (1H, dd, J=9.0, 3.7 Hz), 3.72 (3H, s), 3.91-4.00 (2H, m), 4.14 (1H, t, J=8.3 Hz), 4.63-4.68 (1H, m).

cis isomer $^1$H-NMR (CDCl$_3$) δ: 0.05 (3H, s), 0.06 (3H, s), 0.86 (9H, s), 3.07-3.15 (1H, m), 3.70 (3H, s), 3.72 (1H, d, J=2.4 Hz), 3.94 (1H, dd, J=9.4, 4.3 Hz), 4.01 (1H, t, J=8.3 Hz), 4.20 (1H, t, J=9.0 Hz), 4.59-4.64 (1H, m).

Step 4

[trans-4-{[tert-Butyl(dimethyl)silyl]oxy}tetrahydrofuran-3-yl]methanol

The title compound (0.16 g) was obtained as a colorless oil by the same procedure as in Step 2 of Example 33 using the compound obtained in the above Step 3 (0.59 g).

$^1$H-NMR (CDCl$_3$) δ: 0.07 (3H, s), 0.08 (3H, s), 0.89 (9H, s), 1.77 (1H, br s), 2.24-2.35 (1H, m), 3.54-3.69 (4H, m), 3.93 (1H, dd, J=9.1, 5.2 Hz), 4.03 (1H, dd, J=8.8, 6.8 Hz), 4.21-4.27 (1H, m).

Step 5

6-Bromo-1-{[trans-4-{[tert-butyl(dimethyl)silyl]oxy}tetrahydrofuran-3-yl]methyl}-3-cyclohex-1-en-1-yl-1,3-dihydro-2H-imidazo[4,5-b]pyridin-2-one The title compound (229 mg) was obtained by the same procedure as in Step 3 of Example 35 using the compound obtained in Step 2 of Example 35 (200 mg) and the compound obtained in the above Step 4 (160 mg).

$^1$H-NMR (CDCl$_3$) δ: −0.10 (3H, s), −0.06 (3H, s), 0.80 (9H, s), 1.71-1.79 (2H, m), 1.83-1.91 (2H, m), 2.28-2.34 (2H, m), 2.38-2.45 (2H, m), 2.57-2.66 (1H, m), 3.60-3.71 (3H, m), 3.92 (1H, dd, J=14.4, 9.0 Hz), 4.01 (1H, dd, J=9.3, 6.1 Hz), 4.13 (1H, dd, J=9.3, 5.1 Hz), 4.20-4.24 (1H, m), 5.98-6.01 (1H, m), 7.32 (1H, d, J=2.0 Hz), 8.11 (1H, d, J=2.0 Hz).

Step 6

1-{[trans-4-{[tert-Butyl(dimethyl)silyl]oxy}tetrahydrofuran-3-yl]methyl}-3-cyclohex-1-en-1-yl-6-(1H-pyrrolo[2,3-b]pyridin-5-yl)-1,3-dihydro-2H-imidazo[4,5-b]pyridin-2-one The title compound (191 mg) was obtained as a pale yellow amorphous material by the same procedure as in Step 3 of Example 1 using the compound obtained in the above Step 5 (229 mg) and 5-(4,4,5,5-tetramethyl-1,3,2-dioxaborolan-2-yl)-1H-pyrrolo[2,3-b]pyridine (165 mg).

$^1$H-NMR (CDCl$_3$) δ: −0.09 (3H, s), −0.06 (3H, s), 0.78 (9H, s), 1.74-1.82 (2H, m), 1.86-1.95 (2H, m), 2.31-2.38 (2H, m), 2.46-2.54 (2H, m), 2.67-2.76 (1H, m), 3.65 (1H, dd, J=9.3, 2.9 Hz), 3.73-3.82 (2H, m), 3.98-4.08 (2H, m), 4.17 (1H, dd, J=9.3, 5.1 Hz), 4.26-4.30 (1H, m), 6.05-6.10 (1H, m), 6.60 (1H, dd, J=3.4, 2.0 Hz), 7.42 (1H, d, J=1.7 Hz), 7.44-7.47 (1H, m), 8.09 (1H, d, J=2.0 Hz), 8.33 (1H, d, J=1.7 Hz), 8.51 (1H, d, J=2.0 Hz), 10.48 (1H, br s).

Step 7

1-{[trans-4-Hydroxytetrahydrofuran-3-yl]methyl}-3-cyclohex-1-en-1-yl-6-(1H-pyrrolo[2,3-b]pyridin-5-yl)-1,3-dihydro-2H-imidazo[4,5-b]pyridin-2-one The title compound (61 mg) was obtained as a pale brown powder by the same procedure as in Step 6 of Example 35 using the compound obtained in the above Step 6 (191 mg).

MS (ESI) m/z: 352 (M+H)$^+$.

HRMS (ESI) [M+H]$^+$ calculated: C$_{18}$H$_{17}$N$_5$O$_3$ 352.14096. found: 352.14065.

$^1$H-NMR (DMSO-d$_6$) δ: 3.44-3.50 (1H, m), 3.55 (1H, dd, J=8.7, 3.8 Hz), 3.69-3.97 (5H, m), 4.05-4.13 (1H, m), 4.94-4.99 (1H, m), 6.51 (1H, d, J=2.7 Hz), 7.52 (1H, d, J=2.9 Hz), 7.80-7.87 (1H, m), 8.22-8.25 (2H, m), 8.54 (1H, d, J=2.0 Hz), 11.73 (1H, br s).

Example 62

1-{[cis-4-Hydroxytetrahydrofuran-3-yl]methyl}-3-cyclohex-1-en-1-yl-6-(1H-pyrrolo[2,3-b]pyridin-5-yl)-1,3-dihydro-2H-imidazo[4,5-b]pyridin-2-one

[Formula 82]

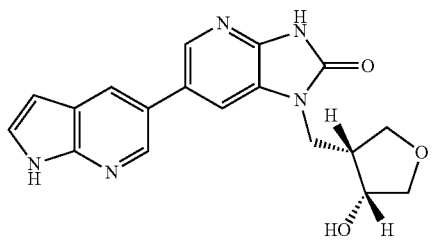

and an enantiomer thereof.

Step 1 cis-4-(Hydroxymethyl)tetrahydrofuran-3-ol

The title compound (0.17 g) was obtained as a colorless oil by the same procedure as in Step 2 of Example 33 using the compound obtained in Step 3 of Example 61 (0.42 g).
$^1$H-NMR (CDCl$_3$) δ: 2.37-2.47 (1H, m), 3.61-3.95 (7H, m), 4.21 (1H, br s), 4.45-4.50 (1H, m).

Step 2 cis-4-({[tert-Butyl(diphenyl)silyl]oxy}methyl)tetrahydrofuran-3-yl]methyl}tetrahydrofuran-3-ol The compound obtained in the above Step 1 (0.39 g) was dissolved in dichloromethane (20 ml). Triethylamine (0.92 ml), dimethylaminopyridine (0.04 g) and tert-butyldiphenylsilyl chloride (1.02 ml) were added under ice-cooling, and the mixture was stirred at room temperature for 65 hours. Water was added to the reaction solution, followed by extraction with chloroform. The organic layer was washed with brine and then dried over anhydrous sodium sulfate, and the solvent was evaporated. The residue was purified by silica gel column chromatography (developed with ethyl acetate-hexane) to give the title compound (1.0 g) as a colorless oil.
$^1$H-NMR (CDCl$_3$) δ: 1.07 (9H, s), 2.37-2.48 (1H, m), 2.85-2.93 (1H, m), 3.67 (1H, t, J=8.8 Hz), 3.77-3.86 (2H, m), 3.86-3.94 (3H, m), 4.46-4.52 (1H, m), 7.36-7.47 (6H, m), 7.64-7.69 (4H, m).

Step 3 tert-Butyl(diphenyl){[cis-4-(tetra-2H-pyran-2-yloxy)tetrahydrofuran-3-yl]methoxy}silane The compound obtained in the above Step 2 (149 mg) was dissolved in dichloromethane (10 ml). 3,4-Dihydro-2H-pyran (0.11 ml) and p-toluenesulfonic acid (14 mg) were added and the mixture was stirred at room temperature for 21 hours. A saturated aqueous sodium bicarbonate solution was added to the reaction solution, followed by extraction with chloroform. The organic layer was washed with brine and then dried over anhydrous sodium sulfate, and the solvent was evaporated. The residue was purified by silica gel column chromatography (developed with ethyl acetate-hexane) to give the title compound (126 mg) as a colorless oil.
$^1$H-NMR (CDCl$_3$) δ: 1.05 (9H, s), 1.34-1.81 (6H, m), 2.43-2.61 (1H, m), 3.36-3.51 (1H, m), 3.56-4.10 (7H, m), 4.33-4.46 (1H, m), 4.62-4.68 (1H, m), 7.34-7.46 (6H, m), 7.62-7.70 (4H, m).

Step 4

[cis-4-(Tetra-2H-pyran-2-yloxy)tetrahydrofuran-3-yl]methanol

The compound obtained in the above Step 3 (126 mg) was dissolved in tetrahydrofuran (5 ml). Tetrabutylammonium fluoride (1.0 M solution in tetrahydrofuran) (0.32 ml) was added and the mixture was stirred at room temperature for one hour. A saturated aqueous sodium bicarbonate solution was added to the reaction solution, followed by extraction with ethyl acetate. The organic layer was washed with brine and then dried over anhydrous sodium sulfate, and the solvent was evaporated. The residue was purified by silica gel column chromatography (developed with methanol-chloroform) to give the title compound (49 mg) as a colorless oil.
$^1$H-NMR (CDCl$_3$) δ: 1.49-1.66 (4H, m), 1.70-1.87 (2H, m), 2.43-2.62 (1.5H, m), 3.48-3.58 (1.5H, m), 3.59-4.01 (7H, m), 4.36-4.43 (0.5H, m), 4.45-4.54 (1H, m), 4.70-4.74 (0.5H, m).

Step 5

6-Bromo-3-cyclohex-1-en-1-yl-1-{[cis-4-(tetra-2H-pyran-2-yloxy)tetrahydrofuran-3-yl]methyl}-1,3-dihydro-2H-imidazo[4,5-b]pyridin-2-one The title compound (91 mg) was obtained by the same procedure as in Step 3 of Example 35 using the compound obtained in Step 2 of Example 35 (71 mg) and the compound obtained in the above Step 4 (49 mg).
$^1$H-NMR (CDCl$_3$) δ: 1.46-1.95 (10H, m), 2.26-2.38 (2H, m), 2.36-2.49 (2H, m), 2.76-2.89 (1H, m), 3.42-3.56 (1H, m), 3.74-4.16 (6H, m), 4.24-4.33 (0.5H, m), 4.45-4.50 (0.5H, m), 4.52-4.58 (0.5H, m), 4.64 (0.5H, dd, J=4.9, 2.7 Hz), 5.98-6.05 (1H, m), 7.36 (0.5H, d, J=2.0 Hz), 7.46 (0.5H, d, J=2.0 Hz), 7.56 (0.5H, d, J=2.0 Hz), 8.06-8.10 (1H, m), 8.11 (0.5H, d, J=2.0 Hz).

Step 6

3-Cyclohex-1-en-1-yl-1-{[cis-4-(tetra-2H-pyran-2-yloxy)tetrahydrofuran-3-yl]methyl}-6-(1H-pyrrolo[2,3-b]pyridin-5-yl)-1,3-dihydro-2H-imidazo[4,5-b]pyridin-2-one The title compound (82 mg) was obtained as a pale yellow oil by the same procedure as in Step 3 of Example 1 using the compound obtained in the above Step 5 (91 mg) and 5-(4,4,5,5-tetramethyl-1,3,2-dioxaborolan-2-yl)-1H-pyrrolo[2,3-b]pyridine (69 mg).
$^1$H-NMR (CDCl$_3$) δ: 1.30-1.66 (4H, m), 1.67-1.84 (4H, m), 1.86-1.95 (2H, m), 2.30-2.38 (2H, m), 2.46-2.54 (2H, m), 2.84-2.96 (1H, m), 3.39-3.55 (1H, m), 3.70-3.78 (0.5H, m), 3.79-4.08 (5.0H, m), 4.11-4.39 (2H, m), 4.51-4.56 (0.5H, m), 4.56-4.60 (0.5H, m), 4.65-4.69 (0.5H, m), 6.06-6.10 (1H, m), 6.58-6.61 (1H, m), 7.41-7.45 (1.5H, m), 7.57 (0.5H, d, J=2.0 Hz), 8.07-8.12 (1H, m), 8.30 (1H, t, J=2.2 Hz), 8.49-8.55 (1H, m), 9.83-9.92 (1H, m).

Step 7

1-{[cis-4-Hydroxytetrahydrofuran-3-yl]methyl}-3-cyclohex-1-en-1-yl-6-(1H-pyrrolo[2,3-b]pyridin-5-yl)-1,3-dihydro-2H-imidazo[4,5-b]pyridin-2-one The title compound (22 mg) was obtained as a pale brown powder by the same procedure as in Step 6 of Example 35 using the compound obtained in the above Step 6 (82 mg).
MS (ESI) m/z: 352 (M+H)$^+$.
HRMS (ESI) [M+H]$^+$ calculated: $C_{18}H_{17}N_5O_3$ 352.14096. found: 352.14081.
$^1$H-NMR (DMSO-$d_6$) δ: 2.53-2.64 (1H, m), 3.56-3.66 (2H, m), 3.73-3.81 (2H, m), 3.94-4.06 (2H, m), 4.15-4.21 (1H, m), 5.17-5.27 (1H, m), 6.51 (1H, d, J=3.4 Hz), 7.50-7.54 (1H, m), 7.86-7.89 (1H, m), 8.24 (2H, d, J=2.0 Hz), 8.54 (1H, d, J=2.0 Hz), 11.66 (1H, br s), 11.73 (1H, br s).

Example 63

1-{[cis-4-Methoxytetrahydrofuran-3-yl]methyl}-3-cyclohex-1-en-1-yl-6-(1H-pyrrolo[2,3-b]pyridin-5-yl)-1,3-dihydro-2H-imidazo[4,5-b]pyridin-2-one

[Formula 83]

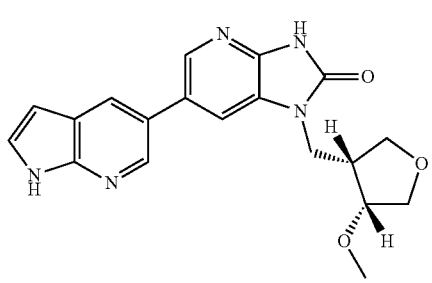

and an enantiomer thereof

Step 1 tert-Butyl{[cis-4-methoxytetrahydrofuran-3-yl]methoxy}diphenylsilane cis-4-({[tert-Butyl(diphenyl)silyl]oxy}methyl)tetrahydrofuran-3-yl]methyl}tetrahydrofuran-3-ol obtained in Step 2 of Example 62 (0.93 g) was dissolved in tetrahydrofuran (30 ml). 55% Sodium hydride (228 mg) was added under nitrogen atmosphere at 0° C. and the mixture was stirred at the same temperature for five minutes and then stirred at room temperature for 30 minutes. Methyl iodide (1.62 ml) was added and the mixture was stirred at room temperature for 15 hours. Water was added under ice-cooling and then tetrahydrofuran was distilled off. The residue was extracted with ethyl acetate. The organic layer was washed with brine and then dried over anhydrous sodium sulfate, and the solvent was evaporated. The residue was purified by silica gel column chromatography (developed with ethyl acetate-hexane) to give the title compound (0.91 g) as a colorless solid.
$^1$H-NMR (CDCl$_3$) δ: 1.05 (9H, s), 2.47-2.58 (1H, m), 3.27 (3H, s), 3.59-3.65 (1H, m), 3.72 (1H, dd, J=10.0, 7.3 Hz), 3.79 (1H, dd, J=10.0, 4.2 Hz), 3.88-3.99 (4H, m), 7.34-7.45 (6H, m), 7.64-7.71 (4H, m).

Step 2

[cis-4-Methoxytetrahydrofuran-3-yl]methanol

The title compound (171 mg) was obtained as a colorless oil by the same procedure as in Step 4 of Example 11 using the compound obtained in the above Step 1 (0.91 g).
$^1$H-NMR (CDCl$_3$) δ: 2.42-2.54 (1H, m), 2.75 (1H, br s), 3.37 (3H, s), 3.76-3.96 (6H, m), 4.01-4.09 (1H, m).

Step 3

6-Bromo-3-cyclohex-1-en-1-yl-1-{[cis-4-methoxytetrahydrofuran-3-yl]methyl}-1,3-dihydro-2H-imidazo[4,5-b]pyridin-2-one The title compound (334 mg) was obtained by the same procedure as in Step 3 of Example 35 using the compound obtained in Step 2 of Example 35 (250 mg) and the compound obtained in the above Step 2 (169 mg).
$^1$H-NMR (CDCl$_3$) δ: 1.68-1.79 (2H, m), 1.83-1.91 (2H, m), 2.27-2.35 (2H, m), 2.38-2.46 (2H, m), 2.78-2.89 (1H, m), 3.31 (3H, s), 3.65-3.78 (3H, m), 3.91-4.07 (4H, m), 5.99-6.04 (1H, m), 7.47 (1H, d, J=1.2 Hz), 8.09 (1H, t, J=1.0 Hz).

Step 4

3-Cyclohex-1-en-1-yl-1-{[cis-4-methoxytetrahydrofuran-3-yl]methyl}-6-(1H-pyrrolo[2,3-b]pyridin-5-yl)-1,3-dihydro-2H-imidazo[4,5-b]pyridin-2-one The title compound (246 mg) was obtained as a pale orange amorphous material by the same procedure as in Step 3 of Example 1 using the compound obtained in the above Step 3 (334 mg) and 5-(4,4,5,5-tetramethyl-1,3,2-dioxaborolan-2-yl)-1H-pyrrolo[2,3-b]pyridine (240 mg).
$^1$H-NMR (CDCl$_3$) δ: 1.73-1.81 (2H, m), 1.86-1.94 (2H, m), 2.30-2.38 (2H, m), 2.48-2.54 (2H, m), 2.89-3.00 (1H, m), 3.29 (3H, s), 3.73-3.81 (2H, m), 3.81-3.86 (1H, m), 3.98-4.07 (3H, m), 4.18 (1H, dd, J=14.3, 7.9 Hz), 6.07-6.11 (1H, m), 6.60 (1H, dd, J=3.5, 1.8 Hz), 7.43-7.47 (1H, m), 7.55 (1H, d, J=2.0 Hz), 8.12 (1H, d, J=2.0 Hz), 8.32 (1H, d, J=2.0 Hz), 8.54 (1H, d, J=2.2 Hz), 10.58 (1H, br s).

Step 5

1-{[cis-4-Methoxytetrahydrofuran-3-yl]methyl}-3-cyclohex-1-en-1-yl-6-(1H-pyrrolo[2,3-b]pyridin-5-yl)-1,3-dihydro-2H-imidazo[4,5-b]pyridin-2-one The title compound (50 mg) was obtained as a colorless powder by the same procedure as in Step 6 of Example 35 using the compound obtained in the above Step 4 (246 mg).
MS (ESI) m/z: 366 (M+H)$^+$.
HRMS (ESI) [M+H]$^+$ calculated: $C_{19}H_{19}N_5O_3$ 366.15661. found: 366.15583.
$^1$H-NMR (DMSO-$d_6$) δ: 2.73-2.85 (1H, m), 3.23 (3H, s), 3.58 (1H, t, J=8.9 Hz), 3.67 (1H, dd, J=9.6, 3.5 Hz), 3.76 (1H, t, J=7.8 Hz), 3.83-3.91 (2H, m), 3.97 (1H, dd, J=14.0, 8.4 Hz), 4.07 (1H, dd, J=14.5, 6.5 Hz), 6.51 (1H, d, J=3.4 Hz), 7.52 (1H, t, J=2.7 Hz), 7.81-7.84 (1H, m), 8.22-8.26 (2H, m), 8.55 (1H, d, J=2.0 Hz), 11.60 (1H, br s), 11.73 (1H, br s).

Example 64

1-{[trans-4-Methoxytetrahydrofuran-3-yl]methyl}-6-(1H-pyrrolo[2,3-b]pyridin-5-yl)-1,3-dihydro-2H-imidazo[4,5-b]pyridin-2-one

[Formula 84]

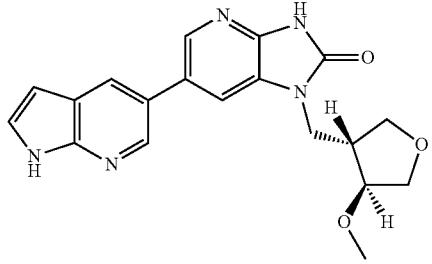

and an enantiomer thereof

Step 1 trans-4-(Hydroxymethyl)tetrahydrofuran-3-ol

The title compound (0.30 g) was obtained as a colorless oil by the same procedure as in Step 2 of Example 33 using the compound obtained in Step 3 of Example 61 (0.89 g).

$^1$H-NMR (CDCl$_3$) δ: 1.66-1.72 (1H, m), 2.31-2.42 (1H, m), 3.55-3.74 (4H, m), 3.87 (1H, t, J=5.6 Hz), 3.94 (1H, dd, J=9.8, 5.1 Hz), 4.09 (1H, dd, J=8.8, 7.3 Hz), 4.33 (1H, br s).

Step 2 trans-4-({[tert-Butyl(diphenyl)silyl]oxy}methyl)tetrahydrofuran-3-yl]methyl}tetrahydrofuran-3-ol The title compound (0.39 g) was obtained as a colorless oil by the same procedure as in Step 2 of Example 62 using the compound obtained in the above Step 1 (0.30 g).

$^1$H-NMR (CDCl$_3$) δ: 1.06 (9H, s), 2.19 (1H, br s), 2.34-2.43 (1H, m), 3.55-3.63 (2H, m), 3.64-3.70 (2H, m), 3.82 (1H, dd, J=9.6, 5.0 Hz), 4.04 (1H, dd, J=8.8, 7.6 Hz), 4.27-4.33 (1H, m), 7.36-7.46 (6H, m), 7.62-7.68 (4H, m).

Step 3 tert-Butyl{[trans-4-methoxytetrahydrofuran-3-yl]methoxy}diphenylsilane

The title compound (0.35 g) was obtained as a colorless oil by the same procedure as in Step 1 of Example 63 using the compound obtained in the above Step 2 (0.39 g).

$^1$H-NMR (CDCl$_3$) δ: 1.06 (9H, s), 2.40-2.50 (1H, m), 3.29 (3H, s), 3.52-3.67 (3H, m), 3.73-3.84 (3H, m), 3.97 (1H, dd, J=8.9, 7.0 Hz), 7.34-7.47 (6H, m), 7.60-7.68 (4H, m).

Step 4

[trans-4-Methoxytetrahydrofuran-3-yl]methanol

The title compound (0.075 g) was obtained as a colorless oil by the same procedure as in Step 4 of Example 62 using the compound obtained in the above Step 3 (0.35 g).

$^1$H-NMR (CDCl$_3$) δ: 1.25 (1H, br s), 2.38-2.47 (1H, m), 3.34 (3H, s), 3.59-3.67 (3H, m), 3.78 (1H, dd, J=9.8, 2.7 Hz), 3.81-3.85 (1H, m), 3.91 (1H, dd, J=9.5, 5.1 Hz), 4.00 (1H, dd, J=9.0, 6.8 Hz).

Step 5

6-Bromo-3-cyclohex-1-en-1-yl-1-{[trans-4-methoxytetrahydrofuran-3-yl]methyl}-1,3-dihydro-2H-imidazo[4,5-b]pyridin-2-one The title compound (118 mg) was obtained by the same procedure as in Step 3 of Example 35 using the compound obtained in Step 2 of Example 35 (166 mg) and [trans-4-methoxytetrahydrofuran-3-yl]methanol obtained in the above Step 4 (75 mg).

$^1$H-NMR (CDCl$_3$) δ: 1.70-1.79 (2H, m), 1.82-1.91 (2H, m), 2.28-2.34 (2H, m), 2.37-2.45 (2H, m), 2.68-2.78 (1H, m), 3.21 (3H, s), 3.62-3.75 (2H, m), 3.78 (1H, dd, J=9.9, 3.1 Hz), 3.81-3.85 (1H, m), 3.91-4.00 (2H, m), 4.09 (1H, dd, J=9.9, 5.2 Hz), 5.98-6.03 (1H, m), 7.35 (1H, d, J=2.0 Hz), 8.12 (1H, d, J=2.0 Hz).

Step 6

3-Cyclohex-1-en-1-yl-1-{[trans-4-methoxytetrahydrofuran-3-yl]methyl}-6-(1H-pyrrolo[2,3-b]pyridin-5-yl)-1,3-dihydro-2H-imidazo[4,5-b]pyridin-2-one The title compound (102 mg) was obtained as a pale yellow solid by the same procedure as in Step 3 of Example 1 using the compound obtained in the above Step 5 (119 mg) and 5-(4,4,5,5-tetramethyl-1,3,2-dioxaborolan-2-yl)-1H-pyrrolo[2,3-b]pyridine (197 mg).

$^1$H-NMR (CDCl$_3$) δ: 1.73-1.82 (2H, m), 1.87-1.95 (2H, m), 2.31-2.38 (2H, m), 2.46-2.53 (2H, m), 2.79-2.87 (1H, m), 3.22 (3H, s), 3.72 (1H, dd, J=9.0, 3.7 Hz), 3.77-3.86 (2H, m), 3.87-3.92 (1H, m), 3.97-4.09 (2H, m), 4.12 (1H, dd, J=10.0, 5.1 Hz), 6.06-6.10 (1H, m), 6.60 (1H, dd, J=3.5, 1.8 Hz), 7.41-7.44 (2H, m), 8.09 (1H, d, J=2.0 Hz), 8.32 (1H, d, J=2.0 Hz), 8.51 (1H, d, J=2.0 Hz), 9.84 (1H, br s).

Step 7

1-{[trans-4-Methoxytetrahydrofuran-3-yl]methyl}-6-(1H-pyrrolo[2,3-b]pyridin-5-yl)-1,3-dihydro-2H-imidazo[4,5-b]pyridin-2-one The title compound (26 mg) was obtained as a pale orange powder by the same procedure as in Step 6 of Example 35 using the compound obtained in the above Step 6 (102 mg).

MS (ESI) m/z: 366 (M+H)$^+$.

HRMS (ESI) [M+H]$^+$ calculated: C$_{19}$H$_{19}$N$_5$O$_3$ 366.15661. found: 366.15599.

$^1$H-NMR (DMSO-d$_6$) δ: 2.70-2.79 (1H, m), 3.03 (3H, s), 3.54 (1H, dd, J=9.0, 4.2 Hz), 3.66 (1H, dd, J=9.8, 2.2 Hz), 3.79-3.95 (5H, m), 6.51 (1H, dd, J=3.4, 1.7 Hz), 7.51-7.54 (1H, m), 7.96 (1H, d, J=2.0 Hz), 8.24-8.28 (2H, m), 8.56 (1H, d, J=2.2 Hz), 11.67 (1H, br s), 11.74 (1H, br s).

Example 65

1-{[cis-5-Hydroxytetrahydro-2H-pyran-3-yl]methyl}-6-(1H-pyrrolo[2,3-b]pyridin-5-yl)-1,3-dihydro-2H-imidazo[4,5-b]pyridin-2-one

[Formula 85]

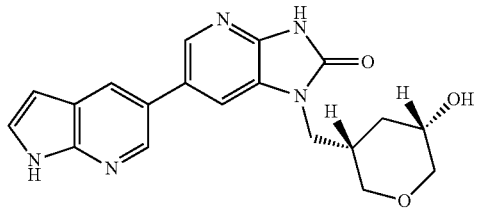

and an enantiomer thereof

Step 1

Methyl 4-anilino-2,5-dihydrofuran-3-carboxylate

The compound obtained in Step 1 of Example 61 (1.0 g) was dissolved in toluene (20 ml). Aniline (0.76 ml) and p-toluenesulfonic acid (0.011 g) were added and the mixture was heated under reflux while dehydrating for 17 hours. After cooling, the solvent was evaporated. The residue was purified by silica gel column chromatography (developed with ethyl acetate-hexane) to give the title compound (1.2 g) as a pale yellow solid.

$^1$H-NMR (CDCl$_3$) δ: 3.76 (3H, s), 4.80 (2H, t, J=3.2 Hz), 4.95 (2H, t, J=3.2 Hz), 6.93 (2H, d, J=8.3 Hz), 7.08 (1H, t, J=7.3 Hz), 7.30 (2H, t, J=7.9 Hz), 9.10 (1H, br s).

Step 2

Methyl (4Z)-3-(iodomethyl)-4-(phenylimino)tetrahydrofuran-3-carboxylate

Potassium tert-butoxide (5.2 g) was suspended in benzene (40 ml). A solution of the compound obtained in the above Step 1 (8.5 g) and 18-crown-6 (12.3 g) in benzene (40 ml) was added under nitrogen atmosphere, and the mixture was stirred at room temperature for 30 minutes. Subsequently, diiodomethane (9.4 ml) was added and the mixture was stirred at room temperature for 24 hours. The reaction solution was diluted with ethyl acetate, washed with a 5% aqueous sodium thiosulfate solution and brine and then dried over anhydrous sodium sulfate, and the solvent was evaporated. The residue was purified by silica gel column chromatography (developed with ethyl acetate-hexane) to give the title compound (3.5 g) as a pale yellow solid.

$^1$H-NMR (CDCl$_3$) δ: 3.61 (1H, d, J=10.1 Hz), 3.79 (1H, d, J=10.1 Hz), 3.85 (3H, s), 4.17 (1H, d, J=9.9 Hz), 4.19 (1H, d, J=16.0 Hz), 4.28 (1H, d, J=16.0 Hz), 4.60 (1H, d, J=9.9 Hz), 6.78-6.83 (2H, m), 7.11-7.16 (1H, m), 7.29-7.35 (2H, m).

Step 3

Methyl 5-oxotetrahydro-2H-pyran-3-carboxylate

The compound obtained in the above Step 2 (3.5 g) was dissolved in benzene (300 ml). A solution of tri-n-butyltin hydride (3.9 ml) and azobisisobutyronitrile (0.3 g) in benzene (300 ml) was added dropwise with heating under reflux under nitrogen atmosphere over 6 hours. The mixture was further heated under reflux for 2 hours. After cooling, the solvent was evaporated. The residue was diluted with chloroform, washed with a 10% aqueous potassium fluoride solution and brine and then dried over anhydrous sodium sulfate, and the solvent was evaporated. The residue was purified by silica gel column chromatography (developed with ethyl acetate-hexane) to give the title compound (1.3 g) as a pale yellow oil.

$^1$H-NMR (CDCl$_3$) δ: 2.69 (1H, dd, J=17.0, 6.2 Hz), 2.84 (1H, dd, J=17.1, 7.3 Hz), 3.14-3.23 (1H, m), 3.75 (3H, s), 4.00 (1H, dd, J=11.7, 6.6 Hz), 4.04 (2H, s), 4.08 (1H, dd, J=11.7, 4.4 Hz).

Step 4

Methyl cis-5-{[tert-butyl(dimethyl)silyl]oxy}tetrahydro-2H-pyran-3-carboxylate

Methyl trans-5-{[tert-butyl(dimethyl)silyl]oxy}tetrahydro-2H-pyran-3-carboxylate The compound obtained in the above Step 3 (1.6 g) was dissolved in methanol (100 ml). Sodium borohydride (0.5 g) was added under ice-cooling and the mixture was stirred at the same temperature for 3 hours. Water was added to the reaction solution, followed by neutralization with acetic acid. Methanol was distilled off. Sodium chloride was added to the residual solution and then extracted with ethyl acetate. The organic layer was washed with brine and then dried over anhydrous sodium sulfate, and the solvent was evaporated. The residue was purified by silica gel column chromatography (developed with methanol-chloroform) to give a crude alcohol (1.5 g).

The title compound cis isomer (2.1 g) and trans isomer (0.18 g) were both obtained as colorless oils by the same procedure as in Step 3 of Example 61 using the resulting crude alcohol (1.5 g).

Cis Isomer $^1$H-NMR (CDCl$_3$) δ: 0.06 (3H, s), 0.07 (3H, s), 0.88 (9H, s), 1.54-1.66 (1H, m), 2.24-2.35 (1H, m), 2.64-2.76 (1H, m), 3.02 (1H, t, J=10.4 Hz), 3.32 (1H, t, J=11.1 Hz), 3.64-3.77 (1H, m), 3.66 (3H, s), 3.80-3.90 (1H, m), 4.01-4.10 (1H, m).

Trans Isomer $^1$H-NMR (CDCl$_3$) δ: 0.08 (3H, s), 0.08 (3H, s), 0.90 (9H, s), 1.76-1.85 (1H, m), 2.06-2.15 (1H, m), 2.87-2.95 (1H, m), 3.41 (1H, dd, J=11.2, 5.9 Hz), 3.59-3.65 (1H, m), 3.70 (3H, s), 3.77-3.86 (2H, m), 3.87-3.94 (1H, m).

Step 5 cis-5-{[tert-Butyl(dimethyl)silyl]oxy}tetrahydro-2H-pyran-3-carboxylic acid

Methyl cis-5-{[tert-butyl(dimethyl)silyl]oxy}tetrahydro-2H-pyran-3-carboxylate obtained in the above Step 4 (300 mg) was dissolved in methanol (15 ml). A 1 N aqueous sodium hydroxide solution (3.2 ml) was added and the mixture was stirred at room temperature for 24 hours. Methanol was distilled off and then a 1 N aqueous hydrochloric acid solution (3.2 ml) was added to the residue, followed by extraction with ethyl acetate. The organic layer was washed with brine and then dried over anhydrous sodium sulfate, and the solvent was evaporated to give the title compound (267 mg) as a colorless solid.

$^1$H-NMR (CDCl$_3$) δ: 0.07 (6H, d, J=3.9 Hz), 0.88 (9H, s), 1.61-1.72 (1H, m), 2.24-2.33 (1H, m), 2.66-2.76 (1H, m), 3.10 (1H, dd, J=10.9, 9.2 Hz), 3.42 (1H, t, J=10.7 Hz), 3.68-3.78 (1H, m), 3.79-3.86 (1H, m), 4.03 (1H, ddd, J=11.4, 4.3, 1.2 Hz), 10.52 (1H, br s).

Step 6

[cis-5-{[tert-Butyl(dimethyl)silyl]oxy}tetrahydro-2H-pyran-3-yl]methanol

The compound obtained in the above Step 5 (267 mg) was dissolved in tetrahydrofuran (10 ml). Triethylamine (0.214 ml) and ethyl chloroformate (0.118 ml) were added under ice-cooling. The mixture was stirred at the same temperature for 30 minutes and then the precipitate was removed by filtration. A solution of sodium borohydride (77.7 mg) in water (2 ml) was added dropwise to the filtrate under ice-cooling, and then the mixture was stirred at room temperature for 22 hours. Tetrahydrofuran was distilled off, and then a saturated aqueous sodium bicarbonate solution was added to the residue, followed by extraction with ethyl acetate. The organic layer was washed with brine and then dried over anhydrous sodium sulfate, and the solvent was evaporated. The residue was purified by silica gel column chromatography (developed with methanol-chloroform) to give the title compound (251 mg) as a colorless oil.

$^1$H-NMR (CDCl$_3$) δ: 0.07 (6H, d, J=3.2 Hz), 0.88 (9H, s), 1.13-1.27 (1H, m), 1.84-1.95 (1H, m), 1.95-2.05 (1H, m), 3.00-3.15 (2H, m), 3.45-3.55 (2H, m), 3.67-3.76 (1H, m), 3.79-3.85 (1H, m), 3.90-3.96 (1H, m).

Step 7

6-Bromo-1-{[cis-5-{[tert-butyl(dimethyl)silyl]oxy}tetrahydro-2H-pyran-3-yl]methyl}-3-cyclohex-1-en-1-yl-1,3-dihydro-2H-imidazo[4,5-b]pyridin-2-one The title compound (405 mg) was obtained by the same procedure as in Step 3 of Example 35 using the compound obtained in Step 2 of Example 35 (200 mg) and the compound obtained in the above Step 6 (251 mg).

$^1$H-NMR (CDCl$_3$) δ: 0.07 (6H, d, J=1.0 Hz), 0.88 (9H, s), 1.51-1.53 (1H, m), 1.70-1.78 (2H, m), 1.82-1.91 (2H, m), 1.99-2.07 (1H, m), 2.17-2.27 (1H, m), 2.27-2.34 (2H, m), 2.38-2.44 (2H, m), 3.11-3.21 (2H, m), 3.65-3.93 (5H, m), 5.98-6.02 (1H, m), 7.31 (1H, d, J=2.0 Hz), 8.10 (1H, d, J=2.0 Hz).

Step 8

1-{[cis-5-{[tert-Butyl(dimethyl)silyl]oxy}tetrahydro-2H-pyran-3-yl]methyl}-3-cyclohex-1-en-1-yl-6-(1H-pyrrolo[2,3-b]pyridin-5-yl)-1,3-dihydro-2H-imidazo[4,5-b]pyridin-2-one The title compound (204 mg) was obtained as a pale yellow oil by the same procedure as in Step 3 of Example 1 using the compound obtained in the above Step 7 (405 mg) and 5-(4,4,5,5-tetramethyl-1,3,2-dioxaborolan-2-yl)-1H-pyrrolo[2,3-b]pyridine (204 mg).

$^1$H-NMR (CDCl$_3$) δ: 0.06 (6H, d, J=2.4 Hz), 0.88 (9H, s), 1.34-1.47 (1H, m), 1.73-1.82 (2H, m), 1.86-1.94 (2H, m), 2.05-2.13 (1H, m), 2.25-2.38 (3H, m), 2.46-2.53 (2H, m), 3.15 (1H, dd, J=10.7, 8.5 Hz), 3.24 (1H, dd, J=11.2, 9.5 Hz), 3.70-3.85 (4H, m), 3.99 (1H, dd, J=14.4, 9.0 Hz), 6.06-6.10 (1H, m), 6.60 (1H, dd, J=3.5, 1.8 Hz), 7.41 (1H, d, J=2.0 Hz), 7.42-7.46 (1H, m), 8.09 (1H, d, J=2.0 Hz), 8.31 (1H, d, J=1.7 Hz), 8.52 (1H, d, J=2.2 Hz), 10.18 (1H, br s).

Step 9

1-{[cis-5-Hydroxytetrahydro-2H-pyran-3-yl]methyl}-6-(1H-pyrrolo[2,3-b]pyridin-5-yl)-1,3-dihydro-2H-imidazo[4,5-b]pyridin-2-one The title compound (10 mg) was obtained as a colorless solid by the same procedure as in Step 6 of Example 35 using the compound obtained in the above Step 8 (204 mg).

MS (ESI) m/z: 366 (M+H)$^+$.

HRMS (ESI) [M+H]$^+$ calculated: C$_{19}$H$_{19}$N$_5$O$_3$ 366.15661. found: 366.15645.

$^1$H-NMR (CD$_3$OD) δ: 1.25-1.36 (1H, m), 2.07-2.16 (1H, m), 2.22-2.35 (1H, m), 3.08 (1H, t, J=10.0 Hz), 3.22 (1H, t, J=10.6 Hz), 3.58-3.68 (1H, m), 3.77-3.92 (3H, m), 3.96 (1H, dd, J=14.5, 7.7 Hz), 6.58 (1H, d, J=3.4 Hz), 7.46 (1H, d, J=3.4 Hz), 7.82 (1H, d, J=1.7 Hz), 8.24 (1H, d, J=1.7 Hz), 8.27 (1H, d, J=2.0 Hz), 8.46 (1H, d, J=2.0 Hz).

Example 66

1-{[trans-5-Hydroxytetrahydro-2H-pyran-3-yl]methyl}-6-(1H-pyrrolo[2,3-b]pyridin-5-yl)-1,3-dihydro-2H-imidazo[4,5-b]pyridin-2-one

[Formula 86]

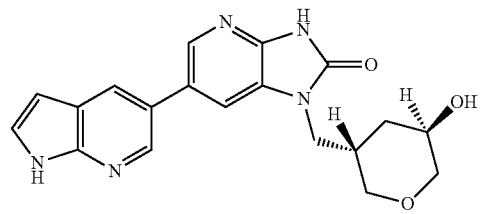

and an enantiomer thereof

Step 1 trans-5-{[tert-Butyl(dimethyl)silyl]oxy}tetrahydro-2H-pyran-3-carboxylic acid

The title compound (165 mg) was obtained as a colorless oil by the same method as in Step 5 of Example 65 using methyl trans-5-{[tert-butyl(dimethyl)silyl]oxy}tetrahydro-2H-pyran-3-carboxylate (184 mg) obtained in Step 4 of Example 65.

$^1$H-NMR (CDCl$_3$) δ: 0.08 (6H, d, J=3.2 Hz), 0.90 (9H, s), 1.79-1.87 (1H, m), 2.07-2.16 (1H, m), 2.91-2.99 (1H, m), 3.41 (1H, dd, J=11.4, 5.7 Hz), 3.65 (1H, dd, J=11.2, 2.7 Hz), 3.79-3.96 (3H, m).

Step 2

[trans-5-{[tert-Butyl(dimethyl)silyl]oxy}tetrahydro-2H-pyran-3-yl]methanol

The title compound (154 mg) was obtained by the same procedure as in Step 6 of Example 65 using the compound obtained in the above Step 1 (165 mg).

¹H-NMR (CDCl₃) δ: 0.06 (6H, s), 0.89 (9H, s), 1.68 (2H, t, J=5.7 Hz), 2.07-2.20 (1H, m), 2.38 (1H, br s), 3.42 (1H, dd, J=11.4, 5.7 Hz), 3.47-3.55 (1H, m), 3.57-3.64 (3H, m), 3.77 (1H, dd, J=11.4, 3.5 Hz), 3.80-3.88 (1H, m).

Step 3

6-Bromo-1-{[trans-5-{[tert-butyl(dimethyl)silyl]oxy}tetrahydro-2H-pyran-3-yl]methyl}-3-cyclohex-1-en-1-yl-1,3-dihydro-2H-imidazo[4,5-b]pyridin-2-one The title compound (167 mg) was obtained by the same procedure as in Step 3 of Example 35 using the compound obtained in Step 2 of Example 35 (183 mg) and the compound obtained in the above Step 2 (154 mg).

¹H-NMR (CDCl₃) δ: 0.03 (6H, d, J=11.7 Hz), 0.85 (9H, s), 1.64-1.70 (2H, m), 1.70-1.78 (2H, m), 1.82-1.90 (2H, m), 2.27-2.34 (2H, m), 2.37-2.43 (2H, m), 2.45-2.55 (1H, m), 3.42 (2H, td, J=10.9, 6.2 Hz), 3.64-3.73 (2H, m), 3.78 (1H, dd, J=14.3, 8.2 Hz), 3.87 (1H, dd, J=14.2, 7.3 Hz), 3.89-3.97 (1H, m), 5.97-6.02 (1H, m), 7.32 (1H, d, J=2.0 Hz), 8.09 (1H, d, J=2.0 Hz).

Step 4

1-{[trans-5-{[tert-Butyl(dimethyl)silyl]oxy}tetrahydro-2H-pyran-3-yl]methyl}-3-cyclohex-1-en-1-yl-6-(1H-pyrrolo[2,3-b]pyridin-5-yl)-1,3-dihydro-2H-imidazo[4,5-b]pyridin-2-one The title compound (138 mg) was obtained as a pale yellow oil by the same procedure as in Step 3 of Example 1 using the compound obtained in the above Step 3 (167 mg) and 5-(4,4,5,5-tetramethyl-1,3,2-dioxaborolan-2-yl)-1H-pyrrolo[2,3-b]pyridine (117 mg).

¹H-NMR (CDCl₃) δ: 0.01 (6H, d, J=11.5 Hz), 0.82 (9H, s), 1.67-1.81 (4H, m), 1.85-1.94 (2H, m), 2.30-2.37 (2H, m), 2.46-2.53 (2H, m), 2.55-2.66 (1H, m), 3.40-3.53 (2H, m), 3.66-3.78 (2H, m), 3.84-4.01 (3H, m), 6.05-6.10 (1H, m), 6.58-6.60 (1H, m), 7.43 (1H, d, J=1.7 Hz), 7.44-7.47 (1H, m), 8.09 (1H, d, J=2.0 Hz), 8.31 (1H, d, J=1.7 Hz), 8.51 (1H, d, J=2.0 Hz), 10.76 (1H, br s).

Step 5

1-{[trans-5-Hydroxytetrahydro-2H-pyran-3-yl]methyl}-6-(1H-pyrrolo[2,3-b]pyridin-5-yl)-1,3-dihydro-2H-imidazo[4,5-b]pyridin-2-one The title compound (50 mg) was obtained as a pale brown powder by the same procedure as in Step 6 of Example 35 using the compound obtained in the above Step 4 (138 mg).

MS (ESI) m/z: 366 (M+H)⁺.

HRMS (ESI) [M+H]⁺ calculated: $C_{19}H_{19}N_5O_3$ 366.15661. found: 366.15579.

¹H-NMR (DMSO-d₆) δ: 1.07-1.13 (1H, m), 1.50-1.62 (2H, m), 3.51 (1H, dd, J=11.5, 2.4 Hz), 3.59 (2H, dd, J=11.2, 2.9 Hz), 3.69-3.79 (3H, m), 4.65 (1H, br s), 6.50 (1H, d, J=3.4 Hz), 7.51 (1H, d, J=3.4 Hz), 7.67-7.72 (1H, m), 8.16-8.19 (1H, m), 8.21 (1H, d, J=2.2 Hz), 8.52 (1H, d, J=2.2 Hz), 11.71 (1H, br s).

Example 67

1-{[cis-5-Methoxytetrahydro-2H-pyran-3-yl]methyl}-6-(1H-pyrrolo[2,3-b]pyridin-5-yl)-1,3-dihydro-2H-imidazo[4,5-b]pyridin-2-one

[Formula 87]

and an enantiomer thereof

Step 1 tert-butyl(dimethyl)({cis-5-[(tetrahydro-2H-pyran-2-yloxy)methyl]tetrahydro-2H-pyran-3-yl}oxy)silane The title compound (222 mg) was obtained as a colorless oil by the same procedure as in Step 3 of Example 62 using the compound obtained in Step 6 of Example 65 (180 mg).

¹H-NMR (CDCl₃) δ: 0.06 (12H, d, J=3.4 Hz), 0.88 (18H, s), 1.13-1.29 (2H, m), 1.46-1.91 (9H, m), 1.95-2.09 (4H, m), 2.95-3.10 (4H, m), 3.17-3.29 (2H, m), 3.46-4.02 (14H, m), 4.51-4.57 (2H, m), 4.93-4.98 (1H, m).

Step 2 cis-5-[(Tetrahydro-2H-pyran-2-yloxy)methyl]tetrahydro-2H-pyran-3-ol

The title compound (136 mg) was obtained as a colorless oil by the same procedure as in Step 4 of Example 62 using the compound obtained in the above Step 1 (222 mg).

¹H-NMR (CDCl₃) δ: 1.17-1.32 (2H, m), 1.47-1.86 (6H, m), 1.97-2.18 (2H, m), 2.37 (1H, br s), 3.02-3.33 (3H, m), 3.46-4.02 (5H, m), 4.53-4.60 (1H, m).

Step 3 cis-3-Methoxy-5-[(tetrahydro-2H-pyran-2-yloxy)methyl]tetrahydro-2H-pyran

The title compound (123 mg) was obtained as a colorless oil by the same procedure as in Step 1 of Example 63 using the compound obtained in the above Step 2 (136 mg).

¹H-NMR (CDCl₃) δ: 1.08-1.20 (1H, m), 1.47-1.63 (4H, m), 1.64-1.74 (1H, m), 1.74-1.86 (1H, m), 1.96-2.08 (1H, m), 2.14-2.25 (1H, m), 2.99-3.15 (2H, m), 3.21-3.37 (2H, m), 3.38 (3H, s), 3.46-3.55 (1H, m), 3.56-3.66 (1H, m), 3.76-3.86 (1H, m), 3.91-4.10 (2H, m), 4.52-4.58 (1H, m).

Step 4

[cis-5-Methoxytetrahydro-2H-pyran-3-yl]methanol

The compound obtained in the above Step 3 (115 mg) was dissolved in methanol (10 ml). p-Toluenesulfonic acid (10 mg) was added and the mixture was stirred at room temperature for 14 hours. After methanol was distilled off, the residue was purified by silica gel column chromatography (developed with ethyl acetate-hexane) to give the title compound (68 mg) as a colorless oil.

¹H-NMR (CDCl₃) δ: 1.14-1.28 (1H, m), 1.83-1.97 (2H, m), 2.13-2.20 (1H, m), 3.11-3.22 (2H, m), 3.28-3.37 (1H, m), 3.38 (3H, s), 3.53-3.61 (2H, m), 3.91-4.02 (2H, m).

Step 5

6-Bromo-3-cyclohex-1-en-1-yl-1-{[cis-5-methoxytetrahydro-2H-pyran-3-yl]methyl}-1,3-dihydro-2H-imidazo[4,5-b]pyridin-2-one The title compound (114 mg) was obtained by the same procedure as in Step 3 of Example 35 using the compound obtained in Step 2 of Example 35 (137 mg) and the compound obtained in the above Step 4 (68 mg).

¹H-NMR (CDCl₃) δ: 1.34-1.47 (1H, m), 1.70-1.80 (2H, m), 1.81-1.91 (2H, m), 2.07-2.17 (1H, m), 2.18-2.36 (3H, m), 2.38-2.45 (2H, m), 3.26-3.36 (3H, m), 3.38 (3H, s), 3.71-3.83 (2H, m), 3.86-3.95 (2H, m), 5.98-6.03 (1H, m), 7.38 (1H, d, J=2.0 Hz), 8.09 (1H, d, J=2.0 Hz).

Step 6

3-Cyclohex-1-en-1-yl-1-{[cis-5-methoxytetrahydro-2H-pyran-3-yl]methyl}-6-(1H-pyrrolo[2,3-b]pyridin-5-yl)-1,3-dihydro-2H-imidazo[4,5-b]pyridin-2-one The title compound (113 mg) was obtained as a pale yellow oil by the same procedure as in Step 3 of Example 1 using the compound obtained in the above Step 5 (114 mg) and 5-(4,4,5,5-tetramethyl-1,3,2-dioxaborolan-2-yl)-1H-pyrrolo[2,3-b]pyridine (99 mg).

¹H-NMR (CDCl₁) δ: 1.37-1.48 (1H, m), 1.72-1.81 (2H, m), 1.83-1.95 (2H, m), 2.15-2.23 (1H, m), 2.28-2.37 (3H, m), 2.47-2.53 (2H, m), 3.27-3.37 (3H, m), 3.37 (3H, s), 3.78-4.03 (4H, m), 6.06-6.11 (1H, m), 6.60 (1H, dd, J=3.5, 1.8 Hz), 7.45-7.48 (2H, m), 8.11 (1H, d, J=2.0 Hz), 8.31 (1H, d, J=2.0 Hz), 8.53 (1H, d, J=2.2 Hz), 10.90 (1H, br s).

Step 7

1-{[cis-5-Methoxytetrahydro-2H-pyran-3-yl]methyl}-6-(1H-pyrrolo[2,3-b]pyridin-5-yl)-1,3-dihydro-2H-imidazo[4,5-b]pyridin-2-one The title compound (68 mg) was obtained as a pale brown powder by the same procedure as in Step 6 of Example 35 using the compound obtained in the above Step 6 (113 mg).

MS (ESI) m/z: 380 (M+H)⁺.

¹H-NMR (DMSO-d₆) δ: 1.07-1.21 (1H, m), 2.09-2.23 (2H, m), 2.95 (1H, t, J=10.1 Hz), 3.10 (1H, t, J=10.5 Hz), 3.17-3.25 (1H, m), 3.24 (3H, s), 3.67-3.95 (4H, m), 6.50-6.53 (1H, m), 7.51-7.55 (1H, m), 7.88-7.90 (1H, m), 8.24 (2H, d, J=1.7 Hz), 8.54 (1H, d, J=2.0 Hz), 11.62 (1H, br s), 11.74 (1H, br s).

Example 68

1-[(4-Methoxytetrahydro-2H-pyran-4-yl)methyl]-6-(1H-pyrrolo[2,3-b]pyridin-5-yl)-1,3-dihydro-2H-imidazo[4,5-b]pyridin-2-one

[Formula 88]

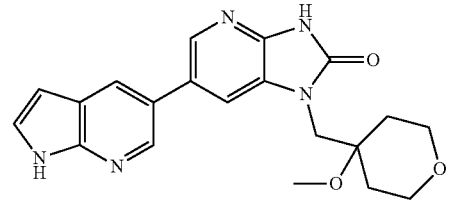

Step 1

4-Methoxytetrahydro-2H-pyran-4-carbaldehyde

The title compound (0.47 g) was obtained by the same procedure as in Step 1 of Example 25 using (4-methoxytetrahydro-2H-pyran-4-yl)methanol obtained by the method described in WO 2008/029825 (0.68 g).

Step 2

5-Bromo-N³-[(4-methoxytetrahydro-2H-pyran-4-yl)methyl]pyridine-2,3-diamine

The title compound (0.11 g) was obtained by the same procedure as in Step 1 of Example 24 using 2,3-diamino-5-bromopyridine (0.56 g) and the compound obtained in the above Step 1 (0.47 g).

MS (ESI) m/z: 316 (M+H)⁺.

Step 3

6-Bromo-1-[(4-methoxytetrahydro-2H-pyran-4-yl)methyl]-1,3-dihydro-2H-imidazo[4,5-b]pyridin-2-one The title compound (0.12 g) was obtained by the same procedure as in Step 2 of Example 1 using the compound obtained in the above Step 2 (0.11 g).

MS (ESI) m/z: 344 (M+H)⁺.

Step 4

1-[(4-Methoxytetrahydro-2H-pyran-4-yl)methyl]-6-(1H-pyrrolo[2,3-b]pyridin-5-yl)-1,3-dihydro-2H-imidazo[4,5-b]pyridin-2-one The title compound (45 mg) was obtained by the same procedure as in Step 3 of Example 1 using the compound obtained in the above Step 3 (115 mg) and 5-(4,4,5,5-tetramethyl-1,3,2-dioxaborolan-2-yl)-1H-pyrrolo[2,3-b]pyridine (82 mg).

HRMS (ESI) [(M+H)⁺]
calculated: C₂₀H₂₂N₅O₃ 380.17226. found: 380.17388.
¹H-NMR (DMSO-d₆) δ: 1.59-1.73 (4H, m), 3.40 (3H, s), 3.42-3.57 (2H, m), 3.61-3.70 (2H, m), 3.91-3.98 (2H, m), 6.49-6.54 (1H, m), 7.50-7.58 (1H, m), 7.82 (1H, d, J=1.8 Hz), 8.19-8.27 (2H, m), 8.50 (1H, dd, J=11.0, 1.8 Hz), 11.74 (1H, br s).

Example 69

1-[(4-Fluorotetrahydro-2H-pyran-4-yl)methyl]-6-(1H-pyrrolo[2,3-b]pyridin-5-yl)-1,3-dihydro-2H-imidazo[4,5-b]pyridin-2-one

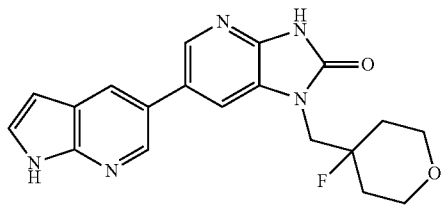

[Formula 89]

Step 1

Methyl 4-fluorotetrahydro-2H-pyran-4-carboxylate

The title compound (0.4 g) was obtained as a pale yellow solid by the same procedure as in Step 1 of Example 51 using methyl tetrahydro-2H-pyran-4-carboxylate (2.0 g).
$^1$H-NMR (CDCl$_3$) δ: 1.83-1.93 (2H, m), 2.07-2.28 (2H, m), 3.71-3.79 (2H, m), 3.82 (3H, s), 3.88 (2H, ddd, J=11.7, 5.1, 2.4 Hz).

Step 2

(4-Fluorotetrahydro-2H-pyran-4-yl)methanol

The title compound (0.15 g) was obtained as a colorless oil by the same procedure as in Step 2 of Example 33 using the compound obtained in the above Step 1 (0.41 g).
$^1$H-NMR (CDCl$_3$) δ: 1.63-1.89 (4H, m), 2.00 (1H, br s), 3.61 (2H, d, J=20.7 Hz), 3.73 (2H, td, J=11.3, 2.4 Hz), 3.79-3.87 (2H, m).

Step 3

6-Bromo-3-cyclohex-1-en-1-yl-1-[(4-fluorotetrahydro-2H-pyran-4-yl)methyl]-1,3-dihydro-2H-imidazo[4,5-b]pyridin-2-one The title compound (353 mg) was obtained by the same procedure as in Step 3 of Example 35 using the compound obtained in Step 2 of Example 35 (200 mg) and the compound obtained in the above Step 2 (134 mg).
$^1$H-NMR (CDCl$_3$) δ: 1.70-1.82 (4H, m), 1.82-2.01 (4H, m), 2.27-2.35 (2H, m), 2.38-2.46 (2H, m), 3.70 (2H, m), 3.82-3.90 (2H, m), 4.01 (2H, d, J=22.9 Hz), 5.99-6.05 (1H, m), 7.48 (1H, m), 8.11 (1H, d, J=1.7 Hz).

Step 4

3-Cyclohex-1-en-1-yl-1-[(4-fluorotetrahydro-2H-pyran-4-yl)methyl]-6-(1H-pyrrolo[2,3-b]pyridin-5-yl)-1,3-dihydro-2H-imidazo[4,5-b]pyridin-2-one The title compound (200 mg) was obtained as a pale yellow solid by the same procedure as in Step 3 of Example 1 using the compound obtained in the above Step 3 (353 mg) and 5-(4,4,5,5-tetramethyl-1,3,2-dioxaborolan-2-yl)-1H-pyrrolo[2,3-b]pyridine (181 mg).
$^1$H-NMR (CDCl$_3$) δ: 1.73-2.06 (8H, m), 2.31-2.39 (2H, m), 2.46-2.53 (2H, m), 3.72 (2H, m), 3.84-3.93 (2H, m), 4.07-4.17 (2H, m), 6.06-6.11 (1H, m), 6.59 (1H, dd, J=3.4, 2.0 Hz), 7.39-7.43 (1H, m), 7.57 (1H, m), 8.09 (1H, J=2.2 Hz), 8.32 (1H, J=2.0 Hz), 8.51 (1H, J=2.0 Hz), 9.50 (1H, br s).

Step 5

1-[(4-Fluorotetrahydro-2H-pyran-4-yl)methyl]-6-(1H-pyrrolo[2,3-b]pyridin-5-yl)-1,3-dihydro-2H-imidazo[4,5-b]pyridin-2-one The title compound (127 mg) was obtained as a pale brown powder by the same procedure as in Step 6 of Example 35 using the compound obtained in the above Step 4 (200 mg).
MS (ESI) m/z: 368 (M+H)$^+$.
HRMS (ESI) [M+H]$^+$ calculated: C$_{19}$H$_{18}$FN$_5$O$_2$ 368.15119. found: 368.15228.
$^1$H-NMR (DMSO-d$_6$) δ: 1.66-1.95 (4H, m), 3.47-3.56 (2H, m), 3.72-3.80 (2H, m), 4.14 (2H, J=22.2 Hz), 6.50-6.54 (1H, m), 7.53 (1H, m), 7.77-7.80 (1H, m), 8.19 (1H, d, J=2.1 Hz), 8.26 (1H, d, J=1.7 Hz) 8.50 (1H, d, J=2.1 Hz), 11.71 (1H, br s), 11.75 (1H, br s).

Example 70

1-[(2,2-Dimethyltetrahydro-2H-pyran-4-yl)methyl]-6-(1H-pyrrolo[2,3-b]pyridin-5-yl)-1,3-dihydro-2H-imidazo[4,5-b]pyridin-2-one

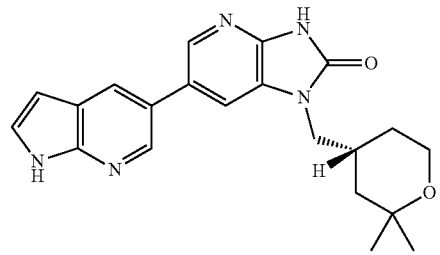

[Formula 90]

and an enantiomer thereof

Step 1

2,2-Dimethyltetrahydro-2H-pyran-4-carbonitrile p-Toluenesulfonylmethyl isocyanide (693 mg) and tert-butanol (438 μl) were added to a solution of 2,2-dimethyltetrahydro-4H-pyran-4-one (350 mg) in dimethoxyethane (10 ml) with stirring. Potassium tert-butoxide (766 mg) were added in three portions under cooling at −20° C. The mixture was heated to room temperature and then stirred for 18 hours. Diethyl ether was added and the mixture was filtered through Celite. Thereafter, the solvent was evaporated under reduced pressure to give the title compound (321 mg).
$^1$H-NMR (CDCl$_3$) δ: 1.21 (3H, s), 1.28 (3H, s), 1.69-1.93 (4H, m), 2.82-2.89 (1H, m), 3.61-3.66 (1H, m), 3.77-3.81 (1H, m).

Step 2

2,2-Dimethyltetrahydro-2H-pyran-4-carboxylic acid

A 2.25 M aqueous potassium hydroxide solution (6 ml) was added to the compound obtained in the above Step 1 (321 mg), and the mixture was heated under reflux overnight. The reaction solution was left to cool to room temperature and then washed with diethyl ether, and concentrated hydrochloric acid was added until the reaction solution was acidic, followed by extraction with ethyl acetate. The organic layer was washed with brine. After drying over anhydrous sodium sulfate, the solvent was evaporated under reduced pressure to give the title compound (264 mg).

$^1$H-NMR (CDCl$_3$) δ: 1.23 (3H, s), 1.26 (3H, s), 1.55-1.71 (2H, m), 1.82 (2H, t, J=13.7 Hz), 2.69-2.75 (1H, m), 3.64-3.69 (1H, m), 3.78-3.81 (1H, m).

Step 3

(2,2-Dimethyltetrahydro-2H-pyran-4-yl)methanol

The title compound (220 mg) was obtained by the same procedure as in Step 2 of Example 33 using the compound obtained in the above Step 2 (264 mg).

$^1$H-NMR (CDCl$_3$) δ: 1.08-1.25 (8H, m), 1.58-1.65 (2H, m), 1.92-1.94 (1H, m), 3.46 (2H, t, J=6.6 Hz), 3.66-3.71 (1H, m), 3.76-3.81 (1H, m).

Step 4

6-Bromo-3-cyclohex-1-en-1-yl-1-[(2,2-dimethyltetrahydro-2H-pyran-4-yl)methyl]-1,3-dihydro-2H-imidazo[4,5-b]pyridin-2-one The title compound (255 mg) was obtained by the same procedure as in Step 3 of Example 35 using the compound obtained in Step 2 of Example 35 (150 mg) and the compound obtained in the above Step 3 (103 mg).

MS (ESI) m/z: 420 (M+H)$^+$.

$^1$H-NMR (CDCl$_3$) δ: 1.19 (3H, s), 1.23 (3H, s), 1.53-1.56 (2H, m), 1.72-1.77 (2H, m), 1.84-1.89 (2H, m), 2.22-2.33 (3H, m), 2.40-2.44 (2H, m), 3.59-3.78 (5H, m), 6.01-6.02 (1H, m), 7.28 (1H, d, J=1.7 Hz), 8.10 (1H, d, J=1.7 Hz).

Step 5

3-Cyclohex-1-en-1-yl-1-[(2,2-dimethyltetrahydro-2H-pyran-4-yl)methyl]-6-(1H-pyrrolo[2,3-b]pyridin-5-yl)-1,3-dihydro-2H-imidazo[4,5-b]pyridin-2-one The title compound (176 mg) was obtained by the same procedure as in Step 3 of Example 1 using the compound obtained in the above Step 4 (255 mg) and 5-(4,4,5,5-tetramethyl-1,3,2-dioxaborolan-2-yl)-1H-pyrrolo[2,3-b]pyridine (108 mg).

MS (ESI) m/z: 458 (M+H)$^+$.

$^1$H-NMR (CDCl$_3$) δ: 1.19 (3H, s), 1.24 (3H, s), 1.57-1.62 (2H, m), 1.76-1.80 (2H, m), 1.88-1.93 (2H, m), 2.32-2.37 (3H, m), 2.49-2.52 (2H, m), 3.63 (1H, t, J=12.3 Hz), 3.73-3.82 (3H, m), 6.08-6.10 (1H, m), 6.60-6.61 (1H, m), 7.35-7.37 (1H, m), 8.07 (1H, s), 8.29-8.30 (1H, m), 8.49-8.50 (1H, m), 9.07 (1H, br s).

Step 6

1-[(2,2-Dimethyltetrahydro-2H-pyran-4-yl)methyl]-6-(1H-pyrrolo[2,3-b]pyridin-5-yl)-1,3-dihydro-2H-imidazo[4,5-b]pyridin-2-one The title compound (57 mg) was obtained by the same procedure as in Step 6 of Example 35 using the compound obtained in the above Step 5 (176 mg).

MS (ESI) m/z: 378 (M+H)$^+$.

HRMS (ESI) [(M+H)$^+$] calculated: $C_{21}H_{23}N_5O_2$ 378.19300.

found: 378.19044.

$^1$H-NMR (DMSO-d$_6$) δ: 1.09 (3H, s), 1.10-1.25 (2H, m), 1.11 (3H, s), 1.47 (2H, t, J=11.2 Hz), 2.22-2.31 (1H, m), 3.47-3.52 (1H, m), 3.59 (1H, dd, J=12.0, 4.0 Hz), 3.72 (2H, d, J=7.4 Hz), 6.51-6.52 (1H, m), 7.52-7.54 (1H, m), 7.91-7.92 (1H, m), 8.23-8.25 (2H, m), 8.55 (1H, d, J=2.3 Hz), 11.59 (1H, br s), 11.75 (1H, br s).

Example 71

1-{[(2R-4r-6S)-2,6-Dimethyltetrahydro-2H-pyran-4-yl]methyl}-6-(1H-pyrrolo-[2,3-b]pyridin-5-yl)-1,3-dihydro-2H-imidazo[4,5-b]pyridin-2-one

[Formula 91]

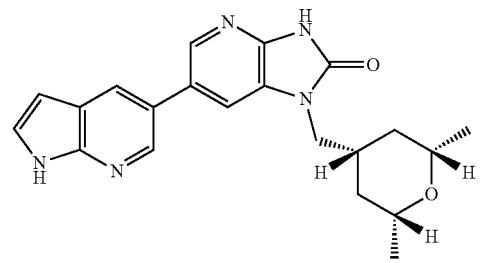

Step 1

6-Bromo-3-cyclohex-1-en-1-yl-1-{[(2R-4r-6S)-2,6-dimethyltetrahydro-2H-pyran-4-yl]methyl}-1,3-dihydro-2H-imidazo[4,5-b]pyridin-2-one The title compound (152 mg) was obtained by the same method as in Step 3 of Example 35 using the compound obtained in Step 2 of Example 35 (150 mg) and [(2R-4r-6S)-2,6-dimethyltetrahydro-2H-pyran-4-yl]methanol (103 mg) obtained by the method described in WO 2007/070201.

MS (ESI) m/z: 420 (M+H)$^+$.

$^1$H-NMR (CDCl$_3$) δ: 0.97-1.05 (2H, m), 1.19 (3H, s), 1.20 (3H, s), 1.58-1.62 (2H, m), 1.72-1.77 (2H, m), 1.84-1.89 (2H, m), 2.10-2.19 (1H, m), 2.29-2.33 (2H, m), 2.41-2.44 (2H, m), 3.42-3.48 (2H, m), 3.69 (2H, d, J=7.4 Hz), 6.01-6.02 (1H, m), 7.26-7.27 (1H, m), 8.10 (1H, d, J=1.7 Hz).

Step 2

3-Cyclohex-1-en-1-yl-1-{[(2R-4r-6S)-2,6-dimethyltetrahydro-2H-pyran-4-yl]methyl}-6-(1H-pyrrolo[2,3-b]pyridin-5-yl)-1,3-dihydro-2H-imidazo[4,5-b]pyridin-2-one The title compound (150 mg) was obtained by the same procedure as in Step 3 of Example 1 using the compound obtained in the above Step 1 (152 mg) and 5-(4,4,5,5-tetramethyl-1,3,2-dioxaborolan-2-yl)-1H-pyrrolo[2,3-b]pyridine (97 mg).

MS (ESI) m/z: 458 (M+H)⁺.

¹H-NMR (CDCl₃) δ: 1.02-1.09 (2H, m), 1.19 (3H, s), 1.20 (3H, s), 1.65-1.68 (2H, m), 1.75-1.80 (2H, m), 1.88-1.93 (2H, m), 2.18-2.27 (1H, m), 2.33-2.36 (2H, m), 2.49-2.52 (2H, m), 3.44-3.48 (2H, m), 3.80 (2H, d, J=6.9 Hz), 6.08-6.09 (1H, m), 6.60 (1H, dd, J=3.4, 1.7 Hz), 7.35 (1H, d, J=1.7 Hz), 8.07 (1H, d, J=2.3 Hz), 8.29 (1H, d, J=1.7 Hz), 8.49 (1H, d, J=2.3 Hz), 8.76 (1H, br s).

Step 3

1-{[(2R-4r-6S)-2,6-Dimethyltetrahydro-2H-pyran-4-yl]methyl}-6-(1H-pyrrolo[2,3-b]pyridin-5-yl)-1,3-dihydro-2H-imidazo[4,5-b]pyridin-2-one The title compound (65 mg) was obtained by the same procedure as in Step 6 of Example 35 using the compound obtained in the above Step 2 (150 mg).

MS (ESI) m/z: 378 (M+H)⁺.

HRMS (ESI) [(M+H)⁺] calculated: $C_{21}H_{23}N_5O_2$ 378.19300.
found: 378.19088.

¹H-NMR (DMSO-d₆) δ: 0.86-0.93 (2H, m), 1.05 (3H, s), 1.06 (3H, s), 1.54-1.57 (2H, m), 2.12-2.21 (1H, m), 3.33-3.39 (2H, m), 3.74 (2H, d, J=7.4 Hz), 6.51-6.52 (1H, m), 7.52-7.53 (1H, m), 7.90 (1H, s), 8.24-8.25 (2H, m), 8.55 (1H, d, J=2.3 Hz), 11.59 (1H, br s), 11.74 (1H, br s).

Example 72

6-(3-Amino-1H-indazol-5-yl)-1-(tetrahydro-2H-pyran-4-ylmethyl)-1,3-dihydro-2H-imidazo[4,5-b]pyridin-2-one

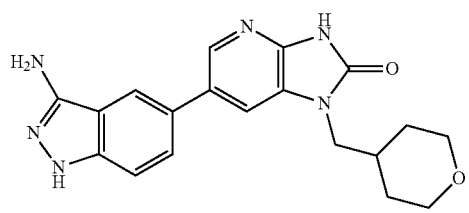

[Formula 92]

Step 1

2-Fluoro-5-[2-oxo-1-(tetrahydro-2H-pyran-4-ylmethyl)-2,3-dihydro-1H-imidazo[4,5-b]pyridin-6-yl]benzonitrile The title compound (56 mg) was obtained by the same procedure as in Step 3 of Example 1 using (3-cyano-4-fluorophenyl)boric acid (35 mg) and the compound obtained in Step 1 of Example 4 (60 mg).

MS (ESI) m/z: 353 (M+H)⁺.

HRMS (ESI) [M+H]⁺ calculated: $C_{19}H_{18}FN_4O_2$ 353.14138. found: 353.14387.

¹H-NMR (DMSO-d₆) δ: 1.21-1.38 (2H, m), 1.43-1.54 (2H, m), 2.01-2.17 (1H, m), 3.19-3.30 (1H, m), 3.71-3.88 (4H, m), 7.61-7.69 (1H, m), 7.93 (1H, d, J=1.8 Hz), 8.12-8.20 (1H, m), 8.28-8.33 (2H, m), 11.72 (1H, br s).

Step 2

6-(3-Amino-1H-indazol-5-yl)-1-(tetrahydro-2H-pyran-4-ylmethyl)-1,3-dihydro-2H-imidazo[4,5-b]pyridin-2-one The compound obtained in the above Step 1 (52 mg) was prepared as a solution in ethanol (3 ml). Hydrazine monohydrate (36 μl) was added thereto and the mixture was heated under reflux for 3 hours. Hydrazine monohydrate (72 μl) was further added and the mixture was heated under reflux for 24 hours. Hydrazine monohydrate (144 μl) was further added and the mixture was heated under reflux for 24 hours. Thereafter, the reaction solution was concentrated and purified by thin-layer chromatography (developed with methanol-dichloromethane) to give the title compound (27 mg).

MS (ESI) m/z: 365 (M+H)⁺.

HRMS (ESI) [M+H]⁺ calculated: $C_{19}H_{20}N_6O_2$ 365.17260. found: 365.17303.

¹H-NMR (DMSO-d₆) δ: 1.22-1.39 (2H, m), 1.46-1.56 (2H, m), 2.02-2.17 (1H, m), 3.19-3.30 (2H, m), 3.72-3.87 (4H, m), 5.40 (2H, s), 7.32 (1H, d, J=8.7 Hz), 7.57 (1H, dd, J=8.7, 1.8 Hz), 7.77 (1H, d, J=1.8 Hz), 8.00 (1H, s), 8.18 (1H, d, J=2.3 Hz), 11.44 (1H, br s), 11.55 (1H, br s).

Example 73

6-Pyrazolo[1,5-a]pyrimidin-6-yl-1-(tetrahydro-2H-pyran-4-ylmethyl)-1,3-dihydro-2H-imidazo[4,5-b]pyridin-2-one

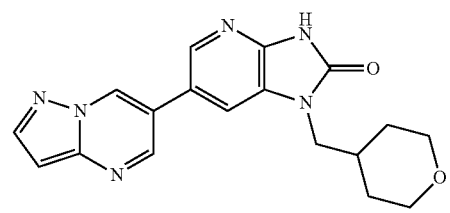

[Formula 93]

Step 1

6-(Trimethylstannyl)pyrazolo[1,5-a]pyrimidine

6-Bromopyrazolo[1,5-a]pyrimidine (150 mg) was dissolved in toluene (3 ml). Hexamethylditin (0.188 ml) and tetrakistriphenylphosphine palladium (92 mg) were added and the mixture was stirred at 115° C. for 2 hours. The reaction solution was cooled to room temperature and then the solvent was evaporated. The resulting residue was purified by thin-layer chromatography (developed with ethyl acetate-hexane) to give the title compound (145 mg).

MS (ESI) m/z: 284 (M+H)⁺.

¹H-NMR (CDCl₃) δ: 0.43 (9H, s), 6.64-6.65 (1H, m), 8.07-8.07 (1H, m), 8.41-8.41 (1H, m), 8.59-8.60 (1H, m).

Step 2

6-Pyrazolo[1,5-a]pyrimidin-6-yl-1-(tetrahydro-2H-pyran-4-ylmethyl)-1,3-dihydro-2H-imidazo[4,5-b]pyridin-2-one Bis(triphenylphosphine)palladium(II) dichloride (36 mg) was added to a solution of the compound obtained in the above Step 1 (145 mg) and the compound obtained in Step 1 of Example 4 (60 mg) in N,N-dimethylformamide (2.6 ml) in a nitrogen atmosphere. The mixture was stirred under microwave irradiation at 150° C. for 15 minutes. The reaction solution was concentrated under reduced pressure and the residue was purified by thin-layer chromatography (developed with methanol-dichloromethane) to give the title compound (28 mg).

MS (ESI) m/z: 351 (M+H)$^+$.

HRMS (ESI) [M+H]$^+$ calculated: $C_{18}H_{19}N_6O_2$ 351.15695. found: 351.16154.

$^1$H-NMR (DMSO-d$_6$) δ: 1.21-1.38 (2H, m), 1.45-1.55 (2H, m), 2.04-2.19 (1H, m), 3.19-3.25 (2H, m), 3.74 (2H, d, J=7.3 Hz), 3.78-3.86 (2H, m), 6.77-6.80 (1H, m), 8.04 (1H, d, J=1.8 Hz), 8.26 (1H, d, J=2.3 Hz), 8.40 (1H, d, J=1.8 Hz), 8.99 (1H, d, J=2.3 Hz), 9.53-9.49 (1H, m), 11.73 (1H, s).

Example 74

6-(1H-Pyrazolo[3,4-b]pyridin-5-yl)-1-(tetrahydro-2H-pyran-4-ylmethyl)-1,3-dihydro-2H-imidazo[4,5-b]pyridin-2-one

[Formula 94]

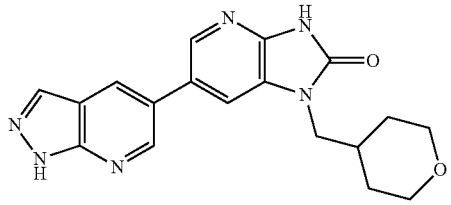

Step 1

5-Bromo-1-{[2-(trimethylsilyl)ethoxy]methyl}-1H-pyrazolo[3,4-b]pyridine

5-Bromo-1H-pyrazolo[3,4-b]pyridine (200 mg) was dissolved in N,N-dimethylformamide (5 ml). 55% Sodium hydride (53 mg) was added at 0° C., and the mixture was stirred at the same temperature for five minutes and then stirred at room temperature for 20 minutes. 2-(Chloromethoxy)ethyltrimethylsilane (0.213 ml) was added and the mixture was stirred at 0° C. for 2 hours. A saturated aqueous ammonium chloride solution was added under ice-cooling, followed by extraction with ethyl acetate. The organic layer was dried over anhydrous sodium sulfate and the solvent was evaporated. The residue was purified by silica gel column chromatography (developed with ethyl acetate-hexane) to give the title compound (0.224 g).

$^1$H-NMR (CDCl$_3$) δ: 0.00 (9H, s), 0.96-1.00 (2H, m), 3.68-3.72 (2H, m), 5.90 (2H, s), 8.07 (1H, s), 8.27 (1H, d, J=2.2 Hz), 8.65 (1H, d, J=2.2 Hz).

Step 2

5-Trimethylstannyl-1-{[2-(trimethylsilyl)ethoxy]methyl}-1H-pyrazolo[3,4-b]pyridine The title compound (115 mg) was obtained by the same procedure as in Step 1 of Example 73 using the compound obtained in the above Step 1 (116 mg).

$^1$H-NMR (CDCl$_3$) δ: 1.71-1.81 (4H, m), 3.43 (3H, s), 3.64-3.67 (2H, m), 3.76-3.79 (2H, m), 4.01 (2H, s), 7.40 (1H, d, J=2.0 Hz), 8.10 (1H, d, J=2.0 Hz), 9.56 (1H, s).

Step 3

1-(Tetrahydro-2H-pyran-4-ylmethyl)-6-(1-{[2-(trimethylsilyl)ethoxy]methyl}-1H-pyrazolo[3,4-b]pyridin-5-yl)-1,3-dihydro-2H-imidazo[4,5-b]pyridin-2-one The title compound (13 mg) was obtained by the same procedure as in Step 2 of Example 73 using the compound obtained in the above Step 2 (85 mg) and the compound obtained in Step 1 of Example 4 (60 mg).

MS (ESI) m/z: 481 (M+H)$^+$.

$^1$H-NMR (CDCl$_3$) δ: 0.04 (9H, s), 0.95-1.03 (2H, m), 1.49-1.58 (2H, m), 1.63-1.73 (2H, m), 2.12-2.29 (1H, m), 3.35-3.45 (2H, m), 3.69-3.76 (2H, m), 3.82-3.89 (2H, m), 3.98-4.07 (2H, m), 5.96 (2H, d, J=1.4 Hz), 7.37-7.41 (1H, m), 8.19 (1H, d, J=1.8 Hz), 8.23-8.26 (1H, m), 8.28-8.31 (1H, m), 8.60 (1H, br s), 8.83-8.79 (1H, m).

Step 4

6-(1H-Pyrazolo[3,4-b]pyridin-5-yl)-1-(tetrahydro-2H-pyran-4-ylmethyl)-1,3-dihydro-2H-imidazo[4,5-b]pyridin-2-one Tetrabutylammonium fluoride (1.0 M solution in tetrahydrofuran) (0.3 ml) was added to a solution of the compound obtained in the above Step 3 (13 mg) in tetrahydrofuran (1 ml), and the mixture was heated under reflux for 8.5 hours. Tetrabutylammonium fluoride (1.0 M solution in tetrahydrofuran) (1 ml) was further added and the mixture was heated under reflux for 8 hours. The reaction solution was concentrated under reduced pressure and the residue was purified by thin-layer chromatography (developed with methanol-dichloromethane) to give the title compound (6 mg).

MS (ESI) m/z: 351 (M+H)$^+$.

HRMS (ESI) [M+H]$^+$ calculated: $C_{18}H_{19}N_6O_2$ 351.15695. found: 351.15591.

$^1$H-NMR (DMSO-d$_6$) δ: 1.24-1.37 (4H, m), 1.44-1.61 (4H, m), 2.03-2.17 (1H, m), 3.10-3.22 (2H, m), 3.70-3.87 (4H, m), 7.95 (1H, d, J=1.8 Hz), 8.21 (1H, s), 8.28 (1H, d, J=1.4 Hz), 8.51 (1H, d, J=2.3 Hz), 8.87 (1H, d, J=2.3 Hz), 11.64 (1H, br s).

Example 75

6-(5H-Pyrrolo[2,3-b]pyrazin-2-yl)-1-(tetrahydro-2H-pyran-4-ylmethyl)-1,3-dihydro-2H-imidazo[4,5-b]pyridin-2-one

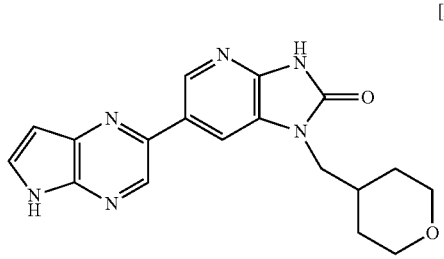

[Formula 95]

Step 1 tert-Butyl 2-bromo-5H-pyrrolo[2,3-b]pyrazine-5-carboxylate

The title compound (244 mg) was obtained by the same procedure as in Step 1 of Example 35 using 2-bromo-5H-pyrrolo[2,3-b]pyrazine (168 mg).
$^1$H-NMR (CDCl$_3$) δ: 1.68 (9H, s), 6.71 (1H, J=4.1 Hz), 7.96 (1H, J=4.1 Hz), 8.49 (1H, s).

Step 2

3-Cyclohex-1-en-1-yl-6-(5H-pyrrolo[2,3-b]pyrazin-2-yl)-1-(tetrahydro-2H-pyran-4-ylmethyl)-1,3-dihydro-2H-imidazo[4,5-b]pyridin-2-one The title compound (131 mg) was obtained as a pale yellow solid by the same procedure as in Step 3 of Example 1 using the compound obtained in the above Step 1 (120 mg) and the compound obtained in Step 4 of Example 35 (216 mg).
MS (ESI) m/z: 432 (M+H)$^+$.
$^1$H-NMR (CDCl$_3$) δ: 1.46-1.57 (2H, m), 1.60-1.67 (2H, m), 1.75-1.80 (2H, m), 1.88-1.94 (2H, m), 2.18-2.24 (1H, m), 2.32-2.37 (2H, m), 2.48-2.52 (2H, m), 3.37 (2H, m), 3.87 (2H, d, J=7.1 Hz), 3.99 (2H, dd, J=11.6, 2.8 Hz), 6.08-6.10 (1H, m), 6.82-6.83 (1H, m), 7.67 (1H, m), 7.96 (1H, d, J=1.7 Hz), 8.64 (1H, d, J=2.0 Hz), 8.71 (1H, s), 8.99 (1H, m).

Step 3

6-(5H-Pyrrolo[2,3-b]pyrazin-2-yl)-1-(tetrahydro-2H-pyran-4-ylmethyl)-1,3-dihydro-2H-imidazo[4,5-b]pyridin-2-one The title compound (54 mg) was obtained as an opal solid by the same procedure as in Step 6 of Example 35 using the compound obtained in the above Step 2 (130 mg).
HRMS (ESI) [M+H]$^+$ calculated: C$_{18}$H$_{19}$N$_6$O$_2$ 351.15695. found: 351.15860.
MS (ESI) m/z: 351 (M+H)$^+$.
$^1$H-NMR (DMSO-d$_6$) δ: 1.29-1.38 (2H, m), 1.50-1.55 (2H, m), 2.07-2.13 (1H, m), 3.22-3.30 (2H, m), 3.79-3.85 (4H, m), 6.69-6.70 (1H, m), 7.91 (1H, m), 8.17 (1H, d, J=2.0 Hz), 8.67 (1H, d, J=1.7 Hz), 8.89 (1H, s), 11.70 (1H, s), 12.11 (1H, m).

Example 76

6-(7H-Pyrrolo[2,3-c]pyridazin-3-yl)-1-(tetrahydro-2H-pyran-4-ylmethyl)-1,3-dihydro-2H-imidazo[4,5-b]pyridin-2-one

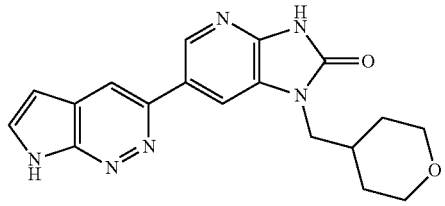

[Formula 96]

Step 1

4-Bromo-6-chloropyridazin-3-amine

3-Amino-6-chloro pyridazine (7.87 g) was dissolved in methanol (115 ml). Sodium bicarbonate (10.2 g) was added and then bromine (3.1 ml) was added dropwise, and the mixture was stirred at room temperature for 16 hours. The reaction solution was filtered and then diluted with water (500 ml), and the aqueous layer was extracted with ethyl acetate three times. The organic layer was dried over anhydrous sodium sulfate. The solvent was evaporated under reduced pressure. The resulting residue was purified by silica gel column chromatography (developed with ethyl acetate-hexane) to give the title compound (5.2 g) as a brown solid.
MS (ESI) m/z: 208 (M+H)$^+$.
$^1$H-NMR (DMSO-d$_6$) δ: 6.98 (2H, br s), 8.00 (1H, s).

Step 2

6-Chloro-4-[(trimethylsilyl)ethynyl]pyridazin-3-amine

The title compound (1.06 g) was obtained as a brown solid by the same procedure as in Step 2 of Example 36 using 4-bromo-6-chloropyridazin-3-amine obtained in the above Step 1 (1.5 g).
MS (ESI) m/z: 226 (M+H)$^+$.
$^1$H-NMR (CDCl$_3$) δ: 0.29 (9H, s), 5.37 (2H, br s), 7.25 (1H, s).

Step 3

N-Acetyl-N-{6-chloro-4-[(trimethylsilyl)ethynyl]pyridazin-3-yl}acetamide

The compound obtained in the above Step 2 (1.06 g) was dissolved in dichloromethane (20 ml). Pyridine (0.57 ml) and acetyl chloride (0.33 ml) were sequentially added under ice-cooling and the mixture was stirred at room temperature overnight. The reaction solution was washed with water and brine in this order and dried over anhydrous sodium sulfate. The solvent was evaporated under reduced pressure. The resulting residue was purified by silica gel column chromatography (developed with ethyl acetate-hexane) to give the title compound (0.45 g) as a pale yellow solid.
MS (ESI) m/z: 310 (M+H)$^+$.

¹H-NMR (CDCl₃) δ: 0.26 (9H, s), 2.33 (6H, s), 7.65 (1H, s).

Step 4

6-Chloro-4-(2,2-dimethoxyethyl)pyridazin-3-amine

The compound obtained in the above Step 3 (310 mg) was dissolved in methanol (20 ml). Potassium carbonate (276 mg) was added and the mixture was stirred overnight. The reaction solution was concentrated, diluted with ethyl acetate, washed with water and brine in this order and dried over anhydrous sodium sulfate. The solvent was evaporated under reduced pressure. The resulting residue was purified by silica gel column chromatography (developed with methanol-chloroform) to give the title compound (233 mg) as a brown oil.
MS (ESI) m/z: 218 (M+H)⁺.
¹H-NMR (CDCl₃) δ: 2.80 (2H, d, J=5.0 Hz), 3.41 (6H, s), 4.53 (1H, t, J=5.0 Hz), 5.25 (2H, s), 7.09 (1H, s).

Step 5

3-Chloro-7H-pyrrolo[2,3-c]pyridazine

The compound obtained in the above Step 4 (250 mg) was dissolved in ethanol (3 ml). A 1 N aqueous hydrochloric acid solution (1 ml) was added and the mixture was stirred at 60° C. for 3 hours. Concentrated hydrochloric acid (0.5 ml) was further added and the mixture was stirred at 80° C. for 2 hours. The reaction solution was neutralized with a saturated aqueous sodium bicarbonate solution and then extracted with a 10% methanol/chloroform mixture three times, and the organic layer was dried over anhydrous sodium sulfate. The solvent was evaporated under reduced pressure. The resulting residue was purified by silica gel column chromatography (developed with methanol-chloroform) to give the title compound (150 mg) as a pale yellow solid.
MS (ESI) m/z: 154 (M+H)⁺.
¹H-NMR (CDCl₃) δ: 6.54 (1H, d, J=3.4 Hz), 7.80 (1H, s), 7.84 (1H, d, J=2.0 Hz), 12.01 (1H, br s).

Step 6

3-Cyclohex-1-en-1-yl-6-(7H-pyrrolo[2,3-c]pyridazin-3-yl)-1-(tetrahydro-2H-pyran-4-ylmethyl)-1,3-dihydro-2H-imidazo[4,5-b]pyridin-2-one The title compound (41 mg) was obtained as a pale yellow oil by the same procedure as in Step 3 of Example 1 using the compound obtained in the above Step 5 (40 mg) and the compound obtained in Step 4 of Example 35 (100 mg).
MS (ESI) m/z: 431 (M+H)⁺.

Step 7

6-(7H-Pyrrolo[2,3-c]pyridazin-3-yl)-1-(tetrahydro-2H-pyran-4-ylmethyl)-1,3-dihydro-2H-imidazo[4,5-b]pyridin-2-one The title compound (8 mg) was obtained as a green solid by the same procedure as in Step 6 of Example 35 using the compound obtained in the above Step 6 (40 mg).
HRMS (ESI) [M+H]⁺ calculated: C₁₈H₁₉N₆O₂ 351.15695. found: 351.15944.
MS (ESI) m/z: 351 (M+H)⁺.
¹H-NMR (DMSO-d₆) δ: 1.29-1.38 (2H, m), 1.51-1.55 (2H, m), 2.08-2.13 (1H, m), 3.24-3.26 (2H, m), 3.80-3.85 (4H, m), 6.60 (1H, d, J=2.9 Hz), 7.92 (1H, m), 8.24 (1H, s), 8.40 (1H, s), 8.67 (1H, d, J=1.7 Hz), 11.70 (1H, s), 12.48 (1H, s).

Example 77

6-(3-Amino-1H-pyrrolo[2,3-b]pyridin-5-yl)-1-(tetrahydro-2H-pyran-4-ylmethyl)-1,3-dihydro-2H-imidazo[4,5-b]pyridin-2-one

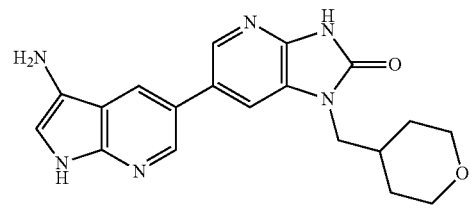

[Formula 97]

Step 1

[2-Oxo-1-(tetrahydro-2H-pyran-4-ylmethyl)-2,3-dihydro-1H-imidazo[4,5-b]pyridin-6-yl]boric acid The title compound (0.98 g) was obtained by the same procedure as in Step 6 of Example 35 using the compound obtained in Step 4 of Example 35 (1.56 g).
MS (ESI) m/z: 278 (M+H)⁺.

Step 2 tert-Butyl (5-bromo-1H-pyrrolo[2,3-b]pyridin-3-yl)carbamate

The title compound (350 mg) was obtained as a brown solid by the same procedure as in Step 1 of Example 35 using 5-bromo-1H-pyrrolo[2,3-b]pyridin-3-amine obtained by the method described in WO 2003/028724 (300 mg).
MS (ESI) m/z: 312 (M+H)⁺.
¹H-NMR (DMSO-d₆) δ: 1.49 (9H, s), 7.54 (1H, s), 8.23 (1H, d, J=2.3 Hz), 8.41 (1H, s), 9.34 (1H, s), 11.52 (1H, s).

Step 3 tert-Butyl {5-[2-oxo-1-(tetrahydro-2H-pyran-4-ylmethyl)-2,3-dihydro-1H-imidazo[4,5-b]pyridin-6-yl]-1H-pyrrolo[2,3-b]pyridin-3-yl}carbamate The title compound (90 mg) was obtained as a pale yellow solid by the same procedure as in Step 3 of Example 1 using the compound obtained in the above Step 2 (150 mg) and the compound obtained in the above Step 1 (173 mg).
MS (ESI) m/z: 465 (M+H)⁺.
¹H-NMR (DMSO-d₆) δ: 1.29-1.37 (2H, m), 1.50 (9H, s), 2.07-2.13 (1H, m), 3.22-3.36 (4H, m), 3.77 (2H, m), 3.82-3.85 (2H, m), 7.53 (1H, s), 7.85 (1H, d, J=1.7 Hz), 8.20 (1H, d, J=1.7 Hz), 8.49 (1H, s), 8.53 (1H, d, J=1.7 Hz), 9.34 (1H, s), 11.35 (1H, s), 11.61 (1H, s).

Step 4

6-(3-Amino-1H-pyrrolo[2,3-b]pyridin-5-yl)-1-(tetrahydro-2H-pyran-4-ylmethyl)-1,3-dihydro-2H-imidazo[4,5-b]pyridin-2-one Trifluoroacetic acid (1 ml) was added dropwise to a solution of the compound obtained in the above Step 3 (90 mg) in dichloromethane under ice-cooling, and the mixture was stirred for 6 hours while gradually returning to room temperature. The reaction solution diluted with water was washed with chloroform. The aqueous layer was neutralized with a saturated aqueous sodium bicarbonate solution and then extracted with a 10% methanol/chloroform mixture three times, and the organic layer was dried over anhydrous sodium sulfate. The solvent was evaporated under reduced pressure, and the resulting solid was washed with ethyl acetate to give the title compound (12 mg) as a pale yellow solid.

HRMS (ESI) [M+H]$^+$ calculated: $C_{19}H_{21}N_6O_2$ 365.17260. found: 365.17097.

MS (ESI) m/z: 365 (M+H)$^+$.

$^1$H-NMR (DMSO-d$_6$) δ: 1.27-1.38 (2H, m), 1.48-1.54 (2H, m), 2.05-2.16 (1H, m), 3.21-3.27 (2H, m), 3.76-3.79 (2H, m), 3.82-3.84 (2H, m), 4.35 (2H, br s), 6.71 (1H, d, J=1.8 Hz), 7.86 (1H, d, J=1.8 Hz), 8.20 (1H, d, J=1.8 Hz), 8.23 (1H, d, J=2.3 Hz), 8.44 (1H, d, J=2.3 Hz), 10.72 (1H, s), 11.59 (1H, s).

Example 78

6-(6-Chloro-1H-pyrrolo[2,3-b]pyridin-5-yl)-1-(tetrahydro-2H-pyran-4-ylmethyl)-1,3-dihydro-2H-imidazo[4,5-b]pyridin-2-one

[Formula 98]

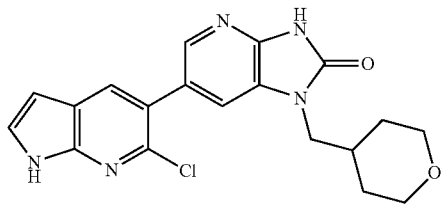

Step 1

5-Bromo-6-chloropyridin-2-amine

6-Chloropyridin-2-amine (2.0 g) was dissolved in acetonitrile (40 ml). N-Bromosuccinimide (3.1 g) was added and the mixture was stirred under shading at room temperature for 13 hours. The reaction solution was concentrated and the resulting residue was purified by silica gel column chromatography (developed with ethyl acetate-hexane) to give the title compound (2.8 g).

MS (ESI) m/z: 207 (M+H)$^+$.

Step 2

5-Bromo-6-chloro-3-iodopyridin-2-amine

The title compound (1.8 g) was obtained by the same procedure as in Step 1 of Example 36 using the compound obtained in the above Step 1 (1.4 g).

MS (ESI) m/z: 333 (M+H)$^+$.

$^1$H-NMR (CDCl$_3$) δ: 5.05 (2H, br s), 7.99 (1H, s).

Step 3

5-Bromo-6-chloro-3-[(trimethylsilyl)ethynyl]pyridin-2-amine

The title compound (1.8 g) was obtained by the same procedure as in Step 2 of Example 36 using the compound obtained in the above Step 2 (1.8 g).

MS (ESI) m/z: 303 (M+H)$^+$.

$^1$H-NMR (CDCl$_3$) δ: 0.26 (9H, s), 5.11 (2H, br s), 7.70 (1H, s).

Step 4

N-{5-Bromo-6-chloro-3-[(trimethylsilyl)ethynyl]pyridin-2-yl}acetamide

The compound obtained in the above Step 3 (1.6 g) was dissolved in pyridine (0.8 ml) and dichloromethane (11 ml). Acetyl chloride (0.4 ml) was slowly added dropwise under ice-cooling, and then the mixture was heated to room temperature and stirred for 4 hours. Water was added to the reaction solution. The organic layer was isolated and dried over anhydrous sodium sulfate, and the solvent was evaporated. The resulting residue was purified by silica gel column chromatography (developed with ethyl acetate-hexane) to give the title compound (0.95 g).

MS (ESI) m/z: 345 (M+H)$^+$.

$^1$H-NMR (CDCl$_3$) δ: 0.29 (9H, s), 2.53 (3H, s), 7.90 (1H, s), 8.02 (1H, s).

Step 5

5-Bromo-6-chloro-1H-pyrrolo[2,3-b]pyridine

The compound obtained in the above Step 4 (0.95 g) was dissolved in tetrahydrofuran (15 ml). Tetrabutylammonium fluoride (1.0 M solution in tetrahydrofuran) (5.5 ml) was added and the mixture was heated under reflux for 1.5 hours. The reaction solution was cooled to room temperature and then tetrahydrofuran was distilled off. The residue was partitioned between ethyl acetate and water. The organic layer was dried over anhydrous sodium sulfate, and the solvent was evaporated. The resulting solid was collected by filtration from chloroform to give the title compound (0.4 g).

MS (ESI) m/z: 231 (M+H)$^+$.

$^1$H-NMR (DMSO-d$_6$) δ: 6.47-6.49 (1H, m), 7.59-7.59 (1H, m), 8.40-8.42 (1H, m), 12.04-12.06 (1H, m).

Step 6

6-(6-Chloro-1H-pyrrolo[2,3-b]pyridin-5-yl)-1-(tetrahydro-2H-pyran-4-ylmethyl)-1,3-dihydro-2H-imidazo[4,5-b]pyridin-2-one The title compound (11 mg) was obtained by the same procedure as in Step 3 of Example 1 using the compound obtained in Step 1 of Example 77 (31 mg) and the compound obtained in the above Step 5 (26 mg).

MS (ESI) m/z: 384 (M+H)$^+$.

HRMS (ESI) [M+H]$^+$ calculated: $C_{19}H_{19}ClN_5O_2$ 384.12273.

found: 384.12511.

$^1$H-NMR (DMSO-d$_6$) δ: 1.24-1.32 (2H, m), 1.45-1.51 (2H, m), 1.99-2.07 (1H, m), 3.22 (2H, t, J=11.2 Hz), 3.68-3.74 (2H, m), 3.80-3.83 (2H, m), 6.54 (1H, d, J=3.4 Hz), 7.58-7.59 (1H, m), 7.69 (1H, s), 7.97 (1H, d, J=1.7 Hz), 8.07 (1H, s), 11.67 (1H, s), 11.96 (1H, br s).

Example 79

6-(6-Fluoro-1H-pyrrolo[2,3-b]pyridin-5-yl)-1-(tetrahydro-2H-pyran-4-ylmethyl)-1,3-dihydro-2H-imidazo[4,5-b]pyridin-2-one

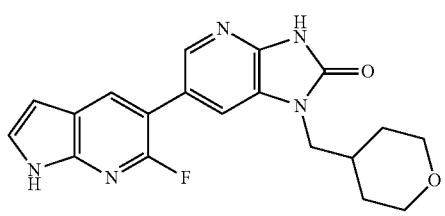

[Formula 99]

Step 1

5-Bromo-6-fluoro-3-iodopyridin-2-amine

The title compound (1.7 g) was obtained by the same procedure as in Step 1 of Example 36 using 5-bromo6-fluoropyridin-2-amine obtained by the method described in US 2008/221149 (1.3 g).

MS (ESI) m/z: 316 (M+H)$^+$.

$^1$H-NMR (CDCl$_3$) δ: 5.01 (2H, br s), 7.99 (1H, d, J=8.3 Hz).

Step 2

5-Bromo-6-fluoro-3-[(trimethylsilyl)ethynyl]pyridin-2-amine

The title compound (0.7 g) was obtained by the same procedure as in Step 2 of Example 36 using 5-bromo-6-fluoro-3-iodopyridin-2-amine obtained in the above Step 1 (1.3 g).

MS (ESI) m/z: 287 (M+H)$^+$.

$^1$H-NMR (CDCl$_3$) δ: 0.27 (9H, s), 5.11 (2H, br s), 7.74 (1H, d, J=8.5 Hz).

Step 3

N-{5-Bromo-6-fluoro-3-[(trimethylsilyl)ethynyl]pyridin-2-yl}acetamide

The title compound (165 mg) was obtained by the same procedure as in Step 4 of Example 78 using the compound obtained in the above Step 2 (707 mg).

MS (ESI) m/z: 329 (M+H)$^+$.

$^1$H-NMR (CDCl$_3$) δ: 0.29 (9H, s), 2.52 (3H, s), 7.95 (1H, d, J=8.3 Hz), 8.07 (1H, br s).

Step 4

5-Bromo-6-fluoro-1H-pyrrolo[2,3-b]pyridine

The title compound (81 mg) was obtained by the same procedure as in Step 5 of Example 78 using the compound obtained in the above Step 3 (165 mg).

MS (ESI) m/z: 215 (M+H)$^+$.

$^1$H-NMR (CDCl$_3$) δ: 6.48-6.49 (1H, m), 7.26-7.29 (1H, m), 8.17 (1H, d, J=8.5 Hz), 8.63 (1H, br s).

Step 5

6-(6-Fluoro-1H-pyrrolo[2,3-b]pyridin-5-yl)-1-(tetrahydro-2H-pyran-4-ylmethyl)-1,3-dihydro-2H-imidazo[4,5-b]pyridin-2-one The title compound (78 mg) was obtained by the same procedure as in Step 3 of Example 1 using the compound obtained in Step 1 of Example 77 (119 mg) and 5-bromo-6-fluoro-1H-pyrrolo[2,3-b]pyridine obtained in the above Step 4 (77 mg).

MS (ESI) m/z: 368 (M+H)$^+$.

HRMS (ESI) [M+H]$^+$ calculated: C$_{19}$H$_{19}$FN$_5$O$_2$ 368.15228. found: 368.15482.

$^1$H-NMR (DMSO-d$_6$) δ: 1.26-1.35 (2H, m), 1.50 (2H, d, J=13.7 Hz), 2.04-2.10 (1H, m), 3.23 (2H, t, J=11.7 Hz), 3.74-3.76 (2H, m), 3.81-3.84 (2H, m), 6.56 (1H, s), 7.49-7.51 (1H, m), 7.78 (1H, s), 8.10 (1H, s), 8.23-8.26 (1H, m), 11.66 (1H, br s), 11.87 (1H, br s).

Example 80

5-[2-Oxo-1-(tetrahydro-2H-pyran-4-ylmethyl)-2,3-dihydro-1H-imidazo[4,5-b]pyridin-6-yl]-1H-indole-2-carboxylic acid

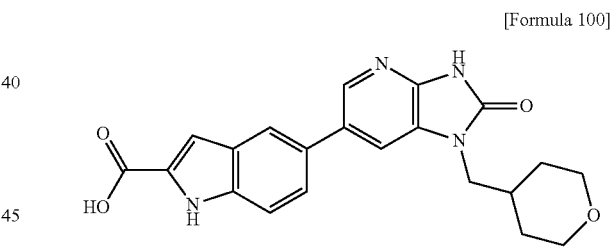

[Formula 100]

Step 1

Benzyl 5-bromo-1H-indole-2-carboxylate

Benzyl bromide (160 μl) and 1,8-diazabicyclo[5.4.0]undec-7-ene (201 μl) were added to a solution of 5-bromo-1H-indole-2-carboxylic acid (161 mg) in acetonitrile (3.5 ml) at room temperature, followed by stirring for 22.5 hours. The reaction solution was concentrated and separated by adding ethyl acetate and distilled water. The resulting organic layer was washed with brine and dried over anhydrous sodium sulfate. The solvent was evaporated under reduced pressure. The resulting residue was solidified from dichloromethane-hexane, collected by filtration and washed with hexane. This was dried under reduced pressure to give the title compound (189 mg).

MS (ESI) m/z: 328 (M+H)$^+$.

$^1$H-NMR (CDCl$_3$) δ: 5.39 (2H, s), 7.18-7.21 (1H, m), 7.27-7.31 (1H, m), 7.34-7.48 (6H, m), 7.81-7.83 (1H, m), 8.91 (1H, br s).

Step 2

2-Benzyl 1-tert-butyl 5-bromo-1H-indole-1,2-dicarboxylate

The title compound (225 mg) was obtained by the same procedure as in Step 1 of Example 35 using benzyl 5-bromo-1H-indole-2-carboxylate obtained in the above Step 1 (184 mg).

$^1$H-NMR (CDCl$_3$) δ: 5.35 (2H, s), 7.03-7.05 (1H, m), 7.32-7.41 (3H, m), 7.41-7.45 (2H, m), 7.46-7.51 (1H, m), 7.70-7.73 (1H, m), 7.98-7.93 (1H, m).

Step 3

2-Benzyl 1-tert-butyl 5-(4,4,5,5-tetramethyl-1,3,2-dioxaborolan-2-yl)-1H-indole-1,2-dicarboxylate The title compound (150 mg) was obtained by the same procedure as in Step 1 of Example 27 using the compound obtained in the above Step 2 (220 mg).

$^1$H-NMR (CDCl$_3$) δ: 1.36 (13H, s), 1.57 (9H, s), 5.36 (2H, d, J=1.8 Hz), 7.14 (1H, d, J=1.8 Hz), 7.31-7.42 (3H, m), 7.45 (2H, d, J=7.3 Hz), 7.84 (1H, d, J=8.3 Hz), 8.05 (1H, d, J=8.3 Hz), 8.08 (1H, s).

Step 4

Benzyl 5-[2-oxo-1-(tetrahydro-2H-pyran-4-ylmethyl)-2,3-dihydro-1H-imidazo[4,5-b]pyridin-6-yl]-1H-indole-2-carboxylate The title compound (52 mg) was obtained by the same procedure as in Step 1 of Example 3 using the compound obtained in the above Step 3 (150 mg) and the compound obtained in Step 1 of Example 4 (98 mg).

MS (ESI) m/z: 483 (M+H)$^+$.

HRMS (ESI) [M+H]$^+$ calculated: C$_{28}$H$_{27}$N$_4$O$_4$ 483.20323. found: 483.20082.

$^1$H-NMR (DMSO-d$_6$) δ: 1.20-1.37 (2H, m), 1.42-1.54 (3H, m), 2.00-2.14 (1H, m), 3.16-3.30 (2H, m), 3.76 (2H, d, J=7.3 Hz), 3.78-3.85 (2H, m), 5.39 (2H, s), 7.24-7.27 (1H, m), 7.33-7.45 (3H, m), 7.47-7.52 (3H, m), 7.54 (1H, d, J=8.7 Hz), 7.61 (1H, dd, J=8.7, 1.8 Hz), 7.82 (1H, d, J=2.3 Hz), 7.95 (1H, s), 8.19 (1H, d, J=1.8 Hz), 11.56 (1H, br s), 12.00 (1H, br s).

Step 5

5-[2-Oxo-1-(tetrahydro-2H-pyran-4-ylmethyl)-2,3-dihydro-1H-imidazo[4,5-b]pyridin-6-yl]-1H-indole-2-carboxylic acid 4 N hydrochloric acid-dioxane (1 ml) and a 10% palladium-carbon catalyst (30 mg) were added to a solution of the compound obtained in the above Step 4 (49 mg) in ethanol (6 ml), and the mixture was stirred in a hydrogen atmosphere for 21 hours. The catalyst was filtered off. After washing with ethanol, the filtrate was concentrated under reduced pressure. The resulting residue was purified by thin-layer chromatography (developed with methanol-water-chloroform) to give the title compound (39 mg).

MS (ESI) m/z: 393 (M+H)$^+$.

HRMS (ESI) [M+H]$^+$ calculated: C$_{21}$H$_{21}$N$_4$O$_4$ 393.15628. found: 363.15310.

$^1$H-NMR (DMSO-d$_6$) δ: 1.19-1.38 (2H, m), 1.42-1.54 (2H, m), 1.99-2.15 (1H, m), 3.18-3.31 (2H, m), 3.72-3.86 (4H, m), 6.71 (1H, s), 7.36-7.47 (2H, m), 7.79-7.81 (2H, m), 8.17 (1H, s), 11.01 (1H, br s), 11.50 (1H, br s).

Example 81

5-[2-Oxo-1-(tetrahydro-2H-pyran-4-ylmethyl)-2,3-dihydro-1H-imidazo[4,5-b]pyridin-6-yl]-1H-indole-3-carbaldehyde

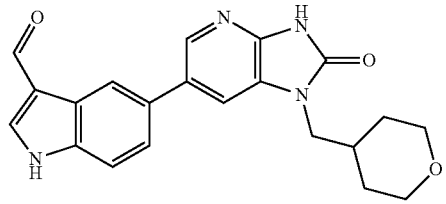

[Formula 101]

Step 1

5-(4,4,5,5-Tetramethyl-1,3,2-dioxaborolan-2-yl)-1H-indole-3-carbaldehyde

The title compound (0.65 g) was obtained by the same procedure as in Step 1 of Example 27 using 5-bromo-1H-indole-3-carbaldehyde (1.5 g).

MS (ESI) m/z: 272 (M+H)$^+$.

$^1$H-NMR (CDCl$_3$) δ: 1.37 (11H, s), 7.43 (1H, d, J=8.3 Hz), 7.77 (1H, d, J=8.3 Hz), 7.86 (1H, d, J=2.8 Hz), 8.81 (1H, s), 8.83 (1H, br s), 10.11 (1H, s).

Step 2

5-[2-Oxo-1-(tetrahydro-2H-pyran-4-ylmethyl)-2,3-dihydro-1H-imidazo[4,5-b]pyridin-6-yl]-1H-indole-3-carbaldehyde The title compound (128 mg) was obtained by the same procedure as in Step 3 of Example 1 using the compound obtained in the above Step 1 (150 mg) and the compound obtained in Step 1 of Example 4 (173 mg).

HRMS (ESI) [M+H]$^+$ calculated: C$_{21}$H$_{21}$N$_4$O$_3$ 377.16136. found: 377.16065.

$^1$H-NMR (DMSO-d$_6$) δ: 1.19-1.32 (2H, m), 1.41-1.49 (2H, m), 1.98-2.11 (1H, m), 3.16-3.25 (2H, m), 3.95-3.97 (4H, m), 7.56 (1H, dd, J=8.3, 2.0 Hz), 7.62 (1H, d, J=8.6 Hz), 7.77 (1H, d, J=1.7 Hz), 8.16 (1H, d, J=2.3 Hz), 8.27 (1H, s), 8.31-8.28 (1H, m), 9.89 (1H, s).

Example 82

6-(1H-Pyrrolo[3,2-b]pyridin-5-yl)-1-(tetrahydro-2H-pyran-4-ylmethyl)-1,3-dihydro-2H-imidazo[4,5-b]pyridin-2-one

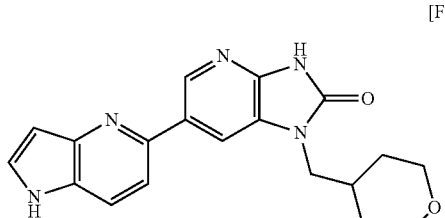

[Formula 102]

Step 1 tert-Butyl 5-chloro-1H-pyrrolo[3,2-b]pyridine-1-carboxylate

The title compound (839 mg) was obtained by the same procedure as in Step 1 of Example 35 using 5-chloro-1H-pyrrolo[3,2-b]pyridine (600 mg).

$^1$H-NMR (CDCl$_3$) δ: 1.68 (9H, s), 6.71 (1H, dd, J=3.7, 0.6 Hz), 7.24 (1H, d, J=8.5 Hz), 7.83 (1H, d, J=3.7 Hz), 8.31-8.33 (1H, m).

Step 2

3-Cyclohex-1-en-1-yl-6-(1H-pyrrolo[3,2-b]pyridin-5-yl)-1-(tetrahydro-2H-pyran-4-ylmethyl)-1,3-dihydro-2H-imidazo[4,5-b]pyridin-2-one The title compound (95 mg) was obtained by the same procedure as in Step 3 of Example 1 using the compound obtained in the above Step 1 (79 mg) and the compound obtained in Step 4 of Example 35 (130 mg).

MS (ESI) m/z: 430 (M+H)$^+$.

$^1$H-NMR (CDCl$_3$) δ: 1.45-1.54 (2H, m), 1.61-1.69 (2H, m), 1.73-1.82 (2H, m), 1.86-1.92 (2H, m), 2.15-2.28 (1H, m), 2.30-2.38 (2H, m), 2.46-2.54 (2H, m), 3.31-3.41 (2H, m), 3.87 (2H, d, J=7.3 Hz), 3.93-4.02 (2H, m), 6.05-6.11 (1H, m), 6.85 (1H, s), 7.49-7.54 (1H, m), 7.59 (1H, d, J=8.7 Hz), 7.79 (1H, d, J=8.7 Hz), 8.04 (1H, d, J=1.8 Hz), 8.33 (1H, br s), 8.59 (1H, d, J=1.8 Hz).

Step 3

6-(1H-Pyrrolo[3,2-b]pyridin-5-yl)-1-(tetrahydro-2H-pyran-4-ylmethyl)-1,3-dihydro-2H-imidazo[4,5-b]pyridin-2-one The title compound (30 mg) was obtained by the same procedure as in Step 6 of Example 35 using the compound obtained in the above Step 2 (90 mg).

MS (ESI) m/z: 350 (M+H)$^+$.

HRMS (ESI) [M+H]$^+$ calculated: C$_{19}$H$_{20}$N$_5$O$_2$ 350.16170. found: 350.16064.

$^1$H-NMR (DMSO-d$_6$) δ: 1.26-1.40 (2H, m), 1.47-1.57 (2H, m), 2.01-2.16 (1H, m), 3.20-3.29 (2H, m), 3.76-3.88 (4H, m), 6.60-6.64 (1H, m), 7.66-7.69 (1H, m), 7.73 (1H, d, J=8.7 Hz), 7.86 (1H, d, J=8.7 Hz), 8.12 (1H, d, J=1.8 Hz), 8.63 (1H, d, J=1.8 Hz), 11.35 (1H, br s), 11.62 (1H, br s).

Example 83

6-(1H-Pyrrolo[2,3-c]pyridin-5-yl)-1-(tetrahydro-2H-pyran-4-ylmethyl)-1,3-dihydro-2H-imidazo[4,5-b]pyridin-2-one

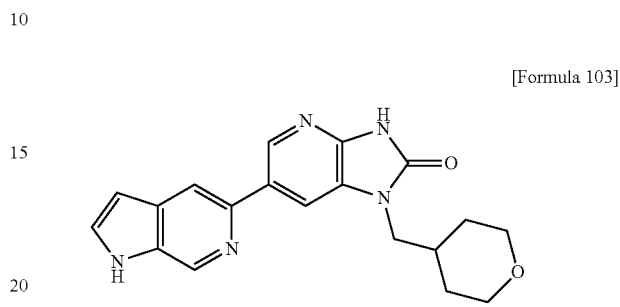

[Formula 103]

Step 1 tert-Butyl 5-chloro-1H-pyrrolo[2,3-c]pyridine-1-carboxylate

The title compound (811 mg) was obtained by the same procedure as in Step 1 of Example 35 using 5-chloro-1H-pyrrolo[2,3-c]pyridine (583 mg).

$^1$H-NMR (CDCl$_3$) δ: 1.69 (9H, s), 6.55 (1H, d, J=3.7 Hz), 7.50-7.51 (1H, m), 7.77-7.78 (1H, m), 9.14 (1H, s).

Step 2

3-Cyclohex-1-en-1-yl-6-(1H-pyrrolo[2,3-c]pyridin-5-yl)-1-(tetrahydro-2H-pyran-4-ylmethyl)-1,3-dihydro-2H-imidazo[4,5-b]pyridin-2-one The title compound (79 mg) was obtained by the same procedure as in Step 3 of Example 1 using the compound obtained in the above Step 1 (85 mg) and the compound obtained in Step 4 of Example 35 (140 mg).

MS (ESI) m/z: 430 (M+H)$^+$.

$^1$H-NMR (CDCl$_3$) δ: 1.43-1.57 (4H, m), 1.73-1.81 (2H, m), 1.86-1.94 (2H, m), 2.13-2.27 (1H, m), 2.30-2.38 (2H, m), 2.47-2.55 (2H, m), 3.31-3.41 (2H, m), 3.85 (2H, d, J=7.3 Hz), 3.93-4.01 (2H, m), 6.06-6.10 (1H, m), 6.67 (3H, d, J=3.2 Hz), 7.45 (1H, d, J=3.2 Hz), 7.98-7.93 (2H, m), 8.61 (1H, d, J=1.8 Hz), 8.67 (1H, br s), 8.92 (1H, s).

Step 3

6-(1H-Pyrrolo[2,3-c]pyridin-5-yl)-1-(tetrahydro-2H-pyran-4-ylmethyl)-1,3-dihydro-2H-imidazo[4,5-b]pyridin-2-one The title compound (58 mg) was obtained by the same procedure as in Step 6 of Example 35 using the compound obtained in the above Step 2 (78 mg).

MS (ESI) m/z: 350 (M+H)$^+$.

HRMS (ESI) [M+H]$^+$ calculated: C$_{19}$H$_{20}$N$_5$O$_2$ 350.16170. found: 350.16216.

$^1$H-NMR (DMSO-d$_6$) δ: 1.22-1.39 (2H, m), 1.45-1.58 (2H, m), 2.02-2.16 (1H, m), 3.21-3.29 (2H, m), 3.79 (2H, d, J=7.4 Hz), 3.81-3.87 (2H, m), 6.54-6.58 (1H, m), 7.62-7.66 (1H, m), 8.12 (1H, d, J=2.9 Hz), 8.15 (1H, s), 8.65 (1H, d, J=2.3 Hz), 8.84 (1H, s), 11.57 (1H, br s), 11.63 (1H, br s).

Example 84

1-(Tetrahydro-2H-pyran-4-ylmethyl)-6-[3-(trifluoromethyl)-1H-pyrrolo[2,3-b]pyridin-5-yl]-1,3-dihydro-2H-imidazo[4,5-b]pyridin-2-one

[Formula 104]

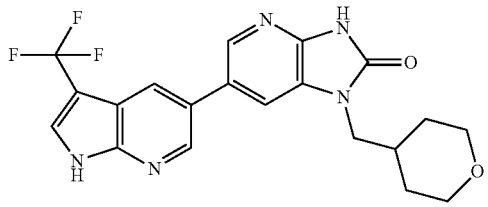

Step 1

5-Bromo-1-[(4-methylphenyl)sulfonyl]-3-(trifluoromethyl)-1H-pyrrolo[2,3-b]pyridine 5-Bromo-3-iodo-1-[(4-methylphenyl)sulfonyl]-1H-pyrrolo[2,3-b]pyridine obtained by the method described in WO 2006/015123 (240 mg) was dissolved in N,N-dimethylformamide (5 ml). Copper iodide (96 mg) and methyl difluoro(fluorosulfonyl)acetate (0.254 ml) were added and the mixture was stirred with heating at 80° C. for 18 hours. The reaction solution was diluted with ethyl acetate and the insoluble matter was separated by filtration. The filtrate was washed with brine, saturated aqueous sodium bicarbonate and brine again. The organic layer was dried over anhydrous sodium sulfate and the solvent was evaporated. The resulting residue was purified by silica gel column chromatography (developed with ethyl acetate-hexane) to give the title compound (140 mg).

MS (ESI) m/z: 419 (M+H)$^+$.

$^1$H-NMR (CDCl$_3$) δ: 2.43 (3H, s), 7.36 (2H, d, J=8.5 Hz), 8.13 (4H, m), 8.56 (1H, d, J=2.2 Hz).

Step 2

3-Cyclohex-1-en-1-yl-6-{1-[(4-methylphenyl)sulfonyl]-3-(trifluoromethyl)-1H-pyrrolo[2,3-b]pyridin-5-yl}-1-(tetrahydro-2H-pyran-4-ylmethyl)-1,3-dihydro-2H-imidazo[4,5-b]pyridin-2-one The title compound (74 mg) was obtained by the same procedure as in Step 3 of Example 1 using the compound obtained in the above Step 1 (122 mg) and the compound obtained in Step 4 of Example 35 (120 mg).

MS (ESI) m/z: 652 (M+H)$^+$.

$^1$H-NMR (CDCl$_3$) δ: 1.24-1.34 (2H, m), 1.41-1.54 (2H, m), 1.72-1.81 (2H, m), 1.86-1.93 (3H, m), 2.07-2.22 (1H, m), 2.29-2.37 (2H, m), 2.42 (3H, s), 2.44-2.52 (2H, m), 3.31-3.41 (2H, m), 3.83 (2H, d, J=6.9 Hz), 3.93-4.03 (2H, m), 6.04-6.09 (1H, m), 7.27 (1H, d, J=2.8 Hz), 7.36 (2H, d, J=8.3 Hz), 8.05-8.08 (1H, m), 8.20-8.15 (3H, m), 8.22 (1H, d, J=2.3 Hz), 8.68 (1H, d, J=1.8 Hz).

Step 3

3-Cyclohex-1-en-1-yl-1-(tetrahydro-2H-pyran-4-ylmethyl)-6-[3-(trifluoromethyl)-1H-pyrrolo[2,3-b]pyridin-5-yl]-1,3-dihydro-2H-imidazo[4,5-b]pyridin-2-one Tetrabutylammonium fluoride (1.0 M solution in tetrahydrofuran) (280 µl) was added to a solution of the compound obtained in the above Step 2 (72 mg) in tetrahydrofuran (1 ml), and the mixture was stirred at room temperature for 2 hours. The reaction solution was concentrated under reduced pressure. The resulting residue was purified by thin-layer chromatography (developed with methanol-dichloromethane) to give the title compound (29 mg).

MS (ESI) m/z: 498 (M+H)$^+$.

$^1$H-NMR (CDCl$_3$) δ: 1.46-1.55 (2H, m), 1.60-1.69 (2H, m), 1.74-1.82 (2H, m), 1.87-1.96 (2H, m), 2.11-2.26 (1H, m), 2.30-2.39 (2H, m), 2.46-2.54 (2H, m), 3.37 (2H, t, J=11.2 Hz), 3.85 (2H, d, J=7.3 Hz), 3.95-4.03 (2H, m), 6.08 (1H, s), 7.34-7.38 (1H, m), 7.75 (1H, s), 8.18 (1H, s), 8.26-8.30 (1H, m), 8.57-8.61 (1H, m), 9.32 (1H, br s).

Step 4

1-(Tetrahydro-2H-pyran-4-ylmethyl)-6-[3-(trifluoromethyl)-1H-pyrrolo[2,3-b]pyridin-5-yl]-1,3-dihydro-2H-imidazo[4,5-b]pyridin-2-one The title compound (19 mg) was obtained by the same procedure as in Step 6 of Example 35 using the compound obtained in the above Step 3 (28 mg).

MS (ESI) m/z: 418 (M+H)$^+$.

HRMS (ESI) [M+H]$^+$ calculated: $C_{20}H_{19}F_3N_5O_2$ 418.14908.

found: 418.14801.

$^1$H-NMR (DMSO-d$_6$) δ: 1.22-1.39 (2H, m), 1.45-1.55 (2H, m), 2.03-2.18 (1H, m), 3.19-3.29 (2H, m), 3.74-3.86 (4H, m), 7.95 (1H, d, J=1.8 Hz), 8.21-8.25 (2H, m), 8.26 (1H, d, J=1.8 Hz), 8.71 (1H, d, J=1.8 Hz), 11.66 (1H, br s).

Example 85

6-(3-Acetyl-1H-pyrrolo[2,3-b]pyridin-5-yl)-1-(tetrahydro-2H-pyran-4-ylmethyl)-1,3-dihydro-2H-imidazo[4,5-b]pyridin-2-one

[Formula 105]

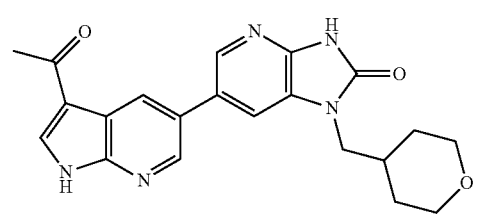

Step 1

1-(5-Bromo-1H-pyrrolo[2,3-b]pyridin-3-yl)ethanone

Aluminum trichloride (846 mg) was added to a solution of 5-bromo-1H-pyrrolo[2,3-b]pyridine (250 mg) in dichloromethane (5 ml) at room temperature over 10 minutes. Subsequently, acetyl chloride (135 μl) was added and the mixture was stirred at room temperature for 5 hours. The reaction solution was poured into ice-cold water and separated by adding dichloromethane. The resulting organic layer was washed with brine and dried over anhydrous sodium sulfate. The solvent was evaporated under reduced pressure. The resulting residue was purified by silica gel column chromatography (developed with methanol-chloroform) to give the title compound (186 mg).

MS (ESI) m/z: 239 (M+H)$^+$.

$^1$H-NMR (CDCl$_3$) δ: 2.55 (3H, s), 7.98 (1H, d, J=2.8 Hz), 8.45 (1H, d, J=2.3 Hz), 8.85 (1H, d, J=1.8 Hz), 10.28 (1H, br s).

Step 2

6-(3-Acetyl-1H-pyrrolo[2,3-b]pyridin-5-yl)-3-cyclohex-1-en-1-yl-1-(tetrahydro-2H-pyran-4-ylmethyl)-1,3-dihydro-2H-imidazo[4,5-b]pyridin-2-one The title compound (26 mg) was obtained by the same procedure as in Step 3 of Example 1 using the compound obtained in the above Step 1 (65 mg) and the compound obtained in Step 4 of Example 35 (113 mg).

MS (ESI) m/z: 472 (M+H)$^+$.

$^1$H-NMR (CDCl$_3$) δ: 1.43-1.54 (2H, m), 1.61-1.70 (2H, m), 1.74-1.83 (2H, m), 1.86-1.96 (2H, m), 2.11-2.25 (1H, m), 2.31-2.38 (2H, m), 2.47-2.54 (2H, m), 2.59 (3H, d, J=2.8 Hz), 3.32-3.43 (2H, m), 3.82-3.89 (2H, m), 3.94-4.04 (2H, m), 6.05-6.12 (1H, m), 7.41 (1H, d, J=1.8 Hz), 8.01-8.06 (1H, m), 8.29-8.33 (1H, m), 8.59 (1H, s), 8.84-8.88 (1H, m), 9.63 (1H, br s).

Step 3

6-(3-Acetyl-1H-pyrrolo[2,3-b]pyridin-5-yl)-1-(tetrahydro-2H-pyran-4-ylmethyl)-1,3-dihydro-2H-imidazo[4,5-b]pyridin-2-one The title compound (5 mg) was obtained by the same procedure as in Step 6 of Example 35 using the compound obtained in the above Step 2 (25 mg).

MS (ESI) m/z: 392 (M+H)$^+$.

HRMS (ESI) [M+H]$^+$ calculated: C$_{21}$H$_{22}$N$_5$O$_3$, 392.17226. found: 392.17437.

$^1$H-NMR (DMSO-d$_6$) δ: 1.27-1.38 (2H, m), 1.46-1.55 (2H, m), 2.03-2.17 (1H, m), 3.19-3.28 (2H, m), 3.79 (2H, d, J=7.4 Hz), 3.80-3.86 (2H, m), 7.74 (1H, d, J=2.9 Hz), 7.97 (1H, d, J=1.7 Hz), 8.18 (1H, d, J=1.7 Hz), 8.28 (1H, d, J=1.7 Hz), 8.65 (1H, d, J=2.3 Hz), 11.63 (1H, br s), 12.09 (1H, br s).

Example 86

6-[2-(Ethoxymethyl)-1H-pyrrolo[2,3-b]pyridin-5-yl]-1-(tetrahydro-2H-pyran-4-ylmethyl)-1,3-dihydro-2H-imidazo[4,5-b]pyridin-2-one

[Formula 106]

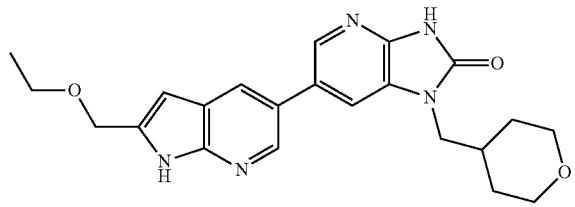

Step 1

5-Bromo-3-(3-{[tert-butyl(dimethyl)silyl]oxy}prop-1-yn-1-yl)pyridin-2-amine

Copper iodide (57 mg) was added to a solution of bis(triphenylphosphine)palladium(II) dichloride (105 mg) in triethylamine (10.4 ml), and the mixture was heated under reflux for 15 minutes. The reaction solution was cooled to 40° C. tert-Butyl(dimethyl)(propyn-2-yn-1-yloxy)silane (752 mg) and subsequently 5-bromo-3-iodopyridin-2-amine (896 mg) were added and the mixture was stirred at the same temperature for one hour. The solvent was evaporated under reduced pressure, and the resulting residue was separated by adding ethyl acetate and distilled water. The resulting organic layer was washed with a 10% aqueous citric acid solution and brine and dried over anhydrous sodium sulfate. The solvent was evaporated under reduced pressure. The residue was purified by silica gel column chromatography (developed with ethyl acetate-hexane) to give the title compound (606 mg).

MS (ESI) m/z: 341 (M+H)$^+$.

$^1$H-NMR (CDCl$_3$) δ: 0.16 (6H, s), 0.93 (9H, s), 4.56 (2H, s), 5.00 (2H, br s), 7.59 (1H, d, J=2.3 Hz), 8.05 (1H, d, J=2.3 Hz).

Step 2

6-[2-({[tert-Butyl(dimethyl)silyl]oxy}methyl)-1H-pyrrolo[2,3-b]pyridin-5-yl]-3-cyclohex-1-en-1-yl-1-(tetrahydro-2H-pyran-4-ylmethyl)-1,3-dihydro-2H-imidazo[4,5-b]pyridin-2-one The title compound (64 mg) was obtained by the same procedure as in Step 3 of Example 1 using the compound obtained in the above Step 1 (114 mg) and the compound obtained in Step 4 of Example 35 (140 mg).

MS (ESI) m/z: 574 (M+H)$^+$.

$^1$H-NMR (CDCl$_3$) δ: 0.15 (6H, s), 0.96 (9H, s), 1.44-1.69 (4H, m), 1.74-1.83 (2H, m), 1.86-1.96 (2H, m), 2.11-2.25 (1H, m), 2.30-2.39 (2H, m), 2.45-2.54 (2H, m), 3.31-3.42 (2H, m), 3.84 (2H, d, J=7.3 Hz), 3.95-4.04 (2H, m), 4.94 (2H, s), 6.04-6.10 (1H, m), 6.33-6.36 (1H, m), 7.36 (1H, d, J=1.8 Hz), 7.98 (1H, d, J=1.8 Hz), 8.28 (1H, d, J=1.8 Hz), 8.43 (1H, d, J=2.3 Hz), 8.90 (1H, br s).

Step 3

6-[2-(Ethoxymethyl)-1H-pyrrolo[2,3-b]pyridin-5-yl]-1-(tetrahydro-2H-pyran-4-ylmethyl)-1,3-dihydro-2H-imidazo[4,5-b]pyridin-2-one The title compound (9 mg) was obtained by the same procedure as in Step 6 of Example 35 using the compound obtained in the above Step 2 (61 mg).

HRMS (ESI) [M+H]$^+$ calculated: $C_{22}H_{26}N_5O_3$ 408.20356. found: 408.20579.

$^1$H-NMR (CDCl$_3$) δ: 1.24-1.31 (3H, m), 1.45-1.54 (2H, m), 1.61-1.68 (2H, m), 3.32-3.42 (2H, m), 3.57-3.66 (2H, m), 3.82 (2H, d, J=7.3 Hz), 3.94-4.03 (2H, m), 4.72 (2H, s), 6.44 (1H, s), 7.34-7.39 (1H, m), 8.00-8.02 (1H, m), 8.24-8.26 (1H, m), 8.44-8.47 (1H, m), 8.99 (1H, br s).

Example 87

6-(2,3-Dimethyl-1H-pyrrolo[2,3-b]pyridin-5-yl)-1-(tetrahydro-2H-pyran-4-ylmethyl)-1,3-dihydro-2H-imidazo[4,5-b]pyridin-2-one

[Formula 107]

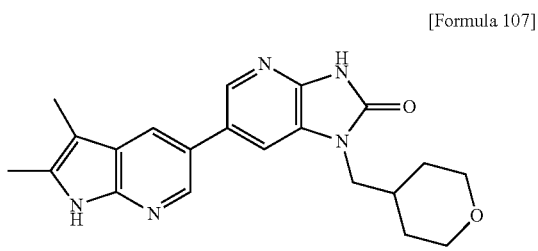 [SMILES: Cc1[nH]c2ncc(-c3cnc4[nH]c(=O)n(CC5CCOCC5)c4c3)cc2c1C]

Step 1

5-Bromo-2,3-dimethyl-1H-pyrrolo[2,3-b]pyridine

2-Butanone (715 μl) was added to a solution of 5-bromo-2-hydrazinopyridine (1000 mg) in ethanol (10 ml), and the mixture was heated under reflux for 2 hours. The reaction solution was concentrated under reduced pressure. Diethylene glycol (10 ml) was added and the mixture was heated under reflux for 23 hours. The reaction solution was concentrated under reduced pressure and separated by adding dichloromethane and distilled water. The resulting organic layer was washed with brine and dried over anhydrous sodium sulfate. The solvent was evaporated under reduced pressure. The resulting residue was purified by silica gel column chromatography (developed with methanol-chloroform) to give the title compound (104 mg).

$^1$H-NMR (CDCl$_3$) δ: 2.17 (3H, s), 2.40 (3H, s), 7.85 (1H, d, J=1.8 Hz), 8.20 (1H, d, J=1.8 Hz), 8.69 (1H, br s).

Step 2

3-Cyclohex-1-en-1-yl-6-(2,3-dimethyl-1H-pyrrolo[2,3-b]pyridin-5-yl)-1-(tetrahydro-2H-pyran-4-ylmethyl)-1,3-dihydro-2H-imidazo[4,5-b]pyridin-2-one The title compound (37 mg) was obtained by the same procedure as in Step 3 of Example 1 using the compound obtained in the above Step 1 (75 mg) and the compound obtained in Step 4 of Example 35 (140 mg).

MS (ESI) m/z: 458 (M+H)$^+$.

$^1$H-NMR (CDCl$_3$) δ: 1.42-1.58 (2H, m), 1.73-1.82 (2H, m), 1.85-1.99 (4H, m), 2.10-2.24 (1H, m), 2.27 (3H, s), 2.31-2.38 (2H, m), 2.44 (3H, s), 2.46-2.54 (2H, m), 3.31-3.42 (2H, m), 3.84 (2H, d, J=6.4 Hz), 3.93-4.03 (2H, m), 6.04-6.11 (1H, m), 7.34-7.38 (1H, m), 7.85 (1H, s), 8.26-8.30 (1H, m), 8.33-8.36 (1H, m), 8.54 (1H, br s).

Step 3

6-(2,3-Dimethyl-1H-pyrrolo[2,3-b]pyridin-5-yl)-1-(tetrahydro-2H-pyran-4-ylmethyl)-1,3-dihydro-2H-imidazo[4,5-b]pyridin-2-one The title compound (17 mg) was obtained by the same procedure as in Step 6 of Example 35 using the compound obtained in the above Step 2 (37 mg).

MS (ESI) m/z: 378 (M+H)$^+$.

HRMS (ESI) [M+H]$^+$ calculated: $C_{21}H_{24}N_5O_2$, 378.19300. found: 378.19290.

$^1$H-NMR (DMSO-d$_6$) δ: 1.22-1.38 (2H, m), 1.46-1.55 (2H, m), 2.04-2.15 (1H, m), 2.22 (3H, s), 2.34 (3H, s), 3.20-3.29 (2H, m), 3.78 (2H, d, J=7.4 Hz), 3.80-3.86 (2H, m), 7.89 (1H, d, J=1.7 Hz), 8.03 (1H, d, J=2.3 Hz), 8.23 (1H, d, J=1.7 Hz), 8.40 (1H, d, J=1.7 Hz), 11.29 (1H, s), 11.57 (1H, br s).

Example 88

6-(1H-Pyrrolo[3,2-b]pyridin-6-yl)-1-(tetrahydro-2H-pyran-4-ylmethyl)-1,3-dihydro-2H-imidazo[4,5-b]pyridin-2-one

[Formula 108]

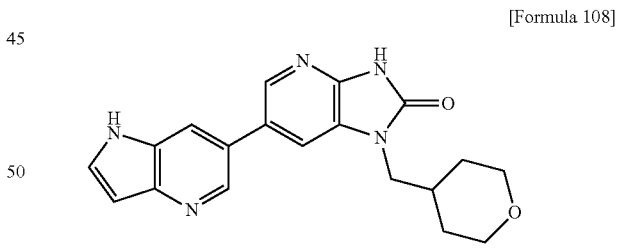

The title compound (33 mg) was obtained by the same procedure as in Step 3 of Example 1 using 6-bromo-1H-pyrrolo[3,2-b]pyridine (100 mg) and the compound obtained in Step 1 of Example 77 (118 mg).

MS (ESI) m/z: 350 (M+H)$^+$.

HRMS (ESI) [M+H]$^+$ calculated: $C_{19}H_{19}N_5O_2$, 350.16170. found: 350.1628.

$^1$H-NMR (DMSO-d$_6$) δ: 1.21-1.39 (2H, m), 1.47-1.55 (2H, m), 2.03-2.17 (1H, m), 3.19-3.29 (2H, m), 3.78 (2H, d, J=7.3 Hz), 3.80-3.87 (2H, m), 6.61 (1H, s), 7.68-7.72 (1H, m), 7.94 (1H, d, J=1.8 Hz), 8.01-8.05 (1H, m), 8.26 (1H, d, J=1.8 Hz), 8.67 (1H, d, J=1.8 Hz), 11.46 (1H, br s), 11.64 (1H, br s).

Example 89

6-{3-[(Dimethylamino)methyl]-1H-pyrrolo[2,3-b]pyridin-5-yl}-1-(tetrahydro-2H-pyran-4-ylmethyl)-1,3-dihydro-2H-imidazo[4,5-b]pyridin-2-one

[Formula 109]

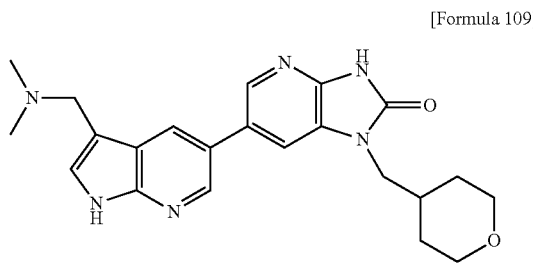

Step 1

3-Cyclohex-1-en-1-yl-6-(1H-pyrrolo[2,3-b]pyridin-5-yl)-1-(tetrahydro-2H-pyran-4-ylmethyl)-1,3-dihydro-2H-imidazo[4,5-b]pyridin-2-one The title compound (100 mg) was obtained by the same procedure as in Step 3 of Example 1 using the compound obtained in Step 4 of Example 35 (200 mg) and 5-bromo-1H-pyrrolo[2,3-b]pyridine (89 mg).
MS (ESI) m/z: 430 (M+H)$^+$.

Step 2

3-Cyclohex-1-en-1-yl-6-{3-[(dimethylamino)methyl]-1H-pyrrolo[2,3-b]pyridin-5-yl}-1-(tetrahydro-2H-pyran-4-ylmethyl)-1,3-dihydro-2H-imidazo[4,5-b]pyridin-2-one Formalin (34 μl) was added to a solution of dimethylamine hydrochloride (40 mg) in acetic acid (0.5 ml) under ice-cooling, and the mixture was stirred at the same temperature for 10 minutes. After warming to room temperature, 3-cyclohex-1-en-1-yl-6-(1H-pyrrolo[2,3-b]pyridin-5-yl)-1-(tetrahydro-2H-pyran-4-ylmethyl)-1,3-dihydro-2H-imidazo[4,5-b]pyridin-2-one obtained in the above Step 1 (100 mg) was added and the mixture was stirred at the same temperature for 16 hours. Acetic acid was distilled off under reduced pressure and water was added, followed by extraction with chloroform. The organic layer was dried over anhydrous sodium sulfate. The solvent was evaporated under reduced pressure. The resulting residue was purified by silica gel column chromatography (developed with methanol-chloroform) to give the title compound (102 mg).
MS (ESI) m/z: 487 (M+H)$^+$.

Step 3

6-{3-[(Dimethylamino)methyl]-1H-pyrrolo[2,3-b]pyridin-5-yl}-1-(tetrahydro-2H-pyran-4-ylmethyl)-1,3-dihydro-2H-imidazo[4,5-b]pyridin-2-one The title compound (48 mg) was obtained by the same procedure as in Step 6 of Example 35 using the compound obtained in the above Step 2 (102 mg).
MS (ESI) m/z: 407 (M+H)$^+$.

HRMS (ESI) [(M+H)$^+$] calculated: $C_{22}H_{27}N_6O_2$ 407.21955.
found: 407.21458.
$^1$H-NMR (DMSO-d$_6$) δ: 1.28-1.36 (2H, m), 1.51 (2H, d, J=10.9 Hz), 2.08-2.12 (1H, m), 2.18 (6H, s), 3.24 (2H, t, J=10.9 Hz), 3.61 (2H, s), 3.78-3.84 (4H, m), 7.40-7.42 (1H, m), 7.88-7.89 (1H, m), 8.20-8.21 (1H, m), 8.22-8.23 (1H, m), 8.52-8.53 (1H, m), 11.59 (1H, br s), 11.61 (1H, br s).

Example 90

6-{3-Isopropyl-1H-pyrrolo[2,3-b]pyridin-5-yl}-1-(tetrahydro-2H-pyran-4-ylmethyl)-1,3-dihydro-2H-imidazo[4,5-b]pyridin-2-one

[Formula 110]

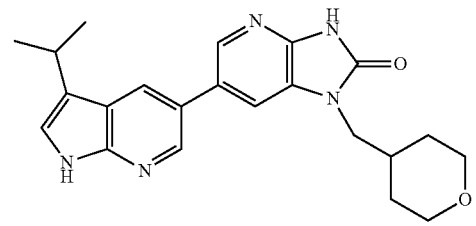

Step 1

5-Bromo-3-isopropenyl-1-[(4-methylphenyl)sulfonyl]-1H-pyrrolo[2,3-b]pyridine

5-Bromo-3-iodo-1-[(4-methylphenyl)sulfonyl]-1H-pyrrolo[2,3-b]pyridine obtained by the method described in WO 2006/015123 (150 mg) was dissolved in a mixed solvent of acetonitrile (1.5 ml) and an aqueous sodium carbonate solution (2 M, 1.5 ml). Isopropenyl-boronic acid pinacol ester (0.071 ml) and bis(triphenylphosphine)palladium(II) dichloride (11 mg) were added, and the mixture was heated with stirring at 60° C. overnight and at 80° C. for 7 hours in a nitrogen atmosphere in a sealed tube. The reaction solution was cooled to room temperature, diluted with ethyl acetate and washed with brine. The organic layer was dried over anhydrous sodium sulfate and the solvent was evaporated. The resulting residue was purified by thin-layer chromatography (developed with toluene) to give the title compound (53 mg).
MS (ESI) m/z: 391 (M+H)$^+$.
$^1$H-NMR (CDCl$_3$) δ: 2.15-2.16 (3H, m), 2.38 (3H, s), 5.21-5.24 (1H, m), 5.40-5.42 (1H, m), 7.29 (2H, d, J=8.1 Hz), 7.71 (1H, s), 8.05 (2H, d, J=8.1 Hz), 8.22 (1H, d, J=2.2 Hz), 8.44 (1H, d, J=2.2 Hz).

Step 2

3-Cyclohex-1-en-1-yl-6-{3-isopropenyl-1-[(4-methylphenyl)sulfonyl]-1H-pyrrolo[2,3-b]pyridin-5-yl}-1-(tetrahydro-2H-pyran-4-ylmethyl)-1,3-dihydro-2H-imidazo[4,5-b]pyridin-2-one The title compound (102 mg) was obtained by the same procedure as in Step 3 of Example 1 using the compound obtained in Step 4 of Example 35 (100 mg) and the compound obtained in the above Step 1 (88 mg).
MS (ESI) m/z: 624 (M+H)$^+$.

Step 3

3-Cyclohex-1-en-1-yl-6-{3-isopropenyl-1H-pyrrolo[2,3-b]pyridin-5-yl}-1-(tetrahydro-2H-pyran-4-ylmethyl)-1,3-dihydro-2H-imidazo[4,5-b]pyridin-2-one The title compound (50 mg) was obtained by the same procedure as in Step 3 of Example 84 using the compound obtained in the above Step 2 (102 mg).
MS (ESI) m/z: 470 (M+H)$^+$.

Step 4

6-{3-Isopropyl-1H-pyrrolo[2,3-b]pyridin-5-yl}-1-(tetrahydro-2H-pyran-4-ylmethyl)-1,3-dihydro-2H-imidazo[4,5-b]pyridin-2-one The title compound (8 mg) was obtained by the same procedure as in Step 6 of Example 35 using the compound obtained in the above Step 3 (50 mg).
MS (ESI) m/z: 392 (M+H)$^+$.
HRMS (ESI) [(M+H)$^+$] calculated: $C_{22}H_{26}N_5O_2$ 392.20865.
found: 392.20520.
$^1$H-NMR (CDCl$_3$) δ: 1.41 (3H, s), 1.42 (3H, s), 1.46-1.57 (2H, m), 1.64-1.71 (2H, m), 2.16-2.26 (1H, m), 3.23-3.30 (1H, m), 3.35-3.41 (2H, m), 3.87 (2H, d, J=7.3 Hz), 3.98-4.02 (2H, m), 7.19-7.20 (1H, m), 7.41-7.42 (1H, m), 8.11 (1H, d, J=1.8 Hz), 8.32 (1H, d, J=1.8 Hz), 8.53 (1H, d, J=1.8 Hz), 9.69 (1H, br s), 10.80 (1H, br s).

Example 91

5-[2-Oxo-1-(tetrahydro-2H-pyran-4-ylmethyl)-2,3-dihydro-1H-imidazo[4,5-b]pyridin-6-yl]-1H-pyrrolo[2,3-b]pyridine-4-carbonitrile

[Formula 111]

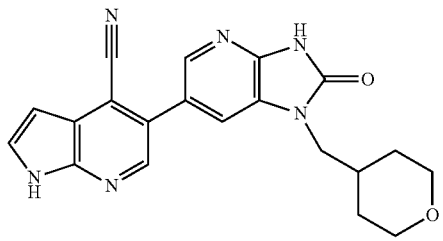

Step 1

2-Amino-5-bromo-3-iodoisonicotinonitrile

The title compound (5.47 g) was obtained by the same procedure as in Step 1 of Example 36 using 2-amino-5-bromo-isonicotinonitrile obtained by the method described in WO 2007/113226 (5.00 g).
MS (ESI) m/z: 324 (M+H)$^+$.

Step 2

2-Amino-5-bromo-3-[(trimethylsilyl)ethynyl]isonicotinonitrile

The title compound (1.38 g) was obtained by the same procedure as in Step 2 of Example 36 using the compound obtained in the above Step 1 (3.00 g).
MS (ESI) m/z: 294 (M+H)$^+$.

Step 3

N-{5-Bromo-4-cyano-3-[(trimethylsilyl)ethynyl]pyridin-2-yl}acetamide

The title compound (646 mg) was obtained by the same procedure as in Step 4 of Example 78 using the compound obtained in the above Step 2 (1.33 g).
MS (ESI) m/z: 336 (M+H)$^+$.

Step 4

5-Bromo-1H-pyrrolo[2,3-b]pyridine-4-carbonitrile

The title compound (78 mg) was obtained by the same procedure as in Step 5 of Example 78 using the compound obtained in the above Step 3 (646 mg).
MS (ESI) m/z: 222 (M+H)$^+$.
$^1$H-NMR (DMSO-d$_6$) δ: 6.65 (1H, d, J=3.5 Hz), 7.90 (1H, d, J=3.5 Hz), 8.55 (1H, s).

Step 5 tert-Butyl 5-bromo-4-cyano-1H-pyrrolo[2,3-b]pyridine-carboxylate

The title compound (108 mg) was obtained by the same procedure as in Step 1 of Example 35 using the compound obtained in the above Step 4 (78 mg).
MS (ESI) m/z: 266 (M-tBu+H)$^+$.

Step 6

5-[3-Cyclohex-1-en-1-yl-2-oxo-1-(tetrahydro-2H-pyran-4-ylmethyl)-2,3-dihydro-1H-imidazo[4,5-b]pyridin-6-yl]-1H-pyrrolo[2,3-b]pyridine-4-carbonitrile

[Formula 112]

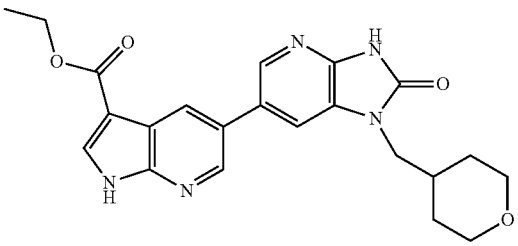

Step 1

5-Bromo-1H-pyrrolo[2,3-b]pyridine-3-carbonitrile

Hydroxylamine hydrochloride (46 mg) was added to a suspension of 5-bromo-1H-pyrrolo[2,3-b]pyridine-3-carbaldehyde obtained by the method of described in WO 2004/101565 (150 mg) in methanol (1.0 ml) under nitrogen atmosphere, and the mixture was stirred at room temperature for one hour. After azeotropic distillation with toluene, thionyl chloride (118 μl) was added to a suspension of the residue in toluene (2 ml), and the mixture was stirred at 80° C. for 16 hours and at 100° C. for 8 hours. After leaving to cool to room temperature, saturated aqueous sodium bicarbonate was added, followed by extraction with ethyl acetate. The organic layer was dried over anhydrous sodium sulfate. The solvent was evaporated under reduced pressure. The resulting residue was purified by silica gel column chromatography (developed with methanol-chloroform) to give the title compound (88 mg).

MS (ESI) m/z: 222 (M+H)$^+$.

$^1$H-NMR (DMSO-d$_6$) δ: 8.38-8.38 (1H, m), 8.47-8.47 (1H, m), 8.50 (1H, s).

Step 2 tert-Butyl 5-bromo-3-cyano-1H-pyrrolo[2,3-b]pyridine-3-carboxylate

The title compound (91 mg) was obtained by the same procedure as in Step 1 of Example 35 using the compound obtained in the above Step 1 (88 mg).

MS (ESI) m/z: 266 (M-tBu+H)$^+$.

Step 3

5-[3-Cyclohex-1-en-1-yl-2-oxo-1-(tetrahydro-2H-pyran-4-ylmethyl)-2,3-dihydro-1H-imidazo[4,5-b]pyridin-6-yl]-1H-pyrrolo[2,3-b]pyridine-3-carbonitrile The title compound (77 mg) was obtained by the same procedure as in Step 3 of Example 1 using the compound obtained in Step 4 of Example 35 (138 mg) and the compound obtained in the above Step 2 (91 mg).

MS (ESI) m/z: 455 (M+H)$^+$.

Step 4

Ethyl 5-[2-oxo-1-(tetrahydro-2H-pyran-4-ylmethyl)-2,3-dihydro-1H-imidazo[4,5-b]pyridin-6-yl]-1H-pyrrolo[2,3-b]pyridine-3-carboxylate The title compound (37 mg) was obtained by the same procedure as in Step 6 of Example 35 using the compound obtained in the above Step 3 (75 mg).

MS (ESI) m/z: 422 (M+H)$^+$.

HRMS (ESI) [(M+H)$^+$] calculated: C$_{22}$H$_{24}$N$_5$O$_4$ 422.18283. found: 422.18716.

$^1$H-NMR (DMSO-d$_6$) δ: 1.29-1.37 (5H, m), 1.50 (2H, d, J=10.9 Hz), 2.06-2.11 (1H, m), 3.22 (2H, t, J=10.9 Hz), 3.77-3.83 (4H, m), 4.31 (2H, q, J=7.1 Hz), 7.92 (1H, d, J=1.7 Hz), 8.21 (1H, d, J=1.7 Hz), 8.26 (1H, s), 8.49 (1H, d, J=2.3 Hz), 8.63 (1H, d, J=2.3 Hz), 11.65 (1H, br s).

Example 93

5-[2-oxo-1-(tetrahydro-2H-pyran-4-ylmethyl)-2,3-dihydro-1H-imidazo[4,5-b]pyridin-6-yl]-1H-pyrrolo[2,3-b]pyridine-3-carboxylic acid The title compound (125 mg) was obtained by the same procedure as in Step 3 of Example 1 using the compound obtained in Step 4 of Example 35 (163 mg) and the compound obtained in the above Step 5 (108 mg).

MS (ESI) m/z: 455 (M+H)±.

Step 7

5-[2-oxo-1-(tetrahydro-2H-pyran-4-ylmethyl)-2,3-dihydro-1H-imidazo[4,5-b]pyridin-6-yl]-1H-pyrrolo[2,3-b]pyridine-4-carbonitrile The title compound (54 mg) was obtained by the same procedure as in Step 6 of Example 35 using the compound obtained in the above Step 6 (125 mg).

MS (ESI) m/z: 375 (M+H)$^+$.

HRMS (ESI) [(M+H)$^+$] calculated: C$_{20}$H$_{19}$N$_6$O$_2$ 375.15695. found: 375.15940.

$^1$H-NMR (DMSO-d$_6$) δ: 1.30-1.33 (2H, m), 1.48-1.52 (2H, m), 2.05-2.12 (1H, m), 3.22 (2H, t, J=11.2 Hz), 3.72-3.75 (2H, m), 3.79-3.83 (2H, m), 6.67-6.69 (1H, m), 7.88-7.90 (2H, m), 8.15-8.17 (1H, m), 8.51-8.52 (1H, m), 11.79 (1H, br s), 12.46 (1H, br s).

Example 92

Ethyl 5-[2-oxo-1-(tetrahydro-2H-pyran-4-ylmethyl)-2,3-dihydro-1H-imidazo[4,5-b]pyridin-6-yl]-1H-pyrrolo[2,3-b]pyridine-3-carboxylate

[Formula 113]

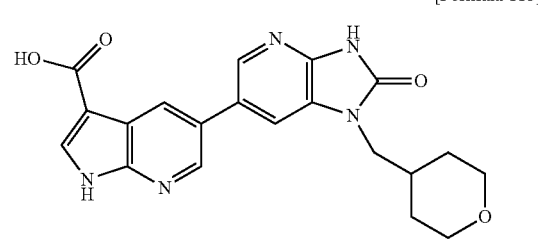

Step 1

5-[2-Oxo-1-(tetrahydro-2H-pyran-4-ylmethyl)-2,3-dihydro-1H-imidazo[4,5-b]pyridin-6-yl]-1H-pyrrolo[2,3-b]pyridine-3-carboxylic acid The aqueous layer in the separation operation in Step 4 of Example 92 was concentrated and purified by thin-layer chromatography (developed with methanol-water-chloroform) to give the title compound (14 mg).

MS (ESI) m/z: 394 (M+H)$^+$.

HRMS (ESI) [(M+H)$^+$] calculated: C$_{20}$H$_{20}$N$_5$O$_4$ 394.15153. found: 394.15466.

$^1$H-NMR (DMSO-d$_6$) δ: 1.27-1.35 (2H, m), 1.49 (2H, d, J=11.5 Hz), 2.05-2.12 (1H, m), 3.19-3.25 (1H, m), 3.77-3.83

(4H, m), 7.91 (1H, d, J=1.7 Hz), 8.16 (1H, s), 8.19 (1H, d, J=1.7 Hz), 8.49-8.50 (1H, m), 8.59-8.60 (1H, m), 11.63 (1H, br s), 12.48 (1H, br s).

Example 94

N-Methyl-5-[2-oxo-1-(tetrahydro-2H-pyran-4-ylmethyl)-2,3-dihydro-1H-imidazo[4,5-b]pyridin-6-yl]-1H-pyrrolo[2,3-b]pyridine-3-carboxamide

[Formula 114]

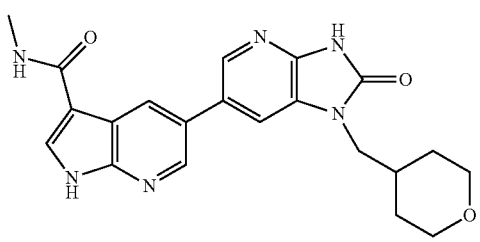

Step 1

N-Methyl-5-[2-oxo-1-(tetrahydro-2H-pyran-4-ylmethyl)-2,3-dihydro-1H-imidazo[4,5-b]pyridin-6-yl]-1H-pyrrolo[2,3-b]pyridine-3-carboxamide The compound obtained in Step 4 of Example 92 (34 mg) was dissolved in a solution of methylamine in methanol (1 M, 20 ml), and the solution was stirred in a sealed tube at 100° C. for 16 hours. The solvent was evaporated under reduced pressure. The residue was dissolved again in a solution of methylamine in methanol (1 M, 20 ml), and the solution was stirred in a sealed tube at 120° C. for 23 hours. After leaving to cool to room temperature, the solvent was concentrated off under reduced pressure and the residue was purified by thin-layer chromatography (developed with methanol-chloroform) to give the title compound (14 mg).

MS (ESI) m/z: 407 (M+H)$^+$.

HRMS (ESI) [(M+H)$^+$] calculated: $C_{21}H_{23}N_6O_3$ 407.18316.

found: 407.18633.

$^1$H-NMR (DMSO-d$_6$) δ: 1.28-1.38 (2H, m), 1.48-1.55 (2H, m), 2.07-2.14 (1H, m), 2.82 (3H, s), 3.25 (2H, t, J=12.0 Hz), 3.79-3.85 (4H, m), 7.91 (1H, s), 8.08 (1H, br s), 8.13 (1H, s), 8.24 (1H, s), 8.60 (1H, s), 8.68 (1H, s), 11.69 (1H, br s), 12.21 (1H, br s).

Example 95

5-[2-Oxo-1-(tetrahydro-2H-pyran-4-ylmethyl)-2,3-dihydro-1H-imidazo[4,5-b]pyridin-6-yl]-1H-pyrrolo[2,3-b]pyridine-3-carbonitrile

[Formula 115]

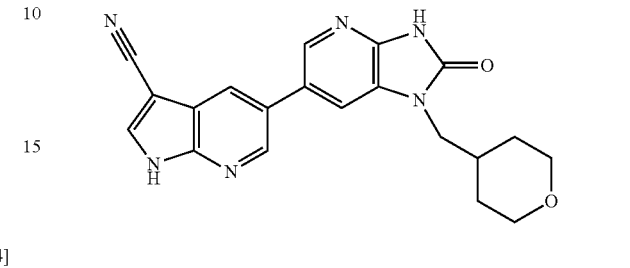

Step 1

5-[2-Oxo-1-(tetrahydro-2H-pyran-4-ylmethyl)-2,3-dihydro-1H-imidazo[4,5-b]pyridin-6-yl]-1H-pyrrolo[2,3-b]pyridine-3-carbonitrile The title compound (62 mg) was obtained by the same procedure as in Step 3 of Example 1 using the compound obtained in Step 1 of Example 77 (112 mg) and the compound obtained in Step 1 of Example 92 (75 mg).

MS (ESI) m/z: 375 (M+H)$^+$.

HRMS (ESI) [(M+H)$^+$] calculated: $C_{20}H_{19}FN_6O_2$ 375.15695.

found: 375.15878.

$^1$H-NMR (DMSO-d$_6$) δ: 1.28-1.37 (2H, m), 1.51 (2H, d, J=10.3 Hz), 2.08-2.14 (1H, m), 3.24 (2H, t, J=10.6 Hz), 3.79 (2H, d, J=7.4 Hz), 3.81-3.85 (2H, m), 7.80 (1H, br s), 8.01 (1H, d, J=2.3 Hz), 8.33 (1H, d, J=2.3 Hz), 8.40 (1H, d, J=2.3 Hz), 8.51 (1H, s), 8.75 (1H, d, J=2.3 Hz), 11.66 (1H, br s).

Example 96

6-(3-Fluoro-1H-pyrrolo[2,3-b]pyridin-5-yl)-1-(tetrahydro-2H-pyran-4-ylmethyl)-1,3-dihydro-2H-imidazo[4,5-b]pyridin-2-one

[Formula 116]

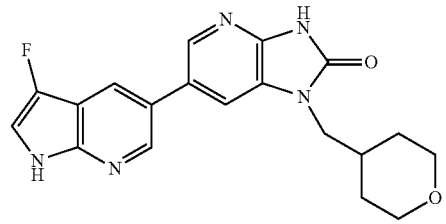

Step 1 tert-Butyl 5-bromo-3-fluoro-1H-pyrrolo[2,3-b]pyridine-1-carboxylate

The title compound (0.52 g) was obtained by the same procedure as in Step 1 of Example 35 using 5-bromo-3- fluoro-1H-pyrrolo[2,3-b]pyridine obtained by the method described in WO 2009/016460 (1.2 g).
¹H-NMR (CDCl₃) δ: 1.66 (9H, s), 7.42 (1H, d, J=2.0 Hz), 8.06 (1H, d, J=2.0 Hz), 8.57 (1H, d, J=2.0 Hz).

Step 2

3-Cyclohex-1-en-1-yl-6-(3-fluoro-1H-pyrrolo[2,3-b]pyridin-5-yl)-1-(tetrahydro-2H-pyran-4-ylmethyl)-1,3-dihydro-2H-imidazo[4,5-b]pyridin-2-one The title compound (104 mg) was obtained by the same procedure as in Step 3 of Example 1 using the compound obtained in Step 4 of Example 35 (192 mg) and the compound obtained in the above Step 1 (125 mg).
MS (ESI) m/z: 448 (M+H)⁺.

Step 3

6-(3-Fluoro-1H-pyrrolo[2,3-b]pyridin-5-yl)-1-(tetrahydro-2H-pyran-4-ylmethyl)-1,3-dihydro-2H-imidazo[4,5-b]pyridin-2-one The title compound (60 mg) was obtained by the same procedure as in Step 6 of Example 35 using the compound obtained in the above Step 2 (104 mg).
MS (ESI) m/z: 368 (M+H)⁺.
HRMS (ESI) [(M+H)⁺] calculated: $C_{19}H_{18}FN_5O_2$ 368.15228.
found: 368.15682.
¹H-NMR (DMSO-d₆) δ: 1.28-1.37 (2H, m), 1.49-1.52 (2H, m), 2.07-2.14 (1H, m), 3.24 (2H, t, J=11.2 Hz), 3.77 (2H, d, J=6.9 Hz), 3.81-3.85 (2H, m), 7.52-7.54 (1H, m), 7.97 (1H, s), 8.29-8.30 (2H, m), 8.63 (1H, d, J=1.7 Hz), 11.59 (1H, br s), 11.62 (1H, br s).

Example 97

1-[(1,1-Dioxidotetrahydro-2H-thiopyran-4-yl)methyl]-6-(1H-pyrrolo[2,3-b]pyridin-5-yl)-1,3-dihydro-2H-imidazo[4,5-b]pyridin-2-one

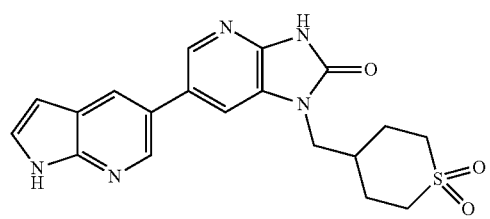

[Formula 117]

Step 1

6-Bromo-3-cyclohex-1-en-1-yl-1-[(1,1-dioxidotetrahydro-2H-thiopyran-4-yl)methyl]-1,3-dihydro-2H-imidazo[4,5-b]pyridin-2-one The title compound (313 mg) was obtained by the same method as in Step 3 of Example 35 using the compound obtained in Step 2 of Example 35 (280 mg) and (1,1-dioxidotetrahydro-2H-thiopyran-4-yl)methanol obtained by the method described in US 2007/82931 (187 mg).

MS (APCI) m/z: 440 [M+H]⁺
¹H-NMR (CDCl₃) δ: 1.71-1.78 (2H, m), 1.83-1.90 (2H, m), 1.96-2.20 (5H, m), 2.28-2.34 (2H, m), 2.38-2.44 (2H, m), 2.97 (2H, dd, J=17.9, 8.7 Hz), 3.11 (2H, d, J=13.4 Hz), 3.78 (2H, d, J=6.8 Hz), 6.00-6.02 (1H, m), 7.28 (1H, d, J=2.0 Hz), 8.12 (1H, d, J=2.0 Hz).

Step 2

3-Cyclohex-1-en-1-yl-1-[(1,1-dioxidotetrahydro-2H-thiopyran-4-yl)methyl]-6-(1H-pyrrolo[2,3-b]pyridin-5-yl)-1,3-dihydro-2H-imidazo[4,5-b]pyridin-2-one The title compound (91 mg) was obtained by the same procedure as in Step 3 of Example 1 using the compound obtained in the above Step 1 (309 mg) and 5-(4,4,5,5-tetramethyl-1,3,2-dioxaborolan-2-yl)-1H-pyrrolo[2,3-b]pyridine (107 mg).
MS (APCI) m/z: 478 [M+H]⁺

Step 3

1-[(1,1-Dioxidotetrahydro-2H-thiopyran-4-yl)methyl]-6-(1H-pyrrolo[2,3-b]pyridin-5-yl)-1,3-dihydro-2H-imidazo[4,5-b]pyridin-2-one The title compound (63 mg) was obtained by the same procedure as in Step 6 of Example 35 using the compound obtained in the above Step 4 (91 mg).
MS (APCI) m/z: 398 [M+H]⁺
¹H-NMR (DMSO-d₆) δ: 1.72-1.84 (2H, m), 1.97-2.00 (2H, br m), 2.21-2.23 (1H, br m), 3.09-3.11 (4H, m), 3.83 (2H, d, J=7.1 Hz), 6.52 (1H, dd, J=3.1, 1.9 Hz), 7.53 (1H, t, J=3.1 Hz), 7.95 (1H, d, J=1.9 Hz), 8.24-8.28 (2H, m), 8.56 (1H, d, J=1.9 Hz), 11.64 (1H, br s), 11.75 (1H, br s).

Example 98

1-[(trans-4-Methoxycyclohexyl)methyl]-6-(1H-pyrrolo[2,3-b]pyridin-5-yl)-1,3-dihydro-2H-imidazo[4,5-b]pyridin-2-one

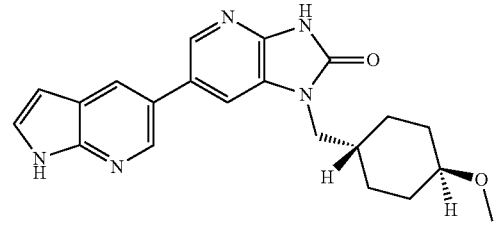

[Formula 118]

Step 1

(trans-4-Methoxycyclohexyl)methanol (cis-4-Methoxycyclohexyl)methanol

The title compound trans isomer (0.59 g) and cis isomer (0.94 g) were obtained by the same procedure as in Step 2 of Example 33 using 4-methoxycyclohexanecarboxylic acid (2.0 g).

Trans Isomer

¹H-NMR (CDCl₃) δ: 0.98-1.02 (2H, m), 1.15-1.25 (2H, m), 1.44-1.50 (1H, m), 1.83-1.87 (2H, m), 2.08-2.13 (2H, m), 3.07-3.12 (1H, m), 3.35 (3H, s), 3.46 (2H, d, J=6.3 Hz).

Cis Isomer

¹H-NMR (CDCl₃) δ: 1.32-1.55 (7H, m), 1.88-1.92 (2H, m), 3.31 (3H, s), 3.43-3.45 (1H, m), 3.47-3.48 (2H, m).

Step 2

6-Bromo-3-cyclohex-1-en-1-yl-1-[(trans-4-methoxycyclohexyl)methyl]-1,3-dihydro-2H-imidazo[4,5-b]pyridin-2-one The title compound (216 mg) was obtained by the same procedure as in Step 3 of Example 35 using the compound obtained in Step 2 of Example 35 (280 mg) and (trans-4-methoxycyclohexyl)methanol obtained in the above Step 1 (164 mg).

MS (APCI) m/z: 420 [M+H]⁺

¹H-NMR (CDCl₃) δ: 1.10-1.23 (5H, m), 1.73-1.88 (7H, m), 2.08-2.11 (2H, m), 2.30-2.31 (2H, m), 2.42-2.43 (2H, m), 3.34 (3H, s), 3.68 (2H, d, J=7.1 Hz), 6.00-6.02 (1H, m), 7.27 (1H, d, J=2.0 Hz), 8.09 (1H, d, J=2.0 Hz).

Step 3

3-Cyclohex-1-en-1-yl-1-[(trans-4-methoxycyclohexyl)methyl]-6-(1H-pyrrolo[2,3-b]pyridin-5-yl)-1,3-dihydro-2H-imidazo[4,5-b]pyridin-2-one The title compound (223 mg) was obtained by the same procedure as in Step 3 of Example 1 using the compound obtained in the above Step 2 (205 mg) and 5-(4,4,5,5-tetramethyl-1,3,2-dioxaborolan-2-yl)-1H-pyrrolo[2,3-b]pyridine (131 mg).

MS (APCI) m/z: 458 [M+H]⁺

Step 4

1-[(trans-4-Methoxycyclohexyl)methyl]-6-(1H-pyrrolo[2,3-b]pyridin-5-yl)-1,3-dihydro-2H-imidazo[4,5-b]pyridin-2-one The title compound (141 mg) was obtained by the same procedure as in Step 6 of Example 35 using the compound obtained in the above Step 3 (223 mg).

MS (APCI) m/z: 378 [M+H]⁺

¹H-NMR (DMSO-d₆) δ: 1.08-1.14 (5H, m), 1.66-1.68 (2H, m), 1.81-1.84 (1H, m), 1.97-1.99 (2H, m), 3.19 (3H, s), 3.72-3.74 (3H, m), 6.52 (1H, dd, J=2.8, 1.9 Hz), 7.53 (1H, t, J=2.8 Hz), 7.86 (1H, d, J=1.9 Hz), 8.24 (2H, t, J=2.3 Hz), 8.55 (1H, d, J=2.3 Hz), 11.58 (1H, br s), 11.74 (1H, br s).

Example 99

1-[(cis-4-Methoxycyclohexyl)methyl]-6-(1H-pyrrolo[2,3-b]pyridin-5-yl)-1,3-dihydro-2H-imidazo[4,5-b]pyridin-2-one

[Formula 119]

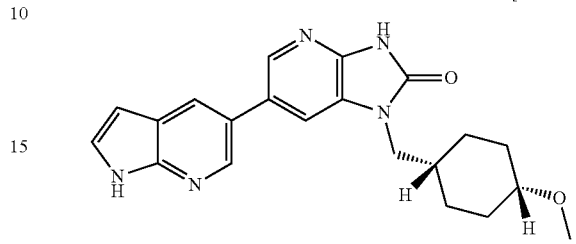

Step 1

6-Bromo-3-cyclohex-1-en-1-yl-1-[(cis-4-methoxycyclohexyl)methyl]-1,3-dihydro-2H-imidazo[4,5-b]pyridin-2-one The title compound (298 mg) was obtained by the same procedure as in Step 3 of Example 35 using the compound obtained in Step 2 of Example 35 (280 mg) and the compound obtained in Step 1 of Example 98 (164 mg).

MS (APCI) m/z: 420 [M+H]⁺

¹H-NMR (CDCl₃) δ: 1.33-1.46 (6H, m), 1.73-1.77 (2H, m), 1.86-1.93 (5H, m), 2.30-2.31 (2H, m), 2.42-2.42 (2H, m), 3.31 (3H, s), 3.43-3.46 (1H, br m), 3.68 (2H, d, J=7.3 Hz), 6.00-6.02 (1H, m), 7.28 (1H, d, J=2.0 Hz), 8.07 (1H, d, J=2.0 Hz).

Step 2

3-Cyclohex-1-en-1-yl-1-[(cis-4-methoxycyclohexyl)methyl]-6-(1H-pyrrolo[2,3-b]pyridin-5-yl)-1,3-dihydro-2H-imidazo[4,5-b]pyridin-2-one The title compound (208 mg) was obtained by the same procedure as in Step 3 of Example 1 using the compound obtained in the above Step 1 (191 mg) and 5-(4,4,5,5-tetramethyl-1,3,2-dioxaborolan-2-yl)-1H-pyrrolo[2,3-b]pyridine (107 mg).

MS (APCI) m/z: 458 [M+H]⁺

Step 3

1-[(cis-4-Methoxycyclohexyl)methyl]-6-(1H-pyrrolo[2,3-b]pyridin-5-yl)-1,3-dihydro-2H-imidazo[4,5-b]pyridin-2-one The title compound (135 mg) was obtained by the same procedure as in Step 6 of Example 35 using the compound obtained in the above Step 2 (208 mg).

MS (APCI) m/z: 378 [M+H]⁺

¹H-NMR (DMSO-d₆) δ: 1.40-1.92 (10H, m), 3.18 (4H, s), 3.73 (3H, d, J=7.1 Hz), 6.51 (1H, dd, J=3.3, 1.8 Hz), 7.52 (1H, t, J=2.8 Hz), 7.88 (1H, d, J=1.8 Hz), 8.24 (2H, dd, J=4.1, 2.1 Hz), 8.54 (1H, d, J=2.1 Hz), 11.57 (1H, br s), 11.73 (1H, br s).

Example 100

4-{[2-Oxo-6-(1H-pyrrolo[2,3-b]pyridin-5-yl)-2,3-dihydro-1H-imidazo[4,5-b]pyridin-1-yl]methyl}tetrahydro-2H-pyran-4-carbonitrile

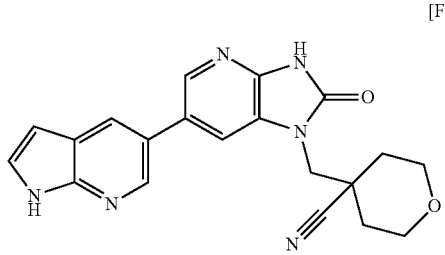

[Formula 120]

Step 1

4-[(6-Bromo-3-cyclohex-1-en-1-yl-2-oxo-2,3-dihydro-1H-imidazo[4,5-b]pyridin-1-yl)methyl]tetrahydro-2H-pyran-4-carbonitrile The title compound (39 mg) was obtained by the same method as in Step 3 of Example 35 using the compound obtained in Step 2 of Example 35 (280 mg) and (4-cyanotetrahydro-2H-pyran-4-yl)methanol obtained by the method described in WO 2008/029825 (161 mg).

MS (APCI) m/z: 417 [M+H]$^+$

Step 2

4-{[3-Cyclohex-1-en-1-yl-2-oxo-6-(1H-pyrrolo[2,3-b]pyridin-5-yl)-2,3-dihydro-1H-imidazo[4,5-b]pyridin-1-yl]methyl}tetrahydro-2H-pyran-4-carbonitrile The title compound (39 mg) was obtained by the same procedure as in Step 3 of Example 1 using the compound obtained in the above Step 1 (39 mg) and 5-(4,4,5,5-tetramethyl-1,3,2-dioxaborolan-2-yl)-1H-pyrrolo[2,3-b]pyridine (25 mg).

MS (APCI) m/z: 455 [M+H]$^+$

Step 3

4-{[2-Oxo-6-(1H-pyrrolo[2,3-b]pyridin-5-yl)-2,3-dihydro-1H-imidazo[4,5-b]pyridin-1-yl]methyl}tetrahydro-2H-pyran-4-carbonitrile The title compound (15 mg) was obtained by the same procedure as in Step 6 of Example 35 using the compound obtained in the above Step 2 (39 mg).

MS (APCI) m/z: 375 [M+H]$^+$ $^1$H-NMR (DMSO-d$_6$) δ: 1.85-1.95 (4H, m), 3.46 (2H, t, J=12.0 Hz), 3.92-3.94 (2H, br m), 4.22 (2H, s), 6.52 (1H, dd, J=3.3, 1.6 Hz), 7.53 (1H, dd, J=2.2, 1.6 Hz), 8.11 (1H, d, J=2.0 Hz), 8.21 (1H, d, J=2.2 Hz), 8.28 (1H, d, J=1.6 Hz), 8.53 (1H, d, J=2.0 Hz), 11.76 (2H, br s).

Example 101

1-[(trans-4-Hydroxycyclohexyl)methyl]-6-(1H-pyrrolo[2,3-b]pyridin-5-yl)-1,3-dihydro-2H-imidazo[4,5-b]pyridin-2-one

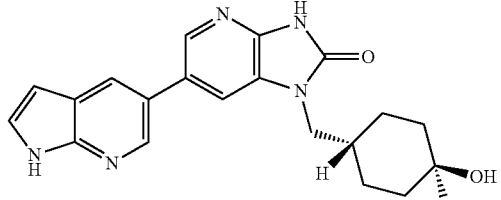

[Formula 121]

Step 1 trans-Ethyl 4-{[tert-butyl(dimethyl)silyl]oxy}cyclohexanecarboxylate cis-Ethyl 4-{[tert-butyl(dimethyl)silyl]oxy}cyclohexanecarboxylate The title compound trans isomer (0.85 g) and cis isomer (1.0 g) were obtained by the same procedure as in Step 2 of Example 62 using ethyl 4-hydroxycyclohexanecarboxylate (2.0 g).

Trans Isomer
$^1$H-NMR (CDCl$_3$) δ: 0.05 (6H, s), 0.88 (9H, s), 1.24 (3H, t, J=7.1 Hz), 1.30-1.32 (2H, m), 1.46-1.49 (2H, m), 1.89-1.96 (4H, m), 2.21-2.23 (1H, m), 3.55-3.58 (1H, m), 4.11 (2H, q, J=7.1 Hz).

Cis Isomer
$^1$H-NMR (CDCl$_3$) δ: 0.03 (6H, s), 0.89 (9H, s), 1.25 (3H, t, J=7.1 Hz), 1.49-1.50 (2H, m), 1.61-1.66 (4H, m), 1.92-1.95 (2H, m), 2.27-2.30 (1H, m), 3.88-3.90 (1H, m), 4.12 (2H, q, J=7.1 Hz).

Step 2

(trans-4-{[tert-Butyl(dimethyl)silyl]oxy}cyclohexyl)methanol

The title compound (0.83 g) was obtained by the same procedure as in Step 2 of Example 33 using trans-ethyl 4-{[tert-butyl(dimethyl)silyl]oxy}cyclohexanecarboxylate obtained in the above Step 1 (0.85 g).

$^1$H-NMR (CDCl$_3$) δ: 0.06 (6H, s), 0.89 (9H, s), 0.97-1.00 (2H, m), 1.27-1.32 (2H, m), 1.45-1.47 (1H, m), 1.78-1.81 (2H, m), 1.87-1.91 (2H, m), 3.45 (2H, d, J=6.3 Hz), 3.51-3.54 (1H, m).

Step 3

6-Bromo-1-[(trans-4-{[tert-butyl(dimethyl)silyl]oxy}cyclohexyl)methyl]-3-cyclohex-1-en-1-yl-1,3-dihydro-2H-imidazo[4,5-b]pyridin-2-one The title compound (273 mg) was obtained by the same procedure as in Step 3 of Example 35 using the compound obtained in Step 2 of Example 35 (280 mg) and the compound obtained in the above Step 2 (279 mg).

MS (APCI) m/z: 520 [M+H]$^+$

Step 4

1-[(trans-4-{[tert-Butyl(dimethyl)silyl]oxy}cyclohexyl)methyl]-3-cyclohex-1-en-1-yl-6-(1H-pyrrolo[2,3-b]pyridin-5-yl)-1,3-dihydro-2H-imidazo[4,5-b]pyridin-2-one The title compound (205 mg) was obtained by the same procedure as in Step 3 of Example 1 using the compound obtained in the above Step 3 (208 mg) and 5-(4,4,5,5-tetramethyl-1,3,2-dioxaborolan-2-yl)-1H-pyrrolo[2,3-b]pyridine (107 mg).
MS (APCI) m/z: 558 [M+H]$^+$

Step 5

1-[(trans-4-Hydroxycyclohexyl)methyl]-6-(1H-pyrrolo[2,3-b]pyridin-5-yl)-1,3-dihydro-2H-imidazo[4,5-b]pyridin-2-one The title compound (96 mg) was obtained by the same procedure as in Step 6 of Example 35 using the compound obtained in the above Step 4 (205 mg).
MS (APCI) m/z: 364 [M+H]$^+$
$^1$H-NMR (DMSO-d$_6$) δ: 1.06-1.14 (5H, m), 1.60-1.63 (2H, br m), 1.81-1.87 (3H, br m), 3.73 (2H, d, J=10.2 Hz), 4.49 (1H, d, J=4.4 Hz), 6.52 (1H, dd, J=3.3, 1.7 Hz), 7.53 (1H, dd, J=2.9, 1.7 Hz), 7.86 (1H, d, J=1.7 Hz), 8.24 (2H, dd, J=2.9, 2.0 Hz), 8.55 (1H, d, J=2.0 Hz), 11.58 (1H, br s), 11.74 (1H, br s).

Example 102

1-[(cis-4-Hydroxycyclohexyl)methyl]-6-(1H-pyrrolo[2,3-b]pyridin-5-yl)-1,3-dihydro-2H-imidazo[4,5-b]pyridin-2-one

[Formula 122]

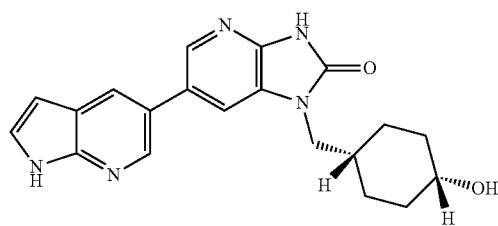

Step 1

(cis-4-{[tert-Butyl(dimethyl)silyl]oxy}cyclohexyl)methanol

The title compound (0.89 g) was obtained by the same procedure as in Step 2 of Example 33 using cis-ethyl 4-{[tert-butyl(dimethyl)silyl]oxy}cyclohexanecarboxylate obtained in Step 1 of Example 101 (1.0 g).
$^1$H-NMR (CDCl$_3$) δ: 0.03 (6H, s), 0.89 (9H, s), 1.26-1.29 (1H, m), 1.46-1.48 (6H, m), 1.65-1.66 (2H, m), 3.46-3.49 (2H, m), 3.96-3.97 (1H, m).

Step 2

6-Bromo-1-[(cis-4-{[tert-butyl(dimethyl)silyl]oxy}cyclohexyl)methyl]-3-cyclohex-1-en-1-yl-1,3-dihydro-2H-imidazo[4,5-b]pyridin-2-one The title compound (251 mg) was obtained by the same procedure as in Step 3 of Example 35 using the compound obtained in Step 2 of Example 35 (280 mg) and the compound obtained in the above Step 1 (279 mg).
MS (APCI) m/z: 520 [M+H]$^+$

Step 3

1-[(cis-4-{[tert-Butyl(dimethyl)silyl]oxy}cyclohexyl)methyl]-3-cyclohex-1-en-1-yl-6-(1H-pyrrolo[2,3-b]pyridin-5-yl)-1,3-dihydro-2H-imidazo[4,5-b]pyridin-2-one The title compound (194 mg) was obtained by the same procedure as in Step 3 of Example 1 using the compound obtained in the above Step 2 (208 mg) and 5-(4,4,5,5-tetramethyl-1,3,2-dioxaborolan-2-yl)-1H-pyrrolo[2,3-b]pyridine (107 mg).
MS (APCI) m/z: 558 [M+H]$^+$

Step 4

1-[(cis-4-Hydroxycyclohexyl)methyl]-6-(1H-pyrrolo[2,3-b]pyridin-5-yl)-1,3-dihydro-2H-imidazo[4,5-b]pyridin-2-one The title compound (92 mg) was obtained by the same procedure as in Step 6 of Example 35 using the compound obtained in the above Step 3 (194 mg).
MS (APCI) m/z: 364 [M+H]$^+$
$^1$H-NMR (DMSO-d$_6$) δ: 1.30-1.98 (6H, m), 3.73-3.81 (3H, m), 4.29 (1H, d, J=3.2 Hz), 6.51-6.52 (1H, m), 7.52 (1H, dd, J=2.8, 1.6 Hz), 7.87 (1H, d, J=6.8 Hz), 8.23-8.26 (2H, m), 8.54 (1H, d, J=2.0 Hz), 11.58 (1H, br s), 11.73 (1H, br s).

Example 103

1-[(4,4-Difluorocyclohexyl)methyl]-6-(1H-pyrrolo[2,3-b]pyridin-5-yl)-1,3-dihydro-2H-imidazo[4,5-b]pyridin-2-one

[Formula 123]

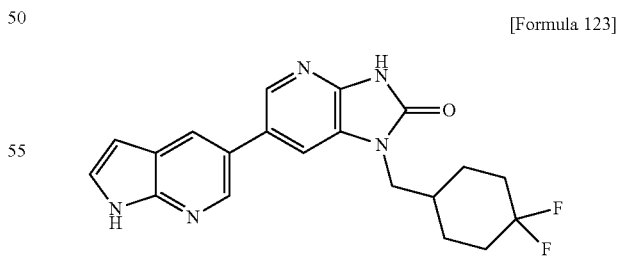

Step 1

(4,4-Difluorocyclohexyl)methanol
The title compound (0.423 g) was obtained by the same procedure as in Step 2 of Example 33 using ethyl 4,4-difluorocyclohexanecarboxylate (1.13 g).

¹H-NMR (CDCl₃) δ: 1.29-1.33 (2H, m), 1.56-1.58 (1H, m), 1.63-1.80 (2H, m), 1.84-1.86 (2H, m), 2.09-2.14 (2H, m), 3.52 (2H, d, J=6.6 Hz).

Step 2

6-Bromo-3-cyclohex-1-en-1-yl-1-[(4,4-difluorocyclohexyl)methyl]-1,3-dihydro-2H-imidazo[4,5-b]pyridin-2-one The title compound (236 mg) was obtained by the same procedure as in Step 3 of Example 35 using the compound obtained in Step 2 of Example 35 (280 mg) and (4,4-difluorocyclohexyl)methanol obtained in the above Step 1 (171 mg).
MS (APCI) m/z: 426 [M+H]⁺

Step 3

3-Cyclohex-1-en-1-yl-1-[(4,4-difluorocyclohexyl)methyl]-6-(1H-pyrrolo[2,3-b]pyridin-5-yl)-1,3-dihydro-2H-imidazo[4,5-b]pyridin-2-one The title compound (108 mg) was obtained by the same procedure as in Step 3 of Example 1 using the compound obtained in the above Step 2 (171 mg) and 5-(4,4,5,5-tetramethyl-1,3,2-dioxaborolan-2-yl)-1H-pyrrolo[2,3-b]pyridine (107 mg).
MS (APCI) m/z: 464 [M+H]⁺

Step 4

1-[(4,4-Difluorocyclohexyl)methyl]-6-(1H-pyrrolo[2,3-b]pyridin-5-yl)-1,3-dihydro-2H-imidazo[4,5-b]pyridin-2-one The title compound (86 mg) was obtained by the same procedure as in Step 6 of Example 35 using the compound obtained in the above Step 3 (108 mg).
MS (APCI) m/z: 384 [M+H]⁺
¹H-NMR (DMSO-d₆) δ: 1.26-1.40 (2H, m), 1.66-1.78 (4H, m), 1.94-2.09 (3H, s), 3.80 (2H, d, J=7.3 Hz), 6.52 (1H, dd, J=3.3, 1.8 Hz), 7.52-7.54 (1H, m), 7.92 (1H, d, J=2.0 Hz), 8.25 (2H, d, J=2.0 Hz), 8.55 (1H, d, J=2.2 Hz), 11.61 (1H, s), 11.74 (1H, s).

Example 104

1-{[trans-3-Methoxycyclohexyl]methyl}-6-(1H-pyrrolo[2,3-b]pyridin-5-yl)-1,3-dihydro-2H-imidazo[4,5-b]pyridin-2-one

[Formula 124]

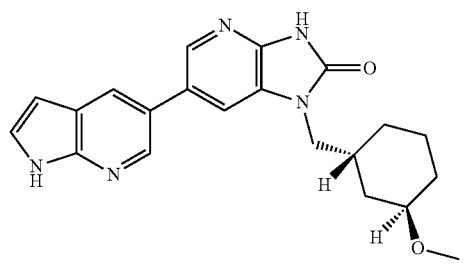

and an enantiomer thereof

Step 1

(trans-3-Methoxycyclohexyl)methanol (cis-3-Methoxycyclohexyl)methanol

The title compound trans isomer (0.41 g) and cis isomer (0.39 g) were obtained by the same procedure as in Step 2 of Example 33 using 3-methoxycyclohexanecarboxylic acid (2.0 g).
trans isomer
¹H-NMR (CDCl₃) δ: 1.02-1.05 (1H, m), 1.14-1.21 (1H, m), 1.25-1.27 (1H, m), 1.33-1.36 (1H, m), 1.49-1.56 (1H, m), 1.71-1.75 (1H, m), 1.84-1.94 (3H, m), 3.31 (3H, s), 3.45-3.47 (2H, m), 3.53-3.54 (1H, m).
cis isomer
¹H-NMR (CDCl₃) δ: 0.85-0.89 (2H, m), 1.09-1.16 (1H, m), 1.23-1.30 (1H, m), 1.53-1.57 (1H, m), 1.70-1.75 (1H, m), 1.82-1.85 (1H, m), 2.05-2.08 (1H, m), 2.13-2.15 (1H, m), 3.13-3.18 (1H, m), 3.36 (3H, s), 3.50-3.51 (2H, m).

Step 2

6-Bromo-3-cyclohex-1-en-1-yl-1-{[trans-4-methoxycyclohexyl]methyl}-1,3-dihydro-2H-imidazo[4,5-b]pyridin-2-one The title compound (281 mg) was obtained by the same procedure as in Step 3 of Example 35 using the compound obtained in Step 2 of Example 35 (280 mg), (trans-3-methoxycyclohexyl)methanol obtained in the above Step 1 (164 mg) and bis(2-methoxyethyl) azodicarboxylate in place of diisopropyl azodicarboxylate (267 mg).
MS (APCI) m/z: 420 [M+H]⁺
¹H-NMR (DMSO-d₆) δ: 1.03-1.05 (1H, m), 1.16-1.22 (1H, m), 1.28-1.33 (1H, m), 1.40-1.43 (2H, m), 1.52-1.55 (1H, m), 1.60-1.76 (6H, m), 2.05-2.10 (1H, m), 2.21-2.22 (2H, m), 2.32-2.32 (2H, m), 3.17 (3H, s), 3.46-3.48 (1H, m), 3.68 (2H, d, J=7.6 Hz), 5.91-5.93 (1H, m), 7.91 (1H, d, J=2.1 Hz), 8.06 (1H, d, J=2.1 Hz).

Step 3

3-Cyclohex-1-en-1-yl-1-{[trans-3-methoxycyclohexyl]methyl}-6-(1H-pyrrolo[2,3-b]pyridin-5-yl)-1,3-dihydro-2H-imidazo[4,5-b]pyridin-2-one The title compound (142 mg) was obtained by the same procedure as in Step 3 of Example 1 using the compound obtained in the above Step 2 (168 mg) and 5-(4,4,5,5-tetramethyl-1,3,2-dioxaborolan-2-yl)-1H-pyrrolo[2,3-b]pyridine (107 mg).
MS (APCI) m/z: 458 [M+H]⁺
¹H-NMR (CDCl₃) δ: 1.09-1.98 (12H, m), 2.25-2.37 (3H, m), 2.47-2.53 (2H, m), 3.25 (4H, s), 3.54-3.59 (1H, m), 3.79 (2H, d, J=7.3 Hz), 6.06-6.09 (1H, m), 6.60 (1H, dd, J=3.7, 1.8 Hz), 7.37 (1H, d, J=1.8 Hz), 7.39-7.42 (1H, m), 8.09 (1H, d, J=1.8 Hz), 8.28 (1H, d, J=1.8 Hz), 8.50 (1H, s), 9.35 (1H, s).

Step 4

1-{[trans-3-Methoxycyclohexyl]methyl}-6-(1H-pyrrolo[2,3-b]pyridin-5-yl)-1,3-dihydro-2H-imidazo[4,5-b]pyridin-2-one The title compound (86 mg) was obtained by the same procedure as in Step 6 of Example 35 using the compound obtained in the above Step 3 (141 mg).

MS (APCI) m/z: 378 [M+H]+

1H-NMR (DMSO-d6) δ: 1.02-1.42 (5H, m), 1.54-1.57 (1H, m), 1.69-1.72 (2H, m), 2.12-2.15 (1H, m), 3.09 (3H, s), 3.44-3.47 (1H, br m), 3.73 (2H, d, J=16.3 Hz), 6.50 (1H, dd, J=3.2, 1.8 Hz), 7.51 (1H, t, J=3.0 Hz), 7.84 (1H, d, J=1.8 Hz), 8.22 (2H, d, J=1.8 Hz), 8.52 (1H, d, J=2.3 Hz), 11.57 (1H, br s), 11.72 (1H, br s).

Example 105

1-{[cis-3-Methoxycyclohexyl]methyl}-6-(1H-pyrrolo[2,3-b]pyridin-5-yl)-1,3-dihydro-2H-imidazo[4,5-b]pyridin-2-one

[Formula 125]

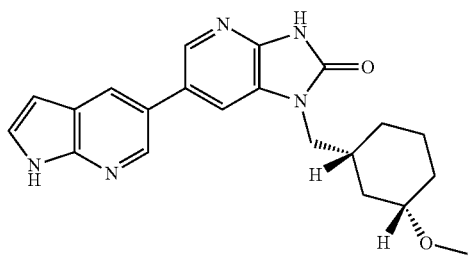

and an enantiomer thereof

Step 1

6-Bromo-3-cyclohex-1-en-1-yl-1-{[cis-4-methoxycyclohexyl]methyl}-1,3-dihydro-2H-imidazo[4,5-b]pyridin-2-one The title compound (215 mg) was obtained by the same procedure as in Step 2 of Example 104 using the compound obtained in Step 2 of Example 35 (280 mg) and (cis-3-methoxycyclohexyl)methanol obtained in Step 1 of Example 104 (164 mg).

MS (APCI) m/z: 420 [M+H]+

1H-NMR (DMSO-d6) δ: 0.83-1.01 (2H, m), 1.13-1.21 (1H, m), 1.51-1.54 (1H, m), 1.67-1.78 (6H, m), 1.94-1.97 (2H, m), 2.21-2.21 (2H, m), 2.32-2.33 (2H, m), 3.06-3.11 (1H, m), 3.21 (3H, s), 3.66-3.77 (2H, m), 5.91-5.93 (1H, m), 7.92 (1H, d, J=2.0 Hz), 8.07 (1H, d, J=2.0 Hz).

Step 2

3-Cyclohex-1-en-1-yl-1-{[cis-3-methoxycyclohexyl]methyl}-6-(1H-pyrrolo[2,3-b]pyridin-5-yl)-1,3-dihydro-2H-imidazo[4,5-b]pyridin-2-one The title compound (124 mg) was obtained by the same procedure as in Step 3 of Example 1 using the compound obtained in the above Step 1 (168 mg) and 5-(4,4,5,5-tetramethyl-1,3,2-dioxaborolan-2-yl)-1H-pyrrolo[2,3-b]pyridine (107 mg).

MS (APCI) m/z: 458 [M+H]+

1H-NMR (CDCl3) δ: 0.98-1.94 (10H, m), 1.97-2.13 (3H, m), 2.32-2.35 (2H, m), 2.49-2.52 (2H, m), 3.11-3.16 (1H, m), 3.33 (3H, s), 3.81 (2H, ddd, J=27.9, 7.2, 3.6 Hz), 6.07-6.09 (1H, m), 6.60 (1H, dd, J=3.7, 1.8 Hz), 7.36 (1H, d, J=1.8 Hz), 7.43 (1H, t, J=2.7 Hz), 8.09 (1H, d, J=2.3 Hz), 8.29 (1H, d, J=1.8 Hz), 8.51 (1H, d, J=2.3 Hz), 9.80 (1H, br s).

Step 3

1-{[cis-3-Methoxycyclohexyl]methyl}-6-(1H-pyrrolo[2,3-b]pyridin-5-yl)-1,3-dihydro-2H-imidazo[4,5-b]pyridin-2-one The title compound (86 mg) was obtained by the same procedure as in Step 6 of Example 35 using the compound obtained in the above Step 2 (123 mg).

MS (APCI) m/z: 378 [M+H]+

1H-NMR (DMSO-d6) δ: 0.86-1.01 (3H, m), 1.11-1.15 (1H, m), 1.52-1.55 (1H, m), 1.67-1.71 (1H, m), 1.83-1.96 (3H, m), 3.02-3.07 (1H, m), 3.17 (3H, s), 3.72-3.77 (2H, m), 6.50 (1H, dd, J=3.4, 1.6 Hz), 7.51 (1H, t, J=3.0 Hz), 7.86 (1H, d, J=1.8 Hz), 8.23 (2H, d, J=1.8 Hz), 8.53 (1H, d, J=2.3 Hz), 11.57 (1H, br s), 11.72 (1H, br s).

Example 106

1-[(4-Oxotetrahydro-2H-pyran-3-yl)methyl]-6-(1H-pyrrolo[2,3-b]pyridin-5-yl)-1,3-dihydro-2H-imidazo[4,5-b]pyridin-2-one

[Formula 126]

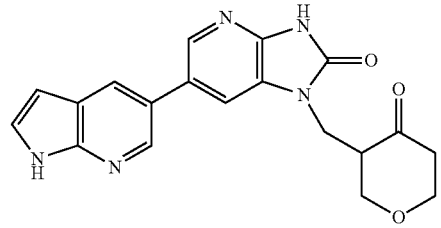

Step 1

Ethyl 4-oxotetrahydro-2H-pyran-3-carboxylate

Lithium diisopropylamide (1.14 mol/l solution in n-hexane/tetrahydrofuran, 2.5 ml) was added dropwise to a solution of tetrahydro-4H-pyran-4-one (260 mg) in tetrahydrofuran (13 ml) at −78° C., and the mixture was stirred for one hour while warming to 0° C. The reaction solution was cooled to −78° C. again, hexamethylphosphoric triamide (452 µl) was added and subsequently ethyl cyanoformate (280 µl) was added at the same temperature. The mixture was stirred over one hour while warming to 0° C. The reaction solution was separated by adding distilled water and ethyl acetate. The resulting organic layer was washed with brine and dried over anhydrous sodium sulfate. The solvent was evaporated under reduced pressure. The resulting residue was purified by silica gel column chromatography (developed with ethyl acetate-hexane) to give the title compound (210 mg).

1H-NMR (CDCl3) δ: 1.30 (3H, t, J=6.9 Hz), 2.36-2.42 (2H, m), 3.82-3.88 (2H, m), 4.23 (3H, q, J=7.3 Hz), 4.29-4.26 (2H, m), 11.86 (1H, s).

Step 2

Ethyl 1,4,8-trioxaspiro[4.5]decane-6-carboxylate

Bis(trimethylsiloxy)ethane (3.68 ml) was added to a solution of the compound obtained in the above Step 1 (860 mg)

in dichloromethane (50 ml) at room temperature. The reaction solution was cooled to −15° C. and trimethylsilyl trifluoromethanesulfonate (92 μl) was added. The mixture was stirred for 2 hours while warming to 0° C. and further stirred at room temperature for 3.5 hours. Pyridine (0.2 ml) was added under ice-cooling, and then the mixture was separated by adding dichloromethane and a saturated aqueous sodium bicarbonate solution. The resulting organic layer was washed with brine and dried over anhydrous sodium sulfate. The solvent was evaporated under reduced pressure. The resulting residue was purified by silica gel column chromatography (developed with ethyl acetate-hexane) to give the title compound (956 mg).

$^1$H-NMR (CDCl$_3$) δ: 1.28 (3H, t, J=7.3 Hz), 1.65-1.75 (1H, m), 2.00-2.09 (1H, m), 2.75-2.82 (1H, m), 3.75-3.85 (2H, m), 3.90-4.03 (6H, m), 4.18 (2H, q, J=6.9 Hz).

Step 3

1,4,8-Trioxaspiro[4.5]dec-6-ylmethanol

The title compound (152 mg) was obtained by the same procedure as in Step 2 of Example 33 using the compound obtained in the above Step 2 (211 mg) and lithium aluminum hydride (60 mg).

$^1$H-NMR (CDCl$_3$) δ: 1.17-1.27 (1H, m), 1.60-1.70 (1H, m), 1.81-1.90 (1H, m), 1.98-2.06 (1H, m), 2.45-2.52 (1H, m), 3.76-3.64 (4H, m), 3.92-3.76 (4H, m).

Step 4

6-Bromo-3-cyclohex-1-en-1-yl-1-(1,4,8-trioxaspiro[4.5]dec-6-ylmethyl)-1,3-dihydro-2H-imidazo[4,5-b]pyridin-2-one The title compound (120 mg) was obtained by the same procedure as in Step 3 of Example 35 using the compound obtained in the above Step 3 (151 mg) and the compound obtained in Step 2 of Example 35 (243 mg).

MS (ESI) m/z: 450 (M+H)$^+$.

$^1$H-NMR (CDCl$_3$) δ: 1.61-1.78 (3H, m), 1.82-1.92 (3H, m), 2.24-2.34 (3H, m), 2.37-2.44 (2H, m), 3.49 (1H, d, J=5.5 Hz), 3.55-3.63 (1H, m), 3.74-3.89 (4H, m), 3.96-4.11 (4H, m), 6.03-5.96 (1H, m), 7.40 (1H, d, J=1.8 Hz), 8.09 (1H, d, J=1.8 Hz).

Step 5

3-Cyclohex-1-en-1-yl-6-(1H-pyrrolo[2,3-b]pyridin-5-yl)-1-(1,4,8-trioxaspiro[4.5]dec-6-ylmethyl)-1,3-dihydro-2H-imidazo[4,5-b]pyridin-2-one The title compound (94 mg) was obtained by the same procedure as in Step 3 of Example 1 using the compound obtained in the above Step 4 (115 mg) and 5-(4,4,5,5-tetramethyl-1,3,2-dioxaborolan-2-yl)-1H-pyrrolo[2,3-b]pyridine (76 mg).

MS (ESI) m/z: 488 (M+H)$^+$.

$^1$H-NMR (CDCl$_3$) δ: 1.62-1.71 (1H, m), 1.73-1.81 (2H, m), 1.85-1.95 (3H, m), 2.30-2.40 (3H, m), 2.45-2.53 (2H, m), 3.62-3.69 (1H, m), 3.77-3.84 (3H, m), 3.92-4.15 (6H, m), 6.03-6.09 (1H, m), 6.58-6.62 (1H, m), 7.36-7.40 (1H, m), 7.50 (1H, d, J=1.8 Hz), 8.08 (1H, d, J=2.3 Hz), 8.28 (1H, d, J=1.8 Hz), 8.50 (1H, d, J=2.3 Hz), 8.75 (1H, br s).

Step 6

1-[(4-Oxotetrahydro-2H-pyran-3-yl)methyl]-6-(1H-pyrrolo[2,3-b]pyridin-5-yl)-1,3-dihydro-2H-imidazo[4,5-b]pyridin-2-one The title compound (11 mg) was obtained by the same procedure as in Step 6 of Example 35 using the compound obtained in the above Step 5 (90 mg).

MS (ESI) m/z: 346 (M+H)$^+$.

HRMS (ESI) [M+H]$^+$ calculated: C$_{19}$H$_{17}$N$_5$O$_3$ 364.14096. found: 364.14502.

$^1$H-NMR (DMSO-d$_6$) δ: 2.34-2.47 (2H, m), 3.20-3.51 (4H, m), 4.59 (2H, s), 6.47-6.52 (1H, m), 7.40-7.44 (1H, m), 7.49-7.53 (1H, m), 7.74 (1H, d, J=2.3 Hz), 8.19 (1H, d, J=1.8 Hz), 8.24 (1H, d, J=1.8 Hz), 8.49 (1H, d, J=2.3 Hz), 11.65 (1H, br s), 11.71 (1H, br s).

Example 107

6-(1H-Pyrrolo[2,3-b]pyridin-5-yl)-1-(tetrahydrofuran-3-ylmethyl)-1,3-dihydro-2H-imidazo[4,5-b]pyridin-2-one

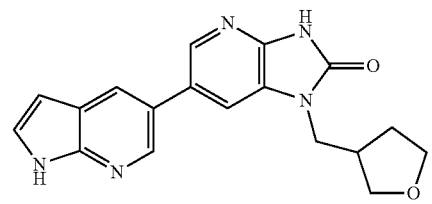

[Formula 127]

Step 1

6-Bromo-3-cyclohex-1-en-1-yl-1-(tetrahydrofuran-3-ylmethyl)-1,3-dihydro-2H-imidazo[4,5-b]pyridin-2-one The title compound (85 mg) was obtained by the same procedure as in Step 3 of Example 35 using the compound obtained in Step 2 of Example 35 (100 mg) and tetrahydrofuran-3-ylmethanol (42 μl).

MS (APCI) m/z: 378 [M+H]$^+$ $^1$H-NMR (CDCl$_3$) δ: 1.71-1.79 (5H, m), 1.86-1.88 (2H, m), 2.01-2.09 (1H, m), 2.30-2.32 (2H, m), 2.39-2.44 (2H, m), 2.78-2.85 (1H, m), 3.64 (1H, dd, J=8.9, 4.8 Hz), 3.77-3.80 (3H, m), 3.90 (1H, dd, J=14.2, 7.6 Hz), 3.99 (1H, td, J=8.2, 5.8 Hz), 6.00-6.03 (1H, m), 7.34 (1H, d, J=2.0 Hz), 8.10 (1H, d, J=2.0 Hz).

Step 2

6-Bromo-1-(tetrahydrofuran-3-ylmethyl)-1,3-dihydro-2H-imidazo[4,5-b]pyridin-2-one The title compound (55 mg) was obtained by the same procedure as in Step 6 of Example 35 using the compound obtained in the above Step 1 (85 mg).

MS (APCI) m/z: 298 [M+H]$^+$

Step 3

6-(1H-Pyrrolo[2,3-b]pyridin-5-yl)-1-(tetrahydrofuran-3-ylmethyl)-1,3-dihydro-2H-imidazo[4,5-b]pyridin-2-one The title compound (39 mg) was obtained by the same procedure as in Step 3 of Example 1 using the compound obtained in the above Step 2 (55 mg) and 5-(4,4,5,5-tetramethyl-1,3,2-dioxaborolan-2-yl)-1H-pyrrolo[2,3-b]pyridine (50 mg).

MS (APCI) m/z: 336 [M+H]$^+$ $^1$H-NMR (DMSO-d$_6$) δ: 1.64-1.67 (1H, m), 1.89-1.94 (1H, m), 2.48-2.50 (4H, m), 2.76-2.82 (1H, m), 3.51 (1H, dd, J=8.4, 5.5 Hz), 3.61-3.67 (2H, m), 3.80 (1H, td, J=8.0, 5.5 Hz), 3.87 (2H, d, J=7.6 Hz), 6.50 (1H, dd, J=3.1, 1.8 Hz), 7.51 (1H, t, J=3.1 Hz), 7.92 (1H, d, J=2.1 Hz), 8.24 (2H, d, J=1.8 Hz), 8.52 (1H, d, J=2.1 Hz), 11.61 (1H, s), 11.71 (1H, br s).

Example 108

1-(Morpholin-3-ylmethyl)-6-(1H-pyrrolo[2,3-b]pyridin-5-yl)-1,3-dihydro-2H-imidazo[4,5-b]pyridin-2-one

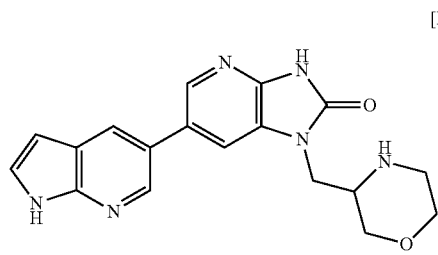

[Formula 128]

Step 1 tert-Butyl 3-[(6-bromo-3-cyclohex-1-en-1-yl-2-oxo-2,3-dihydro-1H-imidazo[4,5-b]pyridin-1-yl)methyl]morpholine-4-carboxylate The title compound (469 mg) was obtained by the same method as in Step 3 of Example 35 using the compound obtained in Step 2 of Example 35 (471 mg) and tert-butyl 3-(hydroxymethyl)morpholine-4-carboxylate obtained by the method described in WO 2006/99352 (521 mg).

MS (APCI) m/z: 493 [M+H]$^+$

Step 2 tert-Butyl 3-{[3-cyclohex-1-en-1-yl-2-oxo-6-(1H-pyrrolo[2,3-b]pyridin-5-yl)-2,3-dihydro-1H-imidazo[4,5-b]pyridin-1-yl]methyl}morpholine-4-carboxylate The title compound (177 mg) was obtained by the same procedure as in Step 3 of Example 1 using the compound obtained in the above Step 1 (197 mg) and 5-(4,4,5,5-tetramethyl-1,3,2-dioxaborolan-2-yl)-1H-pyrrolo[2,3-b]pyridine (107 mg).

MS (APCI) m/z: 531 [M+H]$^+$

Step 3

1-(Morpholin-3-ylmethyl)-6-(1H-pyrrolo[2,3-b]pyridin-5-yl)-1,3-dihydro-2H-imidazo[4,5-b]pyridin-2-one The title compound (64 mg) was obtained by the same procedure as in Step 6 of Example 35 using the compound obtained in the above Step 2 (177 mg).

MS (APCI) m/z: 351 [M+H]$^+$ $^1$H-NMR (DMSO-d$_6$) δ: 2.62-2.65 (1H, m), 2.76 (1H, d, J=10.0 Hz), 3.06-3.08 (1H, m), 3.20 (1H, t, J=9.8 Hz), 3.58 (1H, d, J=11.0 Hz), 3.70-3.79 (4H, m), 6.50 (1H, t, J=1.6 Hz), 7.51 (1H, d, J=2.3 Hz), 7.87 (1H, d, J=1.8 Hz), 8.23 (2H, d, J=1.8 Hz), 8.52 (1H, d, J=1.8 Hz), 11.72 (1H, br s).

Example 109

1-{[(3S)-4-Methyl-5-oxomorpholin-3-yl]methyl}-6-(1H-pyrrolo[2,3-b]pyridin-5-yl)-1,3-dihydro-2H-imidazo[4,5-b]pyridin-2-one

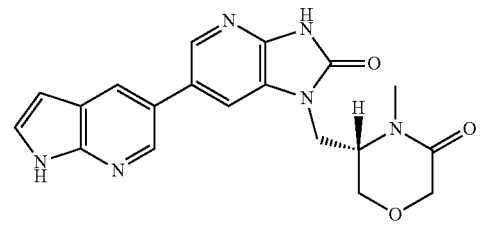

[Formula 129]

Step 1

N-[(1R)-2-(Benzyloxy)-1-(hydroxymethyl)ethyl]-2-chloroacetamide (2R)-2-Amino-3-(benzyloxy)propan-1-ol (2.18 g) was dissolved in acetonitrile (38 ml) and methanol (7 ml), and triethylamine (2.0 ml) was added. The atmosphere was replaced with nitrogen, and then the mixture was cooled to −10° C. A solution of chloroacetyl chloride (1.05 ml) in acetonitrile (9 ml) was added dropwise thereto, and the mixture was stirred for 20 hours to be gradually warmed to room temperature. The reaction solvent was distilled off, and the residue was directly purified by silica gel column chromatography (developed with ethyl acetate-hexane) to give the title compound (2.26 g).

MS (APCI) m/z: 258 [M+H]$^+$ $^1$H-NMR (CDCl$_3$) δ: 3.64 (1H, dd, J=9.5, 4.1 Hz), 3.69-3.73 (2H, m), 3.87 (1H, dd, J=11.3, 4.0 Hz), 4.05 (2H, d, J=2.9 Hz), 4.11-4.13 (1H, m), 4.55 (2H, s), 7.22 (1H, br s), 7.32-7.37 (5H, m).

Step 2

(5S)-5-[(Benzyloxy)methyl]morpholin-3-one

Potassium tert-butoxide (982 mg) was dissolved in 2-methylbutan-2-ol (7 ml). A solution of the compound obtained in the above Step 1 (2.254 g) in 2-methylbutan-2-ol (15 ml) was added dropwise in a nitrogen atmosphere over one hour. After the addition was completed, the mixture was further stirred for one hour and then the reaction solvent was distilled off. The residue was purified by silica gel column chromatography (developed with ethyl acetate-ethanol) to give the title compound (807 mg).

MS (APCI) m/z: 222 [M+H]$^+$ $^1$H-NMR (CDCl$_3$) δ: 3.43 (1H, dd, J=9.0, 8.1 Hz), 3.55 (1H, dd, J=9.0, 5.5 Hz), 3.64 (1H, dd, J=11.7, 5.5 Hz), 3.72-3.76 (1H, m), 3.86 (1H, dd, J=11.7, 3.8 Hz), 4.15 (2H, d, J=4.4 Hz), 4.54 (2H, dd, J=13.4, 11.7 Hz), 6.60 (1H, br s), 7.29-7.39 (5H, m).

Step 3

(5S)-5-[(Benzyloxy)methyl]-4-methylmorpholin-3-one

The compound obtained in the above Step 2 (449 mg) was dissolved in tetrahydrofuran (6 ml), and the solution was ice-cooled under nitrogen atmosphere. 55% Sodium hydride (133 mg) was added and the mixture was stirred under ice-cooling for 30 minutes. After further adding tetrahydrofuran (18 ml), methyl iodide (695 μl) was added and the mixture was stirred for 25 hours to be gradually warmed to room temperature. The reaction solution was extracted once by adding toluene, and the aqueous layer was extracted with ethyl acetate three times. The organic layer was washed with brine and then dried over anhydrous sodium sulfate, and the solvent was evaporated. The residue was purified by silica gel column chromatography (developed with ethyl acetate) to give the title compound (454 mg).

MS (APCI) m/z: 236 [M+H]$^+$ $^1$H-NMR (CDCl$_3$) δ: 3.02 (3H, s), 3.36-3.41 (1H, m), 3.65 (1H, dd, J=9.3, 4.6 Hz), 3.70 (1H, t, J=8.7 Hz), 3.76 (1H, dd, J=11.8, 3.1 Hz), 4.06 (1H, dd, J=12.0, 1.5 Hz), 4.15 (2H, q, J=16.4 Hz), 4.56 (2H, t, J=12.5 Hz), 7.29-7.39 (5H, m).

Step 4

(5S)-5-(Hydroxymethyl)-4-methylmorpholin-3-one

The compound obtained in the above Step 3 (454 mg) was dissolved in ethanol, and 20% palladium hydroxide was added. The mixture was reacted in a hydrogen atmosphere at room temperature for 14 hours. The reaction solvent was filtered through Celite, washed with ethanol and then distilled off. The residue was dissolved in a small amount of acetonitrile, and the solution was filtered through a cotton plug. The filtrate was concentrated to give the title compound (276 mg) as a colorless oil.

MS (APCI) m/z: 146 [M+H]$^+$ $^1$H-NMR (CDCl$_3$) δ: 3.06 (3H, s), 3.28-3.32 (1H, m), 3.81-3.92 (3H, m).

Step 5

6-Bromo-3-cyclohex-1-en-1-yl-1-{[(3S)-4-methyl-5-oxomorpholin-3-yl]methyl}-1,3-dihydro-2H-imidazo[4,5-b]pyridin-2-one The title compound (318 mg) was obtained as colorless needle-like crystals by the same procedure as in Step 3 of Example 35 using the compound obtained in Step 2 of Example 35 (235 mg) and the compound obtained in the above Step 4 (174 mg).

MS (APCI) m/z: 421 [M+H]$^+$ $^1$H-NMR (CDCl$_3$) δ: 1.71-1.79 (2H, m), 1.83-1.91 (2H, m), 2.28-2.46 (4H, m), 3.14 (3H, s), 3.62-3.68 (1H, m), 3.71-3.81 (2H, m), 4.00 (1H, dd, J=14.0, 9.9 Hz), 4.18 (1H, ddd, J=14.2, 3.9, 1.2 Hz), 4.19 (1H, d, J=16.6 Hz), 4.35 (1H, d, J=16.6 Hz), 6.00-6.03 (1H, m), 7.43 (1H, d, J=2.0 Hz), 8.13 (1H, d, J=2.0 Hz).

Step 6

3-Cyclohex-1-en-1-yl-1-{[(3S)-4-methyl-5-oxomorpholin-3-yl]methyl}-6-(1H-pyrrolo[2,3-b]pyridin-5-yl)-1,3-dihydro-2H-imidazo[4,5-b]pyridin-2-one The title compound (133 mg) was obtained by the same procedure as in Step 3 of Example 1 using the compound obtained in the above Step 5 (169 mg) and 5-(4,4,5,5-tetramethyl-1,3,2-dioxaborolan-2-yl)-1H-pyrrolo[2,3-b]pyridine (107 mg).

MS (APCI) m/z: 459 [M+H]$^+$

Step 7

1-{[(3S)-4-Methyl-5-oxomorpholin-3-yl]methyl}-6-(1H-pyrrolo[2,3-b]pyridin-5-yl)-1,3-dihydro-2H-imidazo[4,5-b]pyridin-2-one The compound obtained in the above Step 6 (133 mg) was dissolved in a mixed solvent of ethanol (1 ml), water (0.5 ml) and concentrated sulfuric acid (0.5 ml), and the mixture was stirred at 80° C. for three days. The reaction solution was neutralized with sodium carbonate and then concentrated to dryness. The residue was dissolved in 1,4-dioxane (10 ml) and 4 N hydrochloric acid (10 ml) and the solution was stirred at room temperature for two days. After extraction with dichloromethane/methanol (9/1), the inorganic salt was removed through Porapak™ RxnCX, followed by elution with 5% aqueous ammonia/ethanol. The eluate was concentrated and then dissolved in ethanol (3 ml) and water (1 ml). 4-(4,6-Dimethoxy-1,3,5-triazin-2-yl)-4-methylmorpholinium chloride (160 mg) was added and the mixture was stirred at room temperature for 14 hours. The solvent was concentrated and then water was added, followed by sufficiently stirring. The insoluble matter was collected by filtration, washed with water and ethyl acetate and then dried by suction to give the title compound (30 mg) as ivory crystals.

MS (APCI) m/z: 379 [M+H]$^+$ $^1$H-NMR (DMSO-d$_6$) δ: 2.91 (3H, s), 3.59-4.22 (7H, m), 6.49-6.52 (1H, m), 7.50-7.53 (1H, m), 7.72-7.76 (1H, m), 8.20-8.22 (1H, m), 8.23-8.25 (1H, m), 8.49-8.52 (1H, m), 11.72 (2H, br s).

Example 110

1-[(5-Oxomorpholin-2-yl)methyl]-6-(1H-pyrrolo[2,3-b]pyridin-5-yl)-1,3-dihydro-2H-imidazo[4,5-b]pyridin-2-one

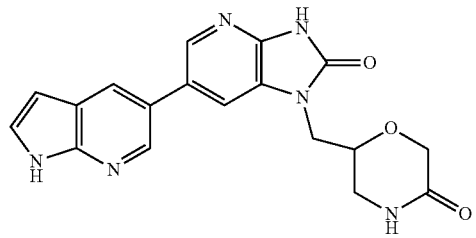

[Formula 130]

Step 1

6-(Hydroxymethyl)morpholin-3-one

Potassium tert-butoxide (1.08 g) was dissolved in 2-methylbutan-2-ol (7.7 ml). A solution of 2-chloro-N-(2,3-dihydroxypropyl)acetamide obtained by the method described in WO 2007/6715 (1.61 g) in 2-methylbutan-2-ol (16.4 ml) was added dropwise in a nitrogen atmosphere over one hour. After the addition was completed, the mixture was further stirred for one hour and then the reaction solvent was distilled off. The residue was purified by silica gel column chromatography (developed with ethyl acetate-ethanol) to give the title compound (488 mg).

MS (APCI) m/z: 132 [M+H]$^+$ $^1$H-NMR (DMSO-d$_6$) δ: 3.07 (1H, t, J=11.2 Hz), 3.13-3.20 (1H, m), 3.38-3.51 (2H, m), 3.62-3.68 (1H, m), 4.00 (2H, d, J=5.6 Hz).

Step 2

6-Bromo-3-cyclohex-1-en-1-yl-1-[(5-oxomorpholin-2-yl)methyl]-1,3-dihydro-2H-imidazo[4,5-b]pyridin-2-one The title compound (285 mg) was obtained by the same procedure as in Step 3 of Example 35 using the compound obtained in Step 2 of Example 35 (235 mg) and the compound obtained in the above Step 1 (157 mg).

MS (APCI) m/z: 407 [M+H]$^+$

Step 3

3-Cyclohex-1-en-1-yl-1-[(5-oxomorpholin-2-yl)methyl]-6-(1H-pyrrolo[2,3-b]pyridin-5-yl)-1,3-dihydro-2H-imidazo[4,5-b]pyridin-2-one The title compound (117 mg) was obtained by the same procedure as in Step 3 of Example 1 using the compound obtained in the above Step 2 (163 mg) and 5-(4,4,5,5-tetramethyl-1,3,2-dioxaborolan-2-yl)-1H-pyrrolo[2,3-b]pyridine (107 mg).

MS (APCI) m/z: 445 [M+H]$^+$

Step 4

1-[(5-Oxomorpholin-2-yl)methyl]-6-(1H-pyrrolo[2,3-b]pyridin-5-yl)-1,3-dihydro-2H-imidazo[4,5-b]pyridin-2-one The title compound (61 mg) was obtained by the same procedure as in Step 7 of Example 109 using the compound obtained in the above Step 3 (117 mg).

MS (APCI) m/z: 365 [M+H]$^+$ $^1$H-NMR (DMSO-d$_6$) δ: 3.93-4.15 (7H, m), 6.49 (1H, dd, J=3.7, 1.8 Hz), 7.51 (1H, t, J=2.3 Hz), 7.84 (1H, d, J=2.3 Hz), 7.98 (1H, d, J=3.7 Hz), 8.22 (1H, d, J=2.3 Hz), 8.24 (1H, d, J=1.8 Hz), 8.52 (1H, d, J=2.3 Hz), 11.64 (1H, br s), 11.71 (1H, br s).

Example 111

2,6-Anhydro-1,3,4-trideoxy-1-[2-oxo-6-(1H-pyrrolo[2,3-b]pyridin-5-yl)-2,3-dihydro-1H-imidazo[4,5-b]pyridin-1-yl]-DL-erythro-hexitol

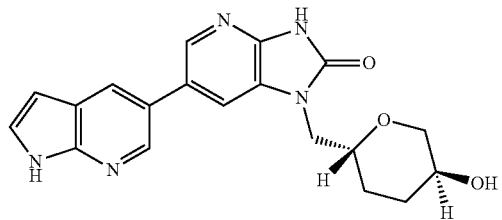

[Formula 131]

and an enantiomer thereof Step 1

2,6-Anhydro-5-O-benzoyl-1-O-[tert-butyl(diphenyl)silyl]-3,4-dideoxy-DL-erythro-hexitol 2,6-Anhydro-1-O-[tert-butyl(diphenyl)silyl]-3,4-dideoxy-DL-erythro-hexitol obtained by the method described in Bioorg. Med. Chem. 2006, 14, 3953 (542 mg) was dissolved in methylene chloride (15 ml). Pyridine (236 μl) and benzoyl chloride (255 μl) were sequentially added under ice-cooling, and the mixture was stirred at room temperature overnight. Water was added to the reaction solution, followed by extraction with ethyl acetate. Then, the organic layer was sequentially washed with a 10% aqueous citric acid solution, a saturated aqueous sodium bicarbonate solution and brine. The resulting organic layer was dried over anhydrous sodium sulfate. The solvent was evaporated under reduced pressure. The resulting residue was purified by silica gel column chromatography (developed with ethyl acetate-hexane) to give the title compound (285 mg) as a brown solid.

$^1$H-NMR (CDCl$_3$) δ: 1.07 (9H, s), 1.52-1.58 (1H, m), 1.60-1.70 (1H, m), 1.88-1.93 (1H, m), 2.28-2.33 (1H, m), 3.35 (1H, t, J=10.4 Hz), 3.43-3.49 (1H, m), 3.59 (1H, dd, J=10.5, 5.6 Hz), 3.76 (1H, dd, J=10.3, 5.4 Hz), 4.13-4.17 (1H, m), 4.98-5.04 (1H, m), 7.37-7.45 (8H, m), 7.54-7.58 (1H, m), 7.66-7.69 (4H, m), 8.01-8.03 (2H, m).

Step 2

2,6-Anhydro-5-O-benzoyl-3,4-dideoxy-DL-erythro-hexitol

The title compound (180 mg) was obtained as a brown solid by the same procedure as in Step 4 of Example 62 using the compound obtained in the above Step 1 (400 mg).

$^1$H-NMR (CDCl$_3$) δ: 1.56-1.61 (1H, m), 1.66-1.76 (2H, m), 1.98 (1H, br s), 2.30-2.35 (1H, m), 3.40 (1H, t, J=10.6 Hz), 3.47-3.52 (1H, m), 3.55-3.59 (1H, m), 3.63-3.67 (1H, m), 4.20-4.23 (1H, m), 4.99-5.06 (1H, m), 7.44 (2H, t, J=7.7 Hz), 7.57 (1H, t, J=7.5 Hz), 8.02 (2H, d, J=6.9 Hz).

Step 3

2,6-Anhydro-5-O-benzoyl-1-(6-bromo-3-cyclohex-1-en-1-yl-2-oxo-2,3-dihydro-1H-imidazo[4,5-b]pyridin-1-yl)-1,3,4-trideoxy-DL-erythro-hexitol The title compound (315 mg) was obtained as a colorless solid by the same procedure as in Step 3 of Example 35 using the compound obtained in Step 2 of Example 35 (200 mg) and the compound obtained in the above Step 2 (176 mg).

MS (ESI) m/z: 512 (M+H)$^+$.

$^1$H-NMR (CDCl$_3$) δ: 1.59-1.78 (4H, m), 1.84-1.89 (2H, m), 1.91-1.96 (1H, m), 2.29-2.34 (3H, m), 2.42-2.45 (2H, m), 3.29 (1H, m), 3.68-3.74 (1H, m), 3.79 (1H, dd, J=14.4, 7.3 Hz), 4.02 (1H, dd, J=14.4, 2.7 Hz), 4.14-4.18 (1H, m), 4.96-5.04 (1H, m), 6.01-6.03 (1H, m), 7.41-7.45 (2H, m), 7.51 (1H, d, J=2.0 Hz), 7.54-7.58 (1H, m), 7.99-8.01 (2H, m), 8.09 (1H, d, J=2.0 Hz).

Step 4

2,6-Anhydro-1-[3-cyclohex-1-en-1-yl-2-oxo-6-(1H-pyrrolo[2,3-b]pyridin-5-yl)-2,3-dihydro-1H-imidazo[4,5-b]pyridin-1-yl]-1,3,4-trideoxy-DL-erythro-hexitol 5-(4,4,5,5-Tetramethyl-1,3,2-dioxaborolan-2-yl)-1H-pyrrolo[2,3-b]pyridine (85 mg) was coupled with the compound obtained in the above Step 3 (150 mg) by the same procedure as in Step 3 of Example 1. Then, the resulting residue was dissolved in methanol (5 ml), potassium carbonate (81 mg) was added under ice-cooling, and the mixture was stirred overnight while gradually returning to room temperature. The reaction solvent was distilled off under reduced pressure, diluted with ethyl acetate and washed with brine. The resulting organic layer was dried over anhydrous sodium sulfate. The solvent was evaporated under reduced pressure. The resulting residue was purified by silica gel column chromatography (developed with methanol-chloroform) to give the title compound (92 mg) as a pale yellow solid.

MS (ESI) m/z: 446 (M+H)$^+$.

$^1$H-NMR (CDCl$_3$) δ: 1.43-1.51 (3H, m), 1.75-1.79 (2H, m), 1.88-1.91 (3H, m), 2.15-2.19 (1H, m), 2.32-2.36 (2H, m), 2.49-2.52 (2H, m), 3.08 (1H, t, J=10.6 Hz), 3.65-3.71 (2H, m), 3.88 (1H, dd, J=14.6, 7.2 Hz), 3.96-4.00 (1H, m), 4.06 (1H, dd, J=14.6, 3.2 Hz), 6.08 (1H, s), 6.58-6.60 (1H, m), 7.38 (1H, t, J=2.9 Hz), 7.57 (1H, d, J=1.7 Hz), 8.07 (1H, d, J=1.7 Hz), 8.28 (1H, d, J=1.7 Hz), 8.49 (1H, d, J=1.7 Hz), 8.88 (1H, br s).

Step 5

2,6-Anhydro-1,3,4-trideoxy-1-[2-oxo-6-(1H-pyrrolo[2,3-b]pyridin-5-yl)-2,3-dihydro-1H-imidazo[4,5-b]pyridin-1-yl]-DL-erythro-hexitol The title compound (7 mg) was obtained as an opal solid by the same procedure as in Step 6 of Example 35 using the compound obtained in the above Step 4 (90 mg).

HRMS (ESI) [M+H]$^+$ calculated: C$_{19}$H$_{20}$N$_5$O$_3$ 366.15661. found: 366.15678.

MS (ESI) m/z: 366 (M+H)$^+$.

$^1$H-NMR (DMSO-d$_6$) δ: 1.24-1.36 (2H, m), 1.69-1.73 (1H, m), 1.92-1.97 (1H, m), 2.89 (1H, t, J=10.4 Hz), 3.37-3.43 (1H, m), 3.58-3.64 (1H, m), 3.72-3.76 (1H, m), 3.82-3.95 (2H, m), 4.76 (1H, d, J=4.9 Hz), 6.52 (1H, dd, J=3.3, 1.8 Hz), 7.53 (1H, t, J=2.8 Hz), 7.80 (1H, d, J=2.0 Hz), 8.22-8.23 (2H, m), 8.52 (1H, d, J=2.0 Hz), 11.59 (1H, br s), 11.74 (1H, br s).

Example 112

2,6-Anhydro-1,3,4-trideoxy-1-[2-oxo-6-(1H-pyrrolo[2,3-b]pyridin-5-yl)-2,3-dihydro-1H-imidazo[4,5-b]pyridin-1-yl]-DL-threo-hexitol

[Formula 132]

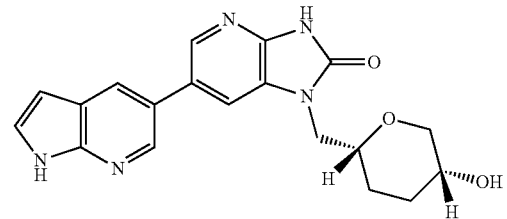

and an enantiomer thereof

Step 1

2,6-Anhydro-5-O-benzoyl-1-O-[tert-butyl(diphenyl)silyl]-3,4-dideoxy-DL-threo-hexitol 2,6-Anhydro-1-O-[tert-butyl(diphenyl)silyl]-3,4-dideoxy-DL-erythro-hexitol obtained by the method described in Bioorg. Med. Chem. 2006, 14, 3953 (4.35 g) was dissolved in tetrahydrofuran (80 ml), and benzoic acid (1.72 g) and triphenylphosphine (3.69 g) were added. Diisopropyl azodicarboxylate (2.87 ml) was added dropwise under ice-cooling, and the mixture was stirred for one hour while gradually returning to room temperature. The reaction solution was diluted with ethyl acetate, and the organic layer was sequentially washed with water, a 10% aqueous citric acid solution, a saturated aqueous sodium bicarbonate solution and brine. The resulting organic layer was dried over anhydrous sodium sulfate. The solvent was evaporated under reduced pressure. The resulting residue was purified by silica gel column chromatography (developed with methanol-chloroform) to give the title compound (2.94 g) as a colorless oil.

$^1$H-NMR (CDCl$_3$) δ: 1.07 (9H, s), 1.62-1.66 (1H, m), 1.82-1.87 (2H, m), 2.13-2.18 (1H, m), 3.48-3.54 (1H, m), 3.64-3.69 (2H, m), 3.78 (1H, dd, J=10.5, 5.1 Hz), 4.11-4.16 (1H, m), 5.06 (1H, s), 7.35-7.44 (8H, m), 7.53-7.58 (1H, m), 7.67-7.71 (4H, m), 8.07-8.09 (2H, m).

Step 2

2,6-Anhydro-5-O-benzoyl-3,4-dideoxy-DL-threo-hexitol

The title compound (0.43 g) was obtained as a colorless oil by the same procedure as in Step 4 of Example 62 using the compound obtained in the above Step 1 (1 g).
MS (ESI) m/z: 237 (M+H)$^+$.
$^1$H-NMR (CDCl$_3$) δ: 1.47-1.51 (1H, m), 1.79-1.93 (2H, m), 2.05 (1H, dd, J=7.5, 4.6 Hz), 2.16-2.20 (1H, m), 3.55-3.69 (3H, m), 3.74 (1H, dd, J=12.9, 1.4 Hz), 4.20 (1H, m), 5.09 (1H, s), 7.44-7.47 (2H, m), 7.56-7.59 (1H, m), 8.08-8.10 (2H, m).

Step 3

2,6-Anhydro-5-O-benzoyl-1-(6-bromo-3-cyclohex-1-en-1-yl-2-oxo-2,3-dihydro-1H-imidazo[4,5-b]pyridin-1-yl)-1,3,4-trideoxy-DL-threo-hexitol The title compound (810 mg) was obtained as a colorless solid by the same procedure as in Step 3 of Example 35 using the compound obtained in Step 2 of Example 35 (480 mg) and the compound obtained in the above Step 2 (424 mg).
MS (ESI) m/z: 512 (M+H)$^+$.
$^1$H-NMR (CDCl$_3$) δ: 1.64-1.68 (1H, m), 1.72-1.78 (3H, m), 1.84-1.89 (3H, m), 2.14-2.19 (1H, m), 2.29-2.31 (2H, m), 2.40-2.43 (2H, m), 3.65 (1H, dd, J=12.9, 1.4 Hz), 3.78-3.82 (1H, m), 3.93-4.01 (2H, m), 4.13-4.17 (1H, m), 5.04 (1H, s), 6.00-6.01 (1H, m), 7.42 (2H, t, J=8.0 Hz), 7.55-7.58 (2H, m), 7.92 (2H, dd, J=8.0, 1.2 Hz), 8.08 (1H, d, J=1.7 Hz).

Step 4

2,6-Anhydro-1-[3-cyclohex-1-en-1-yl-2-oxo-6-(1H-pyrrolo[2,3-b]pyridin-5-yl)-2,3-dihydro-1H-imidazo[4,5-b]pyridin-1-yl]-1,3,4-trideoxy-DL-threo-hexitol The title compound (174 mg) was obtained as a pale yellow oil by the same procedure as in Step 4 of Example 111 using 5-(4,4,5,5-tetramethyl-1,3,2-dioxaborolan-2-yl)-1H-pyrrolo[2,3-b]pyridine (171 mg) and the compound obtained in the above Step 3 (300 mg).
MS (ESI) m/z: 446 (M+H)$^+$.
$^1$H-NMR (CDCl$_3$) δ: 1.62-1.66 (2H, m), 1.73-1.81 (3H, m), 1.88-1.93 (2H, m), 1.95-1.99 (1H, m), 2.14-2.18 (1H, m), 2.33-2.36 (2H, m), 2.49-2.52 (2H, m), 3.56 (1H, dd, J=13.2, 1.7 Hz), 3.74-3.79 (2H, m), 3.89-3.95 (2H, m), 4.06 (1H, dd, J=14.6, 3.2 Hz), 6.07-6.09 (1H, m), 6.59 (1H, dd, J=3.4, 2.3 Hz), 7.39-7.40 (1H, m), 7.60 (1H, d, J=1.7 Hz), 8.07 (1H, d, J=2.3 Hz), 8.28 (1H, d, J=1.7 Hz), 8.49 (1H, d, J=2.3 Hz), 9.20 (1H, br s).

Step 5

2,6-Anhydro-1,3,4-trideoxy-1-[2-oxo-6-(1H-pyrrolo[2,3-b]pyridin-5-yl)-2,3-dihydro-1H-imidazo[4,5-b]pyridin-1-yl]-DL-threo-hexitol The title compound (10 mg) was obtained as a pale yellow solid by the same procedure as in Step 6 of Example 35 using the compound obtained in the above Step 4 (170 mg).
MS (ESI) m/z: 366 (M+H)$^+$.
$^1$H-NMR (DMSO-d$_6$) δ: 1.61-1.73 (2H, m), 3.36-3.39 (1H, m), 3.53-3.70 (3H, m), 3.82-3.86 (1H, m), 3.94-3.99 (1H, m), 4.57 (1H, d, J=4.0 Hz), 6.51 (1H, dd, J=3.4, 1.7 Hz), 7.53 (1H, t, J=2.9 Hz), 7.82 (1H, d, J=1.7 Hz), 8.22 (2H, t, J=2.3 Hz), 8.52 (1H, d, J=2.3 Hz), 11.59 (1H, s), 11.74 (1H, s).

Example 113

2,6-Anhydro-1,3,4-trideoxy-5-O-methyl-1-[2-oxo-6-(1H-pyrrolo[2,3-b]pyridin-5-yl)-2,3-dihydro-1H-imidazo[4,5-b]pyridin-1-yl]-DL-threo-hexitol

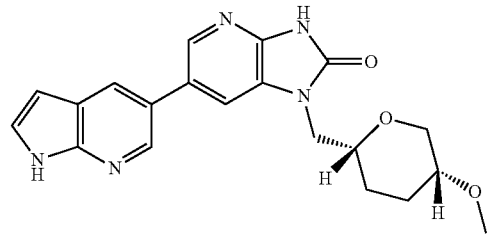

[Formula 133]

and an enantiomer thereof Step 1

2,6-Anhydro-1-O-[tert-butyl(diphenyl)silyl]-3,4-dideoxy-DL-threo-hexitol

The compound obtained in Step 1 of Example 112 (1 g) was dissolved in methanol (20 ml). Potassium carbonate (0.58 g) was added under ice-cooling and the mixture was stirred for a day and a night while gradually returning to room temperature. The reaction solvent was distilled off under reduced pressure and then diluted with ethyl acetate. The organic layer was washed with brine, and the resulting organic layer was dried over anhydrous sodium sulfate. The solvent was evaporated under reduced pressure. The resulting residue was purified by silica gel column chromatography (developed with ethyl acetate-hexane) to give the title compound (0.69 g) as a colorless oil.
MS (ESI) m/z: 393 (M+Na)$^+$.
$^1$H-NMR (CDCl$_3$) δ: 1.06 (9H, s), 1.65-1.70 (2H, m), 1.91-1.95 (1H, m), 2.16-2.18 (1H, m), 3.43-3.48 (1H, m), 3.55-3.60 (2H, m), 3.71-3.76 (2H, m), 3.88 (1H, m), 7.36-7.44 (6H, m), 7.66-7.68 (4H, m).

Step 2

2,6-Anhydro-1-O-[tert-butyl(diphenyl)silyl]-3,4-dideoxy-5-O-methyl-DL-threo-hexitol The title compound (0.69 g) was obtained as a colorless oil by the same procedure as in Step 1 of Example 63 using the compound obtained in the above Step 1 (0.68 g).
MS (ESI) m/z: 407 (M+Na)$^+$.
$^1$H-NMR (CDCl$_3$) δ: 1.05 (9H, s), 1.59-1.64 (3H, m), 2.04-2.08 (1H, m), 3.23 (1H, br s), 3.35 (3H, s), 3.44-3.50 (2H, m), 3.54 (1H, dd, J=10.0, 6.6 Hz), 3.76 (1H, dd, J=10.0, 5.4 Hz), 4.04 (1H, m), 7.35-7.42 (6H, m), 7.66 (4H, dd, J=8.0, 1.2 Hz).

Step 3

2,6-Anhydro-5-O-benzoyl-3,4-dideoxy-DL-threo-hexitol

The title compound (220 mg) was obtained as a colorless oil by the same procedure as in Step 4 of Example 62 using the compound obtained in the above Step 2 (600 mg).

¹H-NMR (CDCl₃) δ: 1.58-1.70 (2H, m), 2.06-2.11 (1H, m), 3.26-3.28 (1H, m), 3.37 (3H, s), 3.46-3.49 (1H, m), 3.49-3.53 (1H, m), 3.56-3.59 (2H, m), 4.11 (1H, m).

Step 4

2,6-Anhydro-1-(6-bromo-3-cyclohex-1-en-1-yl-2-oxo-2,3-dihydro-1H-imidazo[4,5-b]pyridin-1-yl)-1,3,4-trideoxy-5-O-methyl-DL-threo-hexitol The title compound (440 mg) was obtained as a colorless solid by the same procedure as in Step 3 of Example 35 using the compound obtained in Step 2 of Example 35 (330 mg) and the compound obtained in the above Step 3 (180 mg).

MS (ESI) m/z: 424 (M+H)⁺.

¹H-NMR (CDCl₃) δ: 1.52-1.55 (1H, m), 1.57-1.69 (1H, m), 1.71-1.77 (3H, m), 1.83-1.89 (2H, m), 2.12 (1H, m), 2.28-2.32 (2H, m), 2.40-2.44 (2H, m), 3.24 (1H, s), 3.39 (3H, s), 3.41 (1H, dd, J=12.6, 1.6 Hz), 3.65-3.77 (2H, m), 4.00 (1H, dd, J=14.0, 2.5 Hz), 4.03-4.08 (1H, m), 5.99-6.01 (1H, m), 7.60 (1H, d, J=1.8 Hz), 8.06 (1H, d, J=1.8 Hz).

Step 5

2,6-Anhydro-1-[3-cyclohex-1-en-1-yl-2-oxo-6-(1H-pyrrolo[2,3-b]pyridin-5-yl)-2,3-dihydro-1H-imidazo[4,5-b]pyridin-1-yl]-1,3,4-trideoxy-5-O-methyl-DL-threo-hexitol The title compound (210 mg) was obtained as a pale yellow oil by the same procedure as in Step 2 of Example 4 using 5-(4,4,5,5-tetramethyl-1,3,2-dioxaborolan-2-yl)-1H-pyrrolo[2,3-b]pyridine (138 mg) and the compound obtained in the above Step 4 (200 mg).

MS (ESI) m/z: 460 (M+H)⁺.

¹H-NMR (CDCl₃) δ: 1.57-1.67 (3H, m), 1.75-1.80 (2H, m), 1.88-1.92 (2H, m), 2.13 (1H, d, J=13.3 Hz), 2.32-2.37 (2H, m), 2.48-2.52 (2H, br m), 3.24 (1H, br s), 3.37 (3H, s), 3.44 (1H, d, J=12.4 Hz), 3.71-3.77 (1H, m), 3.90 (1H, dd, J=14.7, 7.8 Hz), 4.04-4.10 (2H, m), 6.06-6.09 (1H, m), 6.58-6.60 (1H, m), 7.40 (1H, d, J=1.8 Hz), 7.68 (1H, s), 8.08 (1H, s), 8.28 (1H, s), 8.50 (1H, s), 9.24 (1H, s).

Step 6

2,6-Anhydro-1,3,4-trideoxy-5-O-methyl-1-[2-oxo-6-(1H-pyrrolo[2,3-b]pyridin-5-yl)-2,3-dihydro-1H-imidazo[4,5-b]pyridin-1-yl]-DL-threo-hexitol The title compound (55 mg) was obtained as a pale yellow solid by the same procedure as in Step 6 of Example 35 using the compound obtained in the above Step 5 (210 mg).

MS (ESI) m/z: 380 (M+H)⁺.

¹H-NMR (DMSO-d₆) δ: 1.41-1.45 (1H, m), 1.51-1.64 (2H, m), 1.90-1.94 (1H, m), 3.15-3.17 (1H, m), 3.20 (3H, s), 3.31-3.35 (1H, m), 3.71-3.75 (1H, m), 3.81-3.89 (2H, m), 3.92-3.97 (1H, m), 6.51 (1H, dd, J=3.4, 2.3 Hz), 7.53 (1H, t, J=2.9 Hz), 7.83 (1H, d, J=1.7 Hz), 8.23 (2H, t, J=1.7 Hz), 8.52 (1H, d, J=2.3 Hz), 11.60 (1H, s), 11.74 (1H, s).

Example 114

2,6-Anhydro-1,3,5-trideoxy-4-O-methyl-1-[2-oxo-6-(1H-pyrrolo[2,3-b]pyridin-5-yl)-2,3-dihydro-1H-imidazo[4,5-b]pyridin-1-yl]-DL-threo-hexitol

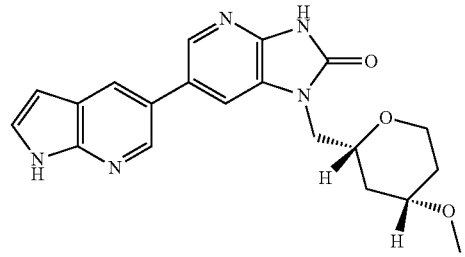

[Formula 134]

and an enantiomer thereof

Step 1

2,6-Anhydro-1-O-benzyl-3,5-dideoxy-DL-threo-hex-5-enitol

2-[(Benzyloxy)methyl]-2,3-dihydro-4H-pyran-4-one obtained by the method described in WO 2001/019831 (1.36 g) and cerium(III) chloride heptahydrate (2.31 g) were dissolved in ethanol (26 ml) and methylene chloride (52 ml). After the atmosphere was replaced with nitrogen, the mixture was cooled to −78° C. and a suspension of sodium borohydride (259 mg) in ethanol (26 ml) was added. After stirring at −78° C. for 90 minutes, a saturated aqueous sodium bicarbonate solution was added. The mixture was warmed to room temperature and then filtered through Celite. The filtrate was extracted with ethyl acetate three times. The organic layer was washed with brine and then dried over anhydrous sodium sulfate, and the solvent was evaporated. The residue was purified by silica gel column chromatography (developed with ethyl acetate-hexane) to give the title compound (1.34 g) as a brown oil.

¹H-NMR (CDCl₃) δ: 1.75-1.77 (2H, m), 2.17-2.23 (1H, m), 3.62 (2H, dq, J=23.2, 5.1 Hz), 4.16-4.22 (1H, m), 4.40-4.41 (1H, m), 4.60 (2H, s), 4.79 (1H, dq, J=6.2, 1.2 Hz), 6.41 (1H, dd, J=6.2, 1.2 Hz), 7.29-7.34 (6H, m).

Step 2

2,6-Anhydro-1-O-benzyl-3,5-dideoxy-DL-threo-hexitol

The compound obtained in the above Step 1 (1.33 mg) was dissolved in ethanol (1 ml), and 10% palladium/carbon was added. The mixture was stirred in a hydrogen atmosphere at room temperature for 3 hours. The reaction solution was filtered through Celite and the filtrate was concentrated. Thereafter, the residue was purified by silica gel column chromatography (developed with ethyl acetate-hexane) to give the title compound (1.22 g) as a colorless oil.

¹H-NMR (CDCl₃) δ: 1.26-1.34 (1H, m), 1.48-1.58 (2H, m), 1.86-1.95 (2H, m), 3.40-3.58 (4H, m), 3.79-3.82 (1H, m), 4.07 (1H, ddd, J=11.8, 2.2, 1.1 Hz), 4.58 (2H, dd, J=19.9, 12.1 Hz), 7.26-7.37 (5H, m).

Step 3

2,6-Anhydro-1-O-benzyl-3,5-dideoxy-4-O-methyl-DL-threo-hexitol

The title compound (569 mg) was obtained as a colorless oil by the same procedure as in Step 1 of Example 63 using the compound obtained in the above Step 2 (546 mg).

$^1$H-NMR (CDCl$_3$) δ: 1.19-1.28 (1H, m), 1.45-1.50 (1H, m), 1.92-2.02 (2H, m), 3.31-3.57 (5H, m), 3, 35 (3H, s), 4.09 (1H, ddd, J=11.7, 4.9, 1.7 Hz), 4.58 (2H, dd, J=34.9, 17.5 Hz), 7.26-7.36 (5H, m).

Step 4

1,5-Anhydro-2,4-dideoxy-3-O-methyl-DL-threo-hexitol

The compound obtained in the above Step 3 (561 mg) was dissolved in ethanol (3 ml), and 20% palladium hydroxide was added. The mixture was stirred in a hydrogen atmosphere at room temperature for 21 hours. The reaction solution was filtered through Celite and washed with ethanol, and the filtrate was concentrated. The oil was dissolved in ethyl acetate, and the solution was filtered through a cotton plug. Thereafter, the filtrate was concentrated to give the title compound (337 mg) as a colorless oil.

$^1$H-NMR (CDCl$_3$) δ: 1.22 (1H, dd, J=23.4, 11.4 Hz), 1.42-1.52 (1H, m), 1.91-2.00 (2H, m), 2.09 (1H, br s), 3.19-3.47 (3H, m), 3.36 (3H, s), 3.57-3.61 (2H, m), 4.08 (1H, ddd, J=11.6, 4.9, 1.5 Hz).

Step 5

3-Cyclohex-1-en-1-yl-6-(1H-pyrrolo[2,3-b]pyridin-5-yl)-1,3-dihydro-2H-imidazo[4,5-b]pyridin-2-one The title compound (1.39 g) was obtained by the same procedure as in Step 3 of Example 1 using 5-(4,4,5,5-tetramethyl-1,3,2-dioxaborolan-2-yl)-1H-pyrrolo[2,3-b]pyridine (1.83 g) and the compound obtained in Step 2 of Example 35 (2.00 g).

MS (APCI) m/z: 332 [M+H]$^+$ $^1$H-NMR (DMSO-d$_6$) δ: 1.65-1.69 (2H, m), 1.75-1.81 (2H, m), 2.23-2.24 (2H, m), 2.39-2.39 (2H, m), 5.93-5.94 (1H, m), 6.51 (1H, dd, J=3.4, 2.0 Hz), 7.52-7.53 (1H, m), 7.56 (1H, d, J=2.0 Hz), 8.19 (1H, d, J=2.0 Hz), 8.24 (1H, d, J=2.0 Hz), 8.48 (1H, d, J=2.2 Hz), 11.27 (1H, br s), 11.74 (1H, br s).

Step 6

2,6-Anhydro-1-[3-cyclohex-1-en-1-yl-2-oxo-6-(1H-pyrrolo[2,3-b]pyridin-5-yl)-2,3-dihydro-1H-imidazo[4,5-b]pyridin-1-yl]-1,3,5-trideoxy-4-O-methyl-DL-threo-hexitol The crude title compound was obtained by the same procedure as in Step 3 of Example 35 using the compound obtained in the above Step 4 (88 mg) and the compound obtained in the above Step 5 (133 mg).

MS (APCI) m/z: 460 [M+H]$^+$

Step 7

2,6-Anhydro-1,3,5-trideoxy-4-O-methyl-1-[2-oxo-6-(1H-pyrrolo[2,3-b]pyridin-5-yl)-2,3-dihydro-1H-imidazo[4,5-b]pyridin-1-yl]-DL-threo-hexitol The title compound (41 mg) was obtained by the same procedure as in Step 6 of Example 35 using the compound obtained in the above Step 7.

MS (APCI) m/z: 380 [M+H]$^+$ $^1$H-NMR (DMSO-d$_6$) δ: 1.08 (1H, dd, J=11.4, 5.7 Hz), 1.20-1.24 (2H, m), 1.84-1.87 (1H, br m), 2.03-2.05 (1H, br m), 3.22 (3H, s), 3.67-3.69 (1H, br m), 3.83-3.88 (2H, m), 3.97 (1H, dd, J=14.2, 7.8 Hz), 6.50 (1H, dd, J=3.4, 1.6 Hz), 7.51 (1H, t, J=3.0 Hz), 7.79 (1H, d, J=1.8 Hz), 8.21 (2H, dd, J=4.4, 2.1 Hz), 8.50 (1H, d, J=2.3 Hz), 11.70 (1H, br s).

Example 115

6-(3-Chloro-1H-pyrrolo[2,3-b]pyridin-5-yl)-1-[(cis-4-methoxycyclohexyl)methyl]-1,3-dihydro-2H-imidazo[4,5-b]pyridin-2-one

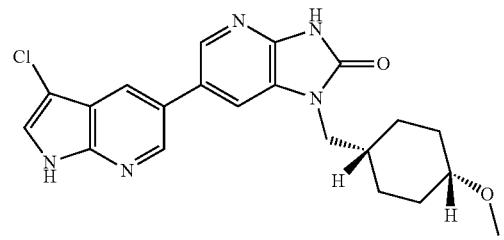

[Formula 135]

Step 1

3-Cyclohex-1-en-1-yl-1-[(cis-4-methoxycyclohexyl)methyl]-6-(4,4,5,5-tetramethyl-1,3,2-dioxaborolan-2-yl)-1,3-dihydro-2H-imidazo[4,5-b]pyridin-2-one The title compound (224 mg) was obtained by the same procedure as in Step 4 of Example 35 using the compound obtained in Step 2 of Example 99 (300 mg).

$^1$H-NMR (CDCl$_3$) δ: 1.36 (12H, s), 1.41-1.44 (6H, m), 1.73-1.76 (2H, m), 1.86-1.88 (2H, m), 1.92-1.94 (3H, m), 2.30-2.32 (2H, m), 2.43-2.44 (2H, m), 3.31 (3H, s), 3.42-3.45 (1H, m), 3.71 (2H, d, J=7.3 Hz), 6.01-6.02 (1H, m), 7.48 (1H, d, J=1.5 Hz), 8.43 (1H, d, J=1.5 Hz).

Step 2

6-(3-Chloro-1H-pyrrolo[2,3-b]pyridin-5-yl)-3-cyclohex-1-en-1-yl-1-[(cis-4-methoxycyclohexyl)methyl]-1,3-dihydro-2H-imidazo[4,5-b]pyridin-2-one The title compound (145 mg) was obtained by the same procedure as in Step 3 of Example 1 using the compound obtained in Step 1 of Example 35 (167 mg) and the compound obtained in the above Step 1 (224 mg).

MS (ESI) m/z: 492 (M+H)$^+$.

$^1$H-NMR (CDCl$_3$) δ: 1.34-1.55 (6H, m), 1.73-1.82 (2H, m), 1.86-2.01 (5H, m), 2.29-2.38 (2H, m), 2.46-2.54 (2H, m), 3.30 (3H, s), 3.41-3.47 (1H, m), 3.79 (2H, d, J=7.3 Hz), 6.05-6.11 (1H, m), 7.36 (2H, d, J=2.8 Hz), 7.38 (2H, d, J=1.8 Hz), 8.07 (1H, d, J=1.8 Hz), 8.27 (1H, d, J=1.8 Hz), 8.53 (1H, d, J=1.8 Hz), 8.81 (1H, br s).

Step 3

6-(3-Chloro-1H-pyrrolo[2,3-b]pyridin-5-yl)-1-[(cis-4-methoxycyclohexyl)methyl]-1,3-dihydro-2H-imidazo[4,5-b]pyridin-2-one The title compound (87 mg) was obtained by the same procedure as in Step 6 of Example 35 using the compound obtained in the above Step 2 (143 mg).
HRMS (ESI) [M+H]$^+$ calculated: $C_{21}H_{23}ClN_5O_2$ 412.15403.
found: 412.15085.
$^1$H-NMR (DMSO-$d_6$) δ: 1.27-1.40 (7H, m), 1.73-1.85 (2H, m), 1.87-1.98 (1H, m), 3.19 (3H, s), 3.75 (2H, d, J=7.4 Hz), 7.74 (1H, d, J=2.9 Hz), 7.95 (1H, d, J=2.3 Hz), 8.18 (1H, d, J=2.3 Hz), 8.27 (1H, d, J=1.7 Hz), 8.64 (1H, d, J=1.7 Hz), 11.61 (1H, s), 12.09 (1H, br s).

Example 116

6-(3-Chloro-1H-pyrrolo[2,3-b]pyridin-5-yl)-1-[(cis-4-hydroxycyclohexyl)methyl]-1,3-dihydro-2H-imidazo[4,5-b]pyridin-2-one

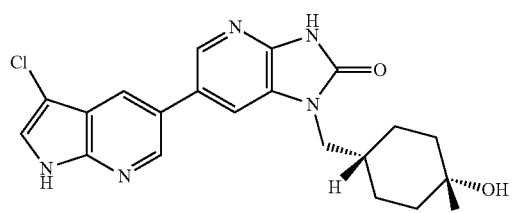

[Formula 136]

Step 1

1-[(cis-4-{[tert-Butyl(dimethyl)silyl]oxy}cyclohexyl)methyl]-3-cyclohex-1-en-1-yl-6-(4,4,5,5-tetramethyl-1,3,2-dioxaborolan-2-yl)-1,3-dihydro-2H-imidazo[4,5-b]pyridin-2-one The title compound (288 mg) was obtained by the same procedure as in Step 4 of Example 35 using the compound obtained in Step 2 of Example 102 (400 mg).
$^1$H-NMR (CDCl$_3$) δ: 0.03 (6H, s), 0.89 (9H, s), 1.36 (12H, s), 1.40-1.43 (4H, m), 1.54-1.54 (2H, m), 1.65-1.77 (4H, m), 1.84-1.90 (3H, m), 2.28-2.33 (2H, m), 2.42-2.46 (2H, m), 3.73 (2H, d, J=7.6 Hz), 3.94-3.96 (1H, m), 6.00-6.02 (1H, m), 7.48 (1H, d, J=1.2 Hz), 8.43 (1H, d, J=1.2 Hz).

Step 2

1-[(cis-4-{[tert-Butyl(dimethyl)silyl]oxy}cyclohexyl)methyl]-6-(3-chloro-1H-pyrrolo[2,3-b]pyridin-5-yl)-3-cyclohex-1-en-1-yl-1,3-dihydro-2H-imidazo[4,5-b]pyridin-2-one The title compound (116 mg) was obtained by the same procedure as in Step 3 of Example 1 using the compound obtained in Step 1 of Example 35 (143 mg) and the compound obtained in the above Step 1 (245 mg).
$^1$H-NMR (CDCl$_3$) δ: 1.34-1.55 (6H, m), 1.73-1.82 (2H, m), 1.86-2.01 (5H, m), 2.29-2.38 (2H, m), 2.46-2.54 (2H, m), 3.30 (3H, s), 3.41-3.47 (1H, m), 3.79 (2H, d, J=7.3 Hz), 6.05-6.11 (1H, m), 7.36 (2H, d, J=2.8 Hz), 7.38 (2H, d, J=1.8 Hz), 8.07 (1H, d, J=1.8 Hz), 8.27 (1H, d, J=1.8 Hz), 8.53 (1H, d, J=1.8 Hz), 8.81 (1H, br s).

Step 3

6-(3-Chloro-1H-pyrrolo[2,3-b]pyridin-5-yl)-1-[(cis-4-hydroxycyclohexyl)methyl]-1,3-dihydro-2H-imidazo[4,5-b]pyridin-2-one The title compound (34 mg) was obtained by the same procedure as in Step 6 of Example 35 using the compound obtained in the above Step 2 (115 mg).
HRMS (ESI) [M+H]$^+$ calculated: $C_{20}H_{21}ClN_5O_2$ 398.13838.
found: 398.13773.
$^1$H-NMR (DMSO-$d_6$) δ: 0.99-1.15 (2H, m), 1.21-1.49 (4H, m), 1.51-1.70 (2H, m), 1.73-1.85 (1H, m), 3.67-3.85 (3H, m), 7.74 (1H, d, J=1.8 Hz), 7.85-7.97 (1H, m), 8.16-8.20 (1H, m), 8.27 (1H, d, J=1.8 Hz), 8.64 (1H, d, J=1.8 Hz), 11.61 (1H, br s), 12.09 (1H, br s).

Example 117

6-(4-Chloro-1H-pyrrolo[2,3-b]pyridin-5-yl)-1-[(2S)-1,4-dioxan-2-ylmethyl]-1,3-dihydro-2H-imidazo[4,5-b]pyridin-2-one

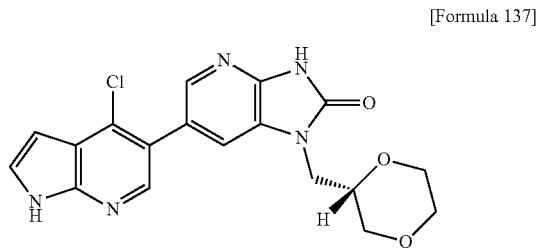 [SMILES: O=c1[nH]c2ncc(-c3cnc4[nH]ccc4c3Cl)cc2n1C[C@H]1COCCO1]

[Formula 137]

Step 1

6-(4-Chloro-1H-pyrrolo[2,3-b]pyridin-5-yl)-3-cyclohex-1-en-1-yl-1-[(2S)-1,4-dioxan-2-ylmethyl]-1,3-dihydro-2H-imidazo[4,5-b]pyridin-2-one The title compound (120 mg) was obtained by the same procedure as in Step 3 of Example 1 using 5-bromo-4-chloro-1H-pyrrolo[2,3-b]pyridine (189 mg) and the compound obtained in Step 1 of Example 41 (300 mg).
MS (ESI) m/z: 466 (M+H)$^+$.
$^1$H-NMR (CDCl$_3$) δ: 1.73-1.82 (2H, m), 1.86-1.96 (3H, m), 2.30-2.39 (2H, m), 2.47-2.55 (2H, m), 3.37-3.45 (1H, m), 3.49 (2H, s), 3.53-3.62 (1H, m), 3.65-3.80 (3H, m), 3.86-4.02 (3H, m), 6.07-6.12 (1H, m), 6.66-6.71 (1H, m), 7.39-7.43 (1H, m), 7.56 (1H, d, J=1.8 Hz), 8.16 (1H, d, J=1.8 Hz), 8.27 (1H, s), 8.91 (1H, br s).

Step 2

6-(4-Chloro-1H-pyrrolo[2,3-b]pyridin-5-yl)-1-[(2S)-1,4-dioxan-2-ylmethyl]-1,3-dihydro-2H-imidazo[4,5-b]pyridin-2-one The title compound (71 mg) was obtained by the same procedure as in Step 6 of Example 35 using the compound obtained in the above Step 1 (119 mg).
HRMS (ESI) [M+H]$^+$ calculated: $C_{18}H_{17}ClN_5O_3$, 386.10199.
found: 386.10206.
$^1$H-NMR (DMSO-d$_6$) δ: 2.42-2.47 (1H, m), 3.37-3.62 (4H, m), 3.66-3.97 (4H, m), 6.53-6.59 (1H, m), 7.63-7.67 (2H, m), 8.01 (1H, d, J=1.8 Hz), 8.24 (1H, s), 11.72 (1H, br s), 12.13 (1H, br s).

Example 118

1-[(2S)-1,4-Dioxan-2-ylmethyl]-6-(3-fluoro-1H-pyrrolo[2,3-b]pyridin-5-yl)-1,3-dihydro-2H-imidazo[4,5-b]pyridin-2-one

[Formula 138]

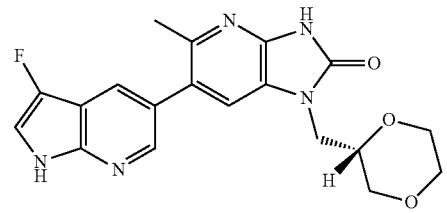

Step 1

3-Cyclohex-1-en-1-yl-1-[(2S)-1,4-dioxan-2-ylmethyl]-6-(3-fluoro-1H-pyrrolo[2,3-b]pyridin-5-yl)-1,3-dihydro-2H-imidazo[4,5-b]pyridin-2-one The title compound (144 mg) was obtained by the same procedure as in Step 3 of Example 1 using the compound obtained in Step 1 of Example 41 (350 mg) and the compound obtained in Step 1 of Example 96 (275 mg).
MS (ESI) m/z: 450 (M+H)$^+$.

Step 2

1-[(2S)-1,4-Dioxan-2-ylmethyl]-6-(3-fluoro-1H-pyrrolo[2,3-b]pyridin-5-yl)-1,3-dihydro-2H-imidazo[4,5-b]pyridin-2-one The title compound (83 mg) was obtained by the same procedure as in Step 6 of Example 35 using the compound obtained in the above Step 1 (144 mg).
MS (ESI) m/z: 370 (M+H)$^+$.

Step 3

1-[(2S)-1,4-Dioxan-2-ylmethyl]-6-(3-fluoro-1H-pyrrolo[2,3-b]pyridin-5-yl)-1,3-dihydro-2H-imidazo[4,5-b]pyridin-2-one dimethanesulfonate Methanesulfonic acid (29 μl) was added dropwise to a suspension of the compound obtained in the above Step 2 (83 mg) in chloroform (1.5 ml). Subsequently, methanol was added dropwise until a homogeneous solution was formed. After stirring at room temperature for 30 minutes, the solvent was evaporated under reduced pressure and hexane was added, followed by stirring. The solid was collected by filtration and dried under reduced pressure overnight while warming to 50° C. to give the title compound (106 mg).
MS (ESI) m/z: 370 (M+H)$^+$.
HRMS (ESI) [(M+H)$^+$] calculated: $C_{18}H_{17}FN_5O_3$ 370.13154.
found: 370.13332.
$^1$H-NMR (DMSO-d$_6$) δ: 2.34 (6H, s), 3.31-3.38 (1H, m), 3.43-3.56 (2H, m), 3.61 (1H, d, J=10.9 Hz), 3.70-4.02 (5H, m), 7.53-7.55 (1H, m), 7.91 (1H, d, J=2.3 Hz), 8.29-8.31 (2H, m), 8.62 (1H, d, J=2.3 Hz), 11.61 (1H, br s), 11.68 (1H, br s).

Example 119

1-[(2S)-1,4-Dioxan-2-ylmethyl]-6-(3-fluoro-1H-pyrrolo[2,3-b]pyridin-5-yl)-5-methyl-1,3-dihydro-2H-imidazo[4,5-b]pyridin-2-one

[Formula 139]

Step 1

3-Cyclohex-1-en-1-yl-1-[(2S)-1,4-dioxan-2-ylmethyl]-6-(3-fluoro-1H-pyrrolo[2,3-b]pyridin-5-yl)-5-methyl-1,3-dihydro-2H-imidazo[4,5-b]pyridin-2-one The title compound (60 mg) was obtained by the same procedure as in Step 2 of Example 4 using the compound obtained in Step 1 of Example 96 (70 mg) and the compound obtained in Step 1 of Example 45 (111 mg).
MS (ESI) m/z: 464 (M+H)$^+$.
$^1$H-NMR (CDCl$_3$) δ: 1.75-1.79 (2H, m), 1.87-1.91 (2H, m), 2.31-2.35 (2H, m), 2.47 (3H, s), 2.52-2.55 (2H, m), 3.39 (1H, dd, J=11.7, 9.5 Hz), 3.53-3.58 (1H, m), 3.65-3.70 (2H, m), 3.73-3.76 (1H, m), 3.84-3.94 (4H, m), 6.06-6.08 (1H, m), 7.14 (1H, t, J=2.6 Hz), 7.23 (1H, s), 7.91 (1H, d, J=2.3 Hz), 8.27-8.29 (1H, m), 8.30 (1H, d, J=1.7 Hz).

Step 2

1-[(2S)-1,4-Dioxan-2-ylmethyl]-6-(3-fluoro-1H-pyrrolo[2,3-b]pyridin-5-yl)-5-methyl-1,3-dihydro-2H-imidazo[4,5-b]pyridin-2-one The title compound (25 mg) was obtained by the same procedure as in Step 6 of Example 35 using the compound obtained in the above Step 1 (60 mg).
HRMS (ESI) [M+H]$^+$ calculated: $C_{19}H_{19}FN_5O_3$ 384.14719. found: 384.14985.
MS (ESI) m/z: 384 (M+H)$^+$.

$^1$H-NMR (DMSO-d$_6$) δ: 2.38 (3H, s), 3.27-3.31 (1H, m), 3.41-3.52 (2H, m), 3.59 (1H, d, J=11.5 Hz), 3.68-3.80 (3H, m), 3.84-3.93 (2H, m), 7.44 (1H, s), 7.54 (1H, t, J=2.3 Hz), 8.00 (1H, d, J=1.7 Hz), 8.29 (1H, d, J=2.3 Hz), 11.52 (1H, s), 11.61 (1H, s).

Example 120

1-[(2S)-1,4-Dioxan-2-ylmethyl]-6-(4-fluoro-1H-pyrrolo[2,3-b]pyridin-5-yl)-1,3-dihydro-2H-imidazo[4,5-b]pyridin-2-one

[Formula 140]

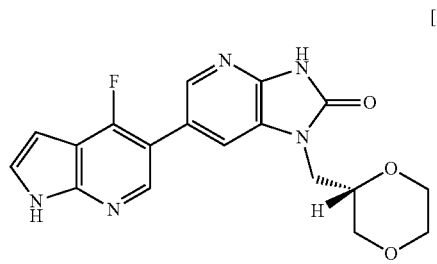

Step 1

5-Bromo-4-fluoro-1H-pyrrolo[2,3-b]pyridine

5-Bromo-4-fluoro-1-(triisopropylsilyl)-1H-pyrrolo[2,3-b]pyridine obtained by the method described in Tetrahedron Lett. 45, 2317-2319 (2004) (230 mg) was dissolved in tetrahydrofuran (5.0 ml). Tetrabutylammonium fluoride (1.0 M solution in tetrahydrofuran) (810 µl) was added and the mixture was stirred at room temperature for one hour. Water was added to the reaction solution, followed by extraction with ethyl acetate. The organic layer was washed with brine and then dried over anhydrous sodium sulfate, and the solvent was evaporated. The residue was purified by silica gel column chromatography (developed with ethyl acetate-hexane) to give the title compound (103 mg).
MS (ESI) m/z: 215 (M+H)$^+$.

Step 2

3-Cyclohex-1-en-1-yl-1-[(2S)-1,4-dioxan-2-ylmethyl]-6-(4-fluoro-1H-pyrrolo[2,3-b]pyridin-5-yl)-1,3-dihydro-2H-imidazo[4,5-b]pyridin-2-one The title compound (212 mg) was obtained by the same procedure as in Step 3 of Example 1 using the compound obtained in Step 1 of Example 41 (254 mg) and the compound obtained in the above Step 1 (103 mg).
MS (ESI) m/z: 450 (M+H)$^+$.

Step 3

1-[(2S)-1,4-Dioxan-2-ylmethyl]-6-(4-fluoro-1H-pyrrolo[2,3-b]pyridin-5-yl)-1,3-dihydro-2H-imidazo[4,5-b]pyridin-2-one The title compound (20 mg) was obtained by the same procedure as in Step 6 of Example 35 using the compound obtained in the above Step 2 (212 mg).
MS (ESI) m/z: 370 (M+H)$^+$.
HRMS (ESI) [(M+H)$^+$] calculated: C$_{18}$H$_{17}$FN$_5$O$_3$ 370.13154.
found: 370.13107.
$^1$H-NMR (DMSO-d$_6$) δ: 3.33-3.62 (4H, m), 3.70-3.97 (5H, m), 6.59-6.61 (1H, m), 7.57-7.59 (1H, m), 7.74 (1H, s), 8.12 (1H, s), 8.35-8.36 (1H, m), 11.71 (1H, br s), 12.10 (1H, br s).

Example 121

6-(2,3-Dihydro-1H-pyrrolo[2,3-b]pyridin-5-yl)-1-[(2S)-1,4-dioxan-2-ylmethyl]-1,3-dihydro-2H-imidazo[4,5-b]pyridin-2-one

[Formula 141]

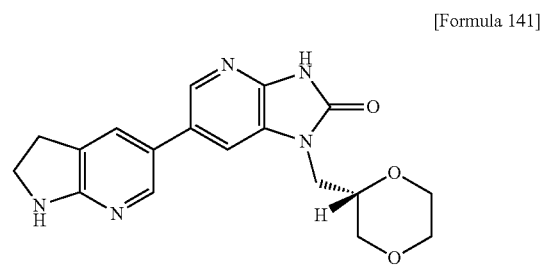 [SMILES: O=c1[nH]c2ncc(-c3cnc4c(c3)CCN4)cc2n1C[C@H]1COCCO1]

Step 1

3-Cyclohex-1-en-1-yl-6-(2,3-dihydro-1H-pyrrolo[2,3-b]pyridin-5-yl)-1-[(2S)-1,4-dioxan-2-ylmethyl]-1,3-dihydro-2H-imidazo[4,5-b]pyridin-2-one The title compound (118 mg) was obtained by the same procedure as in Step 3 of Example 1 using the compound obtained in Step 1 of Example 41 (319 mg) and 5-bromo-2,3-dihydro-1H-pyrrolo[2,3-b]pyridine (199 mg).
MS (ESI) m/z: 434 (M+H)$^+$.

Step 2

6-(2,3-Dihydro-1H-pyrrolo[2,3-b]pyridin-5-yl)-1-[(2S)-1,4-dioxan-2-ylmethyl]-1,3-dihydro-2H-imidazo[4,5-b]pyridin-2-one The title compound (28 mg) was obtained by the same procedure as in Step 6 of Example 35 using the compound obtained in the above Step 1 (118 mg).
MS (ESI) m/z: 354 (M+H)$^+$.
HRMS (ESI) [(M+H)$^+$] calculated: C$_{18}$H$_{20}$N$_5$O$_3$ 354.15661.
found: 354.15597.
$^1$H-NMR (DMSO-d$_6$) δ: 3.04 (2H, t, J=8.6 Hz), 3.32-3.62 (6H, m), 3.71-3.96 (5H, m), 6.52 (1H, s), 7.57-7.59 (1H, m), 7.66-7.67 (1H, m), 8.00-8.01 (1H, m), 8.08 (1H, d, J=2.3 Hz), 11.54 (1H, br s).

Example 122

1-[(2S)-1,4-Dioxan-2-ylmethyl]-6-(4-(trifluoromethyl)-1H-pyrrolo[2,3-b]pyridin-5-yl)-1,3-dihydro-2H-imidazo[4,5-b]pyridin-2-one

[Formula 142]

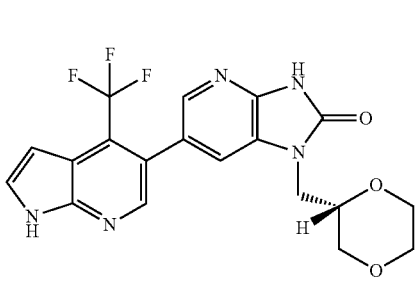

Step 1

5-Bromo-4-iodo-1-[(4-methylphenyl)sulfonyl]-1H-pyrrolo[2,3-b]pyridine

55% Sodium hydride (170 mg) and 4-methylbenzenesulfonyl chloride (740 mg) were added to a solution of 5-bromo-4-iodo-1H-pyrrolo[2,3-b]pyridine obtained by the method described in WO 2008/150914 (1.14 g) in N,N-dimethylformamide (12 ml) in an ice bath, and the mixture was stirred at room temperature for 3 hours. An aqueous ammonium chloride solution was added to the reaction solution, and the precipitated solid was collected by filtration and washed with water. This was dissolved in dichloromethane and dried over anhydrous sodium sulfate. The solvent was evaporated under reduced pressure to give the title compound (1.68 g).
$^1$H-NMR (CDCl$_3$) δ: 2.39 (3H, s), 6.51 (1H, d, J=4.0 Hz), 7.26 (2H, d, J=8.6 Hz), 7.79 (1H, d, J=4.0 Hz), 8.04 (2H, d, J=8.6 Hz), 8.43 (1H, s).

Step 2

5-Bromo-1-[(4-methylphenyl)sulfonyl]-4-(trifluoromethyl)-1H-pyrrolo[2,3-b]pyridine The title compound (168 mg) was obtained by the same procedure as in Step 1 of Example 84 using the compound obtained in the above Step 1 (300 mg).
$^1$H-NMR (CDCl$_3$) δ: 2.39 (3H, s), 6.79-6.84 (1H, m), 7.31 (2H, d, J=8.3 Hz), 7.88 (1H, d, J=4.1 Hz), 8.05 (2H, d, J=8.3 Hz), 8.62 (1H, s).

Step 3

3-Cyclohex-1-en-1-yl-1-[(2S)-1,4-dioxan-2-ylmethyl]-6-{1-[(4-methylphenyl)sulfonyl]-4-(trifluoromethyl)-1H-pyrrolo[2,3-b]pyridin-5-yl}-1,3-dihydro-2H-imidazo[4,5-b]pyridin-2-one The title compound (172 mg) was obtained by the same procedure as in Step 2 of Example 4 using the compound obtained in the above Step 2 (242 mg) and the compound obtained in Step 1 of Example 41 (306 mg).
MS (ESI) m/z: 654 (M+H)$^+$.
$^1$H-NMR (CDCl$_3$) δ: 1.68-2.54 (8H, m), 2.41 (3H, s), 3.29-3.99 (9H, m), 6.07-6.11 (1H, m), 6.87 (1H, s), 7.34 (2H, d, J=7.8 Hz), 7.43-7.49 (1H, m), 7.96 (2H, s), 8.12 (2H, d, J=8.3 Hz), 8.40 (1H, s).

Step 4

3-Cyclohex-1-en-1-yl-1-[(2S)-1,4-dioxan-2-ylmethyl]-6-[4-(trifluoromethyl)-1H-pyrrolo[2,3-b]pyridin-5-yl]-1,3-dihydro-2H-imidazo[4,5-b]pyridin-2-one A 1 N aqueous sodium hydroxide solution (0.52 ml) was added to a solution of the compound obtained in the above Step 3 (170 mg) in methanol (2.6 ml), and the mixture was stirred at room temperature for 17 hours. The reaction solution was separated by adding an aqueous ammonium chloride solution and ethyl acetate. The resulting organic layer was washed with brine and dried over anhydrous sodium sulfate. The solvent was evaporated under reduced pressure. The resulting residue was purified by silica gel column chromatography (developed with ethyl acetate-hexane) to give the title compound (58 mg).
$^1$H-NMR (CDCl$_3$) δ: 1.73-1.82 (2H, m), 1.86-1.95 (2H, m), 2.29-2.39 (2H, m), 2.46-2.57 (2H, m), 3.33-4.00 (9H, m), 6.07-6.13 (1H, m), 6.78-6.83 (1H, m), 7.41-7.43 (1H, m), 7.54 (1H, s), 8.05 (1H, d, J=2.0 Hz), 8.29 (1H, s), 9.13 (1H, brs).

Step 5

1-[(2S)-1,4-Dioxan-2-ylmethyl]-6-(4-(trifluoromethyl)-1H-pyrrolo[2,3-b]pyridin-5-yl)-1,3-dihydro-2H-imidazo[4,5-b]pyridin-2-one The title compound (17 mg) was obtained by the same procedure as in Step 6 of Example 35 using the compound obtained in the above Step 4 (56 mg).
MS (ESI) m/z: 420 (M+H)$^+$.
$^1$H-NMR (DMSO-d$_6$) δ: 3.24-3.97 (9H, m), 6.62-6.67 (1H, m), 7.55 (1H, s), 7.83 (1H, s), 7.90 (1H, d, J=1.8 Hz), 8.27 (1H, s), 11.74 (1H, s), 12.37 (1H, s).

Example 123

1-[(2S)-1,4-Dioxan-2-ylmethyl]-6-(4-ethyl-1H-pyrrolo[2,3-b]pyridin-5-yl)-1,3-dihydro-2H-imidazo[4,5-b]pyridin-2-one

[Formula 143]

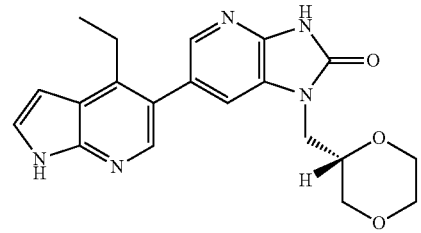

Step 1

5-Bromo-4-ethyl-1-[(4-methylphenyl)sulfonyl]-1H-pyrrolo[2,3-b]pyridine

A [1,1'-bis(diphenylphosphino)ferrocene]palladium(II) chloride-dichloromethane complex (26 mg), potassium carbonate (130 mg) and triethylborane (1 M solution in hexane)

(0.75 ml) were added to a solution of the compound obtained in Step 1 of Example 122 (300 mg) in N,N-dimethylformamide (12 ml). The mixture was stirred under nitrogen atmosphere at 80° C. for 24 hours. The reaction solution was cooled to room temperature and then separated by adding ethyl acetate and distilled water. The resulting organic layer was washed with brine and dried over anhydrous sodium sulfate. The solvent was evaporated under reduced pressure. The resulting residue was purified by silica gel column chromatography (developed with ethyl acetate-hexane) to give the title compound (147 mg).

MS (ESI) m/z: 380 (M+H)$^+$.

$^1$H-NMR (CDCl$_3$) δ: 1.21 (3H, t, J=7.5 Hz), 2.38 (3H, s), 2.94 (2H, q, J=7.5 Hz), 6.60 (1H, d, J=4.1 Hz), 7.28 (2H, d, J=8.3 Hz), 7.70 (1H, d, J=4.1 Hz), 8.05 (2H, d, J=8.3 Hz), 8.43 (1H, s).

Step 2

3-Cyclohex-1-en-1-yl-1-[(2S)-1,4-dioxan-2-ylmethyl]-6-{4-ethyl-1-[(4-methylphenyl)sulfonyl]-1H-pyrrolo[2,3-b]pyridin-5-yl}-1,3-dihydro-2H-imidazo[4,5-b]pyridin-2-one The title compound (122 mg) was obtained by the same procedure as in Step 3 of Example 1 using the compound obtained in the above Step 1 (145 mg) and the compound obtained in Step 1 of Example 41 (183 mg).

MS (ESI) m/z: 614 (M+H)$^+$.

$^1$H-NMR (CDCl$_3$) δ: 1.14 (3H, t, J=7.5 Hz), 1.72-1.82 (2H, m), 1.86-1.94 (2H, m), 2.30-2.37 (2H, m), 2.39 (3H, s), 2.46-2.54 (2H, m), 2.81 (2H, q, J=7.5 Hz), 3.33-3.41 (1H, m), 3.49-3.58 (1H, m), 3.62-3.75 (3H, m), 3.80-3.99 (4H, m), 6.08 (1H, s), 6.68 (1H, d, J=4.1 Hz), 7.29-7.34 (3H, m), 7.77 (1H, d, J=4.1 Hz), 7.97 (1H, d, J=1.4 Hz), 8.13 (2H, d, J=8.3 Hz), 8.26 (1H, s).

Step 3

3-Cyclohex-1-en-1-yl-1-[(2S)-1,4-dioxan-2-ylmethyl]-6-(4-ethyl-1H-pyrrolo[2,3-b]pyridin-5-yl)-1,3-dihydro-2H-imidazo[4,5-b]pyridin-2-one The title compound (75 mg) was obtained by the same procedure as in Step 4 of Example 122 using the compound obtained in the above Step 2 (120 mg).

MS (ESI) m/z: 460 (M+H)$^+$.

$^1$H-NMR (CDCl$_3$) δ: 1.24 (3H, t, J=7.3 Hz), 1.74-1.82 (2H, m), 1.87-1.95 (2H, m), 2.31-2.39 (2H, m), 2.48-2.56 (2H, m), 2.91 (2H, q, J=7.3 Hz), 3.35-4.01 (9H, m), 6.07-6.13 (1H, m), 6.59-6.63 (1H, m), 7.34-7.38 (1H, m), 7.39 (1H, d, J=1.8 Hz), 8.06 (1H, d, J=1.8 Hz), 8.17 (1H, s), 9.21 (1H, brs).

Step 4

1-[(2S)-1,4-Dioxan-2-ylmethyl]-6-(4-ethyl-1H-pyrrolo[2,3-b]pyridin-5-yl)-1,3-dihydro-2H-imidazo[4,5-b]pyridin-2-one The title compound (27 mg) was obtained by the same procedure as in Step 6 of Example 35 using the compound obtained in the above Step 3 (75 mg).

MS (ESI) m/z: 380 (M+H)$^+$.

$^1$H-NMR (DMSO-d$_6$) δ: 1.14 (3H, t, J=7.5 Hz), 2.84 (2H, q, J=7.5 Hz), 3.25-3.97 (9H, m), 6.56-6.60 (1H, m), 7.47-7.50 (1H, m), 7.51 (1H, d, J=1.4 Hz), 7.88 (1H, d, J=1.4 Hz), 8.04 (1H, s), 11.66 (2H, s).

Example 124

6-(3,4-Dimethyl-1H-pyrrolo[2,3-b]pyridin-5-yl)-1-[(2S)-1,4-dioxan-2-ylmethyl]-1,3-dihydro-2H-imidazo[4,5-b]pyridin-2-one

[Formula 144]

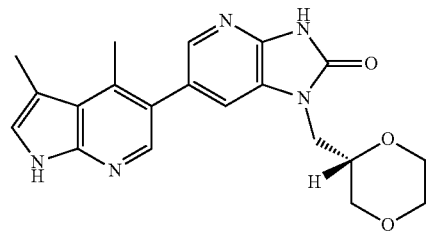

Step 1

5-Bromo-3,4-dimethyl-2-(trimethylsilyl)-1H-pyrrolo[2,3-b]pyridine

The compound obtained in step 1 of Example 36 (1.8 g) was dissolved in N,N-dimethylformamide (40 ml), and potassium acetate (1.7 g) and lithium chloride (0.3 g) were added. After replacing the atmosphere in the system with nitrogen, palladium acetate (0.13 g) and 1-trimethylsilyl-1-propyne (4.3 ml) were added and the mixture was stirred at 90° C. for three days. The reaction solution was cooled to room temperature and then N,N-dimethylformamide was distilled off. The resulting residue was diluted with ethyl acetate and then washed with brine. The organic layer was dried over anhydrous sodium sulfate and the solvent was evaporated to give the crude title compound (2.4 g).

MS (ESI) m/z: 297 (M+H)$^+$.

Step 2

5-Bromo-3,4-dimethyl-1H-pyrrolo[2,3-b]pyridine

The compound obtained in the above Step 1 (2.4 g) was dissolved in tetrahydrofuran (25 ml). A 2 M aqueous hydrochloric acid solution (10 ml) was added and the mixture was heated under reflux for 18 hours. The reaction solution was cooled to room temperature, neutralized with saturated aqueous sodium bicarbonate and then extracted with ethyl acetate. The organic layer was dried over anhydrous sodium sulfate and the solvent was evaporated. The resulting residue was purified by silica gel column chromatography (developed with ethyl acetate-hexane) to give the title compound (0.2 g).

MS (ESI) m/z: 225 (M+H)$^+$.

$^1$H-NMR (CDCl$_3$) δ: 2.46 (3H, s), 2.76 (3H, s), 7.00 (1H, s), 8.29 (1H, s).

Step 3

3-Cyclohex-1-en-1-yl-6-(3,4-dimethyl-1H-pyrrolo[2,3-b]pyridin-5-yl)-1-[(2S)-1,4-dioxan-2-ylmethyl]-1,3-dihydro-2H-imidazo[4,5-b]pyridin-2-one The title compound (145 mg) was obtained by the same procedure as in Step 3 of Example 1 using the compound obtained in Step 1 of Example 41 (306 mg) and the compound obtained in the above Step 2 (142 mg).

MS (ESI) m/z: 460 (M+H)⁺.

Step 4

6-(3,4-Dimethyl-1H-pyrrolo[2,3-b]pyridin-5-yl)-1-[(2S)-1,4-dioxan-2-ylmethyl]-1,3-dihydro-2H-imidazo[4,5-b]pyridin-2-one The title compound (135 mg) was obtained by the same procedure as in Step 6 of Example 35 using the compound obtained in the above Step 3 (222 mg).

MS (ESI) m/z: 380 (M+H)⁺.

HRMS (ESI) [(M+H)⁺] calculated: $C_{23}H_{21}N_5O_3$ 380.17226.

found: 380.17247.

¹H-NMR (DMSO-d₆) δ: 2.46 (3H, s), 2.58 (3H, s), 3.29-3.33 (1H, m), 3.42-3.54 (2H, m), 3.59-3.61 (1H, m), 3.70-3.72 (1H, m), 3.76-3.95 (4H, m), 7.20 (1H, s), 7.51 (1H, d, J=1.7 Hz), 7.88 (1H, d, J=1.7 Hz), 8.00 (1H, s), 11.27-11.28 (1H, m), 11.64 (1H, s).

Example 125

6-(3-Chloro-4-methyl-1H-pyrrolo[2,3-b]pyridin-5-yl)-1-[(2S)-1,4-dioxan-2-ylmethyl]-1,3-dihydro-2H-imidazo[4,5-b]pyridin-2-one

[Formula 145]

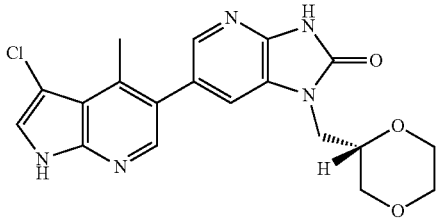

Step 1

5-Bromo-3-chloro-4-methyl-1H-pyrrolo[2,3-b]pyridine

The compound obtained in Step 3 of Example 36 (323 mg) was dissolved in tetrahydrofuran (6 ml). N-Chlorosuccinimide (225 mg) was added and the mixture was stirred at room temperature for three days. Water was added to the reaction solution, followed by extraction with chloroform. The organic layer was dried over anhydrous sodium sulfate, and the solvent was evaporated to give the title compound (364 mg).

MS (ESI) m/z: 245 (M+H)⁺.

Step 2 tert-Butyl 5-bromo-3-chloro-4-methyl-1H-pyrrolo[2,3-b]pyridine-1-carboxylate

The title compound (430 mg) was obtained by the same procedure as in Step 1 of Example 35 using the compound obtained in the above Step 1 (364 mg).

MS (ESI) m/z: 345 (M+H)⁺.

¹H-NMR (CDCl₃) δ: 1.66 (9H, s), 2.84 (3H, s), 7.59 (1H, s), 8.55 (1H, s).

Step 3

6-(3-Chloro-4-methyl-1H-pyrrolo[2,3-b]pyridin-5-yl)-3-cyclohex-1-en-1-yl-1-[(2S)-1,4-dioxan-2-ylmethyl]-1,3-dihydro-2H-imidazo[4,5-b]pyridin-2-one The title compound (125 mg) was obtained by the same procedure as in Step 3 of Example 1 using the compound obtained in Step 1 of Example 41 (302 mg) and the compound obtained in the above Step 2 (215 mg).

MS (ESI) m/z: 480 (M+H)⁺.

Step 4

6-(3-Chloro-4-methyl-1H-pyrrolo[2,3-b]pyridin-5-yl)-1-[(2S)-1,4-dioxan-2-ylmethyl]-1,3-dihydro-2H-imidazo[4,5-b]pyridin-2-one The title compound (77 mg) was obtained by the same procedure as in Step 6 of Example 35 using the compound obtained in the above Step 3 (125 mg).

MS (ESI) m/z: 400 (M+H)⁺.

HRMS (ESI) [(M+H)⁺] calculated: $C_{19}H_{19}ClN_5O_3$ 400.11764.

found: 400.12198.

¹H-NMR (DMSO-d₆) δ: 2.66 (3H, s), 3.28-3.97 (9H, m), 7.55 (1H, d, J=1.8 Hz), 7.66 (1H, d, J=2.7 Hz), 7.91 (1H, d, J=1.8 Hz), 8.13 (1H, s), 11.67 (1H, br s), 12.00 (1H, br s).

Example 126

1-[(2S)-1,4-Dioxan-2-ylmethyl]-6-(3-fluoro-4-methyl-1H-pyrrolo[2,3-b]pyridin-5-yl)-1,3-dihydro-2H-imidazo[4,5-b]pyridin-2-one

[Formula 146]

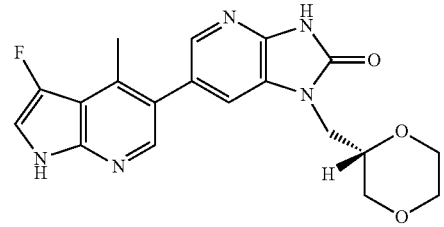

Step 1

5-Bromo-3-fluoro-4-methyl-1H-pyrrolo[2,3-b]pyridine

The compound obtained in Step 3 of Example 36 (3.0 g) was dissolved in acetonitrile (400 ml) and acetic acid (80 ml).

Selectfluoro (7.6 g) was added and the mixture was heated with stirring at 80° C. for 15 hours. The reaction solution was cooled to room temperature, concentrated, diluted with ethyl acetate and sequentially washed with saturated aqueous sodium bicarbonate and brine. After drying over anhydrous sodium sulfate, the solvent was evaporated under reduced pressure. The residue was purified by silica gel column chromatography (developed with methanol-chloroform) to give the title compound (2.0 g).

MS (ESI) m/z: 229 (M+H)$^+$.

$^1$H-NMR (CDCl$_3$) δ: 2.71 (3H, d, J=2.7 Hz), 7.04 (1H, d, J=2.3 Hz), 8.34 (1H, d, J=2.3 Hz), 8.76 (1H, br s).

Step 2 tert-Butyl 5-bromo-3-fluoro-4-methyl-1H-pyrrolo[2,3-b]pyridine-1-carboxylate

The title compound (1.2 g) was obtained by the same procedure as in Step 1 of Example 35 using the compound obtained in the above Step 1 (2.0 g).

$^1$H-NMR (CDCl$_3$) δ: 1.65 (9H, s), 2.67 (3H, s), 7.36-7.37 (1H, m), 8.54 (1H, s).

Step 3

3-Cyclohex-1-en-1-yl-1-[(2S)-1,4-dioxan-2-ylmethyl]-6-(3-fluoro-4-methyl-1H-pyrrolo[2,3-b]pyridin-5-yl)-1,3-dihydro-2H-imidazo[4,5-b]pyridin-2-one The title compound (237 mg) was obtained by the same procedure as in Step 3 of Example 1 using the compound obtained in Step 1 of Example 41 (290 mg) and the compound obtained in the above Step 2 (180 mg).

MS (ESI) m/z: 464 (M+H)$^+$.

Step 4

1-[(2S)-1,4-Dioxan-2-ylmethyl]-6-(3-fluoro-4-methyl-1H-pyrrolo[2,3-b]pyridin-5-yl)-1,3-dihydro-2H-imidazo[4,5-b]pyridin-2-one The title compound (68 mg) was obtained by the same procedure as in Step 6 of Example 35 using the compound obtained in the above Step 3 (237 mg).

MS (ESI) m/z: 384 (M+H)$^+$.

HRMS (ESI) [(M+H)$^+$] calculated: C$_{19}$H$_{19}$FN$_5$O$_3$ 384.14719.

found: 384.14806.

$^1$H-NMR (DMSO-d$_6$) δ: 2.55 (3H, s), 3.28-3.62 (4H, m), 3.69-3.96 (5H, m), 7.44-7.47 (1H, m), 7.56-7.57 (1H, m), 7.92 (1H, d, J=1.4 Hz), 8.13 (1H, s), 11.48 (1H, br s), 11.67 (1H, s).

Example 127

6-(6-Chloro-1H-pyrrolo[2,3-b]pyridin-5-yl)-1-[(2S)-1,4-dioxan-2-ylmethyl]-1,3-dihydro-2H-imidazo[4,5-b]pyridin-2-one

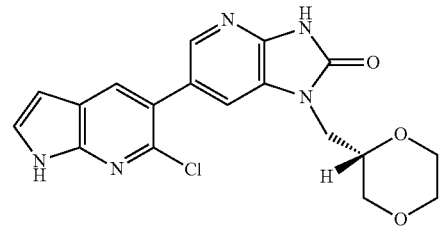

[Formula 147]

Step 1

{1-[(2S)-1,4-Dioxan-2-ylmethyl]-2-oxo-2,3-dihydro-1H-imidazo[4,5-b]pyridin-6-yl}boric acid The title compound (2.2 g) was obtained by the same procedure as in Step 6 of Example 35 using the compound obtained in Step 1 of Example 41 (5.0 g).

MS (ESI) m/z: 280 (M+H)$^+$.

Step 2

6-(6-Chloro-1H-pyrrolo[2,3-b]pyridin-5-yl)-1(tetrahydro-2H-pyran-4-ylmethyl)-1,3-dihydro-2H-imidazo[4,5-b]pyridin-2-one The title compound (107 mg) was obtained by the same procedure as in Step 3 of Example 1 using the compound obtained in the above Step 1 (75 mg) and the compound obtained in Step 5 of Example 78 (68 mg).

MS (ESI) m/z: 386 (M+H)$^+$.

HRMS (ESI) [(M+H)$^+$] calculated: C$_{18}$H$_{17}$ClN$_5$O$_3$ 386.10199.

found: 386.10355.

$^1$H-NMR (DMSO-d$_6$) δ: 3.32-3.62 (4H, m), 3.67-3.97 (5H, m), 6.54 (1H, s), 7.57-7.60 (1H, m), 7.62-7.65 (1H, m), 7.96-7.99 (1H, m), 8.05-8.07 (1H, m), 11.70 (1H, br s), 11.96 (1H, br s).

Example 128

1-[(2S)-1,4-Dioxan-2-ylmethyl]-6-(7-fluoro-4-methyl-1H-indol-5-yl)-1,3-dihydro-2H-imidazo[4,5-b]pyridin-2-one

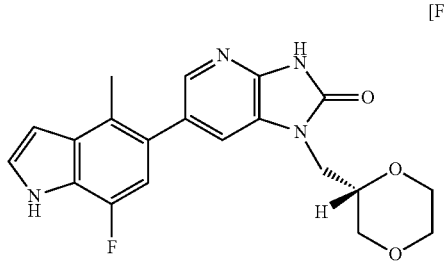

[Formula 148]

Step 1

4-Bromo-6-fluoro-2-iodo-3-methylaniline

The title compound (6.9 g) was obtained by the same procedure as in Step 1 of Example 36 using 4-bromo-6-fluoro-3-methylaniline (5.0 g).
MS (ESI) m/z: 330 (M+H)$^+$.

Step 2

4-Bromo-6-fluoro-2-[(trimethylsilyl)ethynyl]-3-methyl aniline

The title compound (6.9 g) was obtained by the same procedure as in Step 2 of Example 36 using 4-bromo-6-fluoro-2-iodo-3-methylaniline obtained in the above Step 1 (6.9 g).
MS (ESI) m/z: 300 (M+H)$^+$.

Step 3

5-Bromo-7-fluoro-4-methyl-1H-indole

The title compound (3.0 g) was obtained by the same procedure as in Step 3 of Example 36 using the compound obtained in the above Step 2 (6.9 g).
MS (ESI) m/z: 228 (M+H)$^+$.
$^1$H-NMR (CDCl$_3$) δ: 2.54 (3H, s), 6.57-6.59 (1H, m), 7.11 (1H, d, J=10.3 Hz), 7.23 (1H, t, J=2.9 Hz), 8.38 (1H, br s).

Step 4

6-(6-Fluoro-1H-pyrrolo[2,3-b]pyridin-5-yl)-1-(tetrahydro-2H-pyran-4-ylmethyl)-1,3-dihydro-2H-imidazo[4,5-b]pyridin-2-one The title compound (109 mg) was obtained by the same procedure as in Step 3 of Example 1 using the compound obtained in Step 1 of Example 127 (108 mg) and the compound obtained in the above Step 3 (80 mg).
MS (ESI) m/z: 383 (M+H)$^+$.

HRMS (ESI) [(M+H)$^+$] calculated: C$_{20}$H$_{20}$FN$_4$O$_3$ 383.15194.
found: 383.15248.
$^1$H-NMR (DMSO-D$_6$) δ: 2.39 (3H, s), 3.31-3.97 (9H, m), 6.61 (1H, s), 6.87 (1H, d, J=10.9 Hz), 7.44-7.46 (1H, m), 7.51 (1H, s), 7.89-7.90 (1H, m), 11.61 (1H, br s), 11.65 (1H, br s).

Example 129

1-[(2S)-1,4-Dioxan-2-ylmethyl]-6-(6-methyl-1H-pyrrolo[2,3-b]pyridin-5-yl)-1,3-dihydro-2H-imidazo[4,5-b]pyridin-2-one

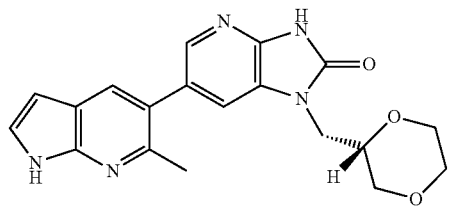

[Formula 149]

Step 1

6-Bromo-1-[(2S)-1,4-dioxan-2-ylmethyl]-1,3-dihydro-2H-imidazo[4,5-b]pyridin-2-one The title compound (0.8 g) was obtained by the same procedure as in Step 6 of Example 35 using the compound obtained in Step 1 of Example 40 (1.4 g).
MS (ESI) m/z: 314 (M+H)$^+$.
$^1$H-NMR (DMSO-d$_6$) δ: 3.26-3.28 (1H, m), 3.45-3.49 (2H, m), 3.59-3.62 (1H, m), 3.70-3.89 (5H, m), 7.75-7.75 (1H, m), 8.00-8.00 (1H, m), 11.79 (1H, br s).

Step 2

1-[(2S)-1,4-Dioxan-2-ylmethyl]-6-(6-methyl-1H-pyrrolo[2,3-b]pyridin-5-yl)-1,3-dihydro-2H-imidazo[4,5-b]pyridin-2-one The title compound (11 mg) was obtained by the same procedure as in Step 3 of Example 1 using the compound obtained in WO 2007/135398 (69 mg) and the compound obtained in the above Step 1 (50 mg).
MS (ESI) m/z: 366 (M+H)$^+$.
HRMS (ESI) [M+H]$^+$ calculated: C$_{19}$H$_{19}$N$_5$O$_3$ 366.15661. found: 366.15746.
$^1$H-NMR (DMSO-d$_6$) δ: 2.48 (3H, s), 3.39-3.94 (9H, m), 6.42 (1H, d, J=3.24 Hz), 7.41-7.42 (1H, m), 7.56 (1H, d, J=1.84 Hz), 7.78 (1H, s), 7.91 (1H, d, J=1.84 Hz), 11.53 (1H, s), 11.63 (1H, s).

Example 130

6-(4-Amino-1H-pyrrolo[2,3-b]pyridin-5-yl)-1-[(2S)-1,4-dioxan-2-ylmethyl]-1,3-dihydro-2H-imidazo[4,5-b]pyridin-2-one

[Formula 150]

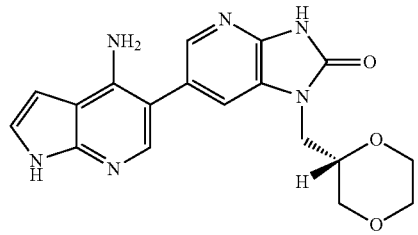

Step 1

4-Azido-5-bromo-1-[(4-methylphenyl)sulfonyl]-1H-pyrrolo[2,3-b]pyridine

The title compound (299 mg) was obtained by the same procedure as in Step 1 of Example 122 using 4-azido-5-bromo-1H-pyrrolo[2,3-b]pyridine obtained by the method described in WO 2008/150914 (199 mg).

$^1$H-NMR (CDCl$_3$) δ: 2.39 (3H, s), 6.85 (1H, d, J=4.0 Hz), 7.29 (2H, d, J=8.3 Hz), 7.73 (1H, d, J=4.0 Hz), 8.04 (2H, d, J=8.3 Hz), 8.39 (1H, s).

Step 2

5-Bromo-1-[(4-methylphenyl)sulfonyl]-1H-pyrrolo[2,3-b]pyridin-4-amine

Sodium borohydride (27 mg) was added to a solution of the compound obtained in the above Step 1 (275 mg) in 2-propanol (14 ml) in an ice bath, and the mixture was stirred at room temperature for 4 hours. The reaction solution was separated by adding an aqueous ammonium chloride solution and ethyl acetate. The resulting organic layer was washed with brine and dried over anhydrous sodium sulfate. The solvent was evaporated under reduced pressure. The resulting residue was purified by silica gel column chromatography (developed with ethyl acetate-hexane) to give the title compound (141 mg).

MS (ESI) m/z: 367 (M+H)$^+$.
$^1$H-NMR (DMSO-d$_6$) δ: 2.34 (3H, s), 6.79 (2H, brs), 6.97 (1H, d, J=4.0 Hz), 7.40 (2H, d, J=8.0 Hz), 7.57 (1H, d, J=4.0 Hz), 7.91 (2H, d, J=8.0 Hz), 8.03 (1H, s).

Step 3

6-{4-Amino-1-[(4-methylphenyl)sulfonyl]-1H-pyrrolo[2,3-b]pyridin-5-yl}-1-[(2S)-1,4-dioxan-2-ylmethyl]-1,3-dihydro-2H-imidazo[4,5-b]pyridin-2-one The title compound (55 mg) was obtained by the same procedure as in Step 3 of Example 1 using the compound obtained in the above Step 2 (50 mg) and the compound obtained in Step 1 of Example 127 (57 mg).

MS (ESI) m/z: 521 (M+H)$^+$.

$^1$H-NMR (CDCl$_3$) δ: 2.39 (3H, s), 3.33-3.97 (9H, m), 4.51 (2H, s), 6.51 (1H, d, J=4.0 Hz), 7.30 (2H, d, J=8.0 Hz), 7.41 (1H, d, J=1.7 Hz), 7.59 (1H, d, J=4.0 Hz), 8.04-8.06 (2H, m), 8.10 (2H, d, J=8.0 Hz), 9.52 (1H, brs).

Step 4

6-(4-Amino-1H-pyrrolo[2,3-b]pyridin-5-yl)-1-[(2S)-1,4-dioxan-2-ylmethyl]-1,3-dihydro-2H-imidazo[4,5-b]pyridin-2-one The title compound (16 mg) was obtained by the same procedure as in Step 4 of Example 122 using the compound obtained in the above Step 3 (43 mg).

MS (ESI) m/z: 367 (M+H)$^+$.
$^1$H-NMR (DMSO-d$_6$) δ: 3.38-3.98 (9H, m), 5.94 (2H, s), 6.63 (1H, s), 7.08-7.12 (1H, m), 7.49-7.53 (1H, m), 7.72 (1H, s), 7.89-7.93 (1H, m), 11.17 (1H, s), 11.59 (1H, s).

Example 131

6-[4-(Dimethylamino)-1H-pyrrolo[2,3-b]pyridin-5-yl]-1-[(2S)-1,4-dioxan-2-ylmethyl]-1,3-dihydro-2H-imidazo[4,5-b]pyridin-2-one

[Formula 151]

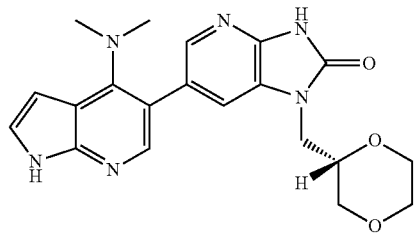

Step 1

5-Bromo-N,N-dimethyl-1-[(4-methylphenyl)sulfonyl]-1H-pyrrolo[2,3-b]pyridin-4-amine 55% Sodium hydride (19 mg) and methyl iodide (0.027 ml) were added to a solution of the compound obtained in Step 2 of Example 130 (64 mg) in N,N-dimethylformamide (3.6 ml) in an ice bath, and the mixture was stirred in an ice bath for 2 hours. The reaction solution was separated by adding an aqueous ammonium chloride solution and ethyl acetate. The resulting organic layer was washed with brine and dried over anhydrous sodium sulfate. The solvent was evaporated under reduced pressure. The resulting residue was purified by silica gel column chromatography (developed with ethyl acetate-hexane) to give the title compound (73 mg).

MS (ESI) m/z: 395 (M+H)$^+$.
$^1$H-NMR (CDCl$_3$) δ: 2.38 (3H, s), 3.13 (6H, s), 6.74 (1H, d, J=4.0 Hz), 7.25-7.29 (2H, m), 7.57 (1H, d, J=4.0 Hz), 8.04 (2H, d, J=8.0 Hz), 8.31 (1H, s).

Step 2

6-{4-(Dimethylamino)-1-[(4-methylphenyl)sulfonyl]-1H-pyrrolo[2,3-b]pyridin-5-yl}-1-[(2S)-1,4-dioxan-2-ylmethyl]-1,3-dihydro-2H-imidazo[4,5-b]pyridin-2-one The title compound (48 mg) was obtained by the same procedure as in Step 3 of Example 1 using the compound obtained in the above Step 1 (59 mg) and the compound obtained in Step 1 of Example 127 (63 mg).

MS (ESI) m/z: 549 (M+H)$^+$.

$^1$H-NMR (CDCl$_3$) δ: 2.39 (3H, s), 2.85 (6H, s), 3.35-3.97 (9H, m), 6.81 (1H, d, J=4.0 Hz), 7.29 (2H, d, J=8.0 Hz), 7.37 (1H, d, J=1.7 Hz), 7.61 (1H, d, J=4.0 Hz), 8.03-8.07 (2H, m), 8.10 (2H, d, J=8.0 Hz), 9.37 (1H, brs).

Step 3

6-[4-(Dimethylamino)-1H-pyrrolo[2,3-b]pyridin-5-yl]-1-[(2S)-1,4-dioxan-2-ylmethyl]-1,3-dihydro-2H-imidazo[4,5-b]pyridin-2-one The title compound (15 mg) was obtained by the same procedure as in Step 4 of Example 122 using the compound obtained in the above Step 2 (47 mg).

MS (ESI) m/z: 395 (M+H)$^+$.

$^1$H-NMR (DMSO-d$_6$) δ: 2.84 (6H, s), 3.27-3.93 (9H, m), 6.64-6.67 (1H, m), 7.28 (1H, s), 7.50 (1H, d, J=1.7 Hz), 7.85 (1H, s), 7.93 (1H, d, J=1.7 Hz), 11.46 (1H, s), 11.57 (1H, s).

Example 132

1-[(2S)-1,4-Dioxan-2-ylmethyl]-6-{4-[(2-hydroxyethyl)(methyl)amino]-1H-pyrrolo[2,3-b]pyridin-5-yl}-1,3-dihydro-2H-imidazo[4,5-b]pyridin-2-one

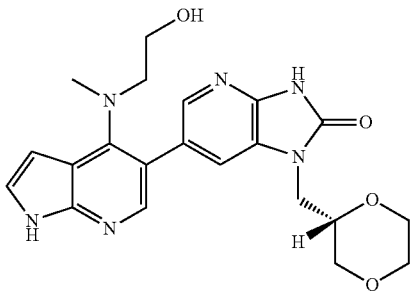

[Formula 152]

Step 1

2-[(5-Bromo-1-{[2-(trimethylsilyl)ethoxy]methyl}-1H-pyrrolo[2,3-b]pyridin-4-yl)(methyl)amino]ethanol 2-(Methylamino)ethanol (1.5 ml) was added to 5-bromo-4-chloro-1-{[2-(trimethylsilyl)ethoxy]methyl}-1H-pyrrolo[2,3-b]pyridine obtained by the method described in WO 2008/150914 (700 mg), and the mixture was heated under reflux at 145° C. for 18 hours. The reaction solution was cooled to room temperature and then concentrated under reduced pressure. The resulting residue was purified by silica gel column chromatography (developed with ethyl acetate-hexane) to give the title compound (472 mg).

MS (ESI) m/z: 401 (M+H)$^+$.

$^1$H-NMR (CDCl$_3$) δ: −0.06 (9H, s), 0.91 (2H, t, J=8.3 Hz), 2.45-2.50 (1H, m), 3.04 (3H, s), 3.50-3.61 (4H, m), 3.74 (2H, s), 5.62 (2H, s), 6.57-6.59 (1H, m), 7.25-7.28 (1H, m), 8.35 (1H, s).

Step 2

1-[(2S)-1,4-Dioxan-2-ylmethyl]-6-(4-[(2-hydroxyethyl)(methyl)amino]-1-{[2-(trimethylsilyl)ethoxy]methyl}-1H-pyrrolo[2,3-b]pyridin-5-yl)-1,3-dihydro-2H-imidazo[4,5-b]pyridin-2-one The title compound (29 mg) was obtained by the same procedure as in Step 3 of Example 1 using the compound obtained in the above Step 1 (100 mg) and the compound obtained in Step 1 of Example 127 (84 mg).

MS (ESI) m/z: 555 (M+H)$^+$.

$^1$H-NMR (CDCl$_3$) δ: −0.04 (9H, s), 0.94 (2H, t, J=8.3 Hz), 2.79 (3H, s), 3.40-4.03 (16H, m), 5.66 (2H, s), 6.67 (1H, d, J=3.4 Hz), 7.27 (1H, s), 7.67 (1H, d, J=1.7 Hz), 8.11 (1H, s), 8.41 (1H, d, J=1.7 Hz), 11.19 (1H, brs).

Step 3

1-[(2S)-1,4-Dioxan-2-ylmethyl]-6-{4-[(2-hydroxyethyl)(methyl)amino]-1H-pyrrolo[2,3-b]pyridin-5-yl}-1,3-dihydro-2H-imidazo[4,5-b]pyridin-2-one Trifluoroacetic acid (0.5 ml) was added to a solution of the compound obtained in the above Step 2 (29 mg) in dichloromethane (0.5 ml), and the mixture was stirred at room temperature for 15 hours. The reaction solution was concentrated under reduced pressure. Dichloromethane (0.5 ml) and ethylenediamine (0.2 ml) were added to the resulting residue, and the mixture was stirred at room temperature for 7 hours. The reaction solution was separated by adding an aqueous ammonium chloride solution and chloroform. The resulting organic layer was dried over anhydrous sodium sulfate. The solvent was evaporated under reduced pressure. The resulting residue was purified by silica gel column chromatography (developed with methanol-dichloromethane) to give the title compound (6 mg).

MS (ESI) m/z: 425 (M+H)$^+$.

$^1$H-NMR (DMSO-d$_6$) δ: 2.74 (3H, s), 3.27-3.93 (13H, m), 4.60 (1H, t, J=5.4 Hz), 6.59 (1H, s), 7.28-7.31 (1H, m), 7.70-7.72 (1H, m), 7.89 (1H, s), 7.98 (1H, d, J=1.7 Hz), 11.46 (1H, s), 11.55 (1H, s).

Example 133

1-[(2S)-1,4-Dioxan-2-ylmethyl]-6-(4-methoxy-1H-pyrrolo[2,3-b]pyridin-5-yl)-1,3-dihydro-2H-imidazo[4,5-b]pyridin-2-one

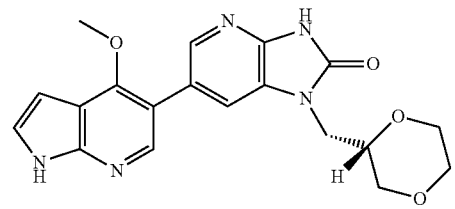

[Formula 153]

Step 1

5-Bromo-4-methoxy-1H-pyrrolo[2,3-b]pyridine

Potassium methoxide (103 mg), lithium methoxide (27 mg) and tert-butanol (40 μl) were added to a solution of 5-bromo-4-chloro-1H-pyrrolo[2,3-b]pyridine (81 mg) in xylene (3.5 ml), and the mixture was heated under reflux at 117° C. for 16 hours. The reaction solution was brought to pH 4 by adding concentrated hydrochloric acid in small portions and separated by adding ethyl acetate and distilled water. The resulting aqueous layer was brought to pH 8 by adding a 5 N aqueous sodium hydroxide solution and separated by adding ethyl acetate. All the resulting organic layers were combined, washed with brine and dried over anhydrous sodium sulfate. The solvent was evaporated under reduced pressure. The resulting residue was purified by thin-layer chromatography (developed with ethyl acetate-hexane) to give the title compound (20 mg).

MS (ESI) m/z: 227 (M+H)$^+$.
$^1$H-NMR (DMSO-$d_6$) δ: 4.29 (3H, s), 6.77-6.82 (1H, m), 7.37-7.42 (1H, m), 8.14 (1H, s), 11.82 (1H, br s).

Step 2

1-[(2S)-1,4-Dioxan-2-ylmethyl]-6-(4-methoxy-1H-pyrrolo[2,3-b]pyridin-5-yl)-1,3-dihydro-2H-imidazo[4,5-b]pyridin-2-one The title compound (26 mg) was obtained by the same procedure as in Step 3 of Example 1 using the compound obtained in the above Step 1 (64 mg) and the compound obtained in Step 1 of Example 127 (79 mg).

MS (ESI) m/z: 382 (M+H)$^+$.
HRMS (ESI) [M+H]$^+$ calculated: $C_{19}H_{20}N_5O_4$ 382.15153. found: 382.15284.
$^1$H-NMR (DMSO-$d_6$) δ: 2.50-2.52 (1H, m), 3.44-3.64 (4H, m), 3.67-3.93 (4H, m), 4.19 (3H, s), 6.76-6.81 (1H, m), 7.37-7.42 (1H, m), 7.57 (1H, d, J=1.8 Hz), 7.97 (1H, d, J=1.4 Hz), 8.04 (1H, s), 11.57 (1H, br s), 11.71 (1H, br s).

Example 134

1-[(2S)-1,4-Dioxan-2-ylmethyl]-6-(3-methoxy-1H-pyrrolo[2,3-b]pyridin-5-yl)-1,3-dihydro-2H-imidazo[4,5-b]pyridin-2-one

[Formula 154]

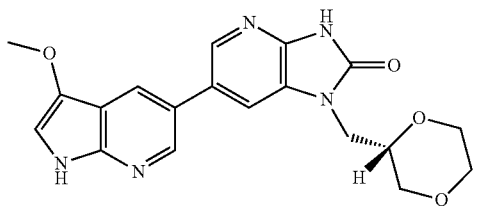

Step 1

5-Bromo-1-[(4-methylphenyl)sulfonyl]-1,2-dihydro-3H-pyrrolo[2,3-b]pyridin-3-one

5-Bromo-1H-pyrrolo[2,3-b]pyridine-3-carbaldehyde obtained by the method described in WO 2004/101565 (4.10 g) was dissolved in THF (100 ml). Triethylamine (3.05 ml) and p-toluenesulfonyl chloride (3.82 g) were added at room temperature and the mixture was stirred overnight. The reaction solvent was distilled off under reduced pressure and then diluted with ethyl acetate. After washing with water and brine in this order, the resulting organic layer was dried over anhydrous sodium sulfate. The solvent was evaporated under reduced pressure. The resulting residue was solidified with (dichloromethane-diethyl ether) and then collected by filtration to give 5-bromo-1-[(4-methylphenyl)sulfonyl]-1H-pyrrolo[2,3-b]pyridine-3-carbaldehyde (2.32 g). Further, the filtrate was concentrated under reduced pressure. The resulting residue was purified by silica gel column chromatography (developed with ethyl acetate-hexane) to give 5-bromo-1-[(4-methylphenyl)sulfonyl]-1H-pyrrolo[2,3-b]pyridine-3-carbaldehyde (2.55 g). The resulting 5-bromo-1-[(4-methylphenyl)sulfonyl]-1H-pyrrolo[2,3-b]pyridine-3-carbaldehyde (2.83 g) was dissolved in methylene chloride (50 ml). 3-Chloroperbenzoic acid (2.13 g) was added under ice-cooling over 3 hours, and the mixture was stirred at room temperature for 2 hours. Thereafter, a 10% aqueous sodium sulfite solution and a saturated aqueous sodium bicarbonate solution were added to the reaction solution, followed by stirring overnight. The reaction solution was diluted with methylene chloride and the insoluble matter was removed by filtration, followed by extraction with methylene chloride three times. The resulting organic layer was dried over anhydrous sodium sulfate. The solvent was evaporated under reduced pressure. The resulting residue was purified by silica gel column chromatography (developed with ethyl acetate-hexane) to give the title compound (0.18 g) as a pale red solid.

MS (ESI) m/z: 366 (M+H)$^+$.
$^1$H-NMR (CDCl$_3$) δ: 2.42 (3H, s), 4.41 (2H, s), 7.32 (2H, d, J=7.1 Hz), 7.99 (2H, d, J=8.5 Hz), 8.02 (1H, d, J=2.7 Hz), 8.64 (1H, d, J=2.0 Hz).

Step 2

5-Bromo-3-methoxy-1-[(4-methylphenyl)sulfonyl]-1H-pyrrolo[2,3-b]pyridine

The compound obtained in the above Step 1 (110 mg) was dissolved in methanol (5 ml) and tetrahydrofuran (5 ml). (Trimethylsilyl)diazomethane (0.75 ml) was added dropwise under ice-cooling, and the mixture was stirred at room temperature for 4 hours. (Trimethylsilyl)diazomethane (0.75 ml) was added dropwise, followed by further stirring overnight. Acetic acid (154 µl) was added to the reaction solution, and then the solvent was evaporated under reduced pressure. The resulting residue was purified by silica gel column chromatography (developed with ethyl acetate-hexane) to give the title compound (40 mg) as a colorless oil.

MS (ESI) m/z: 381 (M+H)$^+$.
$^1$H-NMR (CDCl$_3$) δ: 2.37 (3H, s), 3.88 (3H, s), 7.09 (1H, s), 7.25 (2H, d, J=8.7 Hz), 7.95-7.98 (3H, m), 8.45 (1H, d, J=2.3 Hz).

Step 3

1-[(2S)-1,4-Dioxan-2-ylmethyl]-6-{3-methoxy-1-[(4-methylphenyl)sulfonyl]-1H-pyrrolo[2,3-b]pyridin-5-yl}-1,3-dihydro-2H-imidazo[4,5-b]pyridin-2-one The title compound (45 mg) was obtained as a pale yellow solid by the same procedure as in Step 2 of Example 4 using the compound obtained in the above Step 2 (40 mg) and the compound obtained in Step 1 of Example 127 (38 mg).

MS (ESI) m/z: 536 (M+H)$^+$.

Step 4

1-[(2S)-1,4-Dioxan-2-ylmethyl]-6-(3-methoxy-1H-pyrrolo[2,3-b]pyridin-5-yl)-1,3-dihydro-2H-imidazo[4,5-b]pyridin-2-one The title compound (10 mg) was obtained as a pale yellow solid by the same procedure as in Step 3 of Example 84 using the compound obtained in the above Step 3 (45 mg).
HRMS (ESI) [M+H]$^+$ calculated: $C_{19}H_{20}N_5O_4$ 382.15153. found: 382.15295.
MS (ESI) m/z: 382 (M+H)$^+$.
$^1$H-NMR (DMSO-$d_6$) δ: 3.31-3.37 (2H, m), 3.44-3.54 (2H, m), 3.59-3.62 (1H, m), 3.71-3.80 (2H, m), 3.84-3.94 (4H, m), 3.97-4.02 (1H, m), 7.08 (1H, d, J=2.9 Hz), 7.87 (1H, d, J=1.7 Hz), 8.16 (1H, d, J=2.3 Hz), 8.25 (1H, d, J=2.3 Hz), 8.53 (1H, d, J=2.3 Hz), 11.12 (1H, d, J=1.7 Hz), 11.61 (1H, s).

Example 135

2,6-Anhydro-1,3,4-trideoxy-5-O-methyl-1-[2-oxo-6-(1H-pyrrolo[2,3-b]pyridin-5-yl)-2,3-dihydro-1H-imidazo[4,5-b]pyridin-1-yl]-D-threo-hexitol

[Formula 155]

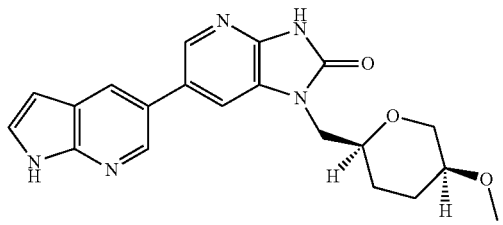

Step 1

2,6-Anhydro-1-(6-bromo-3-cyclohex-1-en-1-yl-2-oxo-2,3-dihydro-1H-imidazo[4,5-b]pyridin-1-yl)-1,3,4-trideoxy-5-O-methyl-D-threo-hexitol 2,6-Anhydro-1-(6-bromo-3-cyclohex-1-en-1-yl-2-oxo-2,3-dihydro-1H-imidazo[4,5-b]pyridin-1-yl)-1,3,4-trideoxy-5-O-methyl-L-threo-hexitol The compound obtained in Step 4 of Example 113 (0.86 g) was optically resolved by HPLC to give the title compound D-isomer (isomer A: 0.35 g) and L-isomer (isomer B: 0.36 g), respectively.
Column: CHIRALPAK AD (5×50 cm)
Eluent: 25% isopropanol/n-hexane
Flow rate: 25 ml/min
Elution time Isomer A: 56 min, isomer B: 71 min

Step 2

2,6-Anhydro-1-[3-cyclohex-1-en-1-yl-2-oxo-6-(1H-pyrrolo[2,3-b]pyridin-5-yl)-2,3-dihydro-1H-imidazo[4,5-b]pyridin-1-yl]-1,3,4-trideoxy-5-O-methyl-D-threo-hexitol The title compound (220 mg) was obtained as a pale yellow oil by the same procedure as in Step 2 of Example 4 using 5-(4,4,5,5-tetramethyl-1,3,2-dioxaborolan-2-yl)-1H-pyrrolo[2,3-b]pyridine (173 mg) and the D-isomer obtained in the above Step 1 (isomer A, 200 mg).
MS (ESI) m/z: 460 (M+H)$^+$.
$^1$H-NMR (CDCl$_3$) δ: 1.57-1.66 (3H, m), 1.75-1.80 (2H, m), 1.88-1.92 (2H, m), 2.11-2.14 (1H, m), 2.32-2.36 (2H, m), 2.49-2.51 (2H, m), 3.23 (1H, s), 3.36 (3H, s), 3.44 (1H, dd, J=12.6, 1.1 Hz), 3.72-3.77 (1H, m), 3.89 (1H, dd, J=14.6, 7.7 Hz), 4.04-4.09 (2H, m), 6.07-6.08 (1H, m), 6.58-6.59 (1H, m), 7.39-7.40 (1H, m), 7.67 (1H, d, J=2.2 Hz), 8.08 (1H, d, J=1.7 Hz), 8.27 (1H, d, J=1.7 Hz), 8.50 (1H, d, J=2.2 Hz), 9.30 (1H, s).

Step 3

2,6-Anhydro-1,3,4-trideoxy-5-O-methyl-1-[2-oxo-6-(1H-pyrrolo[2,3-b]pyridin-5-yl)-2,3-dihydro-1H-imidazo[4,5-b]pyridin-1-yl]-D-threo-hexitol The title compound (55 mg) was obtained as a pale yellow solid by the same procedure as in Step 6 of Example 35 using the compound obtained in the above Step 2 (220 mg).
MS (ESI) m/z: 380 (M+H)$^+$.
$^1$H-NMR (DMSO-$d_6$) δ: 1.40-1.45 (1H, m), 1.54-1.65 (3H, m), 1.89-1.95 (1H, m), 3.15-3.18 (1H, m), 3.20 (3H, s), 3.70-3.76 (1H, m), 3.80-3.98 (2H, m), 6.51 (1H, dd, J=3.2, 1.8 Hz), 7.52-7.53 (1H, m), 7.83 (1H, d, J=1.8 Hz), 8.23 (2H, s), 8.52 (1H, d, J=2.2 Hz), 11.59 (1H, s), 11.74 (1H, s).

Example 136

2,6-Anhydro-1,3,4-trideoxy-5-O-methyl-1-[2-oxo-6-(1H-pyrrolo[2,3-b]pyridin-5-yl)-2,3-dihydro-1H-imidazo[4,5-b]pyridin-1-yl]-L-threo-hexitol

[Formula 156]

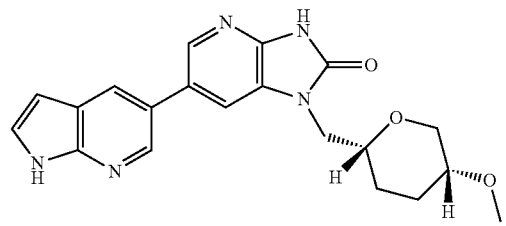

Step 1

2,6-Anhydro-1-[3-cyclohex-1-en-1-yl-2-oxo-6-(1H-pyrrolo[2,3-b]pyridin-5-yl)-2,3-dihydro-1H-imidazo[4,5-b]pyridin-1-yl]-1,3,4-trideoxy-5-O-methyl-L-threo-hexitol The title compound (220 mg) was obtained as a pale yellow oil by the same procedure as in Step 2 of Example 4 using 5-(4,4,5,5-tetramethyl-1,3,2-dioxaborolan-2-yl)-1H-pyrrolo[2,3-b]pyridine (173 mg) and the L-isomer obtained in Step 1 of Example 135 (isomer B, 200 mg).
MS (ESI) m/z: 460 (M+H)$^+$.
$^1$H-NMR (CDCl$_3$) δ: 1.57-1.66 (3H, m), 1.75-1.80 (2H, m), 1.88-1.95 (2H, m), 2.11-2.15 (1H, m), 2.32-2.35 (2H, m), 2.49-2.52 (2H, m), 3.22-3.24 (1H, m), 3.36 (3H, s), 3.44 (1H, dd, J=12.6, 1.7 Hz), 3.72-3.76 (1H, m), 3.89 (1H, dd, J=14.8, 8.0 Hz), 4.04-4.09 (2H, m), 6.06-6.08 (1H, m), 6.59 (1H, dd, J=3.7, 2.0 Hz), 7.39 (1H, dd, J=3.4, 2.2 Hz), 7.67 (1H, d, J=2.2 Hz), 8.08 (1H, d, J=1.7 Hz), 8.27 (1H, d, J=2.2 Hz), 8.50 (1H, d, J=2.2 Hz), 9.13 (1H, s).

Step 2

2,6-Anhydro-1,3,4-trideoxy-5-O-methyl-1-[2-oxo-6-(1H-pyrrolo[2,3-b]pyridin-5-yl)-2,3-dihydro-1H-imidazo[4,5-b]pyridin-1-yl]-L-threo-hexitol The title compound (79 mg) was obtained as a pale yellow solid by the same procedure as in Step 6 of Example 35 using the compound obtained in the above Step 1 (220 mg).
MS (ESI) m/z: 380 (M+H)$^+$.
$^1$H-NMR (DMSO-d$_6$) δ: 1.40-1.44 (1H, m), 1.54-1.64 (2H, m), 1.89-1.95 (1H, m), 3.20 (3H, s), 3.71-3.77 (1H, m), 3.80-3.98 (3H, m), 6.51 (1H, dd, J=3.4, 1.6 Hz), 7.52-7.54 (1H, m), 7.83 (1H, d, J=1.8 Hz), 8.22-8.23 (2H, m), 8.52 (1H, d, J=2.2 Hz), 11.59 (1H, s), 11.74 (1H, s).

Example 137

2,6-Anhydro-1,3,5-trideoxy-4-O-methyl-1-[2-oxo-6-(1H-pyrrolo[2,3-b]pyridin-5-yl)-2,3-dihydro-1H-imidazo[4,5-b]pyridin-1-yl]-L-threo-hexitol

[Formula 157]

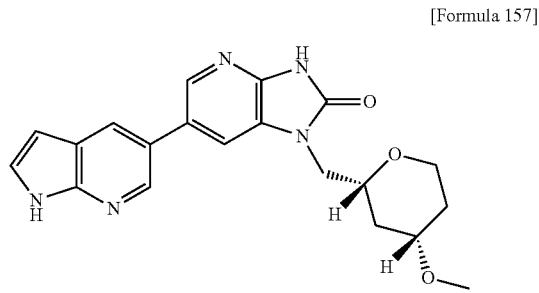 [SMILES: CO[C@H]1CCO[C@@H](Cn2c(=O)[nH]c3ncc(-c4cnc5[nH]ccc5c4)cc32)C1]

Step 1

2,6-Anhydro-1-O-benzyl-3,5-dideoxy-L-threo-hexitol 2,6-Anhydro-1-O-benzyl-3,5-dideoxy-D-threo-hexitol The compound obtained in Step 2 of Example 114 was optically resolved by HPLC to give the title compound L-isomer (isomer A: 0.47 g) and D-isomer (isomer B: 0.47 g), respectively.
Preparative separation;
  Column: CHIRALCEL OD (5×50 cm)
  Eluent: 25% isopropanol/n-hexane
  Flow rate: 25 ml/min
  Elution time Isomer A: 48 min, isomer B: 58 min
Analysis;
  Column: CHIRALCEL OD (0.46×5 cm)
  Eluent: 10% isopropanol/n-hexane
  Flow rate: 1.0 ml/min
  Elution time Isomer A: 12 min, isomer B: 16 min
2,6-Anhydro-1-O-benzyl-3,5-dideoxy-D-threo-hexitol was obtained from a known sugar derivative according to the reference examples shown below.
Analysis result by chiral HPLC; Elution time: 16 min
The isomer B and the isomer A were determined to be a D-isomer and an L-isomer, respectively, based on the above result.

Reference Example 1

2,6-Anhydro-4-O-benzoyl-1-O-benzyl-3-chloro-3,5-dideoxy-D-arabino-hexitol

Sulfonyl chloride (29 μl) was added to a solution of 1,5-anhydro-3-O-benzoyl-6-O-benzyl-2-deoxy-D-arabino-hexitol obtained by the method described in J. Org. Chem. 67. 3346-3354 (2002) (94 mg) in pyridine (27 mg) under ice-cooling, and the mixture was stirred at room temperature for 4 hours. Water was added, followed by extraction with ethyl acetate. Then, the organic layer was dried over anhydrous magnesium sulfate, and the solvent was evaporated under reduced pressure. The resulting residue was purified by silica gel column chromatography (developed with ethyl acetate-hexane) to give the title compound (27 mg).
$^1$H-NMR (CDCl$_3$) δ: 1.82-1.87 (1H, m), 2.32-2.42 (1H, m), 3.60-3.72 (3H, m), 3.84-3.88 (1H, m), 4.13-4.18 (1H, m), 4.52-4.62 (3H, m), 5.26-5.31 (1H, m), 7.27-7.38 (5H, m), 7.44-7.48 (2H, m), 7.57-7.60 (1H, m), 8.07-8.09 (2H, m).

Reference Example 2

2,6-Anhydro-4-O-benzoyl-1-O-benzyl-3,5-dideoxy-D-threo-hexitol

Tributyltin hydride (24 μl) and azobisisobutyronitrile (6 mg) were added to a solution of the compound obtained in the above Reference Example 1 (27 mg) in benzene (1.0 ml), and the mixture was heated under reflux for one hour. Tributyltin hydride (24 μl) and azobisisobutyronitrile (1 mg) were further added and the mixture was heated under reflux for one hour. The reaction solution was concentrated, and then the residue was purified by thin layer chromatography (developed with ethyl acetate-hexane) to give the crude title compound (35 mg).
MS (ESI) m/z: 327 (M+H)$^+$.

Reference Example 3

2,6-Anhydro-1-O-benzyl-3,5-dideoxy-D-threo-hexitol

A solution of sodium methoxide in methanol (5 M, 14 μl) was added dropwise to a solution of the compound obtained in the above Reference Example 2 (35 mg) in methanol (1.0 ml), and the mixture was stirred at room temperature for 6 hours. Saturated aqueous sodium bicarbonate was added, followed by extraction with ethyl acetate. Then, the organic layer was washed with brine and dried over anhydrous sodium sulfate, and the solvent was evaporated under reduced pressure. The resulting residue was purified by silica gel column chromatography (developed with ethyl acetate-hexane) to give the title compound (10 mg).
$^1$H-NMR (CDCl$_3$) δ: 1.30 (1H, dd, J=22.9, 11.5 Hz), 1.49-1.57 (1H, m), 1.86-1.94 (2H, m), 3.41-3.57 (4H, m), 3.77-3.83 (1H, m), 4.05-4.08 (1H, m), 4.55 (2H, d, J=11.6 Hz), 4.60 (1H, d, J=11.6 Hz), 7.27-7.31 (1H, m), 7.33-7.35 (4H, m).

Step 2

2,6-Anhydro-1-O-benzyl-3,5-dideoxy-4-O-methyl-L-threo-hexitol

The title compound (322 mg) was obtained by the same procedure as in Step 1 of Example 63 using the L-isomer obtained in the above Step 1 (isomer A: 466 mg).
MS (ESI) m/z: 237 (M+H)$^+$.

Step 3

1,5-Anhydro-2,4-dideoxy-3-O-methyl-L-threo-hexitol

The title compound (180 mg) was obtained by the same procedure as in Step 4 of Example 114 using the compound obtained in the above Step 2 (322 mg).

Step 4

5-(4,4,5,5-Tetramethyl-1,3,2-dioxaborolan-2-yl)-1-{[2-(trimethylsilyl)ethoxy]methyl}-1H-pyrrolo[2,3-b]pyridine 5-(4,4,5,5-Tetramethyl-1,3,2-dioxaborolan-2-yl)-1H-pyrrolo[2,3-b]pyridine (1.01 g) was dissolved in tetrahydrofuran (10 ml). After the atmosphere was replaced with nitrogen, the solution was ice-cooled. 55% Sodium hydride (216 mg) was added and the mixture was stirred under ice-cooling for 20 minutes. Then, [2-(chloromethoxy)ethyl](trimethyl)silane (875 μl) was added and the mixture was stirred at room temperature for 15.5 hours. The reaction solution was diluted by adding water thereto, neutralized with 1 N hydrochloric acid (0.85 ml) and extracted with ethyl acetate three times. The organic layer was washed with water once and then with brine and dried over anhydrous sodium sulfate, and the solvent was evaporated. The brown oil was purified by silica gel column chromatography (developed with ethyl acetate-hexane) to give the title compound (691 mg) as a colorless oil.

MS (APCI) m/z: 375 [M+H]$^+$ $^1$H-NMR (CDCl$_3$) δ: −0.08 (9H, s), 0.87-0.91 (2H, m), 1.37 (12H, s), 3.49-3.55 (2H, m), 5.70 (2H, s), 6.52 (1H, d, J=3.7 Hz), 7.32 (1H, d, J=3.7 Hz), 8.35 (1H, d, J=1.6 Hz), 8.69 (1H, d, J=1.6 Hz).

Step 5

6-Bromo-3-{[2-(trimethylsilyl)ethoxy]methyl}-1,3-dihydro-2H-imidazo[4,5-b]pyridin-2-one Ethyl 6-bromo-2-oxo-2,3-dihydro-1H-imidazo[4,5-b]pyridine-1-carboxylate obtained under the conditions described in WO 2008/051493 (2.01 g) was dissolved in tetrahydrofuran (40 ml), and [2-(chloromethoxy)ethyl](trimethyl)silane (1.37 ml) was added. After the atmosphere was replaced with nitrogen, the mixture was ice-cooled. 55% Sodium hydride (337 mg) was added and the mixture was stirred for 50 minutes to be gradually warmed to room temperature. The reaction solution was extracted three times by adding water and ethyl acetate. The organic layer was washed with brine and then dried over anhydrous sodium sulfate, and the solvent was evaporated. The resulting brown oil was dissolved in tetrahydrofuran (40 ml). After ice-cooling, isopropylamine (0.9 ml) was added and the mixture was directly stirred for one hour. After distilling off the reaction solvent, the residue was purified by silica gel column chromatography (developed with ethyl acetate-hexane) to give the title compound (1.56 g) as colorless crystals.

MS (APCI) m/z: 344 [M+H]$^+$ $^1$H-NMR (CDCl$_3$) δ: −0.02 (9H, s), 0.98-0.99 (2H, m), 3.70-3.74 (2H, m), 5.41 (2H, s), 7.50 (1H, d, J=2.3 Hz), 8.16 (1H, d, J=2.3 Hz), 10.08 (1H, br s).

Step 6

3-{[2-(Trimethylsilyl)ethoxy]methyl}-6-(1-{[2-(trimethylsilyl)ethoxy]methyl}-1H-pyrrolo[2,3-b]pyridin-5-yl)-1,3-dihydro-2H-imidazo[4,5-b]pyridin-2-one The title compound (195 mg) was obtained by the same procedure as in Step 3 of Example 1 using the compound obtained in the above Step 4 (216 mg) and the compound obtained in the above Step 5 (145 mg).

MS (APCI) m/z: 512 [M+H]$^+$ $^1$H-NMR (CDCl$_3$) δ: −0.05 (9H, s), 0.01 (9H, s), 0.91-0.96 (2H, m), 0.99-1.05 (2H, m), 3.56-3.61 (2H, m), 3.75-3.80 (2H, m), 5.49 (2H, s), 5.72 (2H, s), 6.59 (1H, d, J=3.7 Hz), 7.42 (1H, d, J=3.7 Hz), 7.55 (1H, d, J=2.3 Hz), 8.05 (1H, d, J=2.3 Hz), 8.33 (1H, d, J=2.3 Hz), 8.52 (1H, d, J=2.3 Hz), 9.40 (1H, br s).

Step 7

2,6-Anhydro-1,3,5-trideoxy-4-O-methyl-1-[2-oxo-3-{[2-(trimethylsilyl)ethoxy]methyl}-6-(1-{[2-(trimethylsilyl)ethoxy]methyl}-1H-pyrrolo[2,3-b]pyridin-5-yl)-2,3-dihydro-1H-imidazo[4,5-b]pyridin-1-yl]-L-threo-hexitol The compound obtained in the above Step 6 (130 mg) and the compound obtained in the above Step 3 (60 mg) were stirred at room temperature for 55 minutes by the same procedure as in Step 3 of Example 35, and then the reaction system was ice-cooled. Triethylamine (86 μl) and methanesulfonyl chloride (35 μl) were added and the mixture was stirred under ice-cooling for 30 minutes. Acetonitrile (6 ml) and potassium carbonate (70 mg) were added thereto and the mixture was stirred at 80° C. for 42 hours. The reaction solution was filtered and washed with acetonitrile, and then the filtrate was concentrated. The residue was purified by silica gel column chromatography (developed with ethyl acetate-hexane) to give the title compound (114 mg) as a colorless oil.

MS (APCI) m/z: 640 [M+H]$^+$

Step 8

2,6-Anhydro-1,3,5-trideoxy-4-O-methyl-1-[2-oxo-6-(1H-pyrrolo[2,3-b]pyridin-5-yl)-2,3-dihydro-1H-imidazo[4,5-b]pyridin-1-yl]-L-threo-hexitol dimethanesulfonate The compound obtained in the above Step 7 (109 mg) was dissolved in tetrahydrofuran (3 ml). Tetrabutylammonium fluoride (1.0 M solution in tetrahydrofuran) (1.7 ml) was added and the mixture was stirred at 80° C. for 13 hours. The reaction solvent was distilled off. The residue was purified by silica gel column chromatography (developed with ethyl acetate-ethanol) and then purified by elution with 5% aqueous ammonia/ethanol using PoraPak™ Rxn CX (2 g). The resulting crystals were dissolved in dichloromethane (3 ml)/ethanol (0.5 ml), and methanesulfonic acid (22 μl) was added. The mixture was stirred at room temperature for 15 minutes and then the solvent was evaporated. The residue was solidified from ethyl acetate and collected by filtration in a nitrogen atmosphere to give the title compound (27 mg).

MS (APCI) m/z: 380 [M+H]$^+$ $^1$H-NMR (DMSO-d$_6$) δ: 1.04-1.13 (1H, m), 1.15-1.27 (1H, m), 1.82-1.90 (1H, m), 2.00-2.08 (1H, m), 2.44 (6H, s), 3.18-

3.38 (2H, m), 3.22 (3H, s), 3.64-3.73 (1H, br m), 3.82-3.91 (2H, br m), 3.98 (1H, dd, J=14.7, 7.8 Hz), 6.76 (1H, dd, J=3.7, 1.8 Hz), 7.74 (1H, t, J=2.7 Hz), 7.90 (1H, d, J=1.8 Hz), 8.30 (1H, d, J=1.8 Hz), 8.72 (2H, s), 12.46 (1H, br s).

Example 138

2,6-Anhydro-1,3,5-trideoxy-4-O-methyl-1-[2-oxo-6-(1H-pyrrolo[2,3-b]pyridin-5-yl)-2,3-dihydro-1H-imidazo[4,5-b]pyridin-1-yl]-D-threo-hexitol

[Formula 158]

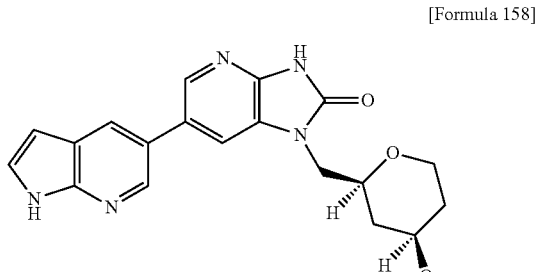

Step 1

2,6-Anhydro-1-O-benzyl-3,5-dideoxy-4-O-methyl-D-threo-hexitol

The title compound (340 mg) was obtained by the same procedure as in Step 1 of Example 63 using the D-isomer obtained in Step 1 of Example 137 (isomer B: 468 mg).
MS (ESI) m/z: 237 (M+H)$^+$.

Step 2

1,5-Anhydro-2,4-dideoxy-3-O-methyl-D-threo-hexitol

The title compound (195 mg) was obtained by the same procedure as in Step 4 of Example 114 using the compound obtained in the above Step 1 (340 mg).

Step 3

2,6-Anhydro-1,3,5-trideoxy-4-O-methyl-1-[2-oxo-3-{[2-(trimethylsilyl)ethoxy]methyl}-6-(1-{[2-(trimethylsilyl)ethoxy]methyl}-1H-pyrrolo[2,3-b]pyridin-5-yl)-2,3-dihydro-1H-imidazo[4,5-b]pyridin-1-yl]-D-threo-hexitol The compound obtained in the above Step 2 (60 mg) was dissolved in ethyl acetate (6 ml). Triethylamine (86 μl) and methanesulfonyl chloride (35 μl) were added and the mixture was stirred under ice-cooling for 30 minutes. The precipitate was removed by filtration. After washing with ethyl acetate, the filtrate was concentrated. Acetonitrile (6 ml), N,N-dimethylformamide (2 ml), the compound obtained in Step 6 of Example 137 (130 mg) and potassium carbonate (70 mg) were added thereto, and the mixture was stirred at 80° C. for 35 hours. The reaction solution was filtered and washed with acetonitrile, and then the filtrate was concentrated. The residue was purified by silica gel column chromatography (developed with ethyl acetate-hexane) to give the title compound (128 mg) as a colorless oil.
MS (APCI) m/z: 640 [M+H]$^+$ $^1$H-NMR (CDCl$_3$) δ: −0.04 (9H, s), 0.00 (9H, s), 0.91-0.96 (2H, m), 0.98-1.03 (2H, m), 1.19-1.29 (1H, m), 1.44 (1H, ddd, J=23.3, 12.4, 4.6 Hz), 1.90-1.97 (1H, m), 2.14-2.21 (1H, m), 3.29-3.39 (2H, m), 3.36 (3H, s), 3.57-3.62 (2H, m), 3.65-3.78 (3H, m), 3.92 (1H, dd, J=14.8, 7.8 Hz), 3.99 (1H, dd, J=11.4, 4.6 Hz), 4.07 (1H, dd, J=14.8, 2.7 Hz), 5.47 (2H, s), 5.74 (2H, s), 6.60 (1H, d, J=3.7 Hz), 7.43 (1H, d, J=3.7 Hz), 7.61 (1H, d, J=1.8 Hz), 8.09 (1H, d, J=1.8 Hz), 8.29 (1H, d, J=1.8 Hz), 8.52 (1H, d, J=1.8 Hz).

Step 4

2,6-Anhydro-1,3,5-trideoxy-4-O-methyl-1-[2-oxo-6-(1H-pyrrolo[2,3-b]pyridin-5-yl)-2,3-dihydro-1H-imidazo[4,5-b]pyridin-1-yl]-D-threo-hexitol dimethanesulfonate The title compound (24 mg) was obtained by the same procedure as in Step 8 of Example 137 using the compound obtained in the above Step 3 (121 mg).
MS (APCI) m/z: 380 [M+H]$^+$
$^1$H-NMR (DMSO-d$_6$) δ: 1.04-1.13 (1H, m), 1.15-1.27 (1H, m), 1.82-1.90 (1H, m), 2.00-2.08 (1H, m), 2.44 (6H, s), 3.18-3.38 (2H, m), 3.22 (3H, s), 3.64-3.73 (1H, br m), 3.82-3.91 (2H, br m), 3.98 (1H, dd, J=14.7, 7.8 Hz), 6.76 (1H, dd, J=3.7, 1.8 Hz), 7.74 (1H, t, J=2.7 Hz), 7.90 (1H, d, J=1.8 Hz), 8.30 (1H, d, J=1.8 Hz), 8.72 (2H, s), 12.46 (1H, br s).

Example 139

2,6-Anhydro-1,3,5-trideoxy-4-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol

[Formula 159]

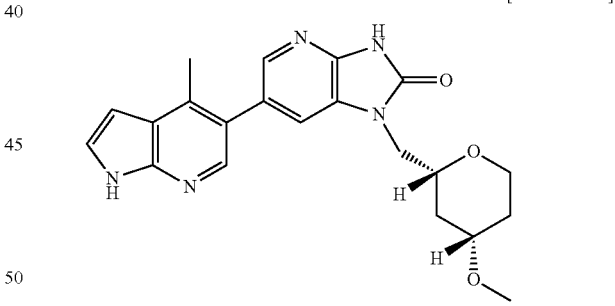

Step 1

2,6-Anhydro-3,5-dideoxy-4-O-methyl-1-O-(methanesulfonyl)-L-threo-hexitol

Triethylamine (137 μl) was added to a solution of the compound obtained in Step 3 of Example 137 (120 mg) in dichloromethane (2.5 ml), and methanesulfonyl chloride (70 μl) was added dropwise under ice-cooling. After stirring at room temperature for 2 hours, phosphate buffer (pH 7.0) was added, followed by dilution with dichloromethane. The organic layer was washed with brine. After drying over anhydrous sodium sulfate, the solvent was evaporated under reduced pressure to give the title compound (179 mg).

Step 2

2,6-Anhydro-1-(6-bromo-3-cyclohex-1-en-1-yl-2-oxo-2,3-dihydro-1H-imidazo[4,5-b]pyridin-1-yl)-1,3,5-trideoxy-4-O-methyl-L-threo-hexitol The compound obtained in Step 2 of Example 35 (235 mg) and potassium carbonate (221 mg) were added to a mixed solution of the compound obtained in the above Step 1 (179 mg) in acetonitrile-N,N-dimethylformamide (2:1, 7.5 ml), and the mixture was stirred at 80° C. overnight. After dilution with ethyl acetate, the organic layer was sequentially washed with water and brine and dried over anhydrous sodium sulfate. The solvent was evaporated under reduced pressure. The resulting residue was purified by silica gel column chromatography (developed with ethyl acetate-hexane) to give the title compound (314 mg).
MS (ESI) m/z: 422 (M+H)$^+$.

Step 3

2,6-Anhydro-1-[3-cyclohex-1-en-1-yl-2-oxo-6-(4,4,5,5-tetramethyl-1,3,2-dioxaborolan-2-yl)-2,3-dihydro-1H-imidazo[4,5-b]pyridin-1-yl]-1,3,5-trideoxy-4-O-methyl-L-threo-hexitol The title compound (174 mg) was obtained by the same procedure as in Step 4 of Example 35 using the compound obtained in the above Step 2 (314 mg).
MS (ESI) m/z: 470 (M+H)$^+$.

Step 4

2,6-Anhydro-1-[3-cyclohex-1-en-1-yl-6-(4-methyl-1H-pyrrolo[2,3-b]pyridin-5-yl)-2-oxo-2,3-dihydro-1H-imidazo[4,5-b]pyridin-1-yl]-1,3,5-trideoxy-4-O-methyl-L-threo-hexitol The title compound (111 mg) was obtained by the same procedure as in Step 3 of Example 1 using the compound obtained in the above Step 3 (174 mg) and the compound obtained in Step 3 of Example 36 (94 mg).
MS (ESI) m/z: 474 (M+H)$^+$.

Step 5

2,6-Anhydro-1,3,5-trideoxy-4-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol The title compound (47 mg) was obtained by the same procedure as in Step 6 of Example 35 using the compound obtained in the above Step 4 (111 mg).
MS (ESI) m/z: 394 (M+H)$^+$.

Step 6

2,6-Anhydro-1,3,5-trideoxy-4-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol dimethanesulfonate The title compound (62 mg) was obtained by the same procedure as in Step 3 of Example 118 using the compound obtained in the above Step 5 (47 mg).
MS (ESI) m/z: 394 (M+H)$^+$.

HRMS (ESI) [(M+H)$^+$] calculated: $C_{21}H_{24}N_5O_3$ 394.18791.
found: 394.18724.
$^1$H-NMR (DMSO-d$_6$) δ: 1.02-1.09 (1H, m), 1.16-1.25 (1H, m), 1.85-1.90 (1H, m), 2.02-2.06 (1H, m), 2.32 (6H, s), 2.54 (3H, s), 3.22 (3H, s), 3.23-3.28 (1H, m), 3.31-3.37 (1H, m), 3.62-3.99 (4H, m), 6.73-6.75 (1H, m), 7.57-7.57 (1H, m), 7.60-7.62 (1H, m), 7.94 (1H, d, J=1.7 Hz), 8.21 (1H, s), 11.69 (1H, br s), 12.08 (1H, br s).

Example 140

2,6-Anhydro-1,3,5-trideoxy-4-O-methyl-1-[6-(4-methyl-1H-pyrrolo[2,3-b]pyridin-5-yl)-2-oxo-2,3-dihydro-1H-imidazo[4,5-b]pyridin-1-yl]-D-threo-hexitol

[Formula 160]

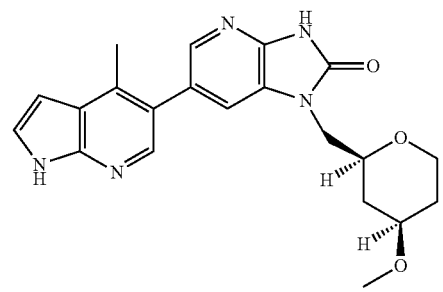

Step 1

2,6-Anhydro-3,5-dideoxy-4-O-methyl-1-O-(methanesulfonyl)-D-threo-hexitol

The title compound (189 mg) was obtained by the same procedure as in Step 1 of Example 139 using the compound obtained in Step 2 of Example 138 (128 mg).

Step 2

2,6-Anhydro-1-(6-bromo-3-cyclohex-1-en-1-yl-2-oxo-2,3-dihydro-1H-imidazo[4,5-b]pyridin-1-yl)-1,3,5-trideoxy-4-O-methyl-D-threo-hexitol The title compound (343 mg) was obtained by the same procedure as in Step 2 of Example 139 using the compound obtained in the above Step 1 (189 mg) and the compound obtained in Step 2 of Example 35 (248 mg).
MS (ESI) m/z: 422 (M+H)$^+$.

Step 3

2,6-Anhydro-1-[3-cyclohex-1-en-1-yl-2-oxo-6-(4,4,5,5-tetramethyl-1,3,2-dioxaborolan-2-yl)-2,3-dihydro-1H-imidazo[4,5-b]pyridin-1-yl]-1,3,5-trideoxy-4-O-methyl-D-threo-hexitol The title compound (215 mg) was obtained by the same procedure as in Step 4 of Example 35 using the compound obtained in the above Step 2 (341 mg).
MS (ESI) m/z: 470 (M+H)$^+$.

Step 4

2,6-Anhydro-1-[3-cyclohex-1-en-1-yl-6-(4-methyl-1H-pyrrolo[2,3-b]pyridin-5-yl)-2-oxo-2,3-dihydro-1H-imidazo[4,5-b]pyridin-1-yl]-1,3,5-trideoxy-4-O-methyl-D-threo-hexitol The title compound (150 mg) was obtained by the same procedure as in Step 3 of Example 1 using the compound obtained in the above Step 3 (215 mg) and the compound obtained in Step 3 of Example 36 (116 mg).
MS (ESI) m/z: 474 (M+H)$^+$.

Step 5

2,6-Anhydro-1,3,5-trideoxy-4-O-methyl-1-[6-(4-methyl-1H-pyrrolo[2,3-b]pyridin-5-yl)-2-oxo-2,3-dihydro-1H-imidazo[4,5-b]pyridin-1-yl]-D-threo-hexitol The title compound (76 mg) was obtained by the same procedure as in Step 6 of Example 35 using the compound obtained in the above Step 4 (150 mg).
MS (ESI) m/z: 394 (M+H)$^+$.

Step 6

2,6-Anhydro-1,3,5-trideoxy-4-O-methyl-1-[6-(4-methyl-1H-pyrrolo[2,3-b]pyridin-5-yl)-2-oxo-2,3-dihydro-1H-imidazo[4,5-b]pyridin-1-yl]-D-threo-hexitol dimethanesulfonate The title compound (106 mg) was obtained by the same procedure as in Step 3 of Example 118 using the compound obtained in the above Step 5 (76 mg).
MS (ESI) m/z: 394 (M+H)$^+$.
HRMS (ESI) [(M+H)$^+$] calculated: $C_{21}H_{24}N_5O_3$ 394.18791.
found: 394.18758.
$^1$H-NMR (DMSO-D$_6$) δ: 1.02-1.09 (1H, m), 1.16-1.25 (1H, m), 1.85-1.89 (1H, m), 2.02-2.06 (1H, m), 2.34 (6H, s), 2.57 (3H, s), 3.23 (3H, s), 3.23-3.28 (1H, m), 3.31-3.37 (1H, m), 3.62-3.99 (4H, m), 6.80-6.82 (1H, m), 7.58 (1H, d, J=2.3 Hz), 7.65-7.66 (1H, m), 7.95 (1H, d, J=1.7 Hz), 8.26 (1H, s), 11.72 (1H, br s), 12.24 (1H, br s).

Example 141

2,6-Anhydro-1,3,4-trideoxy-1-[6-(4-methyl-1H-pyrrolo[2,3-b]pyridin-5-yl)-2-oxo-2,3-dihydro-1H-imidazo[4,5-b]pyridin-1-yl]-DL-threo-hexitol

[Formula 161]

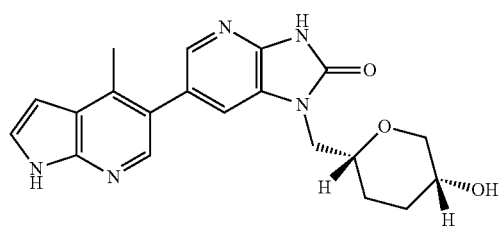

and an enantiomer thereof

Step 1

4-Methyl-5-(4,4,5,5-tetramethyl-1,3,2-dioxaborolan-2-yl)-1H-pyrrolo[2,3-b]pyridine The title compound (0.34 g) was obtained as a colorless solid by the same procedure as in Step 4 of Example 35 using the compound obtained in Step 3 of Example 36 (1 g).
MS (ESI) m/z: 259 (M+H)$^+$.
$^1$H-NMR (CDCl$_3$) δ: 1.38 (9H, s), 2.78 (3H, s), 6.57 (1H, d, J=3.6 Hz), 7.28 (1H, d, J=3.2 Hz), 8.66 (1H, s), 10.24 (1H, s).

Step 2

2,6-Anhydro-5-O-benzoyl-1-[3-cyclohex-1-en-1-yl-6-(4-methyl-1H-pyrrolo[2,3-b]pyridin-5-yl)-2-oxo-2,3-dihydro-1H-imidazo[4,5-b]pyridin-1-yl]-1,3,4-trideoxy-DL-threo-hexitol The title compound (120 mg) was obtained as a pale yellow oil by the same procedure as in Step 2 of Example 4 using the compound obtained in the above Step 1 (113 mg) and the compound obtained in Step 3 of Example 112 (150 mg).
MS (ESI) m/z: 564 (M+H)$^+$.
$^1$H-NMR (CDCl$_3$) δ: 1.69-1.74 (1H, m), 1.76-1.81 (2H, m), 1.84-1.91 (3H, m), 2.13-2.19 (1H, m), 2.33-2.37 (2H, m), 2.40 (3H, s), 2.48-2.55 (2H, m), 3.65 (1H, d, J=12.8 Hz), 3.82-3.87 (1H, m), 4.03-4.12 (3H, m), 5.04 (1H, s), 6.09 (1H, s), 6.52 (1H, d, J=2.2 Hz), 7.31-7.36 (3H, m), 7.46-7.52 (2H, m), 7.84 (2H, d, J=8.2 Hz), 8.04 (1H, s), 8.11 (1H, s), 8.92 (1H, br s).

Step 3

2,6-Anhydro-1,3,4-trideoxy-1-[6-(4-methyl-1H-pyrrolo[2,3-b]pyridin-5-yl)-2-oxo-2,3-dihydro-1H-imidazo[4,5-b]pyridin-1-yl]-DL-threo-hexitol The title compound (10 mg) was obtained as a pale yellow solid by the same procedure as in Step 6 of Example 35 using the compound obtained in the above Step 2 (120 mg).
MS (ESI) m/z: 380 (M+H)$^+$.
$^1$H-NMR (DMSO-d$_6$) δ: 1.38-1.41 (1H, m), 1.61-1.71 (3H, m), 2.47 (3H, s), 3.30-3.38 (1H, m), 3.52-3.54 (1H, m), 3.62-3.66 (2H, m), 3.80-3.93 (2H, m), 4.54 (1H, d, J=4.0 Hz), 6.56-6.57 (1H, m), 7.48 (1H, t, J=2.8 Hz), 7.54 (1H, d, J=1.7 Hz), 7.90 (1H, d, J=1.7 Hz), 8.08 (1H, s), 11.61 (1H, s), 11.65 (1H, s).

Example 142

2,6-Anhydro-1,3,4-trideoxy-5-O-methyl-1-[6-(4-methyl-1H-pyrrolo[2,3-b]pyridin-5-yl)-2-oxo-2,3-dihydro-1H-imidazo[4,5-b]pyridin-1-yl]-DL-threo-hexitol

[Formula 162]

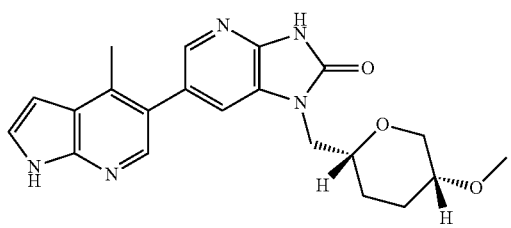

and an enantiomer thereof

Step 1

2,6-Anhydro-1-[3-cyclohex-1-en-1-yl-6-(4-methyl-1H-pyrrolo[2,3-b]pyridin-5-yl)-2-oxo-2,3-dihydro-1H-imidazo[4,5-b]pyridin-1-yl]-1,3,4-trideoxy-5-O-methyl-DL-threo-hexitol The title compound (170 mg) was obtained as a pale yellow oil by the same procedure as in Step 2 of Example 4 using the compound obtained in Step 1 of Example 141 (138 mg) and the compound obtained in Step 4 of Example 113 (150 mg).
MS (ESI) m/z: 474 (M+H)$^+$.
$^1$H-NMR (CDCl$_3$) δ: 1.55-1.65 (4H, m), 1.74-1.80 (2H, m), 1.87-1.93 (2H, m), 2.08-2.13 (1H, m), 2.32-2.36 (2H, m), 2.50-2.53 (4H, m), 3.21 (1H, s), 3.33 (3H, d, J=1.3 Hz), 3.42 (1H, d, J=12.8 Hz), 3.71 (1H, t, J=8.9 Hz), 3.84 (1H, dd, J=14.6, 7.7 Hz), 3.99-4.08 (2H, m), 6.08-6.10 (1H, m), 6.57-6.59 (1H, m), 7.35 (1H, s), 7.48 (1H, s), 8.03 (1H, t, J=1.8 Hz), 8.18 (1H, s), 9.14 (1H, s).

Step 2

2,6-Anhydro-1,3,4-trideoxy-5-O-methyl-1-[6-(4-methyl-1H-pyrrolo[2,3-b]pyridin-5-yl)-2-oxo-2,3-dihydro-1H-imidazo[4,5-b]pyridin-1-yl]-DL-threo-hexitol The title compound (53 mg) was obtained as a pale yellow solid by the same procedure as in Step 6 of Example 35 using the compound obtained in the above Step 1 (170 mg).
MS (ESI) m/z: 394 (M+H)$^+$.

Step 3

2,6-Anhydro-1,3,4-trideoxy-5-O-methyl-1-[6-(4-methyl-1H-pyrrolo[2,3-b]pyridin-5-yl)-2-oxo-2,3-dihydro-1H-imidazo[4,5-b]pyridin-1-yl]-DL-threo-hexitol dimethanesulfonate The title compound (78 mg) was obtained as a pale yellow solid by the same procedure as in Step 3 of Example 118 using the compound obtained in the above Step 2 (53 mg).
MS (ESI) m/z: 394 (M+H)$^+$.
$^1$H-NMR (DMSO-d$_6$) δ: 1.39-1.43 (1H, m), 1.48-1.62 (2H, m), 1.89-1.93 (1H, m), 2.36-2.41 (9H, m), 2.60-2.62 (2H, m), 3.19 (3H, s), 3.32-3.35 (1H, m), 3.66-3.71 (1H, m), 3.79-3.92 (3H, m), 6.87-6.91 (1H, m), 7.61 (1H, d, J=4.0 Hz), 7.70-7.73 (1H, m), 7.96-7.97 (1H, m), 8.32-8.36 (1H, m), 11.74 (1H, s), 12.41 (1H, s).

Example 143

2,6-Anhydro-1,3,4-trideoxy-1-[6-(4-methyl-1H-pyrrolo[2,3-b]pyridin-5-yl)-2-oxo-2,3-dihydro-1H-imidazo[4,5-b]pyridin-1-yl]-L-threo-hexitol

[Formula 163]

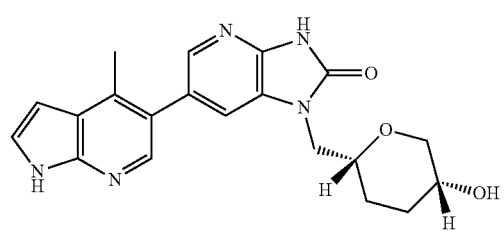

Step 1

2-[(Benzyloxy)methyl]-3,4-dihydro-2H-pyran 3,4-Dihydro-2H-pyran-2-ylmethanol (5.0 g) was dissolved in tetrahydrofuran (100 ml). 55% Sodium hydride (2.3 g) and benzyl bromide (8.2 g) were added under ice-cooling, followed by stirring for 17 hours. A saturated aqueous ammonium chloride solution was added, followed by extraction with ethyl acetate and washing with brine. The organic layer was dried over anhydrous sodium sulfate and then the solvent was evaporated under reduced pressure. The residue was purified by silica gel column chromatography (developed with ethyl acetate-hexane) to give the title compound (8.5 g) as a pale yellow oil.
MS (ESI) m/z: 205 (M+H)$^+$.
$^1$H-NMR (CDCl$_3$) δ: 1.66-1.78 (1H, m), 1.85-1.92 (1H, m), 1.96-2.05 (1H, m), 2.07-2.18 (1H, m), 3.56 (1H, dd, J=4.3, 10.3 Hz), 3.63 (1H, dd, J=6.2, 10.3 Hz), 4.03-4.10 (1H, m), 4.61 (1H, d, J=12.4 Hz), 4.65 (1H, d, J=12.4 Hz), 4.69-4.74 (1H, m), 6.42-6.45 (1H, m), 7.28-7.40 (m, 5H).

Step 2

2,6-Anhydro-1-O-benzyl-3,4-dideoxy-DL-erythro-hexitol

The compound obtained in the above Step 1 (8.9 g) was dissolved in tetrahydrofuran (290 ml). A 0.5 N solution of 9-borabicyclo[3.3.1]nonane in tetrahydrofuran (122.5 ml) was added and the mixture was stirred at room temperature for 17 hours. A 3 N aqueous sodium hydroxide solution (43.8 ml), a 35% aqueous hydrogen peroxide solution (17 ml) and potassium carbonate (30.2 g) were added to the reaction solution, followed by stirring for one hour. Then, the reaction solution was diluted with ethyl acetate and washed with brine. The organic layer was dried over anhydrous sodium sulfate and then the solvent was evaporated under reduced pressure. The residue was purified by silica gel column chromatography (developed with ethyl acetate-hexane) to give the title compound (7.2 g) as a pale yellow oil.

¹H-NMR (CDCl₃) δ: 1.34-1.48 (2H, m), 1.51-1.57 (1H, m), 1.65-1.75 (1H, m), 3.15 (1H, t, J=10.53 Hz), 3.37-3.54 (3H, m), 3.65-3.78 (1H, m), 4.01-4.09 (1H, m), 4.54 (1H, d, J=12.4 Hz), 4.60 (1H, d, J=12.4 Hz), 7.24-7.37 (5H, m).

Step 3

2,6-Anhydro-1-O-benzyl-3,4-dideoxy-5-O-(phenylcarbonyl)-L-threo-hexitol 2,6-Anhydro-1-O-benzyl-3,4-dideoxy-5-O-(phenylcarbonyl)-D-threo-hexitol The title compound was obtained as a racemate by the same procedure as in Step 1 of Example 112 using the compound obtained in the above Step 2 (6.6 g) and benzoic acid (4.32 g).
MS (ESI) m/z: 327 (M+H)⁺.
¹H-NMR (CDCl₃) δ: 1.52-1.59 (1H, m), 1.76-1.92 (2H, m), 2.12-2.21 (1H, m), 3.48 (1H, dd, J=10.1, 3.7 Hz), 3.59 (1H, dd, J=10.1, 6.4 Hz), 3.64-3.77 (2H, m), 4.21 (1H, dt, J=13.0, 2.0 Hz), 4.57 (1H, d, J=12.4 Hz), 4.64 (1H, d, J=12.4 Hz), 5.05-5.09 (1H, m), 7.27-7.38 (5H, m), 7.40-7.47 (2H, m), 7.53-7.59 (1H, m), 8.07-8.11 (2H, m).
The resulting racemate was optically resolved by HPLC to give the title compound L-isomer (isomer A: 4.0 g) and D-isomer (isomer B: 3.7 g), respectively.
Column: CHIRALCEL OD (5×50 cm)
Eluent: 25% isopropanol/n-hexane
Flow rate: 25 ml/min
Elution time Isomer A: 52 min, isomer B: 72 min
The above compound can also be synthesized from a known compound and its absolute configuration can be identified.

Step 4

1,5-Anhydro-3,4-dideoxy-2-O-(phenylcarbonyl)-L-threo-hexitol

The L-isomer obtained in the above Step 3 (isomer A, 3.5 g) was dissolved in methanol (53 ml). 5% Palladium-carbon (1.1 g) was added and the mixture was stirred in a hydrogen atmosphere at room temperature for 22 hours. The reaction solution was filtered and the filtrate was concentrated under reduced pressure to give the title compound (2.3 g) as a colorless oil.
¹H-NMR (CDCl₃) δ: 1.45-1.53 (1H, m), 1.78-1.94 (2H, m), 2.14-2.22 (1H, m), 3.53-3.69 (3H, m), 3.74 (1H, d, J=12.8 Hz), 4.20 (1H, d, J=12.8 Hz), 5.07-5.11 (1H, br m), 7.45 (2H, t, J=7.8 Hz), 7.57 (1H, t, J=7.8 Hz), 8.09 (2H, d, J=7.8 Hz).

Step 5

2,6-Anhydro-1-(6-bromo-3-cyclohex-1-en-1-yl-2-oxo-2,3-dihydro-1H-imidazo[4,5-b]pyridin-1-yl)-1,3,4-trideoxy-5-O-(phenylcarbonyl)-L-threo-hexitol The title compound (3.4 g) was obtained by the same procedure as in Step 3 of Example 35 using the compound obtained in the above Step 4 (1.5 g) and the compound obtained in Step 2 of Example 35 (2.5 g).
¹H-NMR (CDCl₃) δ: 1.63-1.67 (1H, m), 1.70-1.80 (3H, m), 1.81-1.92 (3H, m), 2.12-2.20 (1H, m), 2.27-2.34 (2H, m), 2.38-2.45 (2H, m), 3.65 (1H, dd, J=13.0, 1.5 Hz), 3.76-3.84 (1H, m), 3.97 (1H, t, J=4.4 Hz), 4.92-5.06 (3H, m), 5.98-6.04 (1H, m), 7.42 (2H, t, J=7.7 Hz), 7.53-7.60 (2H, m), 7.90-7.94 (2H, m), 8.08 (1H, d, J=2.0 Hz).

Step 6

2,6-Anhydro-1-(6-bromo-3-cyclohex-1-en-1-yl-2-oxo-2,3-dihydro-1H-imidazo[4,5-b]pyridin-1-yl)-1,3,4-trideoxy-L-threo-hexitol The compound obtained in the above Step 5 (3.4 g) was dissolved in methanol (44 ml). Potassium carbonate (2.7 g) was added and the mixture was stirred for 4 hours. The reaction solution was diluted with ethyl acetate, washed with brine and dried over anhydrous sodium sulfate. The solvent was evaporated under reduced pressure. The resulting residue was purified by silica gel column chromatography (developed with ethyl acetate-hexane) to give the title compound (2.0 g).
MS (ESI) m/z: 408 (M+H)⁺.
¹H-NMR (CDCl₃) δ: 1.69-1.80 (4H, m), 1.82-1.91 (2H, m), 1.93-1.99 (1H, m), 2.01-2.04 (1H, m), 2.27-2.35 (2H, m), 2.39-2.46 (2H, m), 3.53 (1H, d, J=12.4 Hz), 3.64-3.73 (1H, m), 3.76-3.81 (2H, m), 3.87-3.93 (1H, m), 3.98 (1H, dd, J=14.7, 2.8 Hz), 5.99-6.04 (1H, m), 7.53 (1H, d, J=1.8 Hz), 8.08 (1H, d, J=1.8 Hz).

Step 7

2,6-Anhydro-1-[3-cyclohex-1-en-1-yl-2-oxo-6-(4,4,5,5-tetramethyl-1,3,2-dioxaborolan-2-yl)-2,3-dihydro-1H-imidazo[4,5-b]pyridin-1-yl]-1,3,4-trideoxy-L-threo-hexitol The title compound (1.2 g) was obtained by the same procedure as in Step 4 of Example 35 using the compound obtained in the above Step 6 (1.1 g).
MS (ESI) m/z: 456 (M+H)⁺.
¹H-NMR (CDCl₃) δ: 1.35 (12H, s), 1.57-1.62 (1H, m), 1.65-1.80 (4H, m), 1.81-1.98 (3H, m), 2.27-2.34 (2H, m), 2.43-2.44 (2H, m), 3.53 (1H, dd, J=12.4, 1.4 Hz), 3.70-3.79 (2H, m), 3.84-3.97 (3H, m), 5.99-6.04 (1H, m), 7.63 (1H, d, J=1.4 Hz), 8.44 (1H, d, J=1.4 Hz).

Step 8

2,6-Anhydro-1-[3-cyclohex-1-en-1-yl-6-(4-methyl-1H-pyrrolo[2,3-b]pyridin-5-yl)-2-oxo-2,3-dihydro-1H-imidazo[4,5-b]pyridin-1-yl]-1,3,4-trideoxy-L-threo-hexitol The title compound (48 mg) was obtained by the same procedure as in Step 3 of Example 1 using the compound obtained in the above Step 7 (150 mg) and the compound obtained in Step 3 of Example 36 (83 mg).
MS (ESI) m/z: 460 (M+H)⁺.
¹H-NMR (CDCl₃) δ: 1.61-1.67 (1H, m), 1.70-1.84 (4H, m), 1.87-1.93 (2H, m), 1.94-2.00 (1H, m), 2.31-2.36 (2H, m), 2.42 (3H, s), 2.49-2.54 (2H, br m), 3.54 (1H, d, J=12.0 Hz), 3.71-3.77 (1H, m), 3.78-3.80 (1H, br m), 3.84-3.89 (2H, m), 4.05 (1H, dd, J=14.6, 3.2 Hz), 6.07-6.11 (1H, m), 6.51-6.55 (1H, br m), 7.33-7.37 (2H, m), 8.03 (1H, s), 8.17 (1H, s), 9.96 (1H, br s).

Step 9

2,6-Anhydro-1,3,4-trideoxy-1-[6-(4-methyl-1H-pyrrolo[2,3-b]pyridin-5-yl)-2-oxo-2,3-dihydro-1H-imidazo[4,5-b]pyridin-1-yl]-L-threo-hexitol The title compound (31 mg) was obtained by the same procedure as in Step 6 of Example 35 using the compound obtained in the above Step 8 (48 mg).

MS (ESI) m/z: 380 (M+H)$^+$.

HRMS (ESI) [M+H]$^+$ calculated: $C_{20}H_{21}N_5O_3$ 380.17226. found: 380.17420.

$^1$H-NMR (DMSO-$d_6$) δ: 1.38-1.43 (1H, m), 1.56-1.75 (3H, m), 2.47 (3H, s), 3.48-3.56 (1H, m), 3.59-3.61 (2H, m), 3.79-3.94 (2H, m), 4.07-4.12 (1H, m), 6.55-6.57 (1H, m), 7.46-7.48 (1H, m), 7.54 (1H, d, J=1.7 Hz), 7.90 (1H, d, J=1.7 Hz), 8.08 (1H, s), 11.6 (1H, s), 11.7 (1H, s).

Example 144

2,6-Anhydro-1,3,4-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-L-threo-hexitol

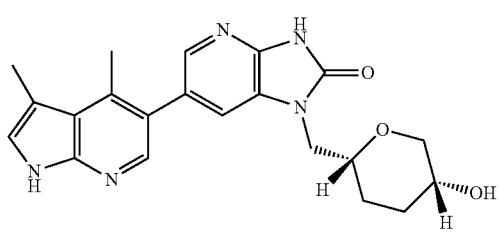

[Formula 164]

Step 1

2,6-Anhydro-1-[3-cyclohex-1-en-1-yl-6-(3,4-dimethyl-1H-pyrrolo[2,3-b]pyridin-5-yl)-2-oxo-2,3-dihydro-1H-imidazo[4,5-b]pyridin-1-yl]-1,3,4-trideoxy-L-threo-hexitol The title compound (57 mg) was obtained by the same procedure as in Step 3 of Example 1 using the compound obtained in Step 7 of Example 143 (150 mg) and the compound obtained in Step 2 of Example 124 (89 mg).

MS (ESI) m/z: 474 (M+H)$^+$.

$^1$H-NMR (CDCl$_3$) δ: 1.60-1.81 (5H, m), 1.87-1.93 (2H, m), 1.94-1.99 (2H, m), 2.31-2.37 (2H, m), 2.48-2.54 (5H, m), 2.58-2.61 (3H, m), 3.54 (1H, d, J=12.6 Hz), 3.69-3.79 (2H, m), 3.82-3.90 (2H, m), 4.04 (1H, d, J=14.9 Hz), 6.08-6.10 (1H, m), 7.05 (1H, s), 7.37 (1H, s), 8.01 (1H, s), 8.09 (1H, s), 8.81 (1H, br s).

Step 2

2,6-Anhydro-1,3,4-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-L-threo-hexitol The title compound (18 mg) was obtained by the same procedure as in Step 6 of Example 35 using the compound obtained in the above Step 1 (57 mg).

MS (ESI) m/z: 394 (M+H)$^+$.

HRMS (ESI) [M+H]$^+$ calculated: $C_{21}H_{23}N_5O_3$ 394.18791. found: 394.18863.

$^1$H-NMR (DMSO-$d_6$) δ: 1.31-1.50 (2H, m), 1.55-1.81 (3H, m), 2.46 (3H, s), 2.57 (3H, s), 3.47-4.06 (5H, m), 7.49 (1H, d, J=1.7 Hz), 7.86 (1H, d, J=1.7 Hz), 7.99 (1H, s), 11.61 (1H, s), 11.26 (1H, s).

Example 145

2,6-Anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,4-trideoxy-L-threo-hexitol

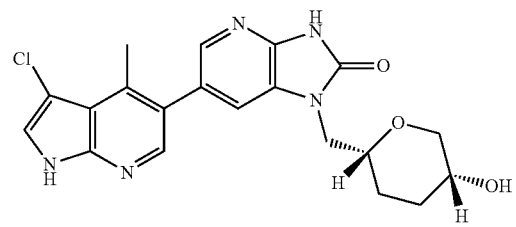

[Formula 165]

Step 1

2,6-Anhydro-1-[6-(3-chloro-4-methyl-1H-pyrrolo[2,3-b]pyridin-5-yl)-3-(cyclohex-1-en-1-yl)-2-oxo-2,3-dihydro-1H-imidazo[4,5-b]pyridin-1-yl]-1,3,4-trideoxy-L-threo-hexitol The title compound (79 mg) was obtained by the same procedure as in Step 3 of Example 1 using the compound obtained in Step 7 of Example 143 (150 mg) and the compound obtained in Step 2 of Example 125 (137 mg).

MS (ESI) m/z: 494 (M+H)$^+$.

$^1$H-NMR (CDCl$_3$) δ: 1.62-2.01 (8H, m), 2.30-2.38 (2H, m), 2.48-2.55 (2H, m), 2.68 (3H, s), 3.55 (1H, d, J=12.2 Hz), 3.70-3.82 (2H, m), 3.84-3.92 (2H, m), 4.06 (1H, dd, J=14.6, 2.7 Hz), 6.07-6.11 (1H, m), 7.30 (1H, s), 7.38 (1H, d, J=1.5 Hz), 8.00 (1H, d, J=1.5 Hz), 8.14 (1H, s).

Step 2

2,6-Anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,4-trideoxy-L-threo-hexitol The title compound (58 mg) was obtained by the same procedure as in Step 6 of Example 35 using the compound obtained in the above Step 1 (79 mg).

MS (ESI) m/z: 380 (M+H)$^+$.

$^1$H-NMR (DMSO-$d_6$) δ: 1.36-1.44 (1H, m), 1.56-1.80 (3H, m), 2.66 (3H, s), 3.50-3.56 (1H, m), 3.59-3.68 (2H, m), 3.70-4.15 (3H, m), 7.53 (1H, d, J=1.8 Hz), 7.66 (1H, d, J=2.8 Hz), 7.89 (1H, d, J=1.8 Hz), 8.13 (1H, s), 11.63 (1H, s), 12.00 (1H, s).

Example 146

2,6-Anhydro-1,3,4-trideoxy-5-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol

[Formula 166]

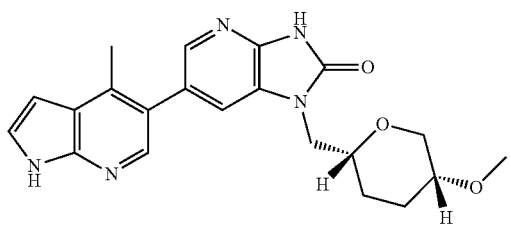

Step 1

2,6-Anhydro-1-[6-bromo-3-cyclohex-1-en-1-yl-2-oxo-2,3-dihydro-1H-imidazo[4,5-b]pyridin-1-yl]-1,3,4-trideoxy-5-O-methyl-L-threo-hexitol The title compound (790 mg) was obtained by the same procedure as in Step 1 of Example 63 using the compound obtained in Step 6 of Example 143 (940 mg).
MS (ESI) m/z: 422 (M+H)⁺.
$^1$H-NMR (CDCl$_3$) δ: 1.52-1.77 (5H, m), 1.83-1.89 (2H, m), 2.08-2.16 (1H, m), 2.27-2.34 (2H, m), 2.39-2.45 (2H, m), 3.22-3.25 (1H, m), 3.37-3.44 (3H, m), 3.38 (1H, s), 3.63-3.78 (2H, m), 3.99 (1H, dd, J=14.0, 2.5 Hz), 4.05 (1H, d, J=12.8 Hz), 5.99-6.02 (1H, m), 7.60 (1H, d, J=1.8 Hz), 8.06 (1H, d, J=1.8 Hz).

Step 2

2,6-Anhydro-1-[3-cyclohex-1-en-1-yl-2-oxo-6-(4,4,5,5-tetramethyl-1,3,2-dioxaborolan-2-yl)-2,3-dihydro-1H-imidazo[4,5-b]pyridin-1-yl]-1,3,4-trideoxy-5-O-methyl-L-threo-hexitol The title compound (812 mg) was obtained by the same procedure as in Step 4 of Example 35 using the compound obtained in the above Step 1 (750 mg).
MS (ESI) m/z: 470 (M+H)⁺.
$^1$H-NMR (CDCl$_3$) δ: 1.35 (12H, s), 1.48-1.65 (2H, m), 1.69-1.80 (3H, m), 1.83-1.90 (2H, m), 2.08-2.13 (1H, m), 2.28-2.34 (2H, m), 2.41-2.47 (2H, m), 3.22-3.25 (1H, m), 3.38 (3H, s), 3.43 (1H, dd, J=12.4, 1.4 Hz), 3.71-3.78 (1H, m), 3.85 (1H, dd, J=14.7, 7.8 Hz), 3.95 (1H, dd, J=14.7, 4.6 Hz), 4.02-4.08 (1H, m), 5.99-6.03 (1H, m), 7.71 (1H, d, J=1.4 Hz), 8.42 (1H, d, J=1.4 Hz).

Step 3

2,6-Anhydro-1-[3-cyclohex-1-en-1-yl-6-(4-methyl-1H-pyrrolo[2,3-b]pyridin-5-yl)-2-oxo-2,3-dihydro-1H-imidazo[4,5-b]pyridin-1-yl]-1,3,4-trideoxy-5-O-methyl-L-threo-hexitol The title compound (67 mg) was obtained by the same procedure as in Step 3 of Example 1 using the compound obtained in the above Step 2 (155 mg) and the compound obtained in Step 3 of Example 36.
MS (ESI) m/z: 474 (M+H)⁺.
$^1$H-NMR (CDCl$_3$) δ: 1.54-1.68 (2H, m), 1.71-1.81 (3H, m), 1.87-1.94 (2H, m), 2.08-2.15 (1H, m), 2.31-2.38 (2H, m), 2.49-2.55 (5H, m), 3.22-3.24 (1H, m), 3.34 (3H, s), 3.43 (1H, d, J=12.4 Hz), 3.69-3.77 (1H, m), 3.88 (1H, dd, J=14.7, 7.8 Hz), 4.02 (1H, d, J=12.8 Hz), 4.07 (1H, dd, J=14.7, 2.8 Hz), 6.09 (1H, t, J=3.7 Hz), 6.56-6.59 (1H, m), 7.37 (1H, t, J=2.5 Hz), 7.48 (2H, d, J=1.8 Hz), 8.04 (1H, d, J=1.8 Hz), 8.18 (1H, s).

Step 4

2,6-Anhydro-1,3,4-trideoxy-5-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol The title compound (17 mg) was obtained by the same procedure as in Step 6 of Example 35 using the compound obtained in the above Step 3 (67 mg).
MS (ESI) m/z: 394 (M+H)⁺.
HRMS (ESI) [M+H]⁺ calculated: C$_{21}$H$_{23}$N$_5$O$_3$ 394.18791. found: 394.18779.
$^1$H-NMR (DMSO-d$_6$) δ: 1.35-1.63 (3H, m), 1.86-1.92 (1H, m), 2.45 (3H, s), 3.28 (3H, s), 3.62-3.91 (6H, m), 6.54-6.56 (1H, m), 7.46 (1H, t, J=2.9 Hz), 7.51 (1H, d, J=2.3 Hz), 7.88 (1H, d, J=2.3 Hz), 8.06 (1H, s), 11.59 (1H, br s), 11.63 (1H, br s).

Example 147

2,6-Anhydro-1,3,4-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-5-O-methyl-L-threo-hexitol

[Formula 167]

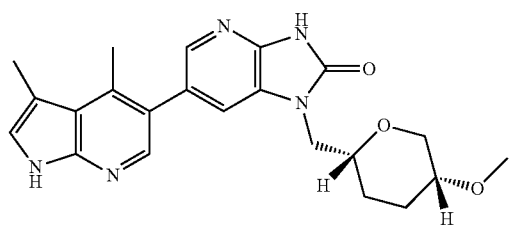

Step 1

2,6-Anhydro-1-[3-cyclohex-1-en-1-yl-6-(3,4-dimethyl-1H-pyrrolo[2,3-b]pyridin-5-yl)-2-oxo-2,3-dihydro-1H-imidazo[4,5-b]pyridin-1-yl]-1,3,4-trideoxy-5-O-methyl-L-threo-hexitol The title compound (74 mg) was obtained by the same procedure as in Step 3 of Example 1 using the compound obtained in Step 2 of Example 146 (155 mg) and the compound obtained in Step 2 of Example 124 (89 mg).
MS (ESI) m/z: 488 (M+H)⁺.
$^1$H-NMR (CDCl$_3$) δ: 1.53-1.95 (7H, m), 2.08-2.15 (1H, m), 2.30-2.38 (2H, m), 2.49-2.55 (5H, m), 2.62 (3H, s), 3.21-3.24 (1H, m), 3.35 (3H, s), 3.43 (1H, dd, J=12.6, 1.1 Hz), 3.69-3.77 (1H, m), 3.86 (1H, dd, J=14.4, 7.8 Hz), 4.02 (2H, d, J=12.4 Hz), 4.06 (2H, dd, J=14.7, 3.7 Hz), 6.07-6.11 (1H, m), 7.07 (1H, s), 7.46 (1H, d, J=1.8 Hz), 8.01 (1H, d, J=1.8 Hz), 8.09 (1H, s), 9.37 (1H, s).

Step 2

2,6-Anhydro-1,3,4-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-5-O-methyl-L-threo-hexitol The title compound (21 mg) was obtained by the same procedure as in Step 6 of Example 35 using the compound obtained in the above Step 1 (74 mg).

MS (ESI) m/z: 408 (M+H)+.

HRMS (ESI) [M+H]+ calculated: $C_{22}H_{25}N_5O_3$ 408.20356. found: 408.20482.

$^1$H-NMR (DMSO-$d_6$) δ: 1.32-1.73 (3H, m), 1.84-1.98 (1H, m), 2.46 (3H, s), 2.58 (3H, s), 3.30 (3H, s), 3.36-3.40 (2H, m), 3.62-3.93 (4H, m), 7.20 (1H, s), 7.48 (1H, d, J=1.7 Hz), 7.86 (1H, d, J=1.7 Hz), 7.99 (1H, s), 11.27 (1H, s), 11.61 (1H, s).

Example 148

2,6-Anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,4-trideoxy-5-O-methyl-L-threo-hexitol

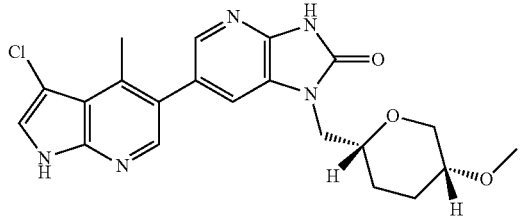

[Formula 168]

Step 1

2,6-Anhydro-1-[6-(3-chloro-4-methyl-1H-pyrrolo[2,3-b]pyridin-5-yl)-3-cyclohex-1-en-1-yl-2-oxo-2,3-dihydro-1H-imidazo[4,5-b]pyridin-1-yl]-1,3,4-trideoxy-5-O-methyl-L-threo-hexitol The title compound (103 mg) was obtained by the same procedure as in Step 3 of Example 1 using the compound obtained in Step 2 of Example 146 (155 mg) and the compound obtained in Step 2 of Example 125 (137 mg).

MS (ESI) m/z: 508 (M+H)+.

$^1$H-NMR (CDCl$_3$) δ: 1.54-1.68 (2H, m), 1.70-1.82 (3H, m), 1.88-1.94 (2H, m), 2.08-2.17 (1H, m), 2.30-2.38 (2H, m), 2.49-2.56 (2H, m), 2.72 (3H, s), 3.23-3.25 (1H, m), 3.35 (3H, s), 3.44 (1H, dd, J=12.6, 1.3 Hz), 3.69-3.77 (1H, m), 3.88 (1H, dd, J=14.4, 8.1 Hz), 4.02 (1H, d, J=12.7 Hz), 4.08 (1H, dd, J=14.6, 2.9 Hz), 6.09-6.11 (1H, m), 7.32 (1H, s), 7.48 (1H, d, J=1.9 Hz), 8.00 (1H, d, J=1.9 Hz), 8.15 (1H, s), 10.58 (1H, s).

Step 2

2,6-Anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,4-trideoxy-5-O-methyl-L-threo-hexitol The title compound (57 mg) was obtained by the same procedure as in Step 6 of Example 35 using the compound obtained in the above Step 1 (103 mg).

MS (ESI) m/z: 428 (M+H)+.

$^1$H-NMR (DMSO-$d_6$) δ: 1.35-1.66 (3H, m), 1.86-1.96 (1H, m), 2.66 (3H, s), 3.30 (3H, s), 3.50-4.02 (6H, m), 7.52 (1H, d, J=1.8 Hz), 7.66 (1H, d, J=2.8 Hz), 7.90 (1H, d, J=1.4 Hz), 8.13 (1H, s), 11.64 (1H, s), 12.00 (1H, s).

Example 149

2,6-Anhydro-1,3,4-trideoxy-1-[5-methyl-2-oxo-6-(1H-pyrrolo[2,3-b]pyridin-5-yl)-2,3-dihydro-1H-imidazo[4,5-b]pyridin-1-yl]-L-threo-hexitol

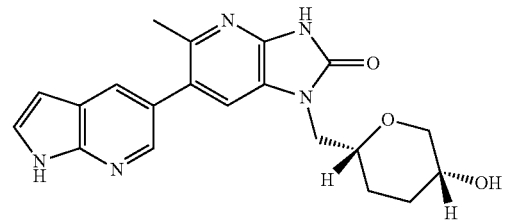

[Formula 169]

Step 1

2,6-Anhydro-1-[6-bromo-3-cyclohex-1-en-1-yl-5-methyl-2-oxo-2,3-dihydro-1H-imidazo[4,5-b]pyridin-1-yl]-1,3,4-trideoxy-5-O-(phenylcarbonyl)-L-threo-hexitol The title compound (1.70 g) was obtained by the same procedure as in Step 3 of Example 35 using the compound obtained in Step 4 of Example 143 (0.76 g) and the compound obtained in Step 1 of Example 44 (1.29 g).

MS (ESI) m/z: 526 (M+H)+.

Step 2

2,6-Anhydro-1-[6-bromo-3-cyclohex-1-en-1-yl-5-methyl-2-oxo-2,3-dihydro-1H-imidazo[4,5-b]pyridin-1-yl]-1,3,4-trideoxy-L-threo-hexitol The title compound (0.627 g) was obtained by the same procedure as in Step 6 of Example 143 using the compound obtained in the above Step 1 (1.70 g).

MS (ESI) m/z: 422 (M+H)+.

$^1$H-NMR (CDCl$_3$) δ: 1.55-1.61 (1H, m), 1.68-1.79 (4H, m), 1.82-1.88 (2H, m), 1.92-1.99 (1H, m), 2.27-2.33 (2H, m), 2.42-2.48 (2H, m), 2.59 (3H, s), 3.52 (1H, d, J=12.0 Hz), 3.66-3.72 (1H, m), 3.76-3.82 (2H, m), 3.89 (1H, dt, J=12.0, 2.3 Hz), 3.94 (1H, dd, J=14.3, 2.9 Hz), 5.99-6.01 (1H, m), 7.51 (1H, s).

Step 3

2,6-Anhydro-1-[3-cyclohex-1-en-1-yl-5-methyl-2-oxo-6-(1H-pyrrolo[2,3-b]pyridin-5-yl)-2,3-dihydro-1H-imidazo[4,5-b]pyridin-1-yl]-1,3,4-trideoxy-L-threo-hexitol The title compound (128 mg) was obtained by the same procedure as in Step 3 of Example 1 using the compound obtained in the above Step 2 (139 mg) and 5-(4,4,5,5-tetramethyl-1,3,2-dioxaborolan-2-yl)-1H-pyrrolo[2,3-b]pyridine (96 mg).
MS (ESI) m/z: 460 (M+H)$^+$.
$^1$H-NMR (CDCl$_3$) δ: 1.56-1.63 (1H, m), 1.65-1.82 (4H, m), 1.83-1.97 (3H, m), 2.28-2.36 (2H, m), 2.48 (3H, s), 2.52-2.58 (2H, m), 3.52 (1H, d, J=11.9 Hz), 3.70-3.79 (2H, m), 3.85-3.93 (2H, m), 3.97 (1H, dd, J=14.7, 3.7 Hz), 6.06-6.10 (1H, m), 6.52-6.55 (1H, m), 7.26 (1H, s), 7.40-7.43 (1H, m), 7.87 (1H, d, J=1.8 Hz), 8.26 (1H, d, J=1.8 Hz), 10.43 (1H, s).

Step 4

2,6-Anhydro-1,3,4-trideoxy-1-[5-methyl-2-oxo-6-(1H-pyrrolo[2,3-b]pyridin-5-yl)-2,3-dihydro-1H-imidazo[4,5-b]pyridin-1-yl]-L-threo-hexitol The title compound (20 mg) was obtained by the same procedure as in Step 6 of Example 35 using the compound obtained in the above Step 3 (151 mg).
MS (ESI) m/z: 380 (M+H)$^+$.
$^1$H-NMR (DMSO-d$_6$) δ: 1.33-1.40 (1H, m), 1.58-1.73 (3H, m), 2.38 (3H, s), 3.35-3.38 (1H, m), 3.50-3.53 (1H, m), 3.59-3.67 (1H, m), 3.77 (1H, dd, J=14.3, 4.0 Hz), 3.87 (1H, dd, J=13.7, 7.4 Hz), 4.51 (1H, d, J=4.0 Hz), 6.48-6.50 (1H, m), 7.38 (1H, s), 7.52-7.54 (1H, m), 7.95 (1H, d, J=2.3 Hz), 8.20 (1H, d, J=2.3 Hz), 11.45 (1H, s), 11.73 (1H, s).

Example 150

2,6-Anhydro-1,3,5-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-L-threo-hexitol

[Formula 170]

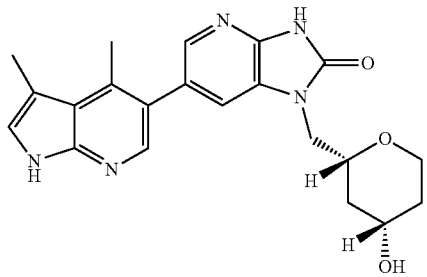

Step 1

2,6-Anhydro-4-O-benzoyl-1-O-benzyl-3,5-dideoxy-L-threo-hexitol

The title compound (2.05 g) was obtained by the same procedure as in Step 1 of Example 111 using the L-isomer obtained in Step 1 of Example 137 (isomer A, 1.48 g).
MS (ESI) m/z: 327 (M+H)$^+$.
$^1$H-NMR (CDCl$_3$) δ: 1.54-1.63 (1H, m), 1.74-1.84 (1H, m), 2.02-2.13 (2H, m), 3.46-3.62 (3H, m), 3.66-3.72 (1H, m), 4.11-4.17 (1H, m), 4.57 (1H, d, J=12.0 Hz), 4.61 (1H, d, J=12.0 Hz), 5.12-5.20 (1H, m), 7.25-7.33 (2H, m), 7.33-7.35 (3H, m), 7.42-7.46 (2H, m), 7.54-7.58 (1H, m), 8.02-8.05 (2H, m).

Step 2

1,5-Anhydro-3-O-benzoyl-2,4-dideoxy-L-threo-hexitol

The title compound (1.48 g) was obtained by the same procedure as in Step 4 of Example 143 using the compound obtained in the above Step 1 (2.05 g).
MS (ESI) m/z: 237 (M+H)$^+$.
$^1$H-NMR (CDCl$_3$) δ: 1.50-1.62 (1H, m), 1.73-1.83 (1H, m), 1.95-1.99 (1H, m), 2.02-2.12 (2H, m), 3.56-3.72 (4H, m), 4.10-4.16 (1H, m), 5.14-5.22 (1H, m), 7.42-7.47 (2H, m), 7.54-7.59 (1H, m), 8.02-8.05 (2H, m).

Step 3

2,6-Anhydro-4-O-benzoyl-1-(6-bromo-3-cyclohex-1-en-1-yl-2-oxo-2,3-dihydro-1H-imidazo[4,5-b]pyridin-1-yl)-1,3,5-trideoxy-L-threo-hexitol The title compound (3.15 g) was obtained by the same procedure as in Step 3 of Example 35 using the compound obtained in the above Step 2 (1.48 g) and the compound obtained in Step 2 of Example 35 (2.40 g).
MS (ESI) m/z: 512 (M+H)$^+$.
$^1$H-NMR (CDCl$_3$) δ: 1.52-1.55 (1H, m), 1.70-1.79 (3H, m), 1.83-1.90 (2H, m), 2.03-2.09 (1H, m), 2.22-2.27 (1H, m), 2.28-2.33 (2H, m), 2.39-2.45 (2H, m), 3.50 (1H, td, J=12.3, 2.3 Hz), 3.78-3.84 (1H, m), 3.88 (1H, dd, J=14.3, 6.9 Hz), 4.00 (1H, dd, J=14.3, 3.1 Hz), 4.06-4.11 (1H, m), 5.12-5.20 (1H, m), 6.01-6.04 (1H, m), 7.42-7.47 (2H, m), 7.52 (1H, d, J=2.3 Hz), 7.54-7.59 (1H, m), 8.01-8.04 (2H, m), 8.09 (1H, d, J=2.3 Hz).

Step 4

2,6-Anhydro-1-(6-bromo-3-cyclohex-1-en-1-yl-2-oxo-2,3-dihydro-1H-imidazo[4,5-b]pyridin-1-yl)-1,3,5-trideoxy-L-threo-hexitol The title compound (1.78 g) was obtained by the same procedure as in Step 6 of Example 143 using the compound obtained in the above Step 3 (3.15 g).
MS (ESI) m/z: 408 (M+H)$^+$.
$^1$H-NMR (CDCl$_3$) δ: 1.24-1.32 (1H, m), 1.46-1.62 (2H, m), 1.71-1.78 (2H, m), 1.83-1.92 (3H, m), 2.03-2.09 (1H, m), 2.28-2.34 (2H, m), 2.39-2.45 (2H, m), 3.35 (1H, td, J=12.0, 2.3 Hz), 3.63-3.69 (1H, m), 3.78-3.86 (2H, m), 3.96-4.03 (2H, m), 5.99-6.03 (1H, m), 7.50 (1H, d, J=1.7 Hz), 8.08 (1H, d, J=1.7 Hz).

Step 5

2,6-Anhydro-1-[3-cyclohex-1-en-1-yl-2-oxo-6-(4,4,5,5-tetramethyl-1,3,2-dioxaborolan-2-yl)-2,3-dihydro-1H-imidazo[4,5-b]pyridin-1-yl]-1,3,5-trideoxy-L-threo-hexitol The title compound (768 mg) was obtained by the same procedure as in Step 4 of Example 35 using the compound obtained in the above Step 4 (800 mg).

MS (ESI) m/z: 456 (M+H)+.

1H-NMR (CDCl3) δ: 1.23-1.29 (1H, m), 1.35 (12H, s), 1.47-1.64 (2H, m), 1.72-1.79 (2H, m), 1.84-1.90 (3H, m), 2.01-2.07 (1H, m), 2.28-2.34 (2H, m), 2.41-2.47 (2H, m), 3.35 (1H, dd, J=12.7, 1.7 Hz), 3.69-4.02 (5H, m), 6.00-6.03 (1H, m), 7.62 (1H, d, J=1.7 Hz), 8.44 (1H, d, J=1.7 Hz).

Step 6

2,6-Anhydro-1-[3-cyclohex-1-en-1-yl-6-(3,4-dimethyl-1H-pyrrolo[2,3-b]pyridin-5-yl)-2-oxo-2,3-dihydro-1H-imidazo[4,5-b]pyridin-1-yl]-1,3,5-trideoxy-L-threo-hexitol The title compound (127 mg) was obtained by the same procedure as in Step 2 of Example 4 using the compound obtained in the above Step 5 (147 mg) and the compound obtained in Step 2 of Example 124 (66 mg).

MS (ESI) m/z: 474 (M+H)+.

1H-NMR (CDCl3) δ: 1.20-2.12 (8H, m), 2.26-2.55 (4H, m), 2.52 (3H, s), 2.64 (3H, s), 3.31-3.40 (1H, m), 3.64-4.08 (5H, m), 6.07-6.11 (1H, m), 7.06 (1H, s), 7.39 (1H, d, J=1.7 Hz), 8.03 (1H, d, J=1.7 Hz), 8.11 (1H, s), 8.62 (1H, brs).

Step 7

2,6-Anhydro-1,3,5-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-L-threo-hexitol The title compound (44 mg) was obtained by the same procedure as in Step 6 of Example 35 using the compound obtained in the above Step 6 (125 mg).

MS (ESI) m/z: 394 (M+H)+.

1H-NMR (DMSO-d6) δ: 1.03-1.13 (1H, m), 1.19-1.30 (1H, m), 1.65-1.72 (1H, m), 1.79-1.87 (1H, m), 2.46 (3H, s), 2.57 (3H, s), 3.21-3.28 (1H, m), 3.52-3.65 (2H, m), 3.76-3.86 (2H, m), 3.92 (1H, dd, J=14.3, 7.4 Hz), 4.77 (1H, d, J=5.2 Hz), 7.19-7.21 (1H, m), 7.48 (1H, d, J=1.7 Hz), 7.87 (1H, d, J=1.7 Hz), 7.99 (1H, s), 11.27 (1H, s), 11.62 (1H, s).

Example 151

2,6-Anhydro-1,3,5-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-4-O-methyl-L-threo-hexitol

[Formula 171]

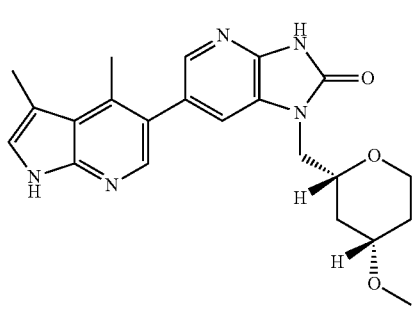

Step 1

2,6-Anhydro-1-[3-cyclohex-1-en-1-yl-6-(3,4-dimethyl-1H-pyrrolo[2,3-b]pyridin-5-yl)-2-oxo-2,3-dihydro-1H-imidazo[4,5-b]pyridin-1-yl]-1,3,5-trideoxy-4-O-methyl-L-threo-hexitol The title compound (113 mg) was obtained by the same procedure as in Step 2 of Example 4 using the compound obtained in Step 3 of Example 139 (165 mg) and the compound obtained in Step 2 of Example 124 (66 mg).

MS (ESI) m/z: 488 (M+H)+.

1H-NMR (CDCl3) δ: 1.10-1.96 (8H, m), 2.32-2.38 (2H, m), 2.50-2.54 (2H, m), 2.52 (3H, s), 2.64 (3H, s), 3.29-3.40 (2H, m), 3.36 (3H, s), 3.65-3.72 (1H, m), 3.84-4.07 (3H, m), 6.07-6.22 (1H, m), 7.05 (1H, s), 7.39 (1H, d, J=1.7 Hz), 8.02 (1H, d, J=1.7 Hz), 8.10 (1H, s), 8.37 (1H, brs).

Step 2

2,6-Anhydro-1,3,5-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-4-O-methyl-L-threo-hexitol The title compound (28 mg) was obtained by the same procedure as in Step 6 of Example 35 using the compound obtained in the above Step 1 (110 mg).

MS (ESI) m/z: 408 (M+H)+.

1H-NMR (DMSO-d6) δ: 1.00-1.11 (1H, m), 1.15-1.26 (1H, m), 1.83-1.90 (1H, m), 2.01-2.07 (1H, m), 2.46 (3H, s), 2.57 (3H, s), 3.23 (3H, s), 3.24-3.40 (2H, m), 3.60-3.68 (1H, m), 3.81-3.98 (3H, m), 7.19-7.21 (1H, m), 7.48 (1H, d, J=1.7 Hz), 7.87 (1H, d, J=1.7 Hz), 7.99 (1H, s), 11.27 (1H, s), 11.61 (1H, s).

Example 152

2,6-Anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,5-trideoxy-4-O-methyl-L-threo-hexitol

[Formula 172]

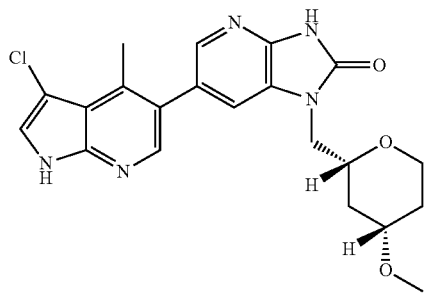

Step 1

2,6-Anhydro-1-{6-[1-(tert-butoxycarbonyl)-3-chloro-4-methyl-1H-pyrrolo[2,3-b]pyridin-5-yl]-3-cyclohex-1-en-1-yl-2-oxo-2,3-dihydro-1H-imidazo[4,5-b]pyridin-1-yl}-1,3,5-trideoxy-4-O-methyl-L-threo-hexitol The title compound (119 mg) was obtained by the same procedure as in Step 2 of Example 4 using the compound obtained in Step 3 of Example 139 (163 mg) and the compound obtained in Step 2 of Example 125 (100 mg).

¹H-NMR (CDCl₃) δ: 1.16-1.26 (1H, m), 1.24 (9H, s), 1.35-1.47 (1H, m), 1.73-1.81 (2H, m), 1.87-1.96 (3H, m), 2.13-2.19 (1H, m), 2.32-2.37 (2H, m), 2.48-2.54 (2H, m), 2.74 (3H, s), 3.30-3.40 (2H, m), 3.36 (3H, s), 3.65-3.71 (1H, m), 3.87 (1H, dd, J=14.9, 8.0 Hz), 3.95-3.99 (1H, m), 4.05 (1H, dd, J=14.9, 2.9 Hz), 6.08-6.11 (1H, m), 7.28-7.30 (1H, m), 7.40 (1H, d, J=1.7 Hz), 8.01 (1H, d, J=1.7 Hz), 8.18 (1H, s).

Step 2

2,6-Anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,5-trideoxy-4-O-methyl-L-threo-hexitol The title compound (28 mg) was obtained by the same procedure as in Step 6 of Example 35 using the compound obtained in the above Step 1 (116 mg).

MS (ESI) m/z: 428 (M+H)⁺.

¹H-NMR (DMSO-d₆) δ: 1.02-1.10 (1H, m), 1.15-1.26 (1H, m), 1.84-1.89 (1H, m), 2.01-2.07 (1H, m), 2.66 (3H, s), 3.23 (3H, s), 3.24-3.38 (2H, m), 3.62-3.68 (1H, m), 3.81-3.87 (2H, m), 3.94 (1H, dd, J=14.5, 7.8 Hz), 7.51-7.53 (1H, m), 7.66 (1H, d, J=2.9 Hz), 7.90 (1H, d, J=2.3 Hz), 8.12 (1H, s), 11.65 (1H, s), 11.98-12.02 (1H, m).

Example 153

1-{[(2S)-6-(Methoxymethyl)-1,4-dioxan-2-yl]methyl}-6-(4-methyl-1H-pyrrolo[2,3-b]pyridin-5-yl)-1,3-dihydro-2H-imidazo[4,5-b]pyridin-2-one

[Formula 173]

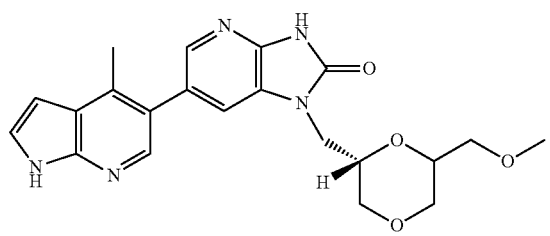

Step 1

(2R)-1-(Allyloxy)-3-chloropropan-2-ol

A boron trifluoride-diethyl ether complex (0.34 ml) was added to allyl alcohol (11 ml), and the mixture was warmed to 45° C. Then, (R)-epichlorohydrin (5.0 g) was added and the mixture was stirred at the same temperature for 1.5 hours. Diethyl ether was added, followed by washing with water and drying over anhydrous magnesium sulfate. The solvent was evaporated under reduced pressure to give the crude title compound (10 g).

¹H-NMR (CDCl₃) δ: 3.54-3.69 (4H, m), 3.97-4.05 (2H, m), 4.16-4.18 (1H, m), 5.15-5.24 (1H, m), 5.27-5.31 (1H, m), 5.85-6.05 (1H, m).

Step 2

(2R)-1-(Allyloxy)-3-(benzyloxy)propan-2-ol

Sodium hydroxide (5.4 g) was dissolved in water (6.4 ml). The compound obtained in the above Step 1 (8.1 g) was added and the mixture was stirred at room temperature for 1.5 hours. Diethyl ether was added, followed by washing with water. The organic layer was dried over anhydrous magnesium sulfate, and the solvent was evaporated under reduced pressure. The resulting residue was dissolved in benzyl alcohol (27 mL), and sodium hydride (55%, 1.8 g) was slowly added under ice-cooling. The mixture was stirred at room temperature for 4.5 hours and the reaction solution was diluted with dichloromethane. Then, the organic layer was sequentially washed with 1 M hydrochloric acid and saturated aqueous sodium bicarbonate. After drying over anhydrous magnesium sulfate, the solvent was evaporated under reduced pressure. The resulting residue was purified by silica gel column chromatography (developed with ethyl acetate-hexane) to give the title compound (2.6 g).

¹H-NMR (CDCl₃) δ: 2.48 (1H, d, J=4.0 Hz), 3.47-3.58 (4H, m), 3.98-4.03 (3H, m), 4.56 (2H, s), 5.17-5.20 (1H, m), 5.25-5.29 (1H, m), 5.86-5.94 (1H, m), 7.30-7.35 (5H, m).

Step 3

(2S)-2-[(Benzyloxy)methyl]-6-(iodomethyl)1,4-dioxane

N-Iodosuccinimide (4.5 g) was added to a solution of the compound obtained in the above Step 2 (2.6 g) in acetonitrile (40 ml), and the mixture was heated under reflux for 2.5 hours. After leaving to cool to room temperature, a saturated aqueous sodium thiosulfate solution was added, followed by extraction with ethyl acetate. After drying over anhydrous sodium sulfate, the solvent was evaporated under reduced pressure. The resulting residue was purified by silica gel column chromatography (developed with ethyl acetate-hexane) to give the title compound (1.7 g).

¹H-NMR (CDCl₃) δ: 3.04-4.28 (10H, m), 4.54-4.59 (2H, m), 7.27-7.37 (5H, m).

Step 4

{(6S)-6-[(Benzyloxy)methyl]-1,4-dioxan-2-yl}methyl 4-nitrobenzoate

Potassium 4-nitrobenzoate (10 g) and 18-crown 6-ether (0.13 g) were added to a solution of the compound obtained in the above Step 3 (1.7 g) in dimethyl sulfoxide (60 ml), and the mixture was stirred at 90° C. for 4 hours. The reaction solution was left to cool to room temperature and diluted with water and diethyl ether. The organic layer was sequentially washed with water and brine. After drying over anhydrous sodium sulfate, the solvent was evaporated under reduced pressure. The resulting residue was purified by silica gel column chromatography (developed with ethyl acetate-hexane) to give the title compound (1.7 g).

¹H-NMR (CD₃OD) δ: 3.35-4.79 (12H, m), 7.24-7.34 (5H, m), 8.21-8.35 (5H, m).

Step 5

{(6S)-6-[(Benzyloxy)methyl]-1,4-dioxan-2-yl}methanol

Concentrated hydrochloric acid (1.0 ml) was added to a solution of the compound obtained in the above Step 4 (1.7 g)

in methanol (40 ml). The mixture was stirred at room temperature for 24 hours and stirred at 50° C. for 8 hours. Concentrated hydrochloric acid (2.0 ml) was further added and the mixture was stirred at the same temperature for 16 hours. Concentrated hydrochloric acid (2.0 ml) was further added and the mixture was stirred at the same temperature for 8 hours. The reaction solution was neutralized with saturated aqueous sodium bicarbonate, and methanol was distilled off under reduced pressure. Water was added, followed by extraction with diethyl ether. Then, the organic layer was washed with brine. After drying over anhydrous sodium sulfate, the solvent was evaporated under reduced pressure. The resulting residue was purified by silica gel column chromatography (developed with ethyl acetate-hexane) to give the title compound (258 mg).

$^1$H-NMR (CDCl$_3$) δ: 1.93-2.01 (1H, m), 3.31-4.03 (10H, m), 4.53-4.60 (2H, m), 7.29-7.37 (5H, m).

Step 6

(2S)-2-[(Benzyloxy)methyl]-6-methoxymethyl-1,4-dioxane

The title compound (261 mg) was obtained by the same procedure as in Step 1 of Example 63 using the compound obtained in the above Step 5 (258 mg).
MS (ESI) m/z: 253 (M+H)$^+$.

Step 7

[(2S)-6-(Methoxymethyl)-1,4-dioxan-2-yl]methanol

The title compound (160 mg) was obtained by the same procedure as in Step 4 of Example 114 using the compound obtained in the above Step 6 (261 mg).

Step 8

[(2S)-6-(Methoxymethyl)-1,4-dioxan-2-yl]methyl methanesulfonate

The title compound (235 mg) was obtained by the same procedure as in Step 1 of Example 139 using the compound obtained in the above Step 7 (160 mg).

Step 9

6-Bromo-3-cyclohex-1-en-1-yl-1-{[(2S)-6-(methoxymethyl)-1,4-dioxan-2-yl]methyl}-1,3-dihydro-2H-imidazo[4,5-b]pyridin-2-one The title compound (440 mg) was obtained by the same procedure as in Step 2 of Example 139 using the compound obtained in the above Step 8 (235 mg) and the compound obtained in Step 2 of Example 35 (288 mg).
MS (ESI) m/z: 438 (M+H)$^+$.

Step 10

3-Cyclohex-1-en-1-yl-1-{[(2S)-6-(methoxymethyl)-1,4-dioxan-2-yl]methyl}-6-(4,4,5,5-tetramethyl-1,3,2-dioxaboran-2-yl)-1,3-dihydro-2H-imidazo[4,5-b]pyridin-2-one The title compound (611 mg) was obtained by the same procedure as in Step 4 of Example 35 using the compound obtained in the above Step 9 (440 mg).
MS (ESI) m/z: 486 (M+H)$^+$.

Step 11

3-Cyclohex-1-en-1-yl-1-{[(2S)-6-(methoxymethyl)-1,4-dioxan-2-yl]methyl}-6-(4-methyl-1H-pyrrolo[2,3-b]pyridin-5-yl)-1,3-dihydro-2H-imidazo[4,5-b]pyridin-2-one The title compound (370 mg) was obtained by the same procedure as in Step 3 of Example 1 using the compound obtained in the above Step 10 (611 mg) and the compound obtained in Step 3 of Example 36 (292 mg).
MS (ESI) m/z: 490 (M+H)$^+$.

Step 12

1-{[(2S)-6-(Methoxymethyl)-1,4-dioxan-2-yl]methyl}-6-(4-methyl-1H-pyrrolo[2,3-b]pyridin-5-yl)-1,3-dihydro-2H-imidazo[4,5-b]pyridin-2-one The title compound (85 mg) (proved to be about 3:2 diastereomer mixture according to NMR) was obtained by the same procedure as in Step 6 of Example 35 using the compound obtained in the above Step 11 (370 mg).
MS (ESI) m/z: 410 (M+H)$^+$.
HRMS (ESI) [(M+H)$^+$] calculated: $C_{21}H_{24}N_5O_4$ 410.18283.
found: 410.18340.
$^1$H-NMR (DMSO-d$_6$) δ: 2.46-2.47 (3H, m), 3.06 (1.8H, s), 3.14 (1.2H, s), 3.15-4.40 (10H, m), 6.56-6.58 (1H, m), 7.47-7.48 (1H, m), 7.54-7.55 (0.6H, m), 7.60-7.62 (0.4H, m), 7.91-7.92 (1H, m), 8.07-8.08 (1H, m), 11.64-11.65 (2H, m).

Example 154

2,6-Anhydro-1,3,5-trideoxy-1-[2-oxo-6-(1H-pyrrolo[2,3-b]pyridin-5-yl)-2,3-dihydro-1H-imidazo[4,5-b]pyridin-1-yl]-D-erythro-hexitol

[Formula 174]

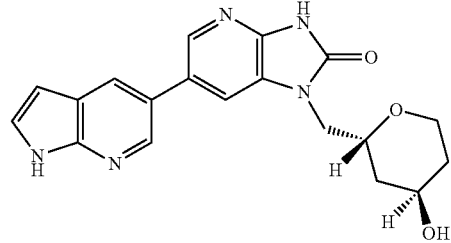

Step 1

2,6-Anhydro-1-O-benzyl-3,5-dideoxy-4-O-(phenylcarbonyl)-D-erythro-hexitol

The title compound (1175 mg) was obtained by the same procedure as in Step 1 of Example 112 using the L-isomer obtained in Step 1 of Example 137 (isomer A, 800 mg) and benzoic acid (571 mg).
MS (ESI) m/z: 327 (M+H)$^+$.
$^1$H-NMR (CDCl$_3$) δ: 1.75-1.82 (1H, m), 1.85-1.92 (2H, m), 1.96-2.04 (1H, m), 3.45-3.53 (2H, m), 3.92-4.08 (3H, m), 4.58 (1H, d, J=12.4 Hz), 4.62 (1H, d, J=12.4 Hz), 5.46-5.50 (1H, m), 7.27-7.32 (1H, m), 7.33-7.40 (4H, m), 7.44-7.50 (2H, m), 7.57-7.62 (1H, m), 8.08 (2H, d, J=7.8 Hz).

Step 2

2,6-Anhydro-3,5-dideoxy-4-O-(phenylcarbonyl)-D-erythro-hexitol

The title compound (71 mg) was obtained by the same procedure as in Step 4 of Example 114 using the compound obtained in Step 1 (120 mg), 20% palladium hydroxide (20 mg), and methanol as solvent.

MS (ESI) m/z: 237 (M+H)$^+$.

Step 3

Ethyl 6-bromo-3-(2-cyanoethyl)-2-oxo-2,3-dihydro-1H-imidazo[4,5-b]pyridine-1-carboxylate The title compound (954 mg) was obtained by the same procedure as in Step 3 of Example 35 using 6-bromo-2-oxo-2,3-dihydro-1H-imidazo[4,5-b]pyridine-1-carboxylate obtained under the conditions described in WO 2008/051493 (1.43 g) and 3-hydroxypropanenitrile (0.51 ml).

MS (APCI) m/z: 339 [M+H]$^+$ $^1$H-NMR (CDCl$_3$) δ: 1.49 (3H, t, J=7.2 Hz), 2.94 (2H, t, J=7.0 Hz), 4.28 (2H, t, J=7.0 Hz), 4.55 (2H, q, J=7.2 Hz), 8.23 (2H, s).

Step 4

3-(6-Bromo-2-oxo-1,2-dihydro-3H-imidazo[4,5-b]pyridin-3-yl)propanenitrile

The compound obtained in the above Step 3 (954 mg) was dissolved in tetrahydrofuran (28 ml). Isopropylamine (362 µl) was added and the mixture was stirred at room temperature for 70 minutes. After distilling off the reaction solvent, hexane was added and sonication was performed. Colorless crystals were collected by filtration to give the title compound (739 mg).

MS (APCI) m/z: 267 [M+H]$^+$ $^1$H-NMR (DMSO-d$_6$) δ: 3.01 (2H, t, J=6.4 Hz), 4.07 (2H, t, J=6.4 Hz), 7.54 (1H, t, J=1.6 Hz), 8.07 (1H, t, J=1.8 Hz).

Step 5

2,6-Anhydro-1-[6-bromo-3-(2-cyanoethyl)-2-oxo-2,3-dihydro-1H-imidazo[4,5-b]pyridin-1-yl]-1,3,5-trideoxy-4-O-(phenylcarbonyl)-D-erythro-hexitol The title compound (96 mg) was obtained by the same procedure as in Step 3 of Example 35 using the compound obtained in the above Step 2 (71 mg) and the compound obtained in the above Step 4 (104 mg).

MS (ESI) m/z: 485 (M+H)$^+$.

$^1$H-NMR (CDCl$_3$) δ: 1.67-1.72 (1H, m), 1.82-1.88 (1H, m), 1.90-1.97 (1H, m), 2.02-2.07 (1H, m), 2.95 (2H, t, J=6.3 Hz), 3.77-3.85 (2H, m), 3.88-3.93 (1H, m), 4.00 (1H, dd, J=14.3, 2.9 Hz), 4.08-4.14 (1H, m), 4.29 (2H, t, J=6.9 Hz), 5.45-5.48 (1H, m), 7.46 (2H, t, J=7.4 Hz), 7.56-7.60 (2H, m), 8.05-8.05 (2H, m), 8.09 (1H, d, J=2.3 Hz).

Step 6

2,6-Anhydro-1-[3-(2-cyanoethyl)-2-oxo-6-(1H-pyrrolo[2,3-b]pyridin-5-yl)-2,3-dihydro-1H-imidazo[4,5-b]pyridin-1-yl]-1,3,5-trideoxy-D-erythro-hexitol The title compound (20 mg) was obtained by the same procedure as in Step 4 of Example 111 using the compound obtained in the above Step 5 (86 mg) and 5-(4,4,5,5-tetramethyl-1,3,2-dioxaborolan-2-yl)-1H-pyrrolo[2,3-b]pyridine (52 mg).

MS (ESI) m/z: 419 (M+H)$^+$.

$^1$H-NMR (CDCl$_3$) δ: 1.52-1.67 (2H, m), 1.76-1.87 (2H, m), 3.01 (2H, t, J=6.8 Hz), 3.73-3.79 (1H, m), 3.84 (1H, dd, J=12.9, 2.2 Hz), 3.87-3.96 (1H, m), 4.01 (1H, dd, J=14.6, 3.4 Hz), 4.15-4.21 (1H, m), 4.28-4.31 (1H, m), 4.37 (2H, t, J=7.1 Hz), 6.58-6.60 (1H, m), 7.42 (1H, dd, J=3.4, 2.2 Hz), 7.64 (1H, d, J=2.0 Hz), 8.09 (1H, d, J=1.7 Hz), 8.26 (1H, d, J=2.0 Hz), 8.49 (1H, d, J=2.2 Hz), 9.90 (1H, s).

Step 7

2,6-Anhydro-1,3,5-trideoxy-1-[2-oxo-6-(1H-pyrrolo[2,3-b]pyridin-5-yl)-2,3-dihydro-1H-imidazo[4,5-b]pyridin-1-yl]-D-erythro-hexitol The compound obtained in the above Step 6 (20 mg) was dissolved in tetrahydrofuran (1 ml). Potassium tert-butoxide (5.3 mg) was added, followed by stirring. Potassium tert-butoxide (11 mg) and acetonitrile (4 ml) were added and then potassium tert-butoxide (33 mg) was further added. The mixture was stirred at room temperature for three days. A saturated aqueous ammonium chloride solution was added, followed by extraction with ethyl acetate three times. The organic layer was dried over anhydrous sodium sulfate and then the solvent was evaporated under reduced pressure. Hexane was added to the residue, and the resulting precipitate was collected by filtration to give the title compound (3 mg).

MS (ESI) m/z: 366 (M+H)$^+$.

$^1$H-NMR (DMSO-d$_6$) δ: 1.36-1.69 (4H, m), 3.58-3.71 (1H, m), 3.79-3.95 (2H, m), 4.00-4.08 (2H, m), 4.62-4.65 (1H, m), 6.51-6.53 (1H, m), 7.52-7.54 (1H, m), 7.78 (1H, d, J=1.7 Hz), 8.21-8.24 (2H, m), 8.51 (1H, d, J=2.0 Hz), 11.60 (1H, s), 11.73 (1H, s).

Example 155

5-Chloro-1-[(2S)-1,4-dioxan-2-ylmethyl]-6-(1H-pyrrolo[2,3-b]pyridin-5-yl)-1,3-dihydro-2H-imidazo[4,5-b]pyridin-2-one

[Formula 175]

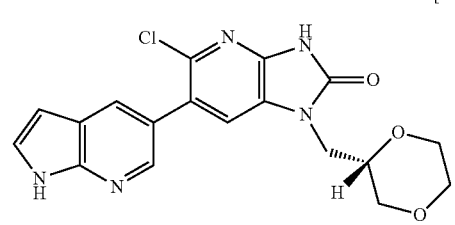

Step 1

6-Bromo-5-chloro-1,3-dihydro-2H-imidazo[4,5-b]pyridin-2-one

5-Bromo-6-chloropyridine-2,3-diamine obtained by the method described in Bioorg. Med. Chem. Lett. 1996, 22, 2749 (0.83 g) was dissolved in tetrahydrofuran (40 ml). 1,1-Carbonyldiimidazole (0.91 g) was added and the mixture was heated under reflux overnight. The reaction solvent was distilled off under reduced pressure. The resulting residue was washed with a hexane/ethyl acetate mixture and then dried under reduced pressure to give the title compound (0.81 g).

MS (ESI) m/z: 248 (M+H)$^+$.
$^1$H-NMR (DMSO-d$_6$) δ: 7.58 (1H, s), 11.18 (1H, s), 11.74 (1H, s).

Step 2

Ethyl 6-bromo-5-chloro-2-oxo-2,3-dihydro-1H-imidazo[4,5-b]pyridine-1-carboxylate The compound obtained in the above Step 1 (300 mg) was dissolved in dimethylformamide (5 ml). Ethyl pyridin-2-yl carbonate obtained by the method described in WO 2008/051493 (242 mg) and potassium carbonate (200 mg) were added and the mixture was stirred at 55° C. for one hour. After cooling the reaction solution to room temperature, water (6 ml) and 1 N aqueous hydrochloric acid (2.9 ml) were added and the mixture was vigorously stirred. The precipitated solid was collected by filtration, washed with water and then dried under reduced pressure to give the title compound (344 mg).

MS (ESI) m/z: 322 (M+H)$^+$.
$^1$H-NMR (DMSO-d$_6$) δ: 1.35 (3H, t, J=7.1 Hz), 4.42 (2H, q, J=7.2 Hz), 8.08 (1H, s), 12.39 (1H, s).

Step 3

6-Bromo-5-chloro-3-[2-(trimethylsilyl)ethyl]-1,3-dihydro-2H-imidazo[4,5-b]pyridin-2-one The compound obtained in the above Step 2 (340 mg) was dissolved in tetrahydrofuran (10 ml). 2-(Trimethylsilyl)ethanol (228 μl) and triphenylphosphine (417 mg) were added and then diisopropyl azodicarboxylate (324 μl) was added dropwise under ice-cooling. The mixture was stirred overnight while gradually warming to room temperature. Thereafter, 2-(trimethylsilyl)ethanol (228 μl) and triphenylphosphine (417 g) were further added and then diisopropyl azodicarboxylate (324 μl) was added dropwise under ice-cooling. The mixture was stirred for 6 hours while gradually warming to room temperature. The reaction solution was cooled in an ice bath again and then isopropylamine (136 μl) was added. The mixture was stirred at room temperature for one hour. The reaction solvent was distilled off under reduced pressure. The resulting residue was purified by silica gel column chromatography (developed with ethyl acetate-hexane) to give the title compound (310 mg).

$^1$H-NMR (CDCl$_3$) δ: 0.09 (9H, s), 1.12-1.16 (2H, m), 3.97-4.01 (2H, m), 7.52 (1H, s), 9.16 (1H, s).

Step 4

6-Bromo-5-chloro-1-[(2S)-1,4-dioxan-2-ylmethyl]-3-[2-(trimethylsilyl)ethyl]-1,3-dihydro-2H-imidazo[4,5-b]pyridin-2-one The title compound (175 mg) was obtained by the same procedure as in Step 3 of Example 35 using the compound obtained in the above Step 3 (150 mg) and (2S)-1,4-dioxan-2-ylmethanol (65 mg).

MS (ESI) m/z: 448 (M+H)$^+$.
$^1$H-NMR (CDCl$_3$) δ: 0.07 (9H, s), 3.31-3.35 (1H, m), 3.52-3.58 (1H, m), 3.64-3.70 (2H, m), 3.76-3.81 (2H, m), 3.84-3.91 (3H, m), 3.98-4.01 (2H, m), 4.96-5.07 (2H, m), 7.56 (1H, s).

Step 5

5-Chloro-1-[(2S)-1,4-dioxan-2-ylmethyl]-6-(1H-pyrrolo[2,3-b]pyridin-5-yl)-3-[2-(trimethylsilyl)ethyl]-1,3-dihydro-2H-imidazo[4,5-b]pyridin-2-one The title compound (160 mg) was obtained by the same procedure as in Step 2 of Example 4 using 5-(4,4,5,5-tetramethyl-1,3,2-dioxaborolan-2-yl)-1H-pyrrolo[2,3-b]pyridine (110 mg) and the compound obtained in the above Step 4 (170 mg).

MS (ESI) m/z: 486 (M+H)$^+$.
$^1$H-NMR (CDCl$_3$) δ: 0.10 (9H, s), 1.18-1.28 (3H, m), 3.33-3.38 (1H, m), 3.50-3.57 (1H, m), 3.65-3.74 (3H, m), 3.84-3.95 (3H, m), 4.05-4.10 (2H, m), 6.58-6.59 (1H, m), 7.38 (2H, dd, J=6.4, 3.7 Hz), 8.03 (1H, d, J=1.8 Hz), 8.36 (1H, d, J=2.3 Hz), 8.87 (1H, s).

Step 6

5-Chloro-1-[(2S)-1,4-dioxan-2-ylmethyl]-6-(1H-pyrrolo[2,3-b]pyridin-5-yl)-1,3-dihydro-2H-imidazo[4,5-b]pyridin-2-one The compound obtained in the above Step 5 (130 mg) was dissolved in tetrahydrofuran (5 ml). Tetrabutylammonium fluoride (1.0 M solution in tetrahydrofuran) (1 ml) was added and the mixture was stirred at 80° C. for three days. The reaction solvent was distilled off under reduced pressure. The resulting residue was purified by silica gel column chromatography (developed with ethyl acetate-hexane). Further, the resulting residue was washed with ethyl acetate and then dried under reduced pressure to give the title compound (50 mg) as a pale yellow solid.

HRMS (ESI) [M+H]$^+$ calculated: C$_{18}$H$_{17}$ClN$_5$O$_3$ 386.10199.
found: 386.10351.
MS (ESI) m/z: 386 (M+H)$^+$.
$^1$H-NMR (DMSO-d$_6$) δ: 3.27-3.31 (1H, m), 3.40-3.53 (2H, m), 3.57-3.61 (1H, m), 3.68-3.72 (1H, m), 3.75-3.89 (3H, m), 3.91-3.96 (1H, m), 6.52 (1H, dd, J=3.7, 1.8 Hz), 7.54-7.56 (1H, m), 7.67 (1H, s), 8.04 (1H, d, J=1.8 Hz), 8.27 (1H, d, J=2.3 Hz), 11.79 (1H, br s), 11.89 (1H, br s).

Formulation Example 1

Hard Capsules

Each standard bipartite hard gelatin capsule is filled with 100 mg of the powdery Example Compound 1, 150 mg of lactose, 50 mg of cellulose and 6 mg of magnesium stearate to produce a unit capsule. The capsule is washed and then dried.

Formulation Example 2

Soft Capsules

A mixture of Example Compound 1 in a digestive oil such as soybean oil, cottonseed oil or olive oil is prepared and injected into a gelatin capsule by a positive displacement pump to give a soft capsule containing 100 mg of the active ingredient. The capsule is washed and then dried.

Formulation Example 3

Tablets

A tablet is produced according to a commonly employed method using 100 mg of Example Compound 1, 0.2 mg of colloidal silicon dioxide, 5 mg of magnesium stearate, 275 mg of microcrystalline cellulose, 11 mg of starch and 98.8 mg of lactose. If desired, a coating is applied to the tablet.

Test Example 1 mTOR Kinase Activity Inhibition Test

The kinase activity of mTOR was measured in the presence or absence of a test compound. A substrate peptide is phosphorylated by mTOR kinase activity. A complex of streptavidin-XL665 and anti-phosphorylated S6K (Thr389) antibody/anti-mouse IgG-cryptate binds to this phosphorylated peptide. At this moment, fluorescence resonance energy transfer takes place from antibody/anti-mouse IgG-cryptate exposed to light excitation to XL665, which results in emission of fluorescence at 665 nm. The mTOR kinase activity is detected using this principle. In the presence of an mTOR inhibitor, phosphorylation of the substrate peptide is inhibited and the aforementioned complex does not bind to the substrate peptide. As a result, fluorescence resonance energy transfer does not occur and fluorescence at 665 nm is decreased.

(1) Sample Preparation and Enzymatic Reaction

An HEK293 cell line that constitutively expresses a His tag fused human mTOR has been established. His tag was introduced into the N terminus of the portion corresponding to 1362-2549aa at the C terminus of human mTOR. Cell lysate was prepared from this HEK293 cell line constitutively expressing His-tagged mTOR (1362C), and His-tagged mTOR (1362C) was purified using the His tag affinity according to a conventional method.

Next, an mTOR enzyme solution was prepared, which contains the aforementioned His-tagged mTOR (1362C) enzyme, 8 μg/mL of biotinylated peptide (Biotin-Ahx-KKANQVFLGFTYVAPSVLESVKE-amide (Sigma)), as well as 50 mM HEPES (pH 7.5), 20 mM MnCl$_2$, 1 mg/ml BSA, an appropriate amount of protease inhibitor cocktail (Complete EDTA free, Roche), 100 ng/ml Calyculin A, 4 μg/ml Cantharidin and 10 mM DTT as other components.

The test compound was dissolved in DMSO, and serial dilutions were prepared with 20 μM ATP solution (50 mM HEPES (pH 7.5), 20 μM ATP) to achieve concentrations necessary for the assay. 5 μL of this compound solution was applied to each well of a 384 well small volume white Greiner plate.

5 μL of mTOR enzyme solution was added to the aforementioned well containing the test compound. After mixing, the mixture was incubated at room temperature for 3 hours to carry out the enzymatic reaction.

The same operation was performed with a solution of DMSO in 20 μM ATP solution as a positive control and with a solution of DMSO in 50 mM HEPES (pH 7.5) as a negative control.

(2) Detection of Enzymatic Reaction

After the enzymatic reaction, 5 μl each of an europium solution (a solution of anti-mouse IgG-cryptate (SCETI Medical Labo K.K.) and anti-phosphorylated S6K (Thr389) antibody (Cell Signaling Technology Inc.) in 50 mM HEPES (pH 7.5), 100 mM EDTA and 1.5 mg/ml BSA) and an XL665 solution (a solution of streptavidin-XL665 (SCETI Medical Labo K.K.) in 50 mM HEPES (pH 7.5), 100 mM EDTA, 0.8 M KF and 1.5 mg/ml BSA) were added in this order and then mixed. The mixture was incubated at 4° C. overnight. On the following day, the mixture was returned to room temperature and irradiated with excitation light at 337 nm. Fluorescence at 620 nm and fluorescence at 665 nm were measured with RUBYstar (BMG).

The mTOR inhibitory activity (%) was calculated using the ratio calculated from the measured values as an index of enzyme activity. Here, the ratio was calculated from the following formula (I).

$$\text{Ratio}=10000\times 665 \text{ nm fluorescence value}/620 \text{ nm fluorescence value} \quad (1)$$

The mTOR enzyme inhibitory activity (%) was calculated from the following formula (2).

$$\text{mTOR enzyme inhibitory activity (\%)}=100\times[(P-S)/(P-N)] \quad (2)$$

P: Ratio in well of positive control
N: Ratio in well of negative control
S: Ratio in well containing test compound Further, an optimal curve was calculated based upon each concentration of the test compound prepared in serial dilutions and the mTOR enzyme inhibitory activity (%) at that concentration. The concentration at which 50% inhibition occurred was calculated as the IC$_{50}$ value of mTOR enzyme inhibitory activity.

The compounds having their IC$_{50}$ values lower than 0.05 μM were the compounds of Example Nos. 1, 3 to 7, 9, 10, 15 to 29, 31 to 55, 58 to 72, 76, 78, 79, 81 to 84, 90, 92, 93, 95 to 130, 133 to 153 and 155. The compounds having their IC$_{50}$ values 0.05 μM or higher and lower than 0.1 μM were the compounds of Example Nos. 57, 75 and 77. The compounds having their IC$_{50}$ values 0.1 μM or higher and lower than 5 μM were the compounds of Example Nos. 2, 8, 11 to 14, 30, 56, 73, 74, 80, 85 to 89, 91, 94, 131 and 132.

Test Example 2

Cell Proliferation Inhibitory Test

WM-266-4 cells (ATCC, USA) were seeded in a 96-well plate and cultured overnight. Then, serial dilutions of the sample containing the test compound were prepared, added to each well and cultured another three days. Thereafter, the cell amount in each well was measured by MTT (MOSMANN, T., Rapid colorimetric assay for cellular growth and survival: application to proliferation and cytotoxicity assays. J. Immunol. Methods, 65, 55-63 (1983)). The 50% cell proliferation inhibitory activity (GI$_{50}$ value) was calculated from the following formula (3).

$$100\times[(T-T_0)/(C-T_0)]=50 \quad (3)$$

Here, T represents values from the test compound added wells, C represents the value from the well to which the test compound was not added for three days, and T$_o$ represents an initial measured value at the time of addition of the test compound.

The compounds that showed GI$_{50}$ values lower than 3 μM were the compounds of Example Nos. 1 to 7, 9, 15 to 21, 23 to 29, 31 to 55, 58, 60 to 65, 67 to 71, 75, 78, 79, 81 to 83, 88, 90 to 92, 96, 98 to 105, 107, 108, 111 to 129, 133 to 153 and 155. The compounds that showed GI$_{50}$ values of 3 μM or higher and lower than 25 μM were the compounds of Example Nos. 8, 10, 14, 56, 57, 59, 72 to 74, 76, 77, 84 to 87, 89, 93 to 95, 97, 109, 110 and 130 to 132.

Test Example 3

In Vivo Antitumor Effect 0.1 mL of a tumor cell suspension adjusted to $3-10\times10^7$ cells/mL or solid tumor sliced into size 3 to 5 mm cubic are subcutaneously transplanted into BALB/c nude mice (6 to 8-week-old), and the mice are kept until the tumor volume reaches more than 100 mm$^3$. The mice are separated into groups based on their tumor volume. The test compound is dissolved or suspended in an appropriate solvent and orally or intraperitoneally administered to the mice. The administration periods are two to four weeks depending on the tumor types. The length (mm) and width (mm) of the tumor is measured with electronic digital calipers, and the estimated tumor volume is calculated using the calculation formula (4) shown below. The tumor growth inhibition rate on the measured day (TGI %) is evaluated. The body weight is measured and the systemic condition is observed during the administration period. The test compound is evaluated to be effective when tumor growth is inhibited without causing death, significant reduction in body weight, or abnormal appearance.

$$TGI (\%)=(1-A/B)\times100 \qquad (4)$$

A: Mean tumor volume of compound-administered group (*) on measurement day.
B: Mean tumor volume of non-treated control group (*) on measurement day.
*: The tumor volume is calculated from: 1/2×[tumor length]×[tumor width]×[tumor width].

INDUSTRIAL APPLICABILITY

The compound of the present invention has strong mTOR inhibitory activity and excellent antitumor activity, and is therefore useful as a medicine, in particular, an antitumor agent.

The invention claimed is:
1. A compound represented by the general formula (I):

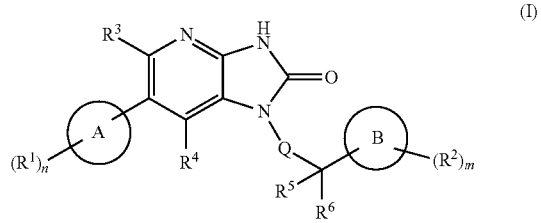

(I)

wherein,
A is an 8- to 10-membered partially saturated or aromatic fused bicyclic nitrogen-containing heterocyclic group having 1 to 3 nitrogen atoms,
A may have the same or different n R$^1$s as substituents,
R$^1$ is a substituent selected from the group consisting of a hydroxy group, a halogen atom, a cyano group, an oxo group, a C$_{1-4}$ alkyl group (wherein the C$_{1-4}$ alkyl group may be substituted with one or two same or different C$_{1-4}$ alkoxy groups or —NR$^{7a}$R$^{7b}$s), a C$_{1-4}$ alkoxy group, a halogeno-C$_{1-4}$ alkyl group, —NR$^{7a}$R$^{7b}$, —C(O)R$^8$ and —C(O)NR$^{9a}$R$^{9b}$, n is any integer of 0 to 3,
R$^{7a}$, R$^{7b}$, R$^{9a}$ and R$^{9b}$ are the same or different and are each a hydrogen atom or a C$_{1-4}$ alkyl group (wherein the C$_{1-4}$ alkyl group may be substituted with 1 or 2 hydroxy groups),
R$^8$ is a hydrogen atom, a hydroxy group, a C$_{1-4}$ alkyl group or a C$_{1-4}$ alkoxy group,
B is a 3- to 7-membered saturated or partially saturated monocyclic hydrocarbon group and may contain 1 or 2 oxygen atoms, sulfur atoms, nitrogen atoms, sulfinyl groups and/or sulfonyl groups as ring constituents,
B may have the same or different m R$^2$s as substituents,
R$^2$ is a substituent present on a carbon atom or nitrogen atom forming B,
R$^2$ is a substituent selected from the group consisting of a hydroxy group, a halogen atom, a cyano group, an oxo group, a C$_{1-4}$ alkyl group (wherein the C$_{1-4}$ alkyl group may be substituted with 1 or 2 C$_{1-4}$ alkoxy groups), a C$_{1-4}$ alkoxy group, a halogeno-C$_{1-4}$ alkyl group, a C$_{1-4}$ alkylsulfonyl group, a C$_{1-4}$ alkylcarbonyl group and —NR$^{10a}$R$^{10b}$ when R$^2$ is a substituent present on a carbon atom forming B, and R$^2$ is a substituent selected from the group consisting of a hydroxy group, a C$_{1-4}$ alkyl group (wherein the C$_{1-4}$ alkyl group may be substituted with 1 or 2 C$_{1-4}$ alkoxy groups), a C$_{1-4}$ alkoxy group, a halogeno-C$_{1-4}$ alkyl group, a C$_{1-4}$ alkylsulfonyl group, a C$_{1-4}$ alkylcarbonyl group and —NR$^{10a}$R$^{10b}$ when R$^2$ is a substituent present on a nitrogen atom forming Ring B,
R$^{10a}$ and R$^{10b}$ are the same or different and are each a hydrogen atom or a C$_{1-4}$ alkyl group,
m is any integer of 0 to 3,
Q is a bond or a C$_{1-4}$ alkylene group,
R$^3$ and R$^4$ are the same or different and are each a hydrogen atom, a halogen atom, a C$_{1-4}$ alkyl group, a halogeno-C$_{1-4}$ alkyl group or a cyano group, and
R$^5$ and R$^6$ are the same or different and are each a hydrogen atom, a halogen atom or a C$_{1-4}$ alkyl group, or R$^5$ and R$^6$ together may form an oxo group or together with the carbon atom to which R$^5$ and R$^6$ are bonded may form a C$_{3-8}$ cycloalkyl group,
or a pharmacologically acceptable salt thereof.

2. The compound or pharmacologically acceptable salt thereof according to claim 1, wherein A is a fused bicyclic nitrogen-containing heterocyclic group having 1 to 3 nitrogen atoms in which:
(a) the ring directly bonded to the imidazopyridine ring is a partially saturated or aromatic 6-membered ring containing 0 to 2 nitrogen atoms and
(b) the ring not directly bonded to the imidazopyridine ring is a partially saturated or aromatic 5-membered ring containing 1 or 2 nitrogen atoms.

3. The compound or pharmacologically acceptable salt thereof according to claim 1, wherein A is an indolyl group, an isoindolyl group, an indazolyl group, a pyrrolopyridyl group, a pyrazolopyridyl group, an imidazopyridyl group, a pyrrolopyridazinyl group, a pyrazolopyridazinyl group, an imidazopyridazinyl group, a pyrrolopyrimidinyl group, a pyrazolopyrimidinyl group, an imidazopyrimidinyl group, a pyrrolopyrazinyl group, a pyrazolopyrazinyl group or an imidazopyrazinyl group.

4. The compound or pharmacologically acceptable salt thereof according to claim 1, wherein R$^1$ is a substituent identically or differently selected from the group consisting of a fluorine atom, a chlorine atom, a cyano group, a methyl group, an ethyl group, an isopropyl group, a methoxy group, an ethoxy group, a trifluoromethyl group, a methoxymethyl group, an ethoxymethyl group, an amino group, a methylamino group, a dimethylamino group, a methylethylamino group, a propylamino group, a (2-hydroxyethyl)(methyl)amino group, a formyl group, an acetyl group, an ethylcarbonyl group, an ethoxycarbonyl group, a carboxyl group, a carbamoyl group and a methylcarbamoyl group and n is any integer of 0 to 2.

5. The compound or pharmacologically acceptable salt thereof according to claim 1, wherein $R^3$ is a hydrogen atom, a fluorine atom, a chlorine atom, a cyano group or a methyl group and $R^4$ is a hydrogen atom.

6. The compound or pharmacologically acceptable salt thereof according to claim 1, wherein Q is a bond or a methylene group.

7. The compound or pharmacologically acceptable salt thereof according to claim 1, wherein $R^5$ and $R^6$ are the same or different and are each a hydrogen atom, a halogen atom or a $C_{1-4}$ alkyl group.

8. The compound or pharmacologically acceptable salt thereof according to claim 1, wherein B is a $C_{3-7}$ cycloalkyl group, a tetrahydrofuryl group, a dihydropyranyl group, a tetrahydropyranyl group, a dioxanyl group, a piperidyl group, a piperazinyl group or a 1,1-dioxidotetrahydrothiopyranyl group.

9. The compound or pharmacologically acceptable salt thereof according to claim 1, wherein $R^2$ is a hydroxy group, a halogen atom, a cyano group, an oxo group, a $C_{1-4}$ alkyl group, a $C_{1-4}$ alkoxy-$C_{1-4}$ alkyl group, a $C_{1-4}$ alkoxy group, a $C_{1-4}$ alkylsulfonyl group or a $C_{1-4}$ alkylcarbonyl group when $R^2$ is a substituent present on a carbon atom forming B, $R^2$ is a $C_{1-4}$ alkyl group, a $C_{1-4}$ alkylsulfonyl group or a $C_{1-4}$ alkylcarbonyl group when $R^2$ is a substituent present on a nitrogen atom forming B, and m is any integer of 0 to 2.

10. The compound according to claim 1, wherein the compound is any one compound selected from:
- 1-[(2S)-1,4-dioxan-2-ylmethyl]-6-(1H-pyrrolo[2,3-b]pyridin-5-yl)-1,3-dihydro-imidazo[4,5-b]pyridin-2-one,
- 1-[(2S)-1,4-dioxan-2-ylmethyl]-6-(4-methyl-1H-pyrrolo[2,3-b]pyridin-5-yl)-1,3-dihydro-imidazo[4,5-b]pyridin-2-one,
- 6-(3,4-dimethyl-1H-pyrrolo[2,3-b]pyridin-5-yl)-1-[(2S)-1,4-dioxan-2-ylmethyl]-1,3-dihydro-2H-imidazo[4,5-b]pyridin-2-one,
- 6-(3-chloro-4-methyl-1H-pyrrolo[2,3-b]pyridin-5-yl)-1-[(2S)-1,4-dioxan-2-ylmethyl]-1,3-dihydro-2H-imidazo[4,5-b]pyridin-2-one,
- 1-[(2S)-1,4-dioxan-2-ylmethyl]-6-(3-fluoro-4-methyl-1H-pyrrolo[2,3-b]pyridin-5-yl)-1,3-dihydro-2H-imidazo[4,5-b]pyridin-2-one,
- 2,6-anhydro-1,3,5-trideoxy-4-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol,
- 2,6-anhydro-1,3,4-trideoxy-5-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol,
- 2,6-anhydro-1,3,4-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-5-O-methyl-L-threo-hexitol,
- 2,6-anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,4-trideoxy-5-O-methyl-L-threo-hexitol,
- 2,6-anhydro-1,3,5-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-4-O-methyl-L-threo-hexitol and
- 2,6-anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,5-trideoxy-4-O-methyl-L-threo-hexitol.

11. 1-[(2S)-1,4-Dioxan-2-ylmethyl]-6-(1H-pyrrolo[2,3-b]pyridin-5-yl)-1,3-dihydro-imidazo[4,5-b]pyridin-2-one.

12. 1-[(2S)-1,4-Dioxan-2-ylmethyl]-6-(4-methyl-1H-pyrrolo[2,3-b]pyridin-5-yl)-1,3-dihydro-imidazo[4,5-b]pyridin-2-one.

13. 6-(3,4-Dimethyl-1H-pyrrolo[2,3-b]pyridin-5-yl)-1-[(2S)-1,4-dioxan-2-ylmethyl]-1,3-dihydro-2H-imidazo[4,5-b]pyridin-2-one.

14. 6-(3-Chloro-4-methyl-1H-pyrrolo[2,3-b]pyridin-5-yl)-1-[(2S)-1,4-dioxan-2-ylmethyl]-1,3-dihydro-2H-imidazo[4,5-b]pyridin-2-one.

15. 1-[(2S)-1,4-Dioxan-2-ylmethyl]-6-(3-fluoro-4-methyl-1H-pyrrolo[2,3-b]pyridin-5-yl)-1,3-dihydro-2H-imidazo[4,5-b]pyridin-2-one.

16. 2,6-Anhydro-1,3,5-trideoxy-4-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol.

17. 2,6-Anhydro-1,3,4-trideoxy-5-O-methyl-1-[6-(4-methyl-1H-pyrrolo[2,3-b]pyridin-5-yl)-2-oxo-2,3-dihydro-1H-imidazo[4,5-b]pyridin-1-yl]-L-threo-hexitol.

18. 2,6-Anhydro-1,3,4-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-5-O-methyl-L-threo-hexitol.

19. 2,6-Anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,4-trideoxy-5-O-methyl-L-threo-hexitol.

20. 2,6-Anhydro-1,3,5-trideoxy-1-[6-(3,4-dimethyl-1H-pyrrolo[2,3-b]pyridin-5-yl)-2-oxo-2,3-dihydro-1H-imidazo[4,5-b]pyridin-1-yl]-4-O-methyl-L-threo-hexitol.

21. 2,6-Anhydro-1-[6-(3-chloro-4-methyl-1H-pyrrolo[2,3-b]pyridin-5-yl)-2-oxo-2,3-dihydro-1H-imidazo[4,5-b]pyridin-1-yl]-1,3,5-trideoxy-4-O-methyl-L-threo-hexitol.

22. A pharmaceutical composition comprising the compound or pharmacologically acceptable salt thereof according to claim 1 as an active ingredient.

23. A pharmaceutical composition comprising the compound of claim 12 or a pharmacologically acceptable salt thereof as an active ingredient.

* * * * *